United States Patent
Dixon et al.

(10) Patent No.: US 6,353,006 B1
(45) Date of Patent: *Mar. 5, 2002

(54) SUBSTITUTED 2-ARYLIMINO HETEROCYCLES AND COMPOSITIONS CONTAINING THEM, FOR USE AS PROGESTERONE RECEPTOR BINDING AGENTS

(75) Inventors: Brian R. Dixon, Woodbridge; Cedo M. Bagi, Branford; Catherine R. Brennan, Milford; David R. Brittelli, Branford; William H. Bullock, Easton; Jinshan Chen, Hamden; William L. Collibee, Bethany; Robert Dally, East Haven; Jeffrey S. Johnson, Branford; Harold C. E. Kluender, Trumbull; William F. Lathrop, Plantsville; Peiying Liu, Madison, all of CT (US); Carol Ann Mase, Ringoes, NJ (US); Anikó M. Redman, Derby; William J. Scott, Guilford, both of CT (US); Klaus Urbahns, Wuppertal (DE); Donald J. Wolanin, Orange, CT (US)

(73) Assignee: Bayer Corporation, Pittsburgh, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/453,613

(22) Filed: Dec. 3, 1999

Related U.S. Application Data

(60) Provisional application No. 60/287,573, filed on Jan. 14, 1999.

(51) Int. Cl.$^7$ .............................................. A01N 43/40
(52) U.S. Cl. ....................... 514/338; 514/342; 514/367; 514/369; 514/370; 546/269.7; 546/270.1; 548/147; 548/161; 548/184; 548/190
(58) Field of Search ................................ 514/338, 342, 514/267, 369, 370; 546/269.7, 270.1; 548/147, 161, 184, 190

(56) References Cited

U.S. PATENT DOCUMENTS

| | | | |
|---|---|---|---|
| 2,784,196 A | 3/1957 | Bacchetti | 260/306.7 |
| 2,902,356 A | 9/1959 | Luckenbaugh | 71/2.5 |
| 3,297,708 A | 1/1967 | Garber et al. | 260/306.7 |
| 3,345,257 A | 10/1967 | Duerr et al. | 167/33 |
| 3,479,351 A | 11/1969 | Metzger, Jr. | 260/246 |
| 3,636,219 A | 1/1972 | Culik et al. | 424/265 |
| 3,640,952 A | 2/1972 | Metzger, Jr. | 260/45.8 |
| 3,651,053 A | 3/1972 | Sagner et al. | 260/243 |
| 3,686,199 A | 8/1972 | Wollweber et al. | 260/307 |
| 3,689,499 A | 9/1972 | Metzger, Jr. | 260/307 |
| 3,737,536 A | 6/1973 | Sagner et al. | 424/246 |
| 3,770,693 A | 11/1973 | Metzger | 260/45.8 |
| 3,787,575 A | 1/1974 | Wollweber et al. | 424/272 |
| 3,804,848 A | 4/1974 | Behner et al. | 260/306.7 |
| 3,860,590 A | 1/1975 | Wollweber et al. | 260/243 |
| 3,898,340 A | 8/1975 | Behner et al. | 424/270 |
| 4,079,144 A | 3/1978 | Dürr et al. | 424/270 |
| 4,140,784 A | 2/1979 | Dürr | 424/270 |
| 4,148,799 A | 4/1979 | Enders | 260/306.7 |
| 4,163,791 A | 8/1979 | Dürr | 424/270 |
| 4,289,778 A | 9/1981 | Balko | 424/263 |
| 4,346,088 A | 8/1982 | Lang et al. | 424/248.51 |
| 4,421,757 A | 12/1983 | Lang et al. | 424/270 |
| 4,581,453 A | 4/1986 | Ippen et al. | 544/331 |
| 4,678,775 A | 7/1987 | Nathanson | 514/47 |
| 4,735,942 A | 4/1988 | Heeres et al. | 514/252 |
| 4,771,062 A | 9/1988 | Raddatz et al. | 514/370 |
| 4,788,209 A | 11/1988 | Baumann et al. | 514/370 |
| 4,806,653 A | 2/1989 | Felix | 548/234 |
| 4,854,961 A | 8/1989 | Wellinga et al. | 71/80 |
| 4,876,265 A | 10/1989 | Schmid | 514/370 |
| 4,877,880 A | 10/1989 | Woolard | 545/190 |
| 4,892,871 A | 1/1990 | Nathanson | 514/227.3 |
| 4,900,351 A | 2/1990 | Felix | 71/88 |
| 4,913,722 A | 4/1990 | Felix et al. | 71/90 |
| 4,931,444 A | 6/1990 | Van Wauwe et al. | 514/252 |
| 5,240,918 A | 8/1993 | Lempert et al. | 514/370 |
| 5,463,069 A | 10/1995 | Masumoto et al. | 548/190 |
| 5,521,145 A | 5/1996 | Takano et al. | 564/228 |
| 5,534,520 A | 7/1996 | Fisher et al. | 514/178 |

FOREIGN PATENT DOCUMENTS

| | | |
|---|---|---|
| DE | 1963192 | 6/1971 |
| DE | 2511731 | 10/1976 |
| DE | 2658138 | 7/1978 |
| DE | 3505432 | 8/1986 |
| EP | 0240680 | 10/1987 |
| EP | 0318253 | 5/1989 |
| EP | 0600489 | 6/1994 |
| EP | 0683160 | 11/1995 |

(List continued on next page.)

OTHER PUBLICATIONS

Streitweiser, A. and Heathcock, C.H., "Introduction to Organic Chemistry, 2nd Ed.", Macmillan, New York, 1981, p. 649.*

Fresenius, P., "Organic Chemical Nomenclature", Ellis Horwood, Chichester, West Sussex, 1989, p. 29.*

Rosen RC, Ashton AK, Arch Sex Behav 1993 Dec;22(6):521–43.*

(List continued on next page.)

*Primary Examiner*—Mukund J. Shah
*Assistant Examiner*—Thomas C McKenzie
(74) *Attorney, Agent, or Firm*—Jerrie L. Chiu

(57) ABSTRACT

This invention relates to 2-arylimino heterocycles, including 2-arylimino-1,3-thiazolidines, 2-arylimino-2,3,4,5-tetrahydro-1,3-thiazines, 2-arylimino-1,3-thiazolidin-4-ones, 2-arylimino-1,3-thiazolidin-5-ones, and 2-arylimino-1,3-oxazolidines, and their use in modulating progesterone receptor mediated processes, and pharmaceutical compositions for use in such therapies.

7 Claims, No Drawings

FOREIGN PATENT DOCUMENTS

| | | |
|---|---|---|
| FR | 1510014 | 12/1967 |
| FR | 1510015 | 12/1967 |
| FR | 1516854 | 2/1968 |
| FR | 2117337 | 7/1972 |
| GB | 1140776 | 1/1969 |
| GB | 1342232 | 1/1974 |
| GB | 1377265 | 12/1974 |
| GB | 1467385 | 3/1977 |
| GB | 1527807 | 10/1978 |
| GB | 1579782 | 11/1980 |
| GB | 1580554 | 12/1980 |
| HU | 171587 | 9/1978 |
| JP | 4315609 | 7/1943 |
| JP | 4421095 | 9/1969 |
| JP | 63041471 A2 * | 2/1988 |
| JP | 7304759 | 11/1995 |
| JP | 07304759 A2 * | 11/1995 |
| SU | 1209688 | 2/1986 |
| WO | 8904595 | 6/1989 |
| WO | 9533717 | 12/1995 |
| WO | 9614842 | 5/1996 |

OTHER PUBLICATIONS

Burke, J.R. et al, Postgraduate medicine, 106, (5), 1999, pp. 85–96.*

Mehta,R.H. and Eagle,K.A., BMJ 1998;316:838–842.*

Noseworthy, J.H., Nature supplement, 399, 1999 pp. A40–A47.*

March, J., "Advanced Organic Chemistry", McGraw–Hill, New York, 1968, p. 877.*

Vollhardt, K.P.C., "Organic Chemistry", Freeman, New York, 1987, p. 857.*

Morrison,, R. T. et al, "Organic Chemistry", Allyn and Bacon, Boston, 1983, p. 627.*

Ambartsumova et al., "1,3–Thiazepines—Reactions of 2–Iminothiazepines with Methyl Acrylate. Crystal and Molecular Structure of 2–Phenylimino–3–(β–Methoxycarbonylethyl)– and 2–Benzyliminohexahydro–1,3–Thiadiazepines", Chemistry of Heterocyclic Compounds, 33(4): 475–480 (1997).

Argay et al., "The Structures of 2–(2, 6–dichlorophenyl)imino–3–methylperhydro–1,3–thiazine, 2–(2,6–Dimethylphenyl)imino–3–methylperhydro–1,3–thiazine and 2–[N–(2,6Dimethylphenyl)–N–methylamino]4, 5dihydro–6H–1,3–thiazine", Acta Cryst., B36: 363–368 (1980).

Arya et al., "Psychoactive Agents: Parts I—Synthetic & Pharmacological Activity of Some Thiazolidines & I,2, 3–Oxathiazolidines Related to Clonidine", Indian J. Chem., 15B:133–140 (Feb. 1977).

Cherbuliez et al., "Aryl(ou aralcoyl ou alcoyl)amino–2–tétrahydro–m–thiazines ou aryl(ou aralcoyl ou alcoyl)amino–2–dihydro–Δ$^2$–m–thiazines et derives", Helvetica Chimica Acta, 50(40): 331–346 (1967).

Chiou et al., "Prevention of Ocular Inflammation Induced by Lens Protein, Endotoxin, and Interleukin–1 with Synthetic Interleukin–1 Blockers,", J. Ocular Pharm., 10(3): 577–586 (1994).

H–G Hahn, "2–iminothiazoline, fungicidal activity", Agriculture Chem. Biotech., 40(1): 139–143 (1997).

Hanefeld et al., "Synthese N–substituierter2–Chlor–5, 6–dihydro–4H–1,3–thiazinium–salze und deren Reaktionen mit primaren Aminoverbindungen", Arch. Pharm. (Weinheim), 321: 199–204 (1988).

Hanefeld et al., "Neuartige Umwandlungen an Terahydro–1, 3–thiazin–2–thionen mittels Thionylchlorid", Arch. Pharm. (Weinheim) 318: 60–69 (1985).

Hanefeld et al., "Zur Darstellbarkeit von 1,2–Oxathietan–2, 2–dioxiden (β–Sultonen) und deren Reaktionen mit Nucleophilen", Arch. Pharm. (Weinheim), 314: 799–810 (1981).

Ignatova et al., "Basicities and Structures of 4,4, 6–Trimethyl–2–Arylamino–5,6–Dihydro–4H–11,3–Thiazines and 4,4,6–Trimethyl–2–Arylamino–5, 6–Dihydro–4H–1,3–Oxazines", English translation of Khim. Geterotsikl. Soedin., 12: 1621–1624 (Dec. 1976) in the Journal of Chemistry of Heterocyclic Compounds, pp. 1333–1336, Plenum Publishing Corporation, New York, NY.

Ignatova et al., "Synthesis of Substituted 2–Amino–5, 6–Dihydro–4H–1,3–Oxazines and 2–Iminotetrahydro–1, 3–Oxazines", English translation of Khim. Geterotsikl. Soedin., 3: 354–356 (Mar. 1974) in the Journal of Chemistry of Heterocyclic Compounds, pp. 307–309 (1975), Plenum Publishing Corporation, New York, NY.

Kalman et al., "On the Tautomerism and Conformational Characteristics of 2–Phenylimino–3,1–Perhydrobenzoxazines and Analogous Benzothiazines: An X–Ray Study", J. Mol. Struct., 161: 125–138 (1987).

Metzger Jr. et al., "Preparation and Reactions of Substituted 2–Imino–1,3–Oxazolidines—their use in retarding hydrolytic degration of polyurethanes", Polym. Prepr., Amer. Chem. Soc., Div. Polym. Chem., 9(2):1572–1579 (1968).

Mizrakh et al., "Reactions of P–Dialkyamido–P–Acetylphosphites with N–Oxyalyl–N+40 –Substituted Thiocarbamides. Synthesis of 2–Iminothiasolidine Derivatives under Mild Conditions", English translation ofZh. Obshch. Khim., 62(7): 1498–1504 (Jul. 1992) in the Journal of Chemistry of Heterocyclic Compounds, pp. 1229–1233 (1989), Plenum Publishing Corporation, New York, NY.

Mizrakh et al., "Reactions of Phosphorous Dialylamides with N'–Substituted N–(Hydroxyalkyl)Thioureas. New method for the synthesis of 2–Iminothiozolidine and Tetrahydro–2–imino–2H–1,3–thiazine Derivatives", English translation of Zh. Obshch. Khim., 58(10): 2246–2251 (Oct. 1988) in the Journal of Chemistry of Heterocyclic Compounds, pp. 1999–2003 (1989), Plenum Publishing Corporation, New York, NY.

Mizrakh et al., "Reaction of Dioxadiazaphosphaspiro–nonanes with Alkyl and Aryl Isothiocyanates. New method of preparing 2–Alkyl– and 2–(Arylimino)–Thiazolidines and some of their derivatives", English translation of Zh. Obshch. Khim., 56(1): 73–81 (Jan. 1986) in the Journal of Chemistry of Heterocyclic Compounds, pp. 62–69 (1986), Plenum Publishing Corporation, New York, NY.

Mohsen et al., "Synthesis and Biological Evaluation of New 2,3–Dihydrothioazole Derivatives for Antimicrobial Antihypertensive, and Anticonvulsant Activities", J. Pharma. Sci., 73(8): 1166–1168 (Aug. 1984).

Okawara et al., "Facile Formation of 1,3–Disubstituted 2,3,5,6–Tetrahydro–2–thioxopyrimidin–4(1H)–ones and 2–N,3–Disubstituted 2,3,5,6–Tetrahydro–2–imino1, 3–thiazin–4–ones from Thioureas and β–Haloacyl Halides", Chem. Pharm. Bull., 31(2): 507–512 (1983).

Olzenko–Piontkowa et al., "1–Thia–3–Azacycloheptane Derivatives", Org. Prep. Proc. Int., 3(1):27–32 (1971).

Peresleni et al., "Structure of 4,46-Trimethyl-2-Arylamino-5,6-Dihydro-4H-1,3-Thiazines and -Oxazines", English translation of Khim. Geterotikl. Soedin., 3: 346–352 (Mar. 1977) in the Journal of Chemistry of Heterocyclic Compounds, pp. 278–284, Plenum Publishing Corporation, New York, NY.

Raman et al., "Substituted Oxothiazolyl Acetic Acids as Antinflammatory Agents", Res. Commun. Chem. Phat. Pharm., 21(1): 177–180 (Jul. 1978).

Reinhoudt D. N., "Synthesis of 1,3-Thiazepines and 1,3-Benzo[e]Thiazepines", Recueil, 92: 20–33 (1973).

Rohde et al., "Effect of Some Phytogenic Agents and Synthetic Compounds on Complement Cascade-Mediated Hemolysis", Ophthalmic Res., 26: 116–123 (1994).

Schwade et al., "Effects of Interleukin-1 Blockers on Ophthalmic Wound Healing in a Rabbit Model of Trabeculectomy", J. Ocular Pharmacology Therapeutics, 11(2): 125–134 (1995).

Singh B. N., "Synthesis of New 5-Arylazo-3-Benzyl-2-Arylimino-4-Thiazolidinones", Asian J. Chem., 5(2): 278–281 (1993).

Singh B. N., "Synthesis of Some New 3-Benzyl-2-Arylimino-4-Thiazolidinone-1,1-Dioxides", Phosphorus and Sulfur, 5: 189–190 (1978).

Solankee et al., "2-Phenylimino-3-Substituted Phenyl-5-(ω-Methoxy-carbonylpropyl)-4-Thiazolidinones. Part II", J. Inst. Chemists (India), 66: 49–50 (Mar. 1994).

Solankee et al., "Synthesis of Some 2-Phenylimino-3-Substituted Phenyl-5-(ω-Methoxy Carbonylheptyl)-4-Thiazolidinones", Indian J. Heterocyclic Chem., 3: 291–292 (Apr.–Jun. 1994).

Solankee et al., "2-Alkyl/Arylimino-3-Substituted Phenyl-5-(ω-Carboxypropyl)-4-Thiazolidinones Part III", J. Inst. Chemists (India), 65: 191 (Nov. 1993).

Toldy et al., "Helyettesített Tiazolin-, Thiazin-És Tiazepin-Származékok Szintékok És Élettani Hatása", Acta Pharmaceutica Hungarica, 43: 195–199 (1973).

Tyukhteneva et al., "Synthesis of 2-(2-Arylamino-3-Alkyloxazolidynyl-4)- and 2-(2-Arylamino-3-Alkylthiazolidynyl-4-N-Alylacetamides from 2(5H)-Furanone", English translation of Khim. Geterotsikl. Soedin., 12: 1629–32 (Dec. 1985) in the Journal of Chemistry of Heterocyclic Compounds, pp. 1339–1342 (1986) Plenum Publishing Corporation, New York, NY.

Xiao et al., "Mechanisms of Antagonism of Interleukin-1α by Synthetic Interleukin-1 Blockers", J. Ocular Pharmacology and Therapeutics, 11(3): 369–377 (1995).

Zawisza et al., "The Reaction of Thiourea Derivatives with Maleic Acid Anhydride", Polish J. Chem., 59:149158 (1985).

Nomura, Ryoki; Nakano, Takahiro; Nishio, Yoshitaka; Ogawa, Sachiko; Ninagawa, Akira; Matsuda, Haruo, Chem. Ber., 122(12), 2407–9 (English) 1989.*

"Advances in Medicinal Chemistry, vol. 33", Academic Press, 1998, New York, p 151 & 158.*

John D. Roberts and Marjorie C. Caserio, "Basic Principles of Organic Chemistry", Benjamin, New York, 1964, p 769.*

* cited by examiner

SUBSTITUTED 2-ARYLIMINO HETEROCYCLES AND COMPOSITIONS CONTAINING THEM, FOR USE AS PROGESTERONE RECEPTOR BINDING AGENTS

CROSS-REFERENCE TO RELATED APPLICATION

This application claims priority to and the benefit oif U.S. Serial No. 60/287,573, filed Jan. 14, 1999.

FIELD

This invention relates to heterocyclic pharmaceuticals, and more particularly, to 2-arylimino heterocycles, pharmaceutical compositions containing them, and their use in modulating progesterone receptor mediated processes.

BACKGROUND

An agent which binds to the progesterone receptor may be employed for a wide variety of indications, including those shown in the lettered paragraphs below:

A1) to enhance bone formation in bone weakening diseases, for the prevention of and/or treatment of osteopenia or osteoporosis (Manzi, et al., J. Soc. Gynecol. Invest., 1, 302 (1994); Scheven, et al., Biochem. Biophys. Res. Commun., 186, 54 (1992); Verhaar, et al., Bone, 15, 307 (1904); Ontjes, In "Calcium and Phosphorus in Health Diseases", Anderson and Garner (Eds.), CRC Press, 207 (1996); Scheven et al., Biochem. Biophys. Res. Commun., 186, 54 (1992)) including corticosteroid-induced osteoporosis (Picardo, et al., Drug Safety 15, 347 (1996)), postmenopausal osteoporosis, or Paget's disease;

A2) as an agent to enhance fracture healing;

B1) as a female contragestive agent, (Cadepond et al., Annu. Rev. Med., 48, 129 (1997); Heikinheimo Clin. Pharmacokinet., 33, 7 (1997); Li et al., Adv. Contracept., 11, 285 (1995); Spitz et al., Adv. Contracept. 8, 1 (1992); Spitz et al., Annu. Rev. Pharmacol. Toxicol., 36, 47 (1996));

B2) for prevention of endometrial implantation (Cadepond et al., Annu. Rev. Med., 48, 129 (1997));

B3) for the induction of labor (Heikinheimo Clin. Pharmacokinet., 33, 7 (1997); Karalis et al., Ann. N. Y. Acad. Sci., 771, 551 (1995)), including the case of foetus mortus (Heikinheimo, Clin. Pharmacokinet., 33, 7 (1997); Cadepond et al., Annu. Rev. Med., 48, 129 (1997));

B4) for treatment of luteal deficiency (Pretzsh et al., Zentralbl. Gynaekol., 119 (Suppl. 2), 25 (1997); Bezer et al., In "Molecular and Cellular Aspects of Periimplantation Processes", Dey (Ed.), Springer-Verlag, p. 27 (1995));

B5) to enhance recognition and maintanence of pregnancy (Bezer et al., In "Molecular and Cellular Aspects of Periimplantation Processes", Dey (Ed.), Springer-Verlag, p. 27 (1995));

B6) for counteracting preeclampsia, eclampsia of pregnancy and preterm labor (Yallampalli et al., WO 97/34,922);

B7) for the treatment of infertility, including promotion of spermatogenesis, the induction of the acrosome reaction, oocyte maturation, and in vitro fertilization of oocytes (Baldi et al., J. Steroid Biochem. Mol. Biol., a53, 199 (1995); Baldi et al., Trends Endocrinol. Metab., 6, 198 (1995); Blackwell et al., Colloq. INSERM, 236, 165 (1995); Blackmore et al., Cell. Signalling, 5, 531 (1993); Cork et al., Zygote, 2, 289 (1994); Meizel, Biol. Reprod., X, 56, 569 (1997));

C1) for treatment of dysmenorrhea (Coll Capdevila et al., Eur. J. Contracept. Reprod. Health Care, 2, 229 (1997); Adashi et al., Keio J. Med., 44, 124 (1995));

C2) for treatment of dysfunctional uterine bleeding (Coll Capdevila et al., Eur. J. Contracept. Reprod. Health Care, 2, 229 (1997); Adashi et al., Keio J. Med., 44, 124 (1995));

C3) for treatment of ovarian hyperandrogynism (Schaison et al., Androg. Excess Disord. Women, 715 (1997));

C4) for treatment of ovarian hyperaldosteronism (Adashi et al., Keio J. Med., 44, 124 (1995));

C5) for treatment of premenstral syndrome and/or premenstral tension (Mortola, Curr. Opin. Endocrinol. Diabetes, 2, 483 (1995)); Adashi et al., Keio J. Med., 44, 124 (1995));

C6) for treatment of perimenstrual behavior disorders (Constant et al., Hormone Res., 40, 141 (1993));

C7) for treatment of climacteric disturbance, i.e. menopause transition (Adashi et al., Keio J. Med., 44, 124 (1995)) including hot flushes (Sarrel, Int. J. Fertil. Women's Med., 42, 78 (1997); Båström et al., Ciba Found. Symp., 121, 171 (1995)), mood changes (Båström et al., Ciba Found. Symp., 121, 171 (1995)), sleep disturbance (Sarrel, Int. J. Fertil. Women's Med., 42, 78 (1997)) and vaginal dryness (Sarrel, Int. J. Fertil. Women's Med., 42, 78 (1997));

C8) for enhancement of female sexual receptivity (Dei et al., Eur. J. Contracept. Reprod. Health Care, 2(4), 253 (1997); McCarthy et al., Trends Endocrinol. Metab., 7, 327–333 (1996); Mani et al., Horm. Behav., 31, 244 (1997)) and male sexual receptivity (Johnson et al., In "Essential Reproduction, $2^{nd}$ ed., Blackwell Scientific Pub., London p177 (1984));

C9) for treatment of post menopausal urinary incontinence (Mäkinen et al., Maturitas, 22, 233 (1995); Batra et al., J. Urology, 138, 1301 (1987));

C10) to improve sensory and motor functions (Båström et al., Ciba Found. Symp., 121, 171 (1995));

C11) to improve short term memory (Båström et al., Ciba Found. Symp., 121, 171 (1995));

C12) for treatment of postpartum depression (Dalton, Practitioner, 229, 507 (1985));

C13) for treatment of genital atrophy (Sarrel, Int. J. Fertil. Women's Med., 42, 78 (1997));

C14) for prevention of postsurgical adhesion formation (Ustun, Gynecol. Obstet. Invest., 46, 202 (1998));

C15) for regulation of uterine immune function (Hansen et al., J. Reprod. Fertil., 49(Suppl.), 69 (1995));

C16) for prevention of myocardial infarction (Sarrel, Int. J. Fertil. Women's Med., 42, 78 (1997));

D1) for hormone replacement therapy (Casper et al., J. Soc. Gynecol. Invest., 3, 225 (1996));

E1) for treatment of cancers, including breast cancer (Cadepond et al., Annu. Rev. Med., 48, 129 (1997); Pike et al., Endocr.-Relat. Cancer, 4, 125 (1997)), uterine cancer (Heikinheimo Clin. Pharmacokinet., 33, 7 (1997)), ovarian cancer (Pike et al., Endocr.-Relat. Cancer, 4, 125 (1997); Hughes, WO 98/10,771), and endometrial cancer (Satyaswaroop, Contrib. Oncol., 50, 258 (1995); Pike et al., Endocr.-Relat. Cancer, 4, 125 (1997));

E2) for treatment of endometriosis (Cadepond et al., Annu. Rev. Med., 48, 129 (1997); Heikinheimo, Clin. Pharmacokinet., 33, 7 (1997); Edmonds, Br, J. Obstet. Gynaecol., 103 (Suppl. 14), 10 (1996); Adashi et al., Keio J. Med., 44, 124 (1995));

E3) for treatment of uterine fibroids (Cadepond et al., Annu. Rev. Med., 48, 129 (1997); Adashi et al., Keio J. Med., 44, 124 (1995));

F1) for treatment of hirsutism (Orentreich et al., U.S. Pat. No. 4,684,635; Azziz et al., J. Clin. Endocrinol. Metab., 80, 3406 (1995));

F2) for inhibition of hair growth (Houssay et al., Acta Physiol. Latinoam., 28, 11 (1978));

G1) as a male contraceptive (Hargreave et al., Int. Congr., Symp. Semin. Ser., 12, 99 (1997); Meriggiola et al., J. Androl., 18, 240 (1997));

G2) as an abortifacient (Michna et al., Pharm. Ztg., 141, 11 (1996)); and

H1) for the promotion of mylin repair (Baulieu et al., Cell. Mol. Neurobiol., 16, 143 (1996); Baulieu et al., Mult. Scler., 3, 105 (1997); Schumaker et al., Dev. Neurosci., 18, 6 (1996); Koenig et al., Science, 268, 1500 (1995)).

Currently, progesterone or progestins alone or in combination with estrogens are clinically indicated: for contraception (Merck Manual; Merck & Co. (1992)); for treatment of gastrointestinal bleeding due to arteriovenous malformations (Merck Manual; Merck & Co. (1992)); for treatment of recurrent metatarsal stress fractures complicated by oligiomenorrhea or amenorrhea (Merck Manual; Merck & Co. (1992)); for treatment of premenstral syndrome (PMS, premenstral tension; Merck Manual; Merck & Co. (1992)); for postmenopausal hormone replacement therapy (Merck Manual; Merck & Co. (1992)); for treatment of hot flashes and subsequent insomnia and fatigue during menopause (Merck Manual; Merck & Co. (1992)); for treatment of dysfunctional uterine bleeding when pregnancy is not desired (Merck Manual; Merck & Co. (1992)); and for suppression of endometriosis (Merck Manual; Merck & Co. (1992)), breast cancer (Merck Manual; Merck & Co. (1992)), endometrial cancer (Merck Manual; Merck & Co. (1992)), or luteal insufficiency (Merck Manual; Merck & Co. (1992)). For example, medroxyprogesterone, a progestin, alone or in combination with estrogens is indicated for prevention of osteoporosis, treatment of vulvar and/or vaginal atrophy, treatment of moderate to severe vasomotor symptoms associated with menopause, treatment of secondary amenorrehea, treatment of abnormal uterine bleeding due to hormonal imbalance in the absence of organic pathology, prevention of pregnancy, or as adjunctive therapy and palliative treatment of inoperable, recurrent, and metastatic endometrial or renal carcinoma (Merck Manual; Merck & Co. (1998)).

SUMMARY

This invention provides nonsteroidal 2-arylimino- and 2-heteroarylimino-heterocyclic compounds which have affinity for the progesterone receptor, and therefore can act as progestins and/or antiprogestins thus modulating progesterone receptor mediated processes.

This invention relates to compounds having the formula (I)

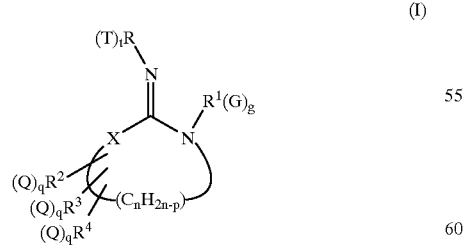

wherein

R is
  aryl of 6–14 carbons; or
  heteroaryl of 3–10 carbons and containing 1–3 heteroatoms selected from the group consisting of N, O, and S, with the proviso that R is other than benzofuran or benzothiophene;

$R^1$ is
  alkyl of 1–10 carbons;
  cycloalkyl of 3–12 carbons and containing 1–3 rings;
  heterocycloalkyl of 4–7 carbons and containing 1–3 rings and 1–3 heteroatoms selected from the group consisting of N, O, and S;
  alkenyl of 2–10 carbons;
  cycloalkenyl of 5–12 carbons and containing 1–3 rings; or
  alkynyl of 3–10 carbons;

$R^2$, $R^3$, and $R^4$ are independently selected from the group consisting of
  H;
  alkyl of 1–10 carbons;
  cycloalkyl of 3–12 carbons;
  alkenyl of 2–10 carbons;
  cycloalkenyl of 5–12 carbons;
  aryl of 6–13 carbons;
  heteroaryl of 3–9 carbons and containing 1–3 heteroatoms selected from the group consisting of N, O, and S;
  $CO_2R^5$; wherein
    $R^5$ is alkyl of 1–4 carbons, haloalkyl of 1–4 carbons, cycloalkyl of 3–6 carbons, or halocycloalkyl of 3–6 carbons;
  halogen; and
  =O, representing two of the groups $R^2$, $R^3$, and $R^4$;

X is O or $S(O)_y$; wherein
  y is 0, 1, or 2;

n is 2, 3, 4, or 5;

p is the sum of non-H substituents $R^2$, $R^3$, and $R^4$;

T is a substituent selected from the group consisting of
  alkyl of 1–4 carbons;
  alkoxy of 1–4 carbons;
  aryl of 6–10 carbons;
  $CO_2H$;
  $CO_2R^5$;
  alkenyl of 2–4 carbons;
  alkynyl of 2–4 carbons;
  $C(O)C_6H_5$;
  $C(O)N(R^6)(R^7)$; wherein
    $R^6$ is H or alkyl of 1–5 carbons; and
    $R^7$ is H or alkyl of 1–5 carbons;
  $S(O)_{y'}R^8$; wherein
    y' is 1 or 2; and
    $R^8$ is alkyl of 1–5 carbons;
  $O_2F$;
  CHO;
  OH;
  $NO_2$;
  CN;
  halogen;
  $OCF_3$;
  N-oxide;
  O—$C(R)_2$—O, the oxygens being connected to adjacent positions on R; and wherein
    $R^9$ is H, halogen, or alkyl of 1–4 carbons;
  C(O)NHC(O), the carbons being connected to adjacent positions on R; and
  $C(O)C_6H_4$, the carbonyl carbon and the ring carbon ortho to the carbonyl being connected to adjacent positions on R;

t is 1–5;
  provided that when substituent moiety T is alkyl of 1–4 carbons, alkoxy of 1–4 carbons, aryl of 6–10 carbons, $CO_2R^5$, alkenyl of 2–4 carbons, alkynyl of 2–4 carbons, $C(O)C_6H^5$, $C(O)N(R^6)(R^7)$, $S(O)_yR^8$, $O-C(R^9)_2-O$, or $C(O)C_6H_4$, then T optionally may bear secondary substituents selected from the group consisting of alkyl of 1–4 carbons; alkoxy of 1–4 carbons; $CO_2R^5$; $CO_2H$; $C(O)N(R^6)(R^7)$; CHO; OH; $NO_2$; CN; halogen; $S(O)_yR^8$; or $=O$, the number of said secondary substituents being 1 or 2 with the exception of halogen, which may be employed up to the perhalo level;

G is a substituent selected from the group consisting of
halogen;
OH;
$OR^5$;
$=O$, representing two substituents G;
alkyl of 1–4 carbons;
alkenyl of 1–4 carbons;
cycloalkyl of 3–7 carbons;
heterocycloalkyl of 3–5 carbons and 1–3 heteroatoms selected from the group consisting of N, O, and S;
cycloalkenyl of 5–7 carbons,
heterocycloalkenyl of 4–6 carbons and 1–3 heteroatoms selected from the group consisting of N, O, and S;
$CO_2R^5$;
$C(O)N(R^6)(R^7)$;
aryl of 6–10 carbons;
heteroaryl of 3–9 carbons and 1–3 heteroatoms selected from the group consisting of N, O, and S;
$NO_2$;
CN;
$S(O)_yR^8$;
$SO_3R^8$; and
$SO_2N(R^6)(R^7)$;

g is 0–4, with the exception of halogen, which may be employed up to the perhalo level;
provided that when substituent 0 is alkyl of 1–4 carbons, alkenyl of 1–4 carbons, cycloalkyl of 3–7 carbons, heterocycloalkyl of 3–5 carbons, cycloalkenyl of 5–7 carbons, or heterocycloalkenyl of 4–6 carbons, then G optionally may bear secondary substituents of halogen up to the perhalo level; and when substituent G is aryl or heteroaryl, then G optionally may bear secondary substituents independently selected from the group consisting of alkyl of 1–4 carbons and halogen, the number of said secondary substituents being up to 3 for alkyl moieties, and up to the perhalo level for halogen;

Q is a substituent selected from the group consisting of
alkyl of 1–4 carbons;
haloalkyl of 1–4 carbons;
cycloalkyl of 3–8 carbons;
alkoxy of 1–8 carbons;
alkenyl of 2–5 carbons;
cycloalkenyl of 5–8 carbons;
aryl of 6–10 carbons;
heteroaryl of 3–9 carbons and containing 1–3 heteroatoms selected from the group consisting of N, O, and S;
$CO_2R^5$;
$=O$, representing two substituents Q;
OH;
halogen;
$N(R^6)(R^7)$;
$S(O)_yR^8$;
$SO_3R^8$; and
$SO_2N(R^6)(R^7)$;

q is 0–4
provided that when substituent Q is aryl or heteroaryl, then Q optionally may bear secondary substituents independently selected from the group consisting of alkyl of 1–4 carbons and halogen, the number of said secondary substituents being up to 3 for alkyl moieties and up to the perhalo level for halogen; and with the further provisos that:
a) two of $(Q)_qR^1$, $(Q)_qR^2$, $(Q)_qR^3$, and $(Q)_qR^4$ may be joined, and taken together with the atom(s) to which they are attached, form a spiro or nonspiro nonaromatic ring of 3–8 members containing 0–2 heteroatoms selected from the group consisting of N, O, and S;
b) when n=2 or 3, at least one of $R^2$, $R^3$, and $R^4$ is other than H;
c) when n=2, and X=O, if t=1, then T is selected from the list of substituents T above excepting alkyl, and the 4-position of the 1,3-oxazolidine ring must bear a substituent;
d) when n=3 and X=O, if t is equal to or greater than 1, then at least one T is selected from the list of substituents T above, excepting alkyl and alkoxy;
e) when n=2 or 3 and X=O or S, then the sum of non-hydrogen atoms in $R^1$, $R^2$, $R^3$, and $R^4$ is at least 5;
f) when n=2, X=O, the 4-position of the 1,3-oxazolidine ring bears a carbonyl group, and R bears halogen at its 2- and 4-positions, then the 5-position of R bears H;
g) when n=2 and X=O, the 4-position of the 1,3-oxazolidine ring may bear a carbonyl only if the 5-position of said ring bears at least one non-H substituent;
h) when n=2, $X=S(O)_y$, the 4-position of the 1,3-thiazolidine ring bears a carbonyl group, $R^1$ is a substituted methyl group, and G is a phenyl group, then said phenyl group bears a secondary substituent;
i) when n=4, X=S, and G is $CO_2R^5$, then $R^5$ contains at least two carbons;

and pharmaceutically acceptable salts thereof.

The invention also relates to pharmaceutical compositions which include a compound of formula (I) as disclosed above, plus a pharmaceutically acceptable carrier.

As a result of their affinity for the progesterone receptor and their resultant ability to act as progestins and/or antiprogestins, and thus modulate progesterone receptor mediated processes, the compounds of this invention, as well as certain related compounds of the prior art, are believed to be useful for the purposes listed in the background section. It is to be noted that the definition of the set of compounds for use in the claimed method of treatment (formula II) is broader than the set of compounds defined by formula I, because the treatment method may employ certain compounds of the prior art which have not been recognized previously as being useful for this purpose. Accordingly, the invention relates further to a method of treating a mammal to achieve an effect, wherein the effect is:

A1) enhancement of bone formation in bone weakening diseases for the treatment or prevention of osteopenia or osteoporosis;
A2) enhancement of fracture healing;
B1) activity as a female contragestive agent;
B2) prevention of endometrial implantation;
B3) induction of labor;
B4) treatment of luteal deficiency;
B5) enhanced recognition and maintanence of pregnancy;
B6) counteracting of preeclampsia, eclampsia of pregnancy, and preterm labor;

B7) treatment of infertility, including promotion of spermatogenesis, induction of the acrosome reaction, maturation of oocytes, or in vitro fertilization of oocytes;
C1) treatment of dysmenorrhea;
C2) treatment of dysfunctional uterine bleeding;
C3) treatment of ovarian hyperandrogynism;
C4) treatment of ovarian hyperaldosteronism;
C5) alleviation of premenstral syndrome and of premenstral tension;
C6) alleviation of perimenstrual behavior disorders;
C7) treatment of climeracteric disturbance, including, menopause transition, mood changes, sleep disturbance, and vaginal dryness;
C8) enhancement of female sexual receptivity and male sexual receptivity;
C9) treatment of post menopausal urinary incontinence;
C10) improvement of sensory and motor functions;
C11) improvement of short term memory;
C12) alleviation of postpartum depression;
C13) treatment of genital atrophy;
C14) prevention of postsurgical adhesion formation;
C15) regulation of uterine immune function;
C16) prevention of myocardial infarction;
D1) therapy for hormone replacement;
E1) treatment of cancers, including breast cancer, uterine cancer, ovarian cancer, and endometrial cancer;
E2) treatment of endometriosis;
E3) treatment of uterine fibroids;
F1) treatment of hirsutism;
F2) inhibition of hair growth;
G1) activity as a male contraceptive;
G2) activity as an abortifacient; and
H1) promotion of mylin repair;
which comprises administering to said mammal an effective amount of a compound of the formula (II)

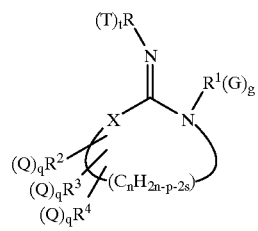

(II)

wherein
R is
  aryl of 6–14 carbons; or
  heteroaryl of 3–10 carbons and containing 1–3 heteroatoms selected from the group consisting of N, O, and S, with the proviso that R is other than benzofuran or benzothiophene;
$R^1$ is
  alkyl of 1–10 carbons;
  cycloalkyl of 3–12 carbons and containing 1–3 rings;
  heterocycloalkyl of 4–7 carbons and containing 1–3 rings and 1–3 heteroatoms selected from the group consisting of N, O, and S;
  aryl of 6–10 carbons;
  heteroaryl of 3–9 carbons and containing 1–3 rings and 1–3 heteroatoms selected from the group consisting of N, O, and S;
  alkenyl of 2–10 carbons;
  cycloalkenyl of 5–12 carbons and containing 1–3 rings; or
  alkynyl of 3–10 carbons;
$R^2$, $R^3$, and $R^4$ are independently selected from the group consisting of
  H;
  alkyl of 1–10 carbons;
  cycloalkyl of 3–12 carbons;
  alkenyl of 2–10 carbons;
  cycloalkenyl of 5–12 carbons;
  aryl of 6–13 carbons;
  heteroaryl of 3–9 carbons and containing 1–3 heteroatoms selected from the group consisting of N, O, and S;
  $CO_2R^5$; wherein
    $R^5$ is alkyl of 1–4 carbons, haloalkyl of 1–4 carbons, cycloalkyl of 3–6 carbons, or halocycloalkyl of 3–6 carbons;
  halogen; and
  =O, representing two of the groups $R^2$, $R^3$, and $R^4$;
X is O or $S(O)_y$; wherein
  y is 0, 1, or 2;
n is 2, 3, 4, or 5;
p is the sum of non-H substituents $R^2$, $R^3$, and $R^4$;
s represents the number of double bonds in the ring, and is 0, 1, or 2;
T is a substituent selected from the group consisting of
  alkyl of 1–4 carbons;
  alkoxy of 1–4 carbons;
  aryl of 6–10 carbons;
  $CO_2H$;
  $CO_2R^5$;
  alkenyl of 2–4 carbons;
  alkynyl of 2–4 carbons;
  $C(O)C_6H_5$;
  $C(O)N(R^6)(R^7)$; wherein
    $R^6$ is H or alkyl of 1–5 carbons; and
    $R^7$ is H or alkyl of 1–5 carbons;
  $S(O)_{y'}R^8$; wherein
    y' is 1 or 2; and
    $R^8$ is alkyl of 1–5 carbons;
  $SO_2F$;
  CHO;
  OH;
  $NO_2$;
  CN;
  halogen;
  $OCF_3$;
  N-oxide;
  O—$C(R^9)_2$—O, the oxygens being connected to adjacent positions on R; and wherein
    $R^9$ is H, halogen, or alkyl of 1–4 carbons;
  C(O)NHC(O), the carbons being connected to adjacent positions on R; and
  $C(O)C_6H_4$, the carbonyl carbon and the ring carbon ortho to the carbonyl being connected to adjacent positions on R;
t is 1–5;
  provided that when substituent moiety T is alkyl of 1–4 carbons; alkoxy of 1–4 carbons; aryl of 6–10 carbons; $CO_2R^5$; alkenyl of 2–4 carbons; alkynyl of 2–4 carbons; $C(O)C_6H_5$; $C(O)N(R^6)(R^7)$; $S(O)_{y'}R^8$; O—$C(R^9)_2$—O, or $C(O)C_6H_4$, then T optionally may bear secondary substituents selected from the group consisting of alkyl of 1–4 carbons; alkoxy of 1–4 carbons; $CO_2R^5$; $CO_2H$; $C(O)N(R^6)(R^7)$; CHO;

OH; $NO_2$; CN; halogen; $S(O)_yR^8$; or =O, the number of said secondary substituents being 1 or 2 with the exception of halogen, which may be employed up to the perhalo level;

G is a substituent selected from the group consisting of
halogen;
OH;
$OR^5$;
=O, representing two substituents G;
alkyl of 1–4 carbons;
alkenyl of 1–4 carbons:
cycloalkyl of 3–7 carbons;
heterocycloalkyl of 3–5 carbons and 1–3 heteroatoms selected from the group consisting of N, O, and S;
cycloalkenyl of 5–7 carbons;
heterocycloalkenyl of 4–6 carbons and 1–3 heteroatoms selected from the group consisting of N, O, and S;
$CO_2R^5$;
$C(O)N(R^6)(R^7)$;
aryl of 6–10 carbons;
heteroaryl of 3–9 carbons and 1–3 heteroatoms selected from the group consisting of N, O, and S;
$NO_2$;
CN:
$S(O)_yR^8$;
$SO_3R^8$; and
$SO_2N(R^6)(R^7)$;
g is 0–4, with the exception of halogen, which may be employed up to the perhalo level;
provided that when substituent G is alkyl of 1–4 carbons, alkenyl of 1–4 carbons, cycloalkyl of 3–7 carbons, heterocycloalkyl of 3–5 carbons, cycloalkenyl of 5–7 carbons, or heterocycloalkenyl of 4–6 carbons, then G optionally may bear secondary substituents of halogen up to the perhalo level; and when substituent G is aryl or heteroaryl, then G optionally may bear secondary substituents independently selected from the group consisting of alkyl of 1–4 carbons and halogen, the number of said secondary substituents being up to 3 for alkyl moieties, and up to the perhalo level for halogen;

Q is a substituent selected from the group consisting of
alkyl of 1–4 carbons;
haloalkyl of 1–4 carbons;
cycloalkyl of 3–8 carbons;
alkoxy of 1–8 carbons;
alkenyl of 2–5 carbons;
cycloalkenyl of 5–8 carbons;
aryl of 6–10 carbons;
heteroaryl of 3–9 carbons and containing 1–3 heteroatoms selected from the group consisting of N, O, and S;
=O, representing two substituents Q;
OH;
halogen;
$N(R^6)(R^7)$;
$S(O)_yR^8$;
$SO_3R^8$; and
$SO_2N(R^6)(R^7)$;
q is 0–4
provided that when substituent Q is aryl or heteroaryl, then Q optionally may bear secondary substituents independently selected from the group consisting of alkyl of 1–4 carbons and halogen, the number of said secondary substituents being up to 3 for alkyl moieties and up to the perhalo level for halogen; and with the further proviso that two of $(Q)_qR^1$, $(Q)_qR^2$, $(Q)_qR^3$, and $(Q)_qR^4$ may be joined, and taken together with the atom(s) to which they are attached, form a spiro or nonspiro nonaromatic ring of 3–8 members containing 0–2 heteroatoms selected from the group consisting of N, O, and S;

and pharmaceutically acceptable salts thereof.

DETAILED DESCRIPTION OF PREFERRED EMBODIMENTS

The compounds of formula (I) have been defined broadly in the summary above. In the compounds of formula (I), the following group preferences apply:

R is preferably phenyl or pyridyl.

$R^1$ is preferably alkyl of 1–10 carbons, cycloalkyl of 3–12 carbons and containing 1–3 rings, alkenyl of 2–10 carbons, cycloalkenyl of 5–12 carbons and containing 1–3 rings, or alkynyl of 3–10 carbons. $R^1$ is more preferably alkyl of 1–10 carbons, cycloalkyl of 3–12 carbons and containing 1–3 rings, alkenyl of 2–10 carbons, or cycloalkenyl of 5–12 carbons and containing 1–3 rings.

$R^2$, $R^3$, and $R^4$ are preferably H, alkyl of 1–10 carbons, cycloalkyl of 3–12 carbons, alkenyl of 2–10 carbons, cycloalkenyl of 5–12 carbons, or =O, in which the carbonyl represents two of the groups $R^2$, $R^3$, and $R^4$. $R^2$, $R^3$, and $R^4$ are more preferably H, alkyl of 1–10 carbons, cycloalkyl of 3–12 carbons, alkenyl of 2–10 carbons, or cycloalkenyl of 5–12 carbons.

X is preferably O or $S(O)_y$, wherein y is 0, 1, or 2.

The subscript n, representing the number of carbons in the ring, is preferably 2 or 3.

The subscript p, representing the sum of non-H substituents $R^2$, $R^3$, and $R^4$, is preferably 1 or 2.

T is a substituent preferably selected from the group consisting of alkyl of 1–4 carbons, alkoxy of 1–4 carbons, alkenyl of 2–4 carbons, alkynyl of 2–4 carbons, $NO_2$, CN, and halogen. T is more preferably alkyl of 1–4 carbons, alkenyl of 2–4 carbons, $NO_2$, CN, or halogen.

The subscript t, representing the number of substituents T, is 1–5, more preferably 1–3.

When substituent moiety T is alkyl of 1–4 carbons, alkoxy of 1–4 carbons, alkenyl of 2–4 carbons, or alkynyl of 2–4 carbons, then T optionally may bear secondary substituents preferably selected from the group consisting of alkyl of 1–4 carbons, alkoxy of 1–4 carbons, $CO_2R^5$, $CO_2H$, $C(O)N(R^6)(R^7)$, CHO, OH, $NO_2$, CN, halogen, $(O)yR^8$, and =O, the number of said secondary substituents being 1 or 2 with the exception of halogen, which may be employed up to the perhalo level.

As employed in this application, the term "secondary substituent" means a substituent on a substituent, not "secondary" as used in defining the degree of substitution at a carbon.

As employed in this application, the terms "haloalkyl" and "halocycloalkyl" are employed to refer to groups which may contain halogen atoms in any number up to the per-halo level.

G is preferably selected from the group consisting of halogen, ORE, alkyl of 1–4 carbons, alkenyl of 1–4 carbons, cycloalkyl of 3–7 carbons, cycloalkenyl of 5–7 carbons, aryl of 6–10 carbons, and CN. G is more preferably halogen, alkyl of 1–4 carbons, alkenyl of 1–4 carbons, cycloalkyl of 3–7 carbons, cycloalkenyl of 5–7 carbons, or aryl of 6–10 carbons.

The subscript g, representing the number of substituents G, is 0–4, more preferably 0–2, with the exception of halogen, which may be employed up to the perhalo level.

Q is preferably selected from the group consisting of alkyl of 1–4 carbons, haloalkyl of 1–4 carbons, cycloalkyl of 3–8 carbons, alkoxy of 1–8 carbons, alkenyl of 2–5 carbons, cycloalkenyl of 5–8 carbons, $CO_2R^5$, =O, 1OH, halogen, $N(R^6)(R^7)$, and $S(O)_y{}^8$. Q is more preferably alkyl of 1–4 carbons, haloalkyl of 1– 4 carbons, cycloalkyl of 3–8 carbons, alkoxy of 1–8 carbons, alkenyl of 2–5 carbons, cycloalkenyl of 5–8 carbons, or halogen.

The present invention also includes pharmaceutically acceptable salts of the compounds of Formula I. Suitable pharmaceutically acceptable salts are well known to those skilled in the art and include basic salts of inorganic and organic acids, such as hydrochloric acid, hydrobromic acid, sulphuric acid, phosphoric acid, methanesulphonic acid, trifluoromethanesulfonic acid, sulphonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, and mandelic acid. In addition, pharmaceutically acceptable salts include acid salts of inorganic bases, such as salts containing alkaline cations (e.g., $Li^+$ $Na^+$ or $K^+$), alkaline earth cations (e.g., $Mg^{+2}$, $Ca^{+2}$ or $Ba^{+2}$), the ammonium cation, as well as acid salts of organic bases, including aliphatic and aromatic substituted ammonium, and quaternary ammonium cations such as those arising from protonation or peralkylation of triethylamine, N,N-diethylamine, N,N-dicyclohexylamine, pyridine, N,N-dimethylaminopyridine (DMAP), 1,4-diazabicyclo[2.2.2] octane (DABCO), 1,5-diazabicyclo[4.3.0]non-5-ene (DBN) and 1,8-diazabicyclo[5.4.0]undec-7-ene (DBU).

A number of the compounds of Formula I possess asymmetric carbons and can therefore exist in racemic and optically active forms. Methods of separation of enantiomeric and diastereomeric mixtures are well known to the skilled in the art. The present invention encompasses any racemic or optically active forms of compounds described in Formula I which possess progesterone receptor binding activity.

The most preferred 2-imino-1,3-thiazolidines and ring expanded homologues of 2-imino-1,3-thiazolidines of the invention are the following:
(4S)-2-(2-methyl-4-nitrophenylimino)-3-isobutyl-4-isopropyl-1,3-thiazolidine;
(4S)-2-(2-methyl-4-nitrophenylimino)-3,4-diisobutyl-1,3-thiazolidine;
(4S)-2-(2-methyl-4-nitrophenylimino)-3-isobutyl-4-(trifluoromethyl)-1,3-thiazolidine;
(4S)-2-(2-methyl-4-nitrophenylimino)-3-cyclopentyl-4-isobutyl-1,3-thiazolidine;
(4S)-2-(2-methyl-4-nitrophenylimino)-3-isobutyl-4-isopropyl-1,3-thiazolidine;
(4S)-2-(2-methyl-4-nitrophenylimino)-3-cyclopentyl-4-isopropyl-1,3-thiazolidine;
(4R)-2-(2-methyl-4-nitrophenylimino)-3-isobutyl-4-isopropyltetrahydro-2H-1,3-thiazine;
(4S)-2-(4-nitro-1-naphthylimino)-3-cyclopentyl-4-((1R)-1-hydroxyethyl)-1,3-thiazolidine;
2-(4-cyano-2-methylphenylimino)-1-cyclopentyl-3-thia-1-azaspiro [4.4]nonane;
2-(4-cyano-2-ethylphenylimino)-1-cyclopentyl-3-thia-1-azaspiro[4.4]nonane;
2-(4-cyanophenylimino)-1-cyclopentyl-3-thia-1-azaspiro [4.4]nonane;
2-(4-cyano-2-methylphenylimino)-1-isobutyl-3thia-1-azaspiro[4.4]nonane;
2-(4-cyano-2,3-dimethylphenylimino)-1-isobutyl-3-thia-1-azaspiro[4.4]nonane;
2-(4-cyano-2-methylphenylimino)-1-(1-ethyl-1-propyl)-3-thia-1-azaspiro[4.4]nonane;
2-(4-cyano-1-naphthylimino)-1-isobutyl-3-thia-1-azaspiro [4.4]nonane;
2-(2-methyl-4-nitrophenylimino)-1-(propenyl)-3-thia-1-azaspiro[4.4]nonane;
2-(2-methyl-4-nitrophenylimino)-1-isopropyl-3-thia-1-azaspiro[4.4]nonane;
2-(2-methyl-4-nitrophenylimino)-1-isobutyl-3-thia-1-azaspiro[4.4]nonane;
2-(2-methyl-4-nitrophenylimino)-1-cyclopentyl-3-thia-1-azaspiro[4.4]nonane;
2-(3-methyl-4-nitrophenylimino)-1-cyclopentyl-3-thia-1-azaspiro[4.4]nonane;
2-(2-methyl-4-nitrophenylimino)-1-cyclohexyl-3-thia-1-azaspiro[4.4]nonane;
2-(2,3-dimethyl-4-nitrophenylimino)-1-cyclopentyl-3-thia-1-azaspiro[4.4]nonane; and
2-(4-cyano-2,3-dimethylphenylimino)-1-cyclopentyl-3-thia-1-azaspiro[4.4]nonane.

The most preferred thiazolidin-4-ones of the invention are the following:
2-(2-methyl-4-nitrophenylimino)-3-isobutyl-1,3-thiazolidin-4-one;
2-(3-methyl-4-nitrophenylimino)-3-isobutyl-1,3-thiazolidin-4-one;
2-(2-methyl-4-nitrophenylimino)-3-benzyl-1,3-thiazolidin-4-one;
2-(3-methyl-4-nitrophenylimino)-3-benzyl-1,3-thiazolidin-4-one;
2-(2-methyl-4-nitrophenylimino)-3-(2-methyl-1-butyl)-1,3-thiazolidin-4-one;
2-(3-methyl-4-nitrophenylimino)-3-(2-methyl-1-butyl)-1,3-thiazolidin-4-one;
2-(2-methyl-4-nitrophenylimino)-3-(2-methyl-1-ethyl)-1,3-thiazolidin-4-one,;
2-(3-methyl-4-nitrophenylimino)-3-(2-cyclohexyl-1-ethyl)-1,3-thiazolidin-4-one;
2-(2-methyl-4-nitrophenylimino)-3-(2-ethyl-1-butyl)-1,3-thiazolidin-4-one;
2-(2-methyl-4-nitrophenylimino)-3-isobutyl-5-methylene-1,3-thiazolidin-4-one; and
1-(2-methyl-4-nitrophenylimino)-3-isobutyl-5-methyl-1,3-thiazolidin-4-one.

The most preferred oxazolidines of the invention are the following:
2-(2-methyl-4-nitrophenylimino)-3-isobutyl-4,4-dimethyl-1,3-oxazolidine;
1-cyclopentyl-2-(4-cyano-2-ethylphenylimino)-3-oxa-1azaspiro[4.4]nonane;
1-cyclopentyl-2-(2-methyl-4-nitrophenylimino)-3-oxa-1-azaspiro[4.4]nonane; and
1-cyclohexyl-2-(2-methyl-4-nitrophenylimino)-3-oxa-1-azaspiro[4.4]nonane.

The therapeutic agents of the invention may be employed alone or concurrently with other therapies. For example, when employed as in A1 or A2, the agent may be used in combination with a calcium source, vitamin D or analogues of vitamin D, and/or antiresorptive therapies such as estrogen replacement therapy, treatment with a fluoride source, treatment with calcitonin or a calcitonin analogue, or treatment with a bisphosphonate such as alendronate. When employed as in B1 through B7, the agent may be used with therapies such as estrogen replacement therapy. When employed as in C1 through C16, E1 through E3, or F1 or F2, the agent may be used concurrently with therapies such as estrogen replacement therapy and/or a gonadotropinreleasing hormone agonist. When employed as in G1 or G2, the agent may be used concurrently with therapies such as an androgen.

The method of the invention is intended to be employed for treatment of progesterone receptor mediated conditions in both humans and other mammals.

The compounds may be administered orally, dermally, parenterally, by injection, by inhalation or spray, or sublingually, rectally or vaginally in dosage unit formulations. The term 'administered by injection' includes intravenous, intraarticular, intramuscular, subcutaneous and parenteral injections, as well as use of infusion techniques. Dermal administration may include topical application or transdermal administration. One or more compounds may be present in association with one or more non-toxic pharmaceutically acceptable carriers and if desired, other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations.

Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions may also be used. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oil phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal or vaginal administration of the drug. These compositions can be prepared by mixing the drug with a suitable non-irritating excipient which is solid at ordinary temperatures but liquid at the rectal or vaginal temperature and will therefore melt in the rectum or vagina to release the drug. Such materials include cocoa butter and polyethylene glycols.

Compounds of the invention may also be administered transdermally using methods known to those skilled in the art (see, for example: Chien; "Transdermal Controlled Systemic Medications"; Marcel Dekker, Inc.; 1987. Lipp et al. WO 94/04157 Mar. 3, 1994). For example, a solution or suspension of a compound of Formula I in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of a compound of Formula I may be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents may also include mixtures one or more materials selected from lower alcohols, lower ketones, lower carboxylic acid esters, polar ethers, lower hydrocarbons, halogenated hydrocarbons.

Suitable penetration enhancing materials for transdermal delivery systems are known to those skilled in the art, and include, for example, monohydroxy or polyhydroxy alcohols such as ethanol, propylene glycol or benzyl alcohol, saturated or unsaturated $C_8$–$C_{18}$ fatty alcohols such as lauryl alcohol or cetyl alcohol, saturated or unsaturated $C_8$–$C_{18}$ fatty acids such as stearic acid, saturated or unsaturated fatty esters with up to 24 carbons such as methyl, ethyl, propyl, isopropyl, n-butyl, sec-butyl isobutyl tert-butyl or monoglycerin esters of acetic acid, capronic acid, lauric acid, myristinic acid, stearic acid, or palmitic acid, or diesters of saturated or unsaturated dicarboxylic acids with a total of up to 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations may also include mixtures one or more materials selected from monohydroxy or polyhydroxy alcohols, saturated or unsaturated $C_8$–$C_{18}$ fatty alcohols, saturated or unsaturated $C_8$–$C_{18}$ fatty acids, saturated or unsaturated fatty esters with up to 24 carbons, diesters of saturated or unsaturated dicarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrene-butadiene copolymers, and natural and synthetic rubbers. Cellulose ethers, derivatized polyethylenes, and silicates may also be used as matrix components. Additional additives, such as viscous resins or oils may be added to increase the viscosity of the matrix.

For all regimens of use disclosed herein for compounds of Formula I, the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily rectal dosage regimen will preferably be from 0.01 to 200 mg/Kg of total body weight. The daily vaginal dosage regimen will preferably be from 0.01 to 200 mg/Kg of total body weight. The daily topical dosage regimen will preferably be from 0.1 to 200 mg administered between one to four times daily. The transdermal concentration will preferably be that required to maintain a daily dose of from 0.01 to 200 mg/Kg. The daily inhalation dosage regimen will preferably be from 0.01 to 10 mg/Kg of total body weight.

It will be appreciated by those skilled in the art that the particular method of administration will depend on a variety of factors, all of which are considered routinely when administering therapeutics. It will also be understood, however, that the specific dose level for any given patient will depend upon a variety of factors, including, but not limited to the activity of the specific compound employed, the age of the patient, the body weigh t of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, i.e., the mode of treatment and the daily number of doses of a compound of Formula I or a pharmaceutically acceptable salt thereof given for a defined number of days, can be ascertained by those skilled in the art using conventional treatment tests.

The entire disclosures of all applications, patents and publications cited above and below are hereby incorporated by reference.

The compounds of Formula I may be prepared by use of known chemical reactions and procedures, from known compounds (or from starting materials which, in turn, are producible from known compounds) through the preparative methods shown below as well as by other reactions and procedures known to the skilled in the art. Nevertheless, the following general preparative methods are presented to aid practitioners in synthesizing the compounds of the invention, with more detailed particular examples being presented in the experimental section. The examples are for illustrative purposes only and are not intended, nor should they be construed, to limit the invention in any way.

List of Abbreviations and Acronyms

As employed herein, the following terms have the indicated meanings.

| | |
|---|---|
| AcOH | acetic acid |
| anh | anhydrous |
| BOC | tert-butoxycarbonyl |
| conc | concentrated |
| dec | decomposition |
| DBU | 1,8-diazabicyclo[5.4.0]undec-7-ene |
| DIBAL | diisobutylaluminum hydride |
| DME | 1,2-dimethoxyethane |
| DMF | N,N-dimethylformamide |
| DMSO | dimethylsulfoxide |
| EtOAc | ethyl acetate |
| EtOH | ethanol (100%) |
| $Et_2O$ | diethyl ether |
| $Et_3N$ | triethylamine |
| $KMnO_4$ | potassium permanganate |
| Magnosil ® | $MgSiO_3 \cdot xH_2O$ |
| m-CPBA | 3-chloroperoxybenzoic acid |
| MeOH | methanol |
| pet. ether | petroleum ether (boiling range 30–60° C.) |
| THF | tetrahydrofuran |
| TFA | trifluoroacetic acid |

General Preparative Methods

Aryl amines, aryl isocyanates, aryl isothiocyanates, unsymmetrical aryl thiourea, aryl isocyanate dichlorides and 2-arylimino-1,3-heterocycles may be synthesized utilizing known methodology (Katritzky, et al. *Comprehensive Heterocyclic Chemistry;* Permagon Press: Oxford, UK (1984). March. *Advanced Organic Chemistry,* 3rd Ed.; John Wiley: New York (1985)). For example, aryl isocyanates (2) are available from the reaction of phosgene, or a phosgene equivalent, such as carbonyl diimidazole, diphosgene or triphosgene, and aryl isothiocyanates (3) are available from reaction of an aryl amine with thiophosgene or a thiophosgene equivalent, such as thiocarbonyl diimidazole (Scheme I). Also, many aryl isocyanates and aryl isothiocyanates are commercially available. Reaction of an aryl isothiocyanate with a primary amine then affords thiourea 4 (Hahn et al. *Han'guk Nonghwa Hakhoechi* 1997,40, 139; Dürr U.S. Pat. No. 4,079,144; Enders U.S. Pat. No. 4,148,799).

Scheme I

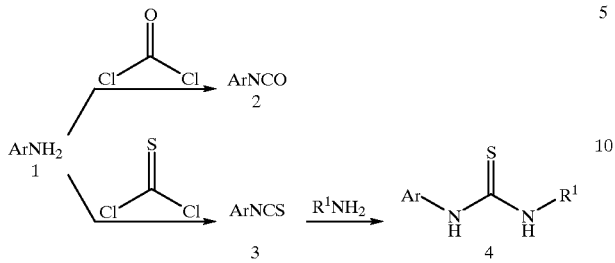

As shown in Scheme II, thioureas react with α-haloketones, e.g. α-bromoketone 5, to afford, after dehydration, the thiazoline (6) (Hahn et al. *Han'guk Nonghwa Hakhoechi* 1997,40, 139; Dürr U.S. Pat. No. 4,079,144; Enders U.S. Pat. No. 4,148,799).

Scheme II

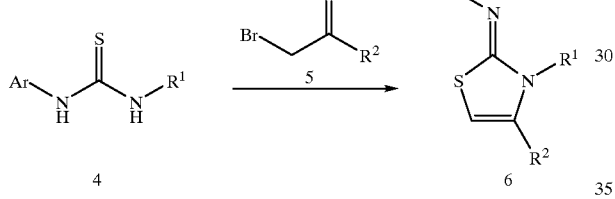

Similarly, thioureas react with α-haloacid halides (Giri et al. *Asian J. Chem.* 1992, 4, 785; Lakhan et al. *Agric. Biol. Chem.* 1982,46, 557), α-haloacids (Dogan et al. *Spectrosc. Lett.* 1983, 16, 499; Seada et al. *Indian J. Heterocycl. Chem.* 1993, 3, 81), and α-haloesters (Seada et al. *Indian J. Heterocycl. Chem.* 1993, 3, 81) to afford 4-thiazolidinones (10).

Scheme III

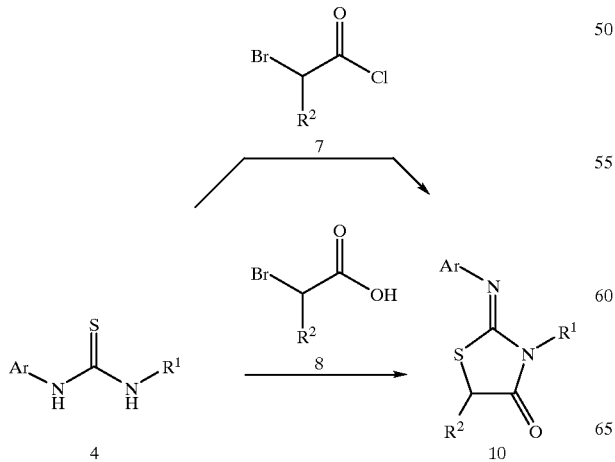

Aryl isothiocyanates (3) also react with allylamines (Tsoi et al. *Zh. Org Khim.* 1983, 19, 2605) and propargylamines (Azerbaev et al. *Khim. Geterotsikl. Soedin.* 1972, 471) to form the corresponding thioureas, which on acid treatment afford the 5-substituted thiazolidines (Scheme IV).

Scheme IV

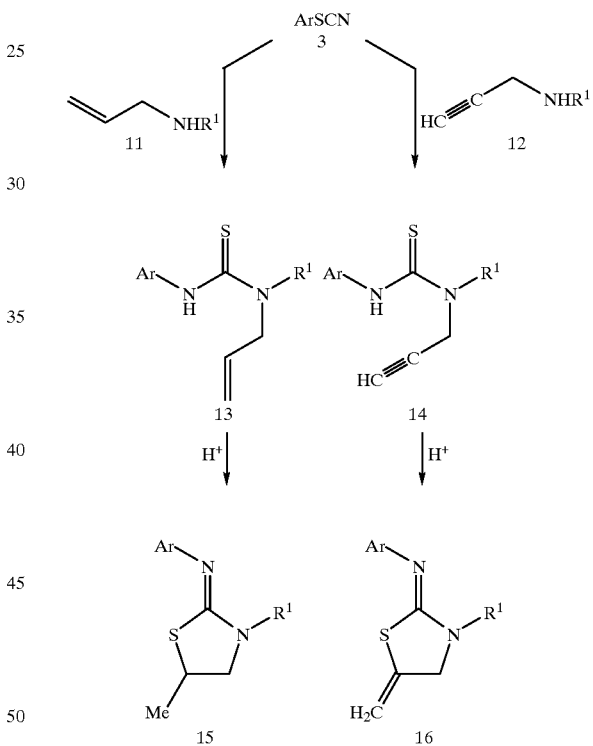

Aryl isothiocyanates may also be reacted with hydroxylamines (17) to form N-hydroxyalkylthiourea 18 (Scheme V). Treatment of the thiourea with acid then leads to 2-imino-1,3-heterocycle 19 (Jen et al. *J.Med Chem.* 1975, 18, 90; Tyukhteneva et al. *Khim. Geterotsikl. Soedin.* 1985, 12, 1629; Olszenko-Piontkowa et al. *Org. Prep. Proced Int.* 11971, 3, 27). Reaction of hydroxyalkylthiourea 18 with $SOCl_2$ affords cloroalkyl analogue 20, which on treatment with base will cyclize to afford heterocycle 19 (Cherbuliez et al. *Helv. Chim. Acta* 1967, 50, 331; Felix et al. U.S. Pat. No. 4,806,053).

Scheme V

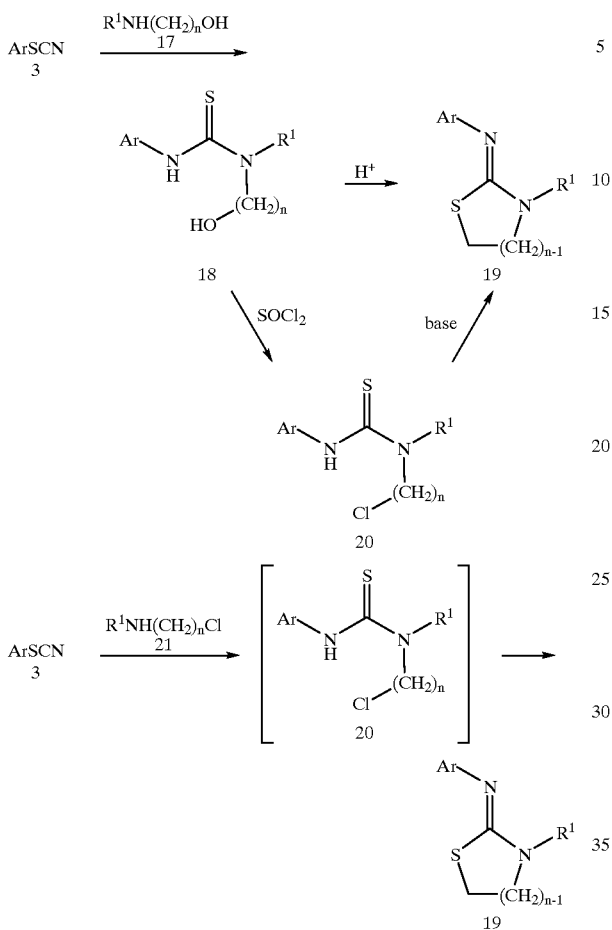

Alternatively, as shown in Scheme VI, treatment of N-hydroxyalkylthiourea 18 with either HgO or an alkylating agent, such as methyl iodide followed by base affords the corresponding oxygen-containing heterocycle (Jen et al. *J.Med. Chem.* 1975, 18, 90; Ignatova et al. *Khim. Geterotsikl. Soedin.* 1974, 354).

Scheme VI

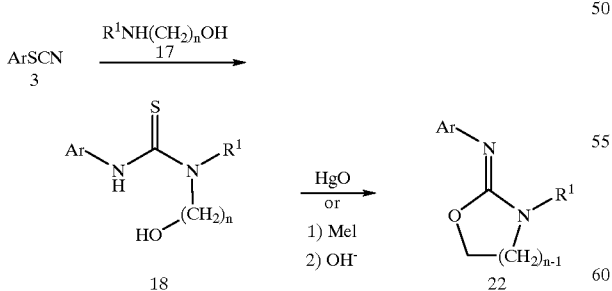

Chloroalkyl isothiocyanates have been reported to react with arylamines to afford the corresponding sulfur 2-phenylimino-1,3-heterocycle (Sagner et al. U.S. Pat. No. 3,651,053; Ibid U.S. Pat. No. 3,737,536).

Scheme VII

Aryl amines react with a formylating source, such as formic acetic anhydride, to form formanilide 25, which may then be oxidatively converted to the aryl isocyanide dichloride (Ferchland et al. DE 3,134,134; for a review, see: Kuehle et al. Angew. Chem. 1967, 79, 663). Aryl isocyanide dichlorides (26) react with hydroxylamines (27) to give oxygen-containing 2-phenylimino-1,3-heterocycle 30 (Wollweber U.S. Pat. No. 3,787,575; Ibid U.S. Pat. No. 3,686,199) and with hydroxylamide 28 to give thiazolidinone 31. In addition, aryl isoyanide dichlorides have been shown to react with aminomercaptans (29) to give the sulfur-containing 2-phenylimino-1,3-heterocycle 32 (Thibault French Patent 1,510,015).

Scheme VIII

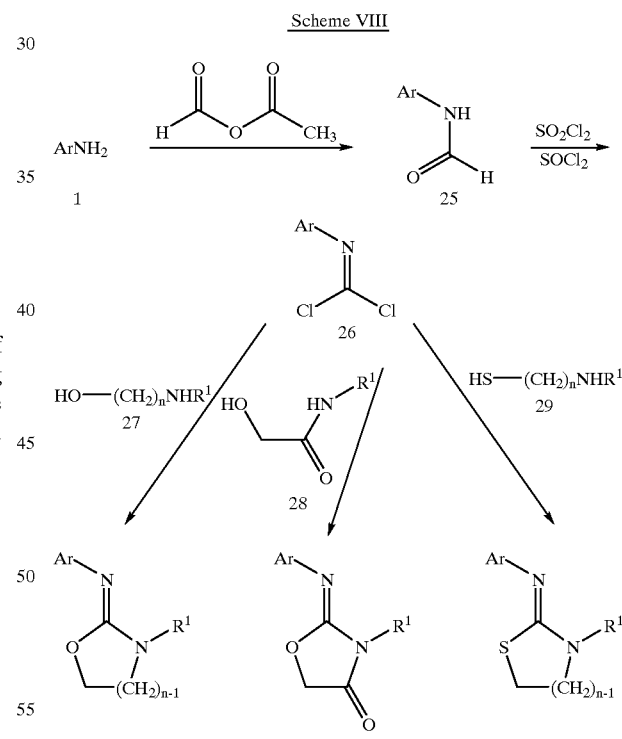

Treatment of hydroxylamines with $CS_2$ in the presence of base will generate the 1,3-thiaza-2-thione (Scheme IX). It has been reported that thione 34 reacts with $SOCl_2$ to give hydroscopically labile imidate 35, which on treatment with an aryl amine affords the sulfur-containing 2-imino-1,3-heterocycle (Hanefeld et al. *Arch. Pharm.* 1985, 318, 60; Ibid 1988, 321, 199).

Scheme IX

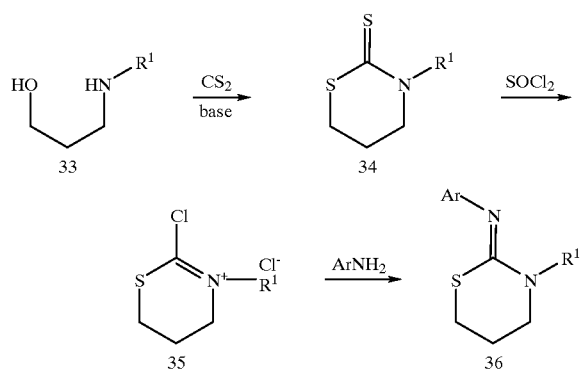

Both oxygen-containing and sulfur-containing 2-imino-1, 3-heterocycles may be further elaborated. Thus, for example, as shown in Scheme X, treatment of N3-unsubstituted 2-phenylimino-1,3-heterocycles with electrophiles, typically in the precense of base, affords the N3-substituted product (Ambartsumova et al. Chem. Heterocycl. Compd. 1997, 33, 475; Mizrakh et a. Khim. Geterotsikl. Soedin. 1990, 563; Olszenko-Piontkowa et al. Org. Prep. Proced. Int. 11971, 3, 27).

Scheme X

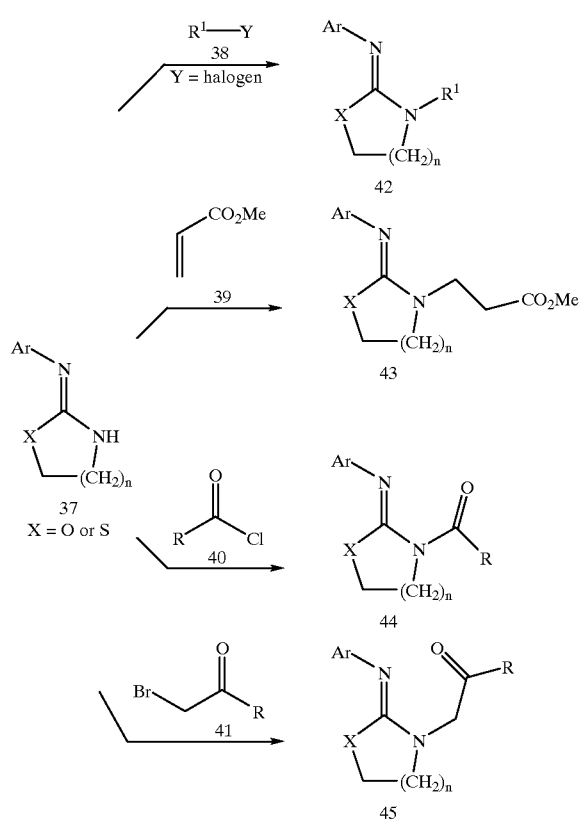

In addition, as shown in Scheme XI, sulfur-containing 2-imino-1,3-heterocycles may be oxidized to the sulfoxide or sulfone (Chizhevskayaet al. Khim. Geterotsikl. Soedin. 1971, 96; Pandey et al. J. Indian Chem. Soc. 1972, 49, 171).

Scheme XI

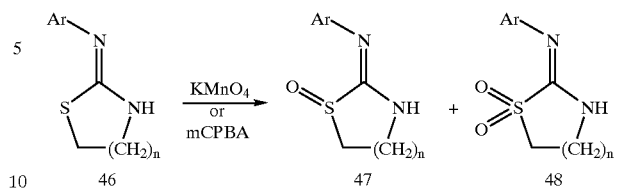

DETAILED EXPERIMENTAL PROCEDURES

Detailed examples of preparations of compounds of the invention are provided in the following detailed synthetic procedures. In the tables of compounds to follow, the synthesis of each compound is referenced back to these exemplary preparative steps.

EXAMPLES

All reactions were carried out in flame-dried or oven-dried glassware under a positive pressure of dry argon or dry nitrogen, and were stirred magnetically unless otherwise indicated. Sensitive liquids and solutions were transferred via syringe or cannula, and indicated into reaction vessels through rubber septa. Commercial grade reagents and solvents were used without further purification.

Unless otherwise stated, the term 'concentration under reduced pressure' refers to use of a Buchi rotary evaporator at approximately 15 mmHg. Bulb-to-bulb concentrations were conducted using an Aldrich Kugelrohr apparatus, and in these cases temperatures refer to oven temperatures. All temperatures are reported uncorrected in degrees Celcius (° C.). Unless otherwise indicated, all parts and percentages are by volume. Thin-layer chromatography (TLC) was performed on Whatman® pre-coated glass-backed silica gel 60A F-254 250 µm plates. Visualization of plates was effected by one or more of the following techniques: (a) ultraviolet illumination, (b) exposure to iodine vapor, (c) immersion of the plate in a 10% solution of phosphomolybdic acid in ethanol followed by heating, (d) immersion of the plate in a cerium sulfate solution followed by heating, and/or (e) immersion of the plate in an acidic ethanol solution of 2,4-dinitrophenylhydrazine followed by heating. Column chromatography (flash chromatography) was performed using 230–400 mesh EM Science® silica gel. Rotary chromatography was performed using pre-cast $SiO_2$ plates (Alltech®) from Harrison Research Chromatotron.

Melting points (mp) were determined using a Thomas-Hoover melting point apparatus or a Mettler FP66 automated melting point apparatus and are uncorrected. Fourier transform infrared sprectra were obtained using a Mattson 4020 Galaxy Series spectrophotometer.

Proton ($^1$H) nuclear magnetic resonance (NMR) spectra were measured with a General Electric GN-Omega 300 (300 MHz) spectrometer with either $Me_4Si$ (δ0.00) or residual protonated solvent ($CHCl_3$ δ7.26; MeOH δ3.30; DMSO δ2.49) as standard. Carbon ($^{13}$C) NMR spectra were measured with a General Electric GN-Omega 300 (75 MHz) spectrometer with solvent ($CDCl_3$ δ77.0; MeOD-$d_3$; δ49.0; DMSO-$d_6$ δ39.5) as standard.

Low resolution mass spectra (MS) and high resolution mass spectra (HRMS) were obtained as electron impact (EI), chemical ionization (CI), or as fast atom bombardment (FAB) mass spectra. Electron impact mass spectra (EI-MS)

were obtained with a Hewlett Packard 5989A mass spectrometer equipped with a Vacumetrics Desorption Chemical Ionization Probe for sample introduction. The ion source was maintained at 250° C. Electron impact ionization was performed with electron energy of 70 eV and a trap current of 300 μA. Liquid-cesium secondary ion mass spectra (FAB-MS), an updated version of fast atom bombardment, were obtained using a Kratos Concept 1-H spectrometer. Chemical ionization mass spectra (CI-MS) were obtained using a Hewlett Packard MS-Engine (5989A) with methane or ammonia as the reagent gas ($1 \times 10^{-4}$ torr to $2.5 \times 10^{-4}$ torr). The direct insertion desorption chemical ionization (DCI) probe (Vaccumetrics, Inc.) was ramped from 0–1.5 amps in 10 sec and held at 10 amps until all traces of the sample disappeared (~1–2 min). Spectra were scanned from 50–800 amu at 2 sec per scan. HPLC—electrospray mass spectra (HPLC ES-MS) were obtained using a Hewlett-Packard 1100 HPLC equipped with a quaternary pump, a variable wavelength detector, a C-18 column, and a Finnigan LCQ ion trap mass spectrometer with electrospray ionization. Spectra were scanned from 120–800 amu using a variable ion time according to the number of ions in the source. Gas chromatography—ion selective mass spectra (GC-MS) were obtained with a Hewlett Packard 5890 gas chromatograph equipped with an HP-1 methyl silicone column (0.33 mM coating; 25 m×0.2 mm) and a Hewlett Packard 5971 Mass Selective Detector (ionization energy 70 eV).

Elemental analyses were conducted by Robertson Microlit Labs, Madison NJ. NMR spectra, LRMS, elemental analyses, and HRMS of the compounds were consistant with the assigned structures.

Examples of preparations of compounds of the invention are provided in the following detailed synthetic procedures. In the tables of compounds to follow, the synthesis of each compound is referenced back to these exemplary preparative steps.

A. Synthesis of Imine Precursors

A1a. General Method of Synthesis of Anilines from Nitrobenzenes

Synthesis of 4-cyano-2-methylaniline

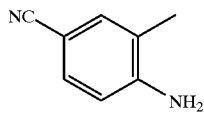

4-Cyano-2-methylaniline was synthesized as previously described (J. Med. Chem. (1991), 34, 3295): To a solution of 3-methyl-4-nitrobenzonitrile (2.0 g, 12.34 mmol) in acetic acid (20 L) was added dropwise a solution of SnCl₂ (9.6 g, 49.38 mmol) in conc. HCl (20 mL). After stirring for 3 h, the mixture was added carefully to a saturated NH₄OH solution (120 mL) at 0° C. The resulting mixture was extracted with EtOAc (4×30 mL). The combined organic layers were sequentially washed with H₂O (30 mL) and a saturated NaCl solution (30 mL), dried (Na₂SO₄), and concentrated under reduced pressure. The residue was purified by flash chromatography (10% EtOAc/hex) to give 4-cyano-2-methylaniline as a white solid (1.48 g, 92%): TLC (30% EtOAc in hexane) R$_f$0.23. This material was used without further purification.

A2a. General Method for the Synthesis of Isothiocyanates
Synthesis of 4-nitro-2-n-propyl isothiocyanate

Step 1

To a solution of 2-n-propylaniline (8.91 g, 66 mmol) and Et₃N (14 mL, 106 mmol) in CH₂Cl₂ (60 mL) was added acetic anhydride (10.9 mL, 99 mmol) dropwise. The resulting mixture was allowed to stir at room temp. overnight, then was treated with a 1N HCl solution (40 mL). The acidic mixture was extracted with CH₂Cl₂ (2×30 mL). The combined organic layers were sequentially washed with H₂O (40 mL), a 1N NaOH solution (40 mL), H₂O (40 mL) and a saturated NaCl solution (40 mL), dried (Na₂SO₄), and concentrated under reduced pressure. The resulting powder was purified by crystalization (EtOAc) to give 2-n-propylacetanilide as white needles (7.85 g, 67%). TLC (30% EtOAc/hex) R$_f$0.37.

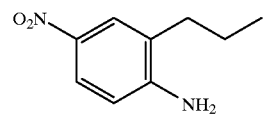

Step 2

To a solution of 2-n-propylacetanilide (1.15 g, 6.50 mmol) in TFA (20 mL) at −5° C. was added NaNO₂ (0.55 g, 6.50 mmol). The mixture was allowed to stir at −5° C. for 3 h, then was treated with H₂O (30 mL). The resulting aqueous solution was extracted with EtOAc (3×20 mL). The combined organic layers were washed with a 1N NaOH solution (30 mL), H₂O (30 mL) and a saturated NaCl solution (40 mL), dried (Na₂SO₄), and concentrated under reduced pressure. The residue was dissolved in a conc. HCl solution (30 mL) and heated at 100° C. overnight. The resulting mixture was cooled to 0° C. with an ice bath, then was carefully adjusted to pH 10 with a 50% NaOH solution. The basic mixture was extracted with EtOAc (4×30 mL). The combined organic layers were sequentially washed with H₂O (30 mL) and a saturated NaCl solution (40 mL), dried (Na₂SO₄), and concentrated under reduced pressure. The residue was purified by flash chromatography (5% EtOAc/hex) to give 2-n-propyl-4-nitroacetanilide as a yellow solid (0.56 g, 48%): TLC (20% EtOAc/hex) R$_f$0.47.

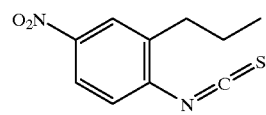

Step 3

To a solution of 2-propyl-4-nitroacetanilide (0.56 g, 0.31 mmol) in toluene (30 mL) was added thiophosgene (0.24 mL, 0.31 mmol) dropwise. The mixture was heated at the reflux temp. overnight, then cooled to room temp. and concentrated under reduced pressure. The residue was purified by flash chromatography (1% EtOAc/hex) to give 2-propyl-4-nitrophenyl isothiocyanate as a yellow oil (0.65 g, 95%): TLC (20% EtOAc/hex) R$_f$0.82.

A2b. General Method for the Synthesis of Isothiocyanates
Synthesis of 4-cyano-2-ethylphenyl isothiocyanate

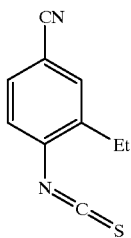

To a solution of 4-amino-3-ethylbenzonitrile, (75 g, 0.51 mol) in toluene (1 L) was added thiophosgene, (43 mL, 0.56 mol, 1.1 equiv.) slowly via syringe. Within 5 min. a viscous slurry formed. The reaction mixture was heated to the reflux temp. and the viscosity diminished. The reaction mixture was heated at the reflux temp. for 5 h then allowed to cool to room temp. The resulting mixture was concentrated under reduced pressure and the residue was treated with $CH_2Cl_2$ (600 mL) and concentrated under reduced pressure to give 4-cyano-2-ethylphenyl isothiocyanate as a light tan crystalline solid (98 g, 100%): $^1$H NMR (DMSO-$d_6$) δ1.18 (t, J=7.4 Hz, 3H), 2.69 (q, J=7.4 Hz, 2H), 7.55 (d, J=7.0 Hz, 1H), 7.75 (d, J=7.0 Hz, 2H), 7.84 (s, 1H); MS (CI-MS) m/z 189 ((M+H)$^+$).

A2c. General Method for the Synthesis of Isothiocyanates
Synthesis of 2,4-dimethyl-3-cyano-5-pyridyl isothiocyanate

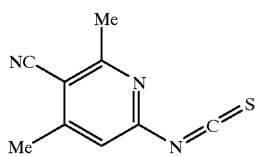

A suspension of 6-amino-3-cyano-2,4-dimethylpyridine (0.1 g, 0.68 mmol) in $CH_2Cl_2$ (1 mL) was added to a vigorously stirred mixture of $CaCO_3$ (0.41 g, 4.11 mmol) in a 1:2 water:$CH_2Cl_2$ mixture (9 mL total) at room temp. The reaction mixture was cooled to 0° C. and thiophosgene (0.09 g, 0.78 mmol) was added dropwise. The resulting mixture was allowed to warm to room temp and was stirred overnight. The resulting aqueous layer was back-extracted with $CH_2Cl_2$ (3×10 mL). The combined organic layers were washed with water (10 mL), dried (MgSO$_4$) and concentrated under reduced pressure. The residue was purified by chromatography (SiO$_2$, 10% EtOAc/hex) to give 2,4-dimethyl-3-cyano-6-pyridyl isothiocyanate (0.12 g, 91%): CI-MS m/z 190 ((M+H)$^+$).

A2d. General Method for the Synthesis of Isothiocyanates
Synthesis of 2,3-dimethyl-4-nitrophenyl isothiocyanate

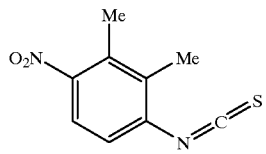

To a solution of 2,3-dimethyl-4-nitroaniline (0.5 g, 1.0 equiv.) in toluene (50 mL) was added thiophosgene (0.3 mL, 1.3 equiv.) and the reaction mixture was heated at the reflux temp. overnight. The resulting mixture was concentrated under reduced pressure and the residue was purified by column chromatography (25% $CH_2Cl_2$/hex) to afford 2,3-dimethyl-4-nitrophenyl isothiocyanate as a light yellow solid (0.30 g, 48%): $^1$H NMR (CDCl$_3$) δ2.39 (s, 3H), 2.41 (s, 3H), 7.20 (d, J=8.4 Hz, 1H); CI-MS m/z 200 ((M+H)$^+$).

A2e. General Method for the Synthesis of Isothiocyanates
Synthesis of 2,3-dimethyl6-nitrophenyl isothiocyanate

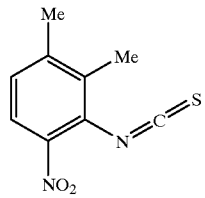

To a solution of 2,3-dimethyl-6-nitroaniline (3.0 g, 1.0 equiv.) in toluene (150 mL) was added thiophosgene (2.5 mL, 1.8 equiv.) and the reaction mixture was heated at the reflux temp. overnight. The resulting mixture was concentrated under reduced pressure and the residue was purified by column chromatography (10% $CH_2Cl_2$/hex) to afford 2,3-dimethyl-6-nitrophenyl isothiocyanate as a light yellow solid (3.63 g, 95%): $^1$H NMR (CDCl$_3$) δ2.39 (s, 3H), 2.40 (s, 3H), 7.17 (d, J=8.4 Hz, 1H), 7.83 (d, J=8.7 Hz, 1H).

A3a. General Method of Synthesis of Aryl Isonitrile Dichlorides
Synthesis of 4-cyano-2-ethylphenyl isocyanide dichloride

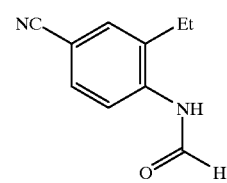

Step 1
Acetic anhydride (235 mL, 2.5 mol, 2.6 equiv.) was added to formic acid (118 mL 3.1 mol, 3.2 equiv.) and the resulting solution was heated at 60° C. for 2 h. After the reaction had cooled to room temp., a solution of 4-amino-3-ethylbenzonitrile (140 g, 0.96 mol) in anh. THF (700 mL) was added at such a rate that the reaction temp. did not exceed 45° C. (approximately 20 min.). When the resulting solution had cooled to room temp. it was concentrated under reduced pressure, treated with EtOH (600 mL), and concentrated again under reduced pressure to afford 4-cyano-2-ethylformanilide as a light tan solid (167 g, 100%): $^1$H NMR (CDCl$_3$) δ1.13 (t, J=7.3 Hz, 3H), 2.48 (q, J=7.3 Hz, 2H), 7.65 (d, J=8.5 Hz, 1H), 8.35 (d, J8.5 Hz, 1H), 8.37 (s, 1H), 9.89 (br s, 1H).

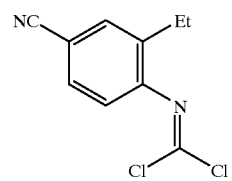

Step 2
To a solution of 4-cyano-2-ethylformanilide (167 g, 0.96 mol, 1.0 equiv.) in SOCl$_2$ (525 mL, 6.05 mol, 6.3 equiv.)

which had been cooled to 0° C. with an ice bath was added sulfuryl chloride, (112 mL, 1.4 mol, 1.4 equiv.) via syringe. The cooling bath was removed and the reaction was heated at 50° C. overnight. The resulting mixture was concentrated under reduced pressure, treated with CH$_2$Cl$_2$ (600 mL), and concentrated again under reduced pressure. The residue was dissolved in Et2O (800 mL) and filtered through a pad of Magnosil® to give 4-cyano-2-ethylphenyl isocyanide dichloride as an oil (210 g, 96%): $^1$H NMR (CDCl$_3$) δ1.13 (t, J=7.3 Hz, 3H), 2.49 (q, 2H, J=7.3 Hz), 7.15 (d, J=8.2 Hz, 1H), 8.35–8.40 (m, 2H).

A3b. General Method of Synthesis of Aryl Isonitrile Dichlorides

Synthesis of 2-methyl-4-nitrophenyl isocyanide dichloride

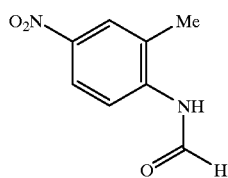

Step 1

Acetic anhydride (400 mL, 4.26 mol, 2.6 equiv.) was added to formic acid (200 mL, 5.25 mol, 3.2 equiv.) and the resulting solution was heated at 60° C. for 2.25 h. After cooling to room temp., a solution of 2-methyl-4-nitroaniline (152 g, 1.64 mol, 1.0 equiv.) in anh. THF (1.2 L) was added at such a rate that the reaction temp. did not exceed 45° C. (approximately 30 min.). When the resulting solution had cooled to room temp. it was concentrated to half the volume under reduced pressure and the reaction product was removed by filtration yielding 2-methyl-4-nitroformanilide as a light tan solid (295 g, 100%): $^1$H NMR (CDCl$_3$) δ2.31 (s, 3H) 8.03 (m, 2H), 8.24 (d, J=8.8 Hz, 1H), 8.39 (br s, 1H), 9.94 (br s, 1H).

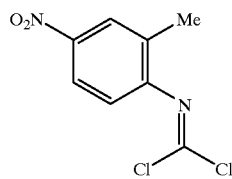

Step2

SOCl$_2$ (525 mL, 6.05 mol, 6.3 equiv.) was added to 2-methyl-4-nitroformanilide (167 g, 0.96 mol) and the resulting solution was cooled to 0° C. Sulfuryl chloride, (112 mL, 1.4 mol, 1.4 equiv.) was added via syringe, the cooling bath was removed and the reaction was heated at 60° C. for 4 h, then allowed cool to room temp. overnight. The reaction mixture was concentrated to half the volume under reduced pressure and the resulting slurry was filtered. The solids were washed with a 50% Et$_2$O/hex solution to yield 2-methyl-4-nitrophenyl isocyanide dichloride as a yellow solid (323 g, 85%): $^1$H NMR (CDCl$_3$) δ2.19 (s, 3H), 7.20 (d, J=8.5 Hz, 1H), 8.15 (d, J=8.5 Hz 1H), 8.2 (s, 1H).

A4a. General Method for the Synthesis of Nitroanilines from Anilines

Synthesis of 2,3-dimethyl-6-nitroaniline and 2,3-dimethyl-4-nitroaniline

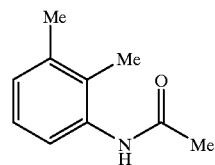

Step 1

To a solution of 2,3-dimethylaniline (1.1 mL, 1.00 equiv.) and Et$_3$N (1.5 mL, 1.30 equiv.) in CH$_2$Cl$_2$ (15 mL) at 0° C. was added acetyl chloride (0.73 mL, 1.25 equiv.) over 30 min. The reaction mixture was allowed to stir overnight at room temp., then was treated with a 2N HCl solution (10 mL) and CH$_2$Cl$_2$ (25 mL). The resulting mixture was extracted with EtOAc (3×25 mL). The combined organics were washed with a 2N HCl solution (2×25 mL), water (2×25 mL), a saturated NaHCO$_3$ solution (2×25 mL) and a saturated NaCl solution (2×25 mL), dried (Na$_2$SO$_4$), and concentrated under reduced pressure to give 2,3-dimethylacetanilide as a white solid (1.25 g, 93%): $^1$H NMR (CDCl$_3$) δ2.05 (s, 3H), 2.15 (s, 3H), 2.25 (s, 3H), 6.95 (d, 7.5 Hz, 1H) 7.02 (app t, J=7.5 Hz, 1H), 7.35 (d, J=6.9 Hz, 1H).

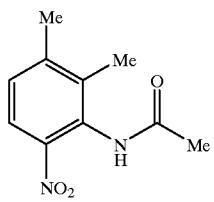 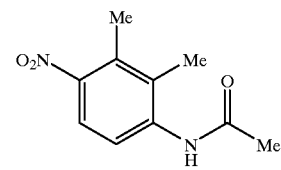

Step 2

To a solution of 2,3-dimethylacetanilide (14.0 g, 1.0 equiv.) in conc. H$_2$SO$_4$ (35 mL) at 0° C. was added HNO$_3$ (5.1 mL, 1.25 equiv) over 30 min. The resulting mixture was allowed to stir at room temp. for 15 min., then was treated with ice water (500 mL) to form a yellow precipitate. The solids were removed and washed with water to afford a 1:1 mixture of 2,3-dimethyl-6-nitroacetanilide and 2,3-dimethyl-4-nitroacetanilide (16.0 g, 90%): $^1$H NMR (CDCl$_3$) δ2.15 (s, 1.5H), 2.22 (s, 1.5H), 2.37 (s, 1.5H), 2.38 (s, 1.5H), 2.41 (s, 1.5H), 5.93 (br s, 1H), 7.15 (d, J=8.7 Hz, 0.5H), 7.63 (d, k8.7 Hz, 0.5H), 7.76 (d, J=8.1 Hz, 1H). This mixture was used in the next step without flirter purification.

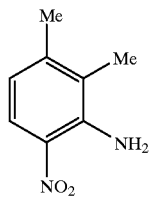 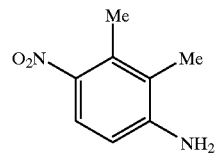

Step 3

To a solution of the mixture of nitroacetanilides (16.0 g, 1.0 equiv.) was added a 60% H$_2$SO$_4$ solution (150 mL). The solution was heated at the reflux temp. for 1 h, then cooled to room temp. and treated with a 2N NaOH solution in ice water (100 mL). The resulting mixture was extracted with EtOAc (3×50 mL). The combined organic layers were washed with a saturated NaHCO₃ solution (2×50 mL) and a saturated NaCl solution (2×50 mL), dried (Na₂SO₄), and concentrated under reduced pressure. The residue was purified by column chromatography (10% CH₂Cl₂/hex) to afford 2,3-dimethyl-6-nitroaniline (5.5 g, 43%), followed by 2,3-dimethyl-4-nitroaniline (1.5 g, 12%). 2,3-Dimethyl-6-nitroaniline (5.5 g, 43%): $^1$H NMR (CDCl₃) δ2.05 (s, 3H), 2.20 (s, 3H), 6.15 (br s, 2H), 6.45 (d, J=8.7 Hz, 1H), 7.63 (d, J=9.0 Hz, 1H); $^1$H NMR (DMSO-d₆) δ2.10 (s, 3H), 2.30 (s, 3H), 6.50 (d, J=8.7 Hz, 1H), 7.15 (br s, 2H), 7.75 (d, J=9.0 Hz, 1H). 2,3-Dimethyl-4-nitroaniline: $^1$H NMR (CDCl₃) δ2.10 (s, 3H), 2.45 (s, 3H), 4.05 (br s, 2H), 6.45 (d, J9.0 Hz, 1H), 7.65 (d, J=8.7 Hz, 1H); $^1$H NMR (DMSO-d₆) δ2.00 (s, 3H), 2.35 (s, 3H), 6.12 (br s, 2H), 6.53 (d, J=9.0 Hz, 1H), 7.63 (d, J=9.0 Hz, 1H).

A5a. General Method for the Synthesis of Iodoanilines
Synthesis of 4-iodo-2-n-propylaniline

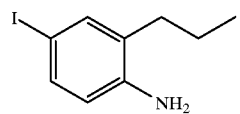

To a solution of 2-n-propylaniline in MeOH (25 mL) was added a solution of NaHCO₃ (5.0 g, 59.5 mmol) in H₂O (25 mL). Iodine (8.4 g, 33.3 mmol) was added portionwise over 70 min. while maintaining the temp. at 10° C., then the mixture was allowed to stir at 10° C. for 30 min. The resulting mixture was diluted with H₂O (30 mL) and extracted with EtOAc (4×40 mL). The combined organic layers were sequentially washed with a 5% Na₂S₂O₃ solution (30 mL) and a saturated NaHCO₃ solution (30 mL), dried (Na2SO₄), and concentrated under reduced pressure to give 4-iodo-2-n-propylaniline (9.4 g, 98%): TLC (20% EtOAc/hex) R$_f$0.43. This material was used in the next step without further purification.

B. Methods for Forming Precursors to 2-Iminoheterocycles
B1a. General Method for the Synthesis of Ethanolamines Via Reduction of Amino Acid Derivatives
Synthesis of 1-amino-1-(hydroxymethyl)cyclohexane

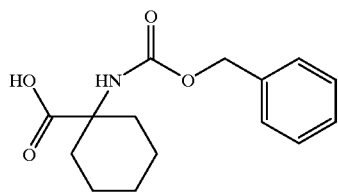

Step 1
To a solution of l-aminocyclohexane-1-carboxylic acid (10.0 g, 70.0 mmol) in a 1M NaOH solution (100 mL) was added benzyl chloroformate (12.0 ml, 84.0 mmol). The reaction mixture was stirred for 2 h while maintaining pH 9 by addition of a 1M NaOH solution as necessary. The resulting solution was washed with Et₂O (2×100 mL), then the aqueous layer was adjusted to pH 0 with a conc. HCl solution and the solution was extracted with EtOAc (3×150 mL). The combined organic layers were dried (MgSO₄) and concentrated under reduced pressure to yield 1-(benzyloxycarbonylamino)cyclohexane-1-carboxylic acid (17.3 g, 89%): TLC (25% EtOAc/hex) R$_f$0.07.

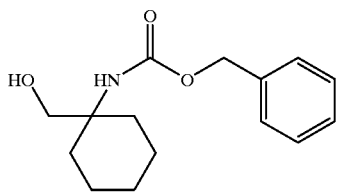

Step 2
To a solution of 1-(benzyloxycarbonylamino) cyclohexane-1-carboxylic acid (4.16 g, 15.0 mmol) and N-methylmorpholine (1.81 mL, 16.5 mmol) in DME (15 mL) at 4° C. was slowly added isobutyl chloroformate (2.14 mL, 16.5 mmol) and the reaction mixture was stirred for 5 min, then filtered into a pre-cooled (4° C.) flask. Sodium borohydride (0.85 g, 22.5 mmol) in water (7 mL) wag added followed immediately by water (500 mL). The reaction was then warmed to 20° C. and stirred for 30 min. The reaction mixture was extracted with CH₂Cl₂ and concentrated under reduced pressure to yield 1-(benzyloxycarbonylamino)-1-(hydroxymethyl)cyclohexane (4.0 g, 100%): TLC (25% EtOAc/hex) R$_f$0.11.

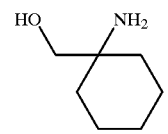

Step 3
A slurry of 1-(benzyloxycarbonylamino)-1-(hydroxymethyl)cyclohexane (4.0 g, 15 mmol) and 10% Pd/C (0.40 g) in MeOH (75 ml) was stirred under H₂ (1 atm.) for 1 h, then treated with Celite®. The resulting mixture was filtered and concentrated under reduced pressure to give 1-amino-1-(hydroxymethyl)cyclohexane.

B1b. General Method for the Synthesis of Ethanolamines Via Reduction of Amino Acid Derivatives
Synthesis of (1S)-1-(hydroxymethyl)-3-methylbutylamine

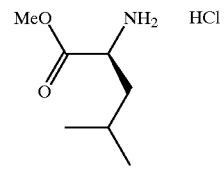

Step 1
To a suspension of (L)-leucine, (315 g, 2.4 mol) in MeOH (3.2 L) at −15° C. was added SOCl₂ (315 mL, 4.32 mol, 1.8 equiv.) dropwise at such a rate that the temp. of the reaction did not exceed 5° C. After the addition was complete, the reaction mixture was allowed to warm to room temp. and was stirred overnight. The resulting mixture was concentrated under reduced pressure and Et₂O (3 L) was slowly added to the residue to produce a precipitate. The mixture was cooled with an ice bath, then treated with additional MeOH (3 L) relatively rapidly. After 1 h at 0° C., the crystals were collected and dried to give (L)-leucine methyl ester HCl salt as a white crystalline solid (394 g, 86%): mp 147–149° C.; $^1$H-NMR (CD₃OD) δ0.78–0.98 (m, 6 h), 1.58–1.72 (m, 3H), 3.76 (g, 3H), 3.92 (t, J=7.3 Hz, 1H).

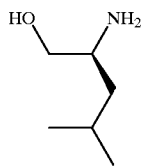

Step 2

To a mixture of (L)-leucine methyl ester HCl salt (254 g, 1.4 mol), NaHCO₃, (118 g, 1.4 mol, 1.0 equiv.) and water (1.8 L) in EtOH (1.8 L) at 5° C. was added NaBH₄, (159 g, 4.2 mol, 3.0 equiv.) in portions at such a rate that the reaction temp. did not exceed 15° C. (approximately 70 min). After the addition of NaBH₄ was complete, the ice bath was removed and the reaction was heated to the reflux temp. overnight. The resulting mixture was cooled to room temp. with the aid of an ice bath. The resulting slurry was filtered and the solids were washed with EtOH (750 mL). The combined filtrates were concentrated to approximately 950 mL under reduced pressure. The residue was diluted with EtOAc (2.5 L) and extracted with a 1N NaOH solution (2×1 L). The aqueous layer was back-extracted with EtOAc (2×750 mL). The combined organics were dried (MgSO₄) and concentrated under reduced pressure to yield (1S)-1-(hydroxymethyl)-3-methylbutylamine as a pale yellow oil (112 g, 65%): ¹H NMR (CDCl₃) δ0.88–0.93 (m, 6H), 1.17 (t, J=7.7 Hz, 2H), 1.68–1.80 (m, 2H), 1.82 (br s, 2H), 2.86–2.91 (m, 1H), 3.22 (dd, J=10.7, 8.1 Hz 1H), 3.56, (dd, J=10.3, 3.6 Hz, 1H).

B1c. General Method for the Synthesis of Ethanolamines Via Reduction of Amino Acid Derivatives Synthesis of 1-hydroxymethylcyclopentanamine

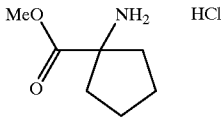

Step 1

To a suspension of 1-aminocyclopentanecarboxylic acid, (675 g, 5.23 mol, 1.0 equiv.) in MeOH (6.5 L) held at −15° C. with an ice/MeOH bath was added SOCl₂ (687 mL, 9.4 mol, 1.8 equiv.), dropwise at such a rate that the reaction temp. did not exceed 7° C. After the addition was complete, cooling was removed, the reaction was allowed to stir at room temp. overnight, then was concentrated under reduced pressure. The residue was treated with CH₂Cl₂ (1 L) and concentrated under reduced pressure to afford methyl 1-aminocyclopentanecarboxylate HCl salt as a white solid (938 g, 100%): ¹H NMR (CD₃OD) d 1.87–1.94 (m, 8H), 3.83 (s, 3H); NMR (DMSO-d₆) δ1.67–1.71 (m, 2H), 1.83–1.98 (m, 4H), 2.06–2.14 (m, 2H), 3.73 (s, 3H), 8.81 (br s 3). This material was used in the next step without further purification.

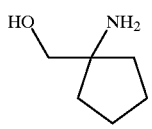

Step 2

A solution of methyl 1-aminocyclopentanecarboxylate HCl salt (310 g, 1.73 mol) in a solution of EtOH (12.5 L) and water (2.5 L) was treated with NaHCO₃ (145 g, 1.73 mol, 1.0 equiv.). The resulting mixture was then cooled to 5° C. with an ice bath and NaBH₄ (196 g, 5.2 mol, 3.0 equiv.) was added in portions at such a rate that the reaction temp. did not exceed 15° C. (approximately 75 min.). After the addition of NaBH₄ was complete, the ice bath was removed and the reaction was heated at the reflux temp. overnight, cooled to room temp. with the aid of an ice bath, and filtered. The resulting solids were washed with EtOH (750 mL) and the combined filtrates were concentrated under reduced pressure. The resulting slurry was then treated with EtOAc (2.5 L). The organic layer was washed with a 1N NaOH solution (2×750 mL) and the aqueous layer was back-extracted with EtOAc (2×500 mL). The combined organic layers were dried (MgSO₄) and concentrated under reduced pressure to afford 1-hydroxymethylcyclopentanamine as a low melting wax (169 g, 85%): ¹H NMR (CDCl₃) δ1.38–1.44 (m, 2H), 1.58–1.69 (m, 4H), 1.70–1.84 (m, 2H), 2.11 (br s, 3H), 3.36 (s, 2H). CI-MS m/z 116 ((M+H)⁺).

B2a. General Method for the N-alkylation of Ethanolamines Via Substitution Reactions Synthesis of 2-(isobutylamino)-2-(hydroxymethyl) norbornane

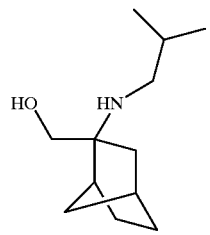

2-Aminonorbornane-2-carboxylic acid was converted into 2-amino-2-(hydroxymethyl)norbornane as a diastereomeric mixture in a manner analogous to Method B1a. A solution of the amino alcohol (0.31 g, 2.16 mmol) and isobutyl bromide (0.23 ml, 2.16 ml) in DMF (3 mL) was heated at 90° C. for 92 h, then cooled to room temp. and partitioned between EtOAc (100 mL) and a saturated NaHCO₃ solution (100 mL). The organic layer was washed with a saturated NaCl solution (50 mL), dried (MgSO₄), and concentrated under reduced pressure to yield 2-(isobutylamino)-2-(hydroxymethyl)norbornane as a diastereomeric mixture (0.24 g, 55%): GC-MS m/z 197 (M⁺).

B2b. General Method for the N-alkylation of Ethanolamines Via Substitution Reactions Synthesis of N-hydroxyethyl-N-cyclohex-1-enylmethylamine

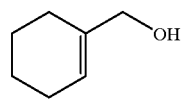

Step 1

To a stirred solution of methyl cyclohex-1-enecarboxylate (4.56 g, 32 mmol) in THF (100 mL) at −78° C. was added DIBAL (1 M in THF, 130 mmol, 130 mL) dropwise. The mixture was allowed to stir at −78° C. for 4 h then treated with a saturated NaHCO₃ solution (40 mL). The aqueous layer was extracted with EtOAc (4×20 mL) and the combined organic layers were washed with H₂O (40 mL) and a saturated NaCl solution (40 mL), dried (Na₂SO₄),and concentrated under reduced pressure. The residual cyclohex-1- enylmethanol was used directly for the next step without purification: TLC (30% EtOAc/hex) $R_f$ 0.44.

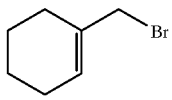

Step 2

To a solution of cyclohex-1-enylmethanol (3.58 g, 32 mmol) in $CH_2Cl_2$ (40 mL) at 0° C. was added $PPh_3$ (36 mmol, 9.39 g) and $CBr_4$ (39 mmol, 12.96 g). The mixture was allowed to stir at room temp. overnight then concentrated under reduced pressure. The residue was diluted with pentane (60 mL) and filtered. The filtrate was concentrated under reduced pressure and purified by column chromatography (5% EtOAc/hex) to give 1-bromomethyl-1-cyclohexene as an oil (3.25 g, 57% over two steps): TLC (30% EtOAc/hex) $R_f$ 0.91.

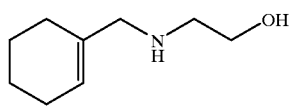

Step 3

A solution of 1-bromomethyl-1-cyclohexene (3.25 g) and 2-aminoethanol (6 mL) in trichloroethylene (40 mL) was heated at the reflux temp. for 3 d, cooled to room temp., and diluted with a 1N NaOH solution (30 mL). The aqueous layer was extracted with $CH_2Cl_2$ (4×20 mL) and the combined organic layers were washed with $H_2O$ (30 mL) and a saturated NaCl solution (30 mL), dried ($Na_2SO_4$) and concentrated under reduced pressure. The residue was purified by vacuum distillation to give N-hydroxyethyl-N-cyclohex-1-enylmethylamine as a colorless oil (1.78 g, 62%): bp 92–94° C. (6 mmHg), B3a. General Method for the N-alkylation of Ethanolamines Via Reductive Alkylation Synthesis of (R)-N-isobutylserine methyl ester HCl salt

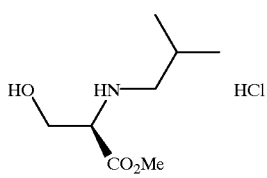

To a suspension of (D)-serine methyl ester HCl salt (2.13 g, 13.7 mmol) in 1,2-dichloroethane was added isobutyraldehyde (1.5 mL, 16.4 mmol) and sodium triacetoxyborohydride (4.3 g, 20.5 mmol). The reaction mixture was stirred at room temp. for 24 h, then partitioned between $Et_2O$ (100 mL) and a saturated $NaHCO_3$ solution (100 mL). The organic layer was washed with a saturated $NaHCO_3$ solution (3×100 mL), dried ($MgSO_4$), and treated with a 1M HCl solution in ether (25 mL). The resulting mixture was concentrated under reduced pressure to yield (R)-N-isobutylserine methyl ester HCl salt (2.27 g, 79%): NMR (DMSO-$d_6$) δ0.94 (dd, J=6.7, 3.0 Hz, 6H); 1.97–2.11 (m, 1H); 2.76–2.91(m, 1H); 3.76 (s, 3H); 3.86 (dd, J=12.1, 4.1 Hz, 1H), 3.99 (dd, J=12.4, 3.2 Hz, 1H), 4.13–4.21 (m, 1H).

B4a. General Method for the N-alkylation of Ethanolamines Via 2-alkyl-1,3-oxazolidine Formation Followed by Reduction Synthesis of 1-(cyclohexylamino)-1-(hydroxymethyl)cyclopentane

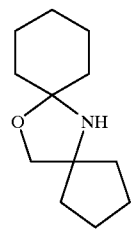

Step 1

To a solution of 1-amino-1-(hydroxymethyl)cyclopentane (Method B1c; 1.44 g, 12.54 mmol) in $CH_2Cl_2$ (10 mL) at 4° C. was added TFA (0.097 mL, 1.25 mmol), cyclohexanone (1.30 mL, 12.54 mmol) and sodium sulfate (2 g) and the reaction was warmed to 20° C. The reaction was stirred for 72 h and was sequentially washed with water (10 mL) and a saturated $NaHCO_3$ solution (20 mL), dried ($MgSO_4$), and concentrated under reduced pressure to give 14-aza-7-oxadispiro[4.2.5.1]tetradecane (2.38 g, 97%): GC-MS m/z 195 ($M^+$).

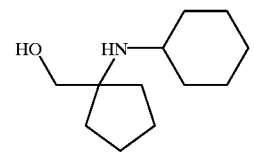

Step 2

To a solution of $LiAlH_4$ (0.93 g, 24.4 mmol) and $AlCl_3$ (3.24 g, 24.4 mmol) in THF at 4° C. was added dropwise a solution of 14-aza-7-oxadispiro[4.2.5.1]tetradecane (2.38 g, 12,2 mmol) in THF (15 mL). The resulting mixture was warmed to 20° C. and stirred for 45 min., then cooled to 4° C. Water (5 mL) was slowly added to quench the reaction and a 1N NaOH solution (85 mL) was added to dissolve the resulting solids. The resulting solution was extracted with $Et_2O$ (200 mL). The organic layer was dried ($Na_2SO_4$) and concentrated under reduced pressure to yield 1-(cyclohexylamino)-1-(hydroxymethyl)cyclopentane 1.89 g (79%): GC-MS m/z 197 ($M^+$).

B4b. General Method for the N-alkylation of Ethanolamines Via 2-alkyl,3-oxazolidine Formation Followed by Reduction Synthesis of N-cyclopentyl-(1,1-dimethyl-2-hydroxyethyl)amine

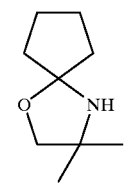

Step 1

A mixture of 2-amino-2-methyl-1-propanol (15.0 g, 0.168 mol), cyclopentanone (14.9 mL, 0.168 mol, 1.0 equiv.) and p-toluenesulfonic acid monohydrate (1.6 g, 8.4 mmol, 0.05 equiv.) in toluene (300 mL) was stirred at the reflux temp. overnight. The reaction mixture was then cooled to room temp., diluted with EtOAc (500 mL), then washed with a saturated NaHCO₃ (250 mL), dried (Na₂SO₄), and concentrated under reduced pressure to yield 4-aza-3,3-dimethyl-1-oxaspiro[4.4]nonane as a pale yellow oil (15.5 g, 60%): ¹H NMR (CDCl₃) δ1.12 (s, 6H), 1.65 (m, 5H), 1.80 (m, 2H), 1.97 (m, 2H), 3.45 (s, 2H).

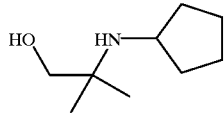

Step 2

To a solution of 4-aza-3,3-dimethyl-1-oxaspiro[4.4] nonane (15.5 g, 0.10 mol) in EtOH (85 mL) at 0° C. was then added NaBH₄ (5.47 g, 0.145 mol, 1.45 equiv.) at a rate that the reaction temp. did not exceed 10° C. (approximately 1 h). The reaction mixture was then allowed to warm to room temp. and stirred for 18 h. The resulting mixture was treated with water (100 mL) and concentrated to a paste under reduced pressure. MeOH (100 mL) was added and the mixture was reconcentrated under reduced pressure. The residue was treated with EtOAc (300 mL) and water (150 mL). The organic layer was dried (Na₂SO₄) and concentrated under reduced pressure to yield N-cyclopentyl-(1,1-dimethyl-2-hydroxyethyl)amine as a pale yellow oil (13.0 g, 83%): ¹H NMR (CDCl₃) δ1.07 (s, 6H), 1.24 (m, 3H), 1.50 (m, 2H), 1.65 (m, 2H), 1.87 (m, 2H), 3.0 (m, 1H), 3.22 (s, 2H); CI-MS m/z 158 ((M+H)⁺).

B4c. General Method for the N-alkylation of Ethanolamines Via 2-alkyl,3-oxazolidine Formation Followed by Reduction Synthesis of (2S)-4-methyl-2-(isobutylamino)pentan-1-ol

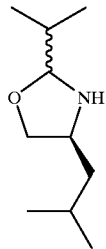

Step 1

A solution of (1S)-1-(hydroxymethyl)-3-methylbutylamine (Method B1b; 152 g, 1.3 mol) and isobutyraldehyde (118 mL, 1.3 mol, 1.0 equiv.) in toluene (1.5 L) was heated at the reflux temp. until the theoretical amount of water had been collected in a Dean-Stark trap (23.4 mL). The reaction mixture was concentrated by distillation to approximately 700 mL. The resulting mixture was cooled to room temp. and was concentrated under reduced pressure to a constant weight to give (4S)-2-isopropyl-4-isobutyl-1,3-oxazolidine as a pale yellow oil (223 g, 100%): ¹H NMR (CDCl₃) δ0.88–0.99 (m, 12H), 1.18–1.35 (m, 1H), 1.42–1.56 (m, 1H), 1.61–1.79 (m, 4H), 3.08 (t, J=7.4 Hz 1H), 3.20–3.34 (m, 1H), 3.85 (t, J=7.4 Hz, 1H), 4.18 (dd, J=7.3, 3.4 Hz, 1H).

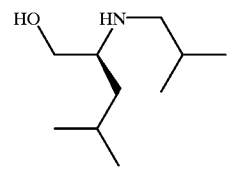

Step 2

To a solution of (4 g)-2-isopropyl-4-isobutyl-1,3-oxazolidine (223g, 1.3 mol) in EtOH (1.1 L) cooled to −13° C. with an ice/MeOH bath was added NaBH₄ (70.3 g, 1.82 mol) in portions at such a rate that the reaction temp. did not exceed 10° C. (approximately 2 h). The reaction mixture was allowed to warm to room temp., stirred overnight, then filtered through a coarse sintered glass funnel. The resulting solids were washed with EtOH. The combined filtrate was concentrated under reduced pressure and the residue was treated with EtOAc (2 L) and water (1 L). The organic layer was dried (Na₂SO₄) and concentrated under reduced pressure to yield (2S)-4-methyl-2-(isobutylamino)pentan-1-ol as a viscous pale yellow oil (192 g, 85%): ¹H NMR (CDCl₃) δ0.90–0.96 (m, 12H), 1.18–1.24 (m, 1H), 1.32–1.39 (m, 1H), 1.58–1.72 (m, 2H), 2.33 (dd, J=11.1, 7.0 Hz, 1H), 2.49 (dd, J=11.1, 7.0 Hz, 1H), 2.61–1.67 (m, 1H), 3.19 (dd, J=10.3, 6.2 Hz, 1H), 3.60 (dd, J=10.3, 6.2 Hz, 1H).

B4d. General Method for the N-alkylation of Ethanolamines Via 2-alkyl,3-oxazolidine Formation Followed by Reduction Synthesis of 1-(cyclopentylamino)-1-(hydroxymethyl) cyclopentane

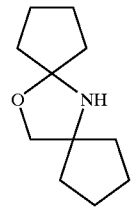

Step 1

A solution of 1-hydroxymethylcyclopentanamine (Method B1c; 263 g, 2.3 mol) and cyclopentanone (220 mL, 1.3 mol, 1.1 equiv.) in toluene (2.7 L) was heated at the reflux temp. with azeotropic removal of water until the theoretical amount of water had been collected (41.4 mL). The reaction mixture was concentrated to 700 mL by simple distillation, then cooled to room temp. and concentrated to constant weight under reduced pressure to give 6-aza-12-oxadispiro[4.1.4.2]tridecane (414 g, 100%) as a pale yellow oil: ¹H NMR (CDCl₃) δ1.55–1.89 (m, 17H), 3.60 (s, 2H).

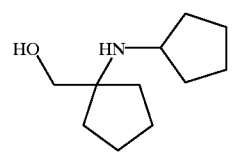

Step 2

To a solution of 6-aza-12-oxadispiro[4.1.4.2]tridecane (124 g, 0.69 mol) dissolved in EtOH (600 mL) held at −13° C. with an ice/MeOH bath was added NaBH₄ (38 g, 1.0 mol, 1.45 equiv.) in portions at a rate that the temp. did not exceed 10° C. (approximately 30 min.). The reaction mixture was allowed to warm to room temp. and stirred overnight. The reaction mixture was diluted with water (500 mL) and concentrated under reduced pressure. The residual paste was separated between EtOAc (1 L) and water (600 mL). The organic layer was dried (Na₂SO₄) and concentrated under reduced pressure to yield 1-(cyclopentylamino)-1-(hydroxymethyl)cyclopentane as a white powder (107 g, 85%): ¹H NMR (CDCl₃) δ1.23–1.28 (m, 2H), 1.46–1.57 (m, 8H), 1.58–1.69 (m, 4H), 1.82–1.86 (m, 2H), 2.94–3.06 (m, 1H,), 3.30 (s, 2H).

B5a. General Method for the Synthesis of Ethanolamines Via Reaction of Amines with Epoxides
Synthesis of N-(hydroxyethyl)-N-(2-butyl)amine

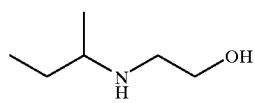

To a solution of sec-butylamine (60 mL, 0.60 mmol) in MeOH (40 mL) at room temp. was added ethylene oxide (10 mL, 0.20 mmol) dropwise via cannula. The mixture was stirred for 4 h at room temp., then concentrated under reduced pressure. The residue was purified by vacuum distillation to give N-(hydroxyethyl)-N-(2-butyl)amine as a colorless oil (16.4 g, 70%): bp 109–112° C. (6 mmHg).

B5b. General Method for the Synthesis of Ethanolamines Via Reaction of Amines with Epoxides
Synthesis of N-(3-phenyl-2-hydroxypropyl)-N-isobutylamine

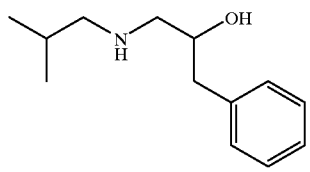

2,3-Epoxypropyl benzene (10 g, 74.5 mmol) and isobutylamine (5.4 g, 74.5 mmol) were mixed then treated with water (2 mL). The mixture was stirred overnight at 110° C., then distilled to yield N-(3-phenyl-2-hydroxypropyl)N-isobutylamine (6.5 g): bp 115–117° C. (1 mmHg).

B6a. General Method for the Synthesis of Propanolamines Via Arndt Eisert Homologation of Amino Acids Followed by Reduction
Synthesis of (R)-3-(tert-butylimino)-4-methylpentanol

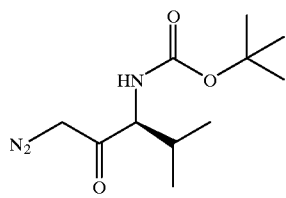

Step 1
To a solution of N-(tert-butoxycarbonyl)-(L)-valine (4.32 g, 19.9 mmol) and N-methylmorpholine (2.3 mL, 20.9 mmol) in DME (30 mL) at −10° C. was added isobutyl chloroformate (2.27 mL, 21.0 mmol). The resulting mixture was stirred at room temp. for 15 min, then filtered, and the solids were washed with cold DME. The filtrate was cooled to −10° C., then treated with a solution of CH₂N₂ in Et₂O until a yellow color persisted, the resulting mixture was warmed to 20° C. and stirred at that temp. for 45 min., then the mixture was concentrated under reduced pressure. The residue was purified by chromatography (SiO₂, gradient from hexane to 30% EtOAc/hex) to yield (S)-3-(tert-butoxycarbonylamino)-1-diazo-4-methylpentan-2-one (1.82 g, 38%): TLC (10% EtOAc/hex) R_f 0.11.

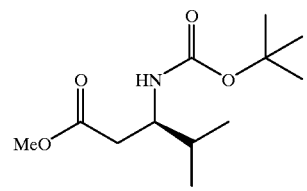

Step 2
A solution of (S)-3-(tert-butoxycarbonylamino)-1-diazo-4-methylpentan-2-one (1.83 g, 7.6 mmol) in MeOH (100 mL) was heated at the reflux temp. and a filtered solution of silver benzoate in Et₃N (0.50 g silver benzoate in 5 mL EON, 0.5 mL) was added. After the initial gas evolution stopped (ca. 0.5 minute) additional silver solution (0.5 mL) was added. This process was repeated until the addition of silver salt caused no more gas to be evolved. The resulting mixture was cooled to 20° C., treated with Celite® and filtered. The filtrate was concentrated under reduced pressure. The residue was dissolved in Et₂O (100 mL) and was sequentially washed with a 1N HCl solution (100 mL), a saturated NaHCO₃ solution (100 mL), and a saturated NaCl solution (50 mL), dried (MgSO₄), and concentrated under reduced pressure to give methyl (R)-3-(tert-butoxycarbonylamino)-4-methylpentanoate (1.63 g, 87%): TLC (10% EtOAc/hex) R_f 0.29.

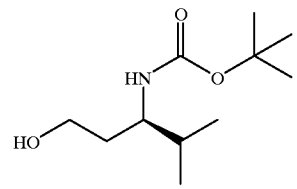

Step 3
Methyl (R)-3-(tert-butoxycarbonylamino)-4-methylpentanoate (1.62 g, 6.6 mmol) was treated with lithium borohydride in a manner analogous to Method B8a, Step 2 to afford (R)-3-(tert-butoxycarbonylamino)-4-methylpentanol (93%).

B7a. General Method for the Synthesis of Chloroethylamines
Synthesis of (1)1-(chloromethyl)-3-methylbutanammonium chloride

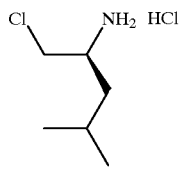

A solution of (1S)-1-(hydroxymethyl)-3-methylbutylamine (Method B1b; 5.40 g, 46.1 mmol) in CH$_2$Cl$_2$ (200 mL) was cooled over an ice bath and saturated with HCl gas. SOCl$_2$ (4.0 mL, 55.3 mmol) was added, the reaction was heated at the reflux temp. for 2.5 h, then cooled to room temp. and concentrated under reduced pressure. The residue was triturated with Et2O to yield (1S)-1-(chloromethyl)-3-methylbutanammonium chloride (5.67 g, 71%): EI-MS m/z 136 ((M+H)$^+$).

B7b. General Method for the Synthesis of Chloroethylamines

Synthesis of 1-(chloromethyl)-1-(cyclohexylamino)cyclopentane HCl Salt

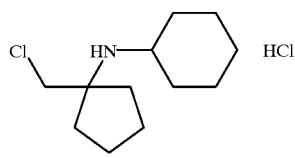

A 4M HCl solution (p-dioxane, 40 mL) containing 1-(cyclohexylamino)-1-(hydroxymethyl)cyclopentane (Method B4a; 1.9 g, 9.6 mmol) and SOCl$_2$ (0.84 mL, 11.5 mmol) was heated to 70° C. for 18 h. The resulting mixture was cooled to room temp. and concentrated under reduced pressure to yield crude 1-(chloromethyl)-1-(cyclohexylamino)cyclopentane HCl salt (2.84 g), which was used in the next step without firer purification.

B7c. General Method for the Synthesis of Chloroethylamines

Synthesis of N-(1S)-(1-(chloromethyl)-3-methylbutyl)-N-(isobutyl)amine HCl Salt

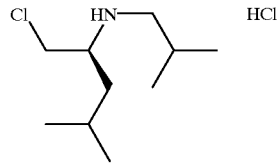

To a solution of (2S)-4-methyl-2-(isobutylamino)pentan-1-ol (Method B4c; 256 g, 1.5 mol) and toluene (2.5 L) was added SOCl$_2$ (167 mL) over 15 min. After the addition of SOCl$_2$ was complete the reaction was heated at 90° C. overnight. The reaction solution was then cooled to room temp. and concentrated under reduced pressure. The dark oily residue was dissolved in CH$_2$Cl$_2$ (2 L) and concentrated under reduced pressure. The red-brown residue was dissolved in Et2O (1 L), and hexane (750 mL) was added dropwise over a period of 8 h. The resulting slurry was stirred overnight, filtered, and washed with a 40% EtOAc/hex solution to give N-(1S)-(1-(chloromethyl)-3-methylbutyl)-N-(isobutyl)amine HCl salt as a dark brown solid (276 g): $^1$H NMR (CDCl$_3$) δ0.93–1.00 (m, 6H), 1.10–1.12 (m, 6H), 1.85 (m, 4H), 2.24–2.34 (m, 2H), 2.80–2.88 (m, 1H), 2.90–3.02 (m, 1H), 3.50–3.57 (m, 1H), 3.96 (dd, J=12.9, 5.6 Hz, 1H), 4.10 (dd, J=13.2, 3.6 Hz, 1H).

B7d. General Method for the Synthesis of Chloroethylamines

Synthesis of 1-(chloromethyl)-1-(cyclopentylamino)cyclopentane HCl salt

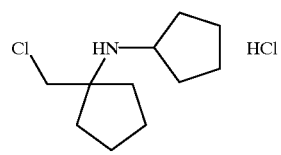

To a solution of 1-(cyclopentylamino)-1-(hydroxymethyl)cyclopentane (Method B1c; 140 g, 0.76 mol, 1.0 equiv.) in toluene (1.4 L). was added SOCl$_2$ (84 mL) over a period of 15 min. After the addition of SOCl$_2$ was complete the reaction mixture, which had already warmed to 40° C., was heated at 60° C. overnight. The resulting solution was cooled to room temp. and treated with HCl (4N in p-dioxane, 100 mL), and the reaction was heated to 60° C. for 3 h then stirred at room temp. overnight. The resulting mixture was concentrated to half of the original volume under reduced pressure, at which time a precipitate began to form. The resulting slurry was diluted with Et$_2$O and allowed stir for 4 h. The resulting precipitate was filtered and washed with Et$_2$O (2×50 mL) to yield 1-(chloromethyl)-1-(cyclopentylamino)cyclopentane HCl salt as an off-white powder (125 g, 70%): $^1$H NMR (CDCl$_3$) δ1.53–1.66 (m, 4H), 1.76–1.94 (m, 2H) 1.95–2.22 (m, 10H), 2.28–2.34 (m, 2H), 3.40 (s, 2H), 3.63–3.73 (m, 1H).

B7e. General Method for the Synthesis of Chloroethylamines

Synthesis of 1-chloromethylcyclopentanamine HCl salt

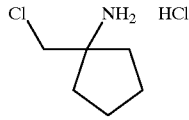

To a solution of 1-hydroxymethylcyclopentanamine HCl salt (Method B1c; 20 g, 0.17 mol) in anh. p-dioxane (65 mL) was added HCl (4M in p-dioxane; 65 mL, 0.26 mol). The resulting solution was stirred for 20 min. at room temp., then SOCl$_2$ (22.7 g, 0.19 mol) was added dropwise. The reaction mixture was heated at 80° C. for 2 d, cooled to room temp., and concentrated under reduced pressure to give 1-chloromethylcyclopentanamine HCl salt (29 g, 100%): CI-MS m/z 171 ((M+H)$^+$).

B8a. General Method for the Synthesis of 2-aminoethylsulfonate Esters

Synthesis of (1R,2R)-1-(methanesulfonyloxymethyl)-2-(tert-butyl)propaneammonium chloride

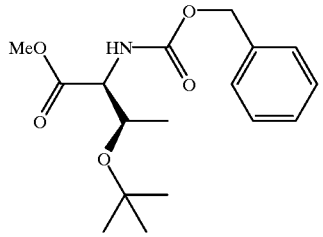

Step 1

A solution of (L)-(1S,2R)-N-(benzyloxycarbonyl)-O-tert-butylthreonine dicyclohexylamine salt (2.15 g, 4.4 mmol) in CH₂Cl₂ (50 mL) was treated with a solution of CH₂N₂ in Et2O until a yellow color persisted. The resulting solution was concentrated under reduced pressure. The residue was dissolved in EtOAc (100 mL) and washed sequentially with a 1N HCl solution (2×100 mL) and a saturated NaCl solution (50 mL), dried (MgSO₄), and concentrated under reduced pressure to yield (1S,2R)-N-(benzyloxycarbonyl)-O-tert-butylthreonine methyl ester (1.44 g, 100%): TLC (25% EtOAc/hex) R$_f$ 0.54.

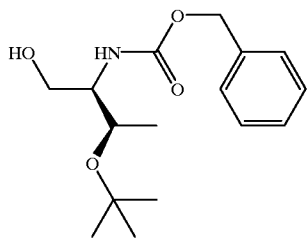

Step 2

To a solution of (1S,2R)-N-(benzyloxycarbonyl)-O-tert-butylthreonine methyl ester (1.4 g, 4.4 mmol) in Et₂O (20 mL) was added a saturated solution of LiBH₄ in Et₂O (9 mL) and the reaction mixture was heated at the reflux temp. for 2 h., then cooled to 20° C. Water (5 mL) was added to the resulting mixture, then a 1N HCl solution was added until no more gas evolved. The ether layer was washed with a saturated NaCl solution (50 mL), dried (MgSO₄), and concentrated under reduced pressure to yield (1R,2R)-N-(benzyloxycarbonyl)-1-(hydroxymethyl)-2-(tert-butoxy) propanamine (1.69 g, 99%): TLC (25% EtOAc/hex) R$_f$ 0.20.

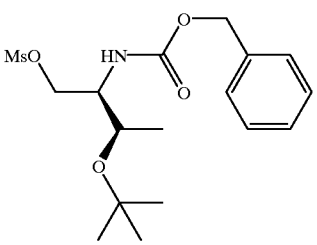

Step 3

To a solution of (1R,2R)-N-(benzyloxycarbonyl)-1-(hydroxymethyl)-2-(tert-butoxy)propanamine (1.6 g, 5.4 mmol) in anh. pyridine (30 mL) at 4° C. was added methanesulfonyl chloride (0.75 mL, 9.7 mmol) dropwise. The reaction was stirred for 5.5 h, then was diluted with EtOAc (200 mL) and washed with a 1N HCl solution (4×200 mL). The combined organic layers were dried (MgSO₄) and concentrated under reduced pressure to yield (1R,2R)-N-(benzyloxycarbonyl)-1-(methanesulfonyloxymethyl)-2-(tert-butoxy)propanamine as an oil (2.03 g, 100%): TLC (25% EtOAc/hex) R$_f$ 0.31.

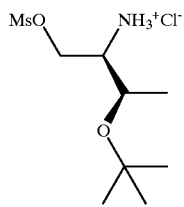

Step 4

To a solution of (1R,2R)-N-(benzyloxycarbonyl)-1-(methanesulfonyloxymethyl)-2-(tert-butoxy)propanamine (2.03 g, 5.5 mmol) in MeOH (50 mL) was added a 4M HCl solution (dioxane; 1.5 mL, 6.0 mmol) and 10% Pd/C (0.20 g). The resulting slurry was stirred under H₂ (1 atm.) for 2 h, then treated with Celite®, filtered and concentrated under reduced pressure to yield (1R,2R)-1-(methanesulfonyloxymethyl)-2-(tert-butoxy) propanammonium chloride (1.6 g, 100%).

B8b. General Method for the Synthesis of 2-aminoethylsulfonate Esters

Synthesis of N-(2-tosyloxyethyl)-2-methylprop-2-en-1-ammonium trifluoroacetate

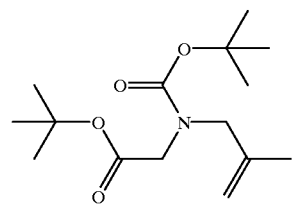

Step 1

To a solution of N-(tert-butoxycarbonyl)glycine tert-butyl ester (3.97 g, 17.2 mmol) in DMF (70 mL) at 0° C. was added sodium hexamethyldisilazide (3.78 g, 20.6 mmol) and the resulting mixture was stirred for 25 min., then allowed to warm to room temp. The resulting solution was treated with 3-bromo-2-methylpropene (2.60 mL, 25.7 mmol), stirred at room temp. for 10 min., and diluted with EtOAc (300 mL). The EtOAc solution was sequentially washed with water (4×500 mL) and a saturated NaCl solution (4×500 mL), dried (MgSO₄), and concentrated under reduced pressure to afford N-(tert-butoxycarbonyl)-N-(2-methylprop-2-enyl)glycine tert-butyl ester (4.03 g, 82%): TLC (10% EtOAc/hex) R$_f$ 0.51.

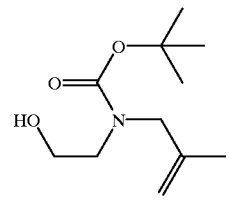

Step 2

A solution of N-(tert-butoxycarbonyl)-N-(2-methylprop-2-enyl)glycine tert-butyl ester (0.26 g, 0.93 mmol) in Et₂O (3 mL) was treated with lithium borohydride (0.011 g), then stirred at room temp. overnight. To the resulting mixture was added water (2 mL), then a 1N HCl was added dropwise until gas evolution stopped. The organic phase was washed with a saturated NaHCO₃ solution (20 mL), dried (MgSO₄), and concentrated under reduced pressure. The residue was purified by chromatography (SiO$_2$, gradient from 10% EtOAc/hex to 50% EtOAc/hex) to give N-(tert-butoxycarbonyl)-N-(2-hydroxyethyl)-1-amino-2-methylprop-2-ene (0.113 g, 57%): TLC (10% EtOAc/hex) R$_f$ 0.66.

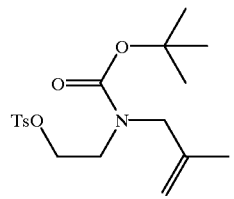

Step 3

To a solution of N-(tert-butoxycarbonyl)-N-(2-hydroxyethyl)-1-amino-2-methylprop-2-ene (21.1 g, 98 mmol) in Et$_2$O (800 mL) at −78° C. was slowly added potassium tert-butoxide (1M in tert-butanol, 103 mL, 103 mmol). The reaction mixture was allowed to warm briefly to −45° C., then was cooled to −78° C., and treated with a solution of p-toluenesulfonyl chloride (18.7 g, 98.0 mmol) in Et$_2$O (100 mL). The resulting mixture was then warmed to −45° C. and treated with water (500 mL). The organic phase was washed with a saturated NaCl solution (800 mL), dried (MgSO$_4$), and concentrated under reduced pressure to give N-(tert-butoxycarbonyl)-N-(2-tosyloxyethyl)-1-amino-2-mohylprop-2-2-ene (36.4 g, 101%): TLC (25% EtOAc/hex) R$_f$ 0.56.

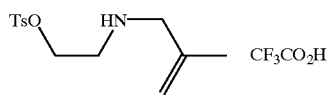

Step 4

Solid N-(tert-butoxycarbonyl)-N-(2-tosyloxyethyl)-1-amino-2-methylprop-2-ene (15 g, 55.7 mmol) was cooled to 0° C. and dissolved in TFA (200 mL). The reaction mixture was allowed to warm to room temp., then was concentrated under reduced pressure. The residual oil was crystallized using Et$_2$O (500 mL) to afford N-(2-tosyloxyethyl)-2-methylprop-2-en-1-ammonium trifluoroacetate (16.7 g, 78%).

B9a. General Method for the Synthesis of 3-chloropropyl- and 4-chlorobutylamines
Synthesis of N-isobutyl-3-chloropropylamine HCl salt

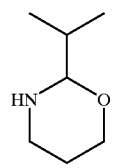

Step 1

To a solution of 3-aminopropanol (91 g, 65.4 mmol) in toluene (100 mL) was added isobutraldehyde (9.0 mL, 99.1 mmol, 1.5 equiv.) and MgSO$_4$ (7.5 g) to generate an exotherm. The slurry was stirred for 30 min. and an additional portion of MgSO$_4$ was added (7.5 g), and the slurry was stirred overnight. The resulting mixture was filtered and concentrated under reduced pressure. The condensate was again concentrated under reduced pressure and the two residues were combined to afford 2isopropyltetrahydro-1,3-oxazine as a colorless oil (5.18 g, 61%) $^1$H NMR (CDCl$_3$) δ0.84–0.88 (m, 6H), 1.24–1.29 (m, 1H), 1.51–1.66 (m, 3H), 2.77–2.87 (m, 1H), 3.07–3.13 (m, 1H), 3.60–3.76 (m, 2H), 4.00–4.05 (m, 1H).

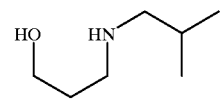

Step 2

To a solution of 2-isopropyltetrahydro-1,3-oxazole (4.94 g, 38.2 mmol) in abs. EtOH (100 mL) at 0° C. was added NaBH$_4$ (2.17 g (57.4 mmol, 1.5 equiv.) in small portions over 15 min. and the resulting mixture was stirred at room temp.overnight. The resulting mixture was concentrated under reduced pressure, then treated with EtOAc (150 mL) and water (100 mL) (CAUTION; gas evolution), and stirred at room temp for 30 min. The resulting organic layer was washed with a saturated NaCl solution. The combined aqueous layers were back-extracted with EtOAc (150 mL). The combined organic layers were dried (Na$_2$SO$_4$) and concentrated under reduced pressure to afford N-isobutyl-3-hydroxypropylamine as a colorless oil (5.04 g, 100%): $^1$H NMR (CDCl$_3$) δ0.84 (d, J=6.6 Hz, 6H), 1.60–1.71 (m, 3H), 2.36 (d, J=6.6 Hz, 2H), 2.80 (dd, J=5.9, 5.9 Hz, 2H), 3.10–3.30 (br s, 2H), 3.74 (dd,, J=5.5, 5.5 Hz, 2H); $^{13}$C NMR (CDCl$_3$) δ20.5, 28.1, 30.6, 50.0, 57.8, 64.1.

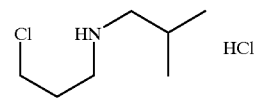

Step 3

To a solution of N-isobutyl-3-hydroxypropylamine (1.01 g, 7.70 mmol) in toluene (100 mL) was added SOCl$_2$ (1.37 g, 11.6 mmol, 1.5 equiv.) and the resulting mixture was stirred at room temp. for 4 h. The resulting slurry was concentrated under reduced pressure to afford N-isobutyl-3-chloropropylamine HCl salt: $^1$H NMR (CDCl$_3$) δ1.12 (s, 9H), 1.28 (t, J=7.0 Hz, 3H), 4.24 (q, J=7.0 Hz, 2H), 4.55 (s, 1H), 5.00 (s, 2H); $^{13}$C NMR (CDCl$_3$) δ13.9, 27.8, 38.2, 61.5, 67.1, 67.3, 117.0, 167.1, 180.7; CI-LRMS m/z (rel abundance) 150 ((M+H)$^+$, 100%).

B10a. General Method for the Synthesis of 2-chlorothiazolidinium Salts
Synthesis of (4S)-2-chloro-3,4-diisobutyl-4,5-dihydro-1,3-thiazolinium chloride

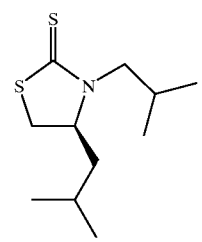

Step 1

To a mixture of (2S)4-methyl-2-(isobutylamino)pentan-1-ol HCl salt (Method B4c; 0.21 g, 1.0 mmol) and CS$_2$ (0.30 mL, 5.0 mmol, 5.0 equiv.) in 2-butanone (20 mL) was added Cs$_2$CO$_3$ (0.72 g, 2.20 mmol, 2.2 equiv.) and the resulting mixture was heated at the reflux temp. overnight. The resulting orange solution was concentrated under reduced pressure and the residue was triturated with EtOAc (25 mL). The remaining solids were washed with EtOAc (25 mL), and the combined EtOAc phases were concentrated under reduced pressure. The residue was absorbed onto SiO$_2$ and purified by MPLC (Biotage 40 S silica gel column; 5% EtOAc/hex) to give (4S)-3,4diisobutyl 1,3-thiazolidin-2-thione as a yellow oil (0.11 g, 52%).

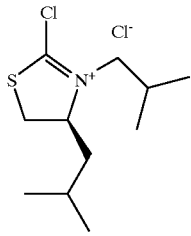

Step 2

A solution of (4S)-3,4-diisobutyl-1,3-thiazolidin-2-thione (5.0 g, 21.6 mmol) in SOCl$_2$ (31 mL, 0.43 mol) and was heated at 70° C. for 2.5 h, then was cooled to room temp. and concentrated under reduced pressure to afford (4S)-2-chloro-3,4-diisobutyl-4,5-dihydro-1,3-thiazolinium chloride as a semisolid: $^1$H NMR δ0.99–1.10 (m, 12H), 1.59–1.67 (m, 1H), 1.72–1.84 (m, 1H), 2.00–2.10 (m, 1H), 2.17–2.29 (br m, 1H), 3.61–3.68 (m, 1H), 3.86–3.95 (br m, 2H), 4.50–4.57 (m, 1H), 4.97–5.06 (br m, 1H). This material was dissolved in dichloroethane (180 mL) to make a 0.12 M stock solution (assuming quantitative conversion to the thiazolidinium chloride).

C. Methods for the Synthesis of Imino Heterocycles

C1a. General Method for the Synthesis of 2-imino-1,3-thiazolidines Via Reaction of 2-chloroethylamines with Isothiocyanates Synthesis of (4S)-2-(2-methyl4-nitrophenylimino)-4-isobutyl-1,3-thiazolidine

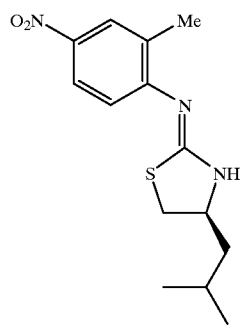

To a mixture of (1S)-1-(chloromethyl)-3-methylbutanammonium chloride (Method B7a; 1.14 g, 3.71 mmol) and 2-methyl-4-nitrophenyl isothiocyanate (0.72 g, 3.71 mmol) suspended in CH$_2$Cl$_2$ (15 mL) was added Et$_3$N (1.08 mL, 7.78 mmol) via syringe. The resulting solution was stirred for 18 h at room temp. The reaction mixture was washed with a saturated NaHCO$_3$ solution and concentrated under reduced pressure. The residue was purified by chromatography (SiO$_2$, gradient from 10% EtOAc/hex to 30% EtOAc/hex) to afford (4S)-2-(2-methyl-4-nitrophenylimino)-4-isobutyl-1,3-thiazolidine (0.91 g, 47%): TLC (25% EtOAc/hex) R$_f$0.46.

C1b. General Method for the Synthesis of 2-imino-1,3-thiazolidines Via Reaction of 2-chloroethylamines with Isothiocyanates Synthesis of (4S)-2-(4-cyano-2-ethylphenylimino)-3,4-diisobutyl-1,3-thiazolidine HCl salt

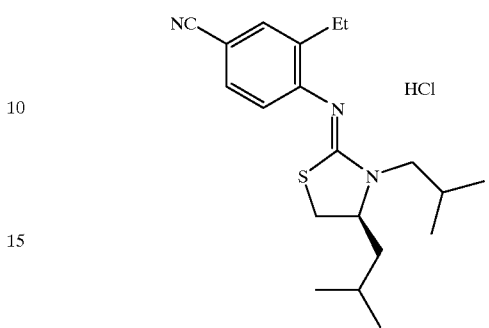

To a solution of N-(1-S)-(1-(chloromethyl)-3-methylbutyl)-N-(isobutyl)amine HCl salt (Method B7c; 95 g, 0.41 mol, 1.08 equiv.) in CH$_2$Cl$_2$ (1.1 L) at 15° C. was added 4-cyano-2-ethylphenyl isothiocyanate (Method A2b; 72 g, 0.38 mol) followed by diisopropylethylamine, (200 mL, 1.15 mol, 3.0 equiv.) generating a slight exotherm. When the reaction had cooled back to room temp., the ice bath was removed and the reaction was stirred at room temp. for 4 h. The reaction was then diluted with CH$_2$Cl$_2$ (500 mL), washed with a 1N NaOH solution 3×500mL), dried (MgSO$_4$) and concentrated under reduced pressure. The residual dark oil (132 g) was dissolved in CH$_2$Cl$_2$ (50 mL) and filtered through a plug of silica gel (5 g SiO$_2$/g crude product) with the aid of a 5% EtOAc/hexane solution to give an oil (120 g), which was dissolved in EtOAc (400 mL) and slowly treated with an HCl solution (1M in Et$_2$O, 500 mL) to give (4S)-2-(4-cyano-2-ethylphenylimino)-3,4-diisobutyl-1,3-thiazolidine HCl salt as a white solid (95 g, 66%): $^1$H NMR (CDCl$_3$) δ0.96 (d, J=5.9 Hz, 3H), 1.02 (d, J=6.3 Hz, 3H), 1.12 (m, 6H), 1.23 (t, J=7.7 Hz, 3H), 1.46–1.76 (m, 3H), 2.10–2.20 (m, 1H), 2.82 (q, J=7.7 Hz, 2H), 3.06–3.14 (m, 2H), 3.55 (dd, J=11.4, 7.7 Hz, 1H), 4.18–4.25 (m, 1H), 5.02 (dd, J=14.3, 8.1 Hz, 1H), 7.32 (d, J=8.1 Hz 1H), 7.51 (dd, 1H, J=8.1, 1.8 Hz, 1H), 7.58 (d, J=1.8 Hz, 1H).

C1c. General Method for the Synthesis of 2-imino-1,3-thiazolidines Via Reaction of 2-chloroethylamines with Isothiocyanates Synthesis of (4S)-2-(2chloro-4-cyano-6-methylphenylimino)-4-isobutyl-1,3-thiazolidine

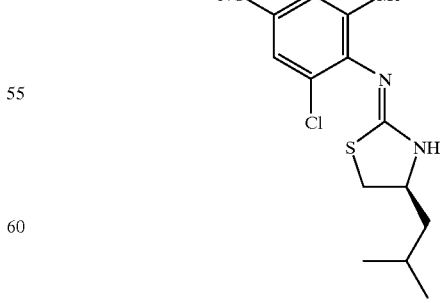

To a slurry of 2-chloro-4-cyano-6-methylphenyl isothiocyanate (0.10 g, 0.50 mmol) and poly(4-vinylpyridine) (0.030 g) in CH$_2$Cl$_2$ was added a solution of (1S)-1-

(chloromethyl)-3-methylbutanammonium chloride (Method B7a; 0.086 g, 0.50 mol, 1.0 equiv) in DMF (2 mL) and the resulting mixture was stirred at 55° C. for 16 h, then concentrated under reduced pressure. The residue was purified by column chromatography (30 g, gradient from 10% EtOAc/hex to 20% EtOAc/hex) to give (4S)-2-(2-chloro-4-cyano-6-methylphenylimino)-4-isobutyl-1,3-thiazolidine (0.052 g, 34%).

C1d. General Method for the Synthesis of 2-imino-1,3-thiazolidines Via Reaction of 2-chloroethylamines with Isothiocyanates Synthesis of (4S)-2-(4-chloro-2-(trifluoromethyl) phenylimino)-3-isobutyl-1,3-thiazolidine

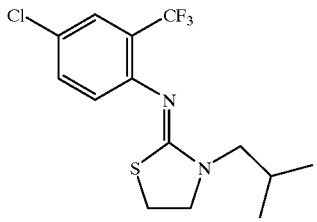

N-(Hydroxyethyl)-N-isobutylamine was converted into N-(chloroethyl)-N-isobutylammonium chloride in a manner analogous to Method B7c. To a slurry of N-(chloroethyl)-N-isobutylammonium chloride (0.10 mmol, 0.10 M) and poly(4-vinylpyridine) (0.030 g) in DMF (1.0 mL) was added a 4-chloro-2-(trifluoromethyl)phenyl isothiocyanate solution (0.25 M in THF, 0.40 mL, 0.10 mmol) and the resulting mixture was heated at 55° C. for 16 h in a sand bath. The resulting slurry was filtered and the filtrate was concentrated under reduced pressure. The residue was purified by preparative reverse phase HPLC (C-18 column, gradient from 0.1% TFA/20% $CH_3CN$/79.9% water to 0.1% TFA/99.9% $CH_3CN$) to furnish (4S)-2-(4-chloro-2-(trifluoromethyl) phenylimino)-3-isobutyl-1,3-thiazolidine (0.020 g, 59%).

C1e. General Method for the Synthesis of 2-imino-1,3-thiazolidines Via Reaction of 2-chloroethylamines with Isothiocyanates Synthesis of 2-(2,4-dimethyl-3-cyano-6-pyridylimino)-3-thia-1-azaspiro[4.4]nonane

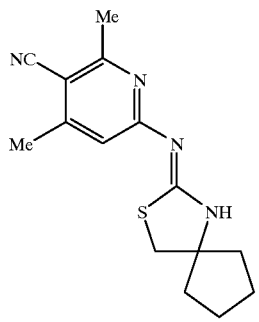

To a solution of 1-chloromethylcyclopentanamine HCl salt (Method B7e; 0.25 g, 1.32 mmol) and 2,4-dimethyl-3-cyano-5-pyridyl isothiocyanate (Method A2c; 0.23 g, 1.32 mmol) in anh. 1,2-dichloroethane (10 mL) was added $Et_3N$ (1 mL) dropwise via syringe. The resulting mixture was heated at 50° C. overnight, then cooled to room temp., and treated with a saturated $NaHCO_3$ solution. The resulting mixture was extracted with $CH_2Cl_2$ (3×25 mL). The combined organic layers were dried ($Na_2SO_4$) and concentrated under reduced pressure. The residue was purified by chromatography ($SiO_2$, 40% EtOAc/hex) to give 2-(2,4-dimethyl-3-cyano-6-pyridylimino)-3-thia-1-azaspiro[4.4] nonane (0.192 g, 51%): CI-MS m/z 287 ((M+H)+).

C1f. General Method for the Synthesis of 2-imino-1,3-thiazolidines Via Reaction of 2-chloroethylamines with Isothiocyanates Synthesis of 2-(3-quinolylimino)-3,5-diisobutyl-1,3-thiazolidine

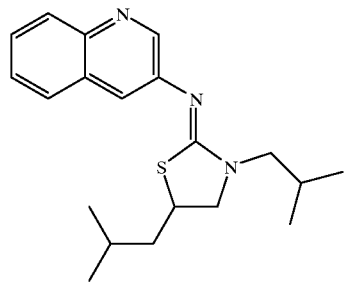

3-Quinoline isothiocyanate was prepared in a manner analogous to Method A2c. To a solution of 3-quinoline isothiocyanate (0.1 g, 0.54 mmol) and N-(1-S)-(1-(chloromethyl)-3-methylbutyl)-N-(isobutyl)amine HCl salt (Method B7c; 0.113g, 0.54 mmol) in anh. $CH_2Cl_2$ (2 mL) was added diisopropylethylamine (0.208 g, 1.61 mmol) dropwise. The resulting mixture was allowed to stir at room temp. overnight, then was concentrated under reduced pressure. The residue was purified by chromatography ($SiO_2$, 30% EtOAc/hex) to give 2-(3-quinolylimino)-3,5-diisobutyl-1,3-thiazolidine (0.02 g, 0.9%): ES-MS m/z 342 ((M+H)+).

C2a. General Method for the Synthesis of 2-imino-1,3-thiazolidines Via Conversion of Ethanolamines into 2-chloroethylamines Followed by Reaction with Isothiocyanates Synthesis of 2-(2-methyl4-nitrophenylimino)-3-thia-1-azaspiro[4.4]nonane

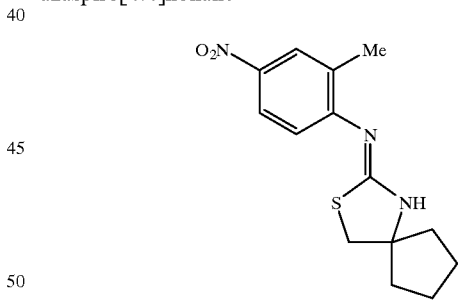

To a solution of 1-amino-1-(hydroxymethyl)cyclopentane (Method B1c; 20.7 g, 180 mmol) and HCl (4M in p-dioxane, 400 mL) was added $SOCl_2$ (15.7 mL, 216 mmol) and the resulting solution was heated at 100° C. for 18 h. The reaction mixture was concentrated under reduced pressure, then treated with 2-methyl4-nitrophenyl isothiocyanate (31.4 g, 162 mmol) and 1,2-dichloroethane (400 ml), followed by N-methylmorpholine (49 mL, 449 mmol). The resulting mixture was heated at 70° C. for 18 h, cooled to room temp. and concentrated under reduced pressure. The residue was treated with hot EtOAc, filtered and concentrated under reduced pressure. The residue was recrystallized (MeOH) to yield 2-(2-methyl-4-nitrophenylimino)-3-thia-1-azaspiro[4.4]nonane (38.3 g, 81%): TLC (25% EtOAc/hex) $R_f$0.27.

C2b. General Method for the Synthesis of 2-imino-1,3-thiazolidines Via Conversion of Ethanolamines into 2-chloroethylamines Followed by Reaction with Isothiocyanates Synthesis of 1-isobutyl-2-(2-methyl-4-nitrophenylimino)-3-thia-1-azaspiro[4.5]decane

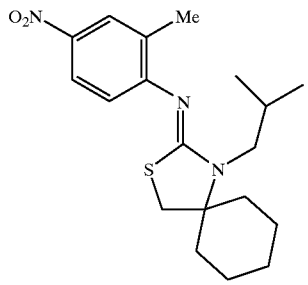

1-Amino-1-(hydroxymethyl)cyclohexane (Method B1a) was dissolved in p-dioxane (80 mL) then treated with SOCl$_2$ followed by 2-methyl-4-nitrophenyl isothiocyanate in a manner analogous to Method C2a to give 2-(2-methyl-4-nitrophenylimino)-3-thia-1-azaspiro[4.5]decane (20%), which was reacted with isobutyl bromide in a manner analogous to Method D2a to yield 1-isobutyl-2-(2-methyl-4-nitrophenylimino)-3-thia-1-azaspiro[4.5]decane (0.026 g, 2%): TLC (20% EtOAc/hex) R$_f$ 0.69.

C2c. General Method for the Synthesis of 2-imino-1,3-thiazolidines Via Conversion of Ethanolamines into 2-chloroethylamines Followed by Reaction with Isothiocyanates Synthesis of 2-(2-methyl-4-nitrophenylimino)-3-isobutylspiro[1,3-thiazolidine-4,2'-bicyclo[2.2.1]heptane]

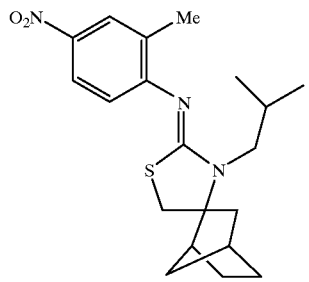

2-(Isobutylamino)-2-(hydroxymethyl)norbornane (Method B2a; 0.24 g, 1.2 mmol) was treated with SOCl$_2$ followed by 2-methyl-4-nitrophenyl isothiocyanate in a manner analogous to Method C2a to yield 2-(2-methyl-4-nitrophenylimino)-3-(2-isobutylspiro[1,3-thiazolidine-4,2'-bicyclo[2.2.1]heptane] as an oil (0.022 g, 5%): TLC (25% EtOAc/hex) R$_f$ 0.72.

C2d. General Method for the Synthesis of 2-imino-1,3-thiazolidines Via Conversion of Ethanolamines into 2-chloroethylamines Followed by Reaction with Isothiocyanates Synthesis of 3-isobutyl-4-methylene-2-(2-methyl4-nitrophenylimino)-1,3-thiazolidin-5-one and (4S)-3-isobutyl-4-carbomethoxy-2-(2-methyl-4-nitrophenylimino)-1,3-thiazolidine HCl salt

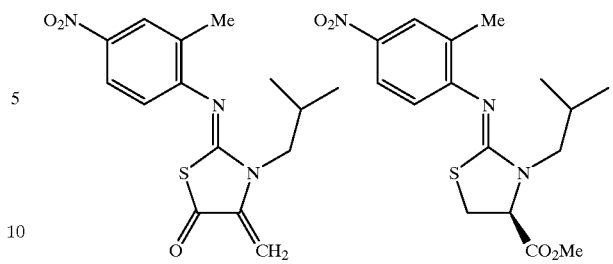

(R)-N-Isobutylserine methyl ester HCl salt (Method B3a; 2.28 g, 10.8 mmol) was treated with SOCl$_2$ followed by 2-methyl-4-nitrophenyl isothiocyanate in a manner analogous to Method C2a. The resulting material was purified by column chromatography (SiO$_2$, gradient from hexane to 10% EtOAc/hex) to give 3-isobutyl-4-methylene-2-(2-methyl-4-nitrophenylimino)-1,3-thiazolidin-5-one (0.028 g, 10%) followed by (S)-3-isobutyl-4-carbomethoxy-2-(2-methyl-4-nitrophenylimino)-1,3-thiazolidine HCl salt (0.192 g, 56%). 3-Isobutyl-4-methylene-2-(2-methyl-4-nitrophenylimino)-1,3-thiazolidin-5-one: TLC (25% EtOAc/hex) R$_f$ 0.40. (S)-3-isobutyl-4-carbomethoxy-2-(2-methyl-4-nitrophenylimino)-1,3-thiazolidine HCl salt: TLC (free base, 25% EtOAc/hex) R$_f$ 0.50.

C2e. General Method for the Synthesis of 2-imino-1,3-thiazolidines Via Conversion of Ethanolamines into 2-chloroethylamines Followed by Reaction with Isothiocyanates Synthesis of 1-cyclohexyl-2-(2-methyl4-nitrophenylimino)-3-thia-1-azaspiro[4.4]nonane

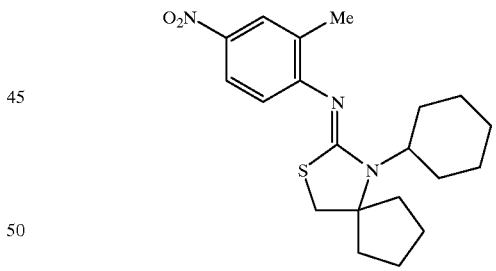

1-(Cyclohexylamino)-1-(hydroxymethyl)cyclopentane (Method B4a; 1.89 g, 9.59 mmol) was reacted with SOCl$_2$ followed by 2-methyl-4-nitrophenyl isothiocyanate in a manner analogous to Method C2a to yield 1-cyclohexyl-2-(2-methyl-4-nitrophenylimino)-3-thia-1-azaspiro[4.4]nonane (0.44 g, 17%): CI-MS m/z 374 ((M+H)$^+$).

C2f. General Method for the Synthesis of 2-imino-1,3-thiazolidines Via Conversion of Ethanolamines into 2-chloroethylamines Followed by Reaction with Isothiocyanates Synthesis of 2-(2-methyl4-nitrophenylimino)-3-isobutyl-4,4-dimethyl-1,3-thiazolidine

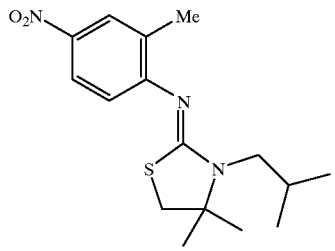

N-Isobutyl-1,1-dimethyl-2-hydroxyethanamine was prepared in a manner analogous to Method B4a. HCl was bubbled into a solution of N-isobutyl-1,1-dimethyl-2-hydroxyethanamine (1.45 g, 10 mmol) in toluene (20 mL) until saturation. SOCl$_2$ (10 mmol) was added to the solution dropwise at room temp., stirred at room temp. for 1 h and at 50° C., for 1 h. The resulting mixture was concentrated under reduced pressure and the residue was dissolved in CHCl$_3$ (20 mL). To the resulting solution was added 2-methyl-4-nitro-phenyl isothiocyanate (1.94 g, 10 mmol), then a solution of Et$_3$N (10 mmol) in CHCl$_3$ (10 mL) was added dropwise at room temp. The resulting mixture was heated at the reflux temp. for 3 h, then concentrated under reduced pressure. The residue was dissolved in EtOAc (100 mL) and the resulting solution was sequentially washed with a 10% aq. NaOH solution (50 mL) and a saturated NaCl solution (50 mL), dried (MgSO$_4$) and concentrated under reduced pressure. The residue was purified by chromatography (9% EtOAc/pet. ether) and the resulting solids were recrystallized (pet. ether) to give 2-(2-methyl-4-nitrophenylimino)-3-isobutyl-4,4-dimethyl-1,3-thiazolidine (0.6 g, 63%): mp 97° C. When appropriate, the product was converted into the HCl salt by dissolving the free base (5 mmol) in Et$_2$O (50 mL) and treating this solution with a 2N ethereal HCl solution until no more solid precipitated. The resulting slurry was filtered and the resulting solids were washed with Et$_2$O (25 mL) followed by EtOAc (25 mL).

C3a. General Method for the Synthesis of 2-imino-113-thiazolidine homologues Via Conversion of Hydroxyalkylamines into Chloroalkylamines Followed by Reaction with Isothiocyanates Synthesis of (R)-4-isopropyl-2-(2-methyl-4-nitrophenylimino)-2,3,4,5-tetrahydro-1,3-thiazine

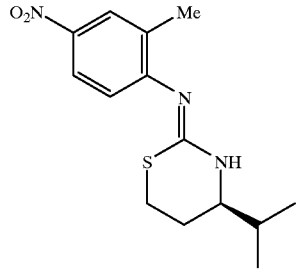

(R)-3-(tert-Butoxycarbonylamino)-4-methylpentanol (Method B6a) was reacted with SOCl$_2$ followed by 2-methyl-4-nitrophenyl isothiocyanate in a manner analogous to Method C2a to afford (R)-4-isopropyl-2-(2-methyl-4-nitrophenylimino)-2,3,4,5-tetrahydro-1,3-thiazine (100%).

C4a. General Method for the Synthesis of 2-imino-1,3-oxazolidines Via Reaction of 2-chloroethylamines with Isocyanates Synthesis of 1-cyclohexyl-2-(2-methyl-4-nitrophenylimino)-3-oxa-1-azaspiro[4.4]nonane

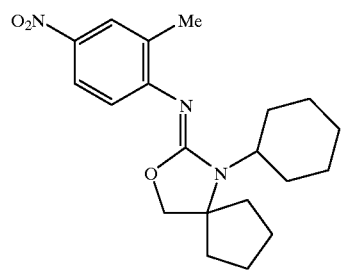

To a solution of 1-(chloromethyl)-1-(cyclohexylamino)cyclopentane HCl salt (Method B7b; 1.06 g, 4.2 mmol) and 2-methyl-4-nitrophenyl isocyanate (0.75 g, 4.2 mmol) in 1,2-dichloroethane (10 mL) was added N-methylmorpholine (0.92 mL, 8.4 mmol). The resulting mixture was heated to 50° C. for 18 h, then cooled to 20° C. and concentrated under reduced pressure. The residue was purified by chromatography (SiO$_2$, gradient from hexane to 10% EtOAc/hex) to yield 1-cyclohexyl-2-(2-methyl-4-nitrophenylimino)-3-oxa-1-azaspiro[4.4]nonane (0.021 g, 1.4%): CI-MS m/z 358 ((M+H)$^+$).

C5a. General Method for the Synthesis of 2-Iminoheterocycles Via Reaction of Aminoethylsulfonate Esters with Isocyanates or Isothiocyanates Synthesis of 2-(2-methyl-4-nitrophenylimino)-3-(2-methylprop-2-enyl)-1,3-oxazolidine

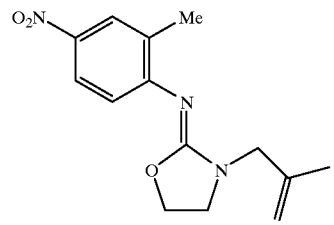

To a solution of N-(2-tosyloxyethyl)-2-methylprop-2-en-1-ammonium trifluoroacetate (Method B8b, Step 4; 0.21 g, 0.548 mmol) in p-dioxane (5 mL) was added 2-methyl-4-nitrophenyl isocyanate (0.0955 g, 0.536 mmol), followed by Et$_3$N (0.080 mL, 1.15 mmol). The resulting mixture was stirred at 37° C. overnight, cooled to room temp., and concentrated under reduced pressure. The residue was dissolved in CH$_2$Cl$_2$ (50 mL) and washed with water (50 mL). The organic layer was extracted with a 2N HCl solution. The aqueous layer was made basic with a 1N NaOH solution, and was extracted with CH$_2$Cl$_2$ (50 mL). The organic phase was dried (Na$_2$SO$_4$) and concentrated under reduced pressure to give 2-(2-methyl-4-nitrophenylimino)-3-(2-methylprop-2-enyl)-1,3-oxazolidine as a yellow oil (0.020 g, 14%) CI-MS m/z 276 ((M+H)$^+$).

C5b. General Method for the Synthesis of 2-Iminoheterocycles Via Reaction of Aminoethylsulfonate Esters with Isocyanates or Isothiocyanates Synthesis of (4S)-4-(1(R)-tert-butoxyethyl)-3-isobutyl-2-(2-methyl-4-nitrophenylimino)-1,3-thiazolidine

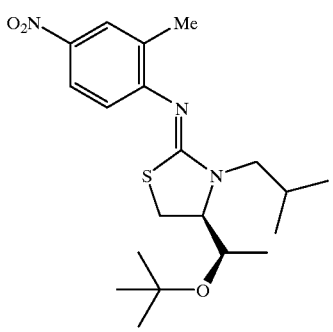

(1R,2R)-1-(Methanesulfonyloxymethyl)-2-(tert-butoxy) propanammonium chloride (Method B8a; 1.5 g, 5.5 mmol) was reacted with 2-methyl-4-nitrophenyl isothiocyanate in a manner analogous to that described in Method C1a to afford 4(S)-(1(R)-tert-butoxyethyl)-2-(2-methyl-4-nitrophenylimino)-1,3-thiazolidine (1.2 g, 67%). The (4S)-2-(2-methyl-4-nitrophenylimino)-4-(1(R)-tert-butoxyethyl)-1,3-thiazolidine was reacted with isobutyl bromide in a manner analogous to Method D2a to yield (4S)-4-(1(R)-tert-butoxyethyl)-3-isobutyl-2-(2-methyl-4-nitrophenylimino)-1,3-thiazolidine (0.26 g, 56%): TLC (25% EtOAc/hex) $R_f$ 0.67.

C6a. General Method for the Synthesis of 2-imino-1,3-thiazolidines Via Conversion of Chloroethylamines into 2-thioethylamines Followed by Reaction with Isocyanide Dichlorides Synthesis of (4S)-2-(4-cyano-2-ethylphenylimino)-3,4-diisobutyl-1,3-thiazolidine HCl salt

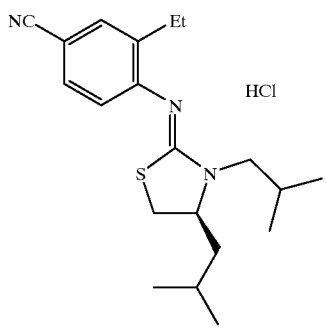

To a solution of sodium hydrogen sulfide (69 g, 1.2 mol, 2.2 equiv.) in water (500 mL) was added N-(1-S)-(1-(chloromethyl)-3-methylbutyl)-N-(isobutyl)amine HCl salt (Method B7c; 126 g, 0.55 mol, 1.0 equiv.). The resulting mixture was stirred at room temp. for 8 h, then 4-cyano-2-ethylphenyl isocyanide dichloride (Method A3a, 125 g, 0.5 mol, 1.0 equiv.) was added followed by isopropyl alcohol (500 mL). The resulting mixture was stirred at room temp. for 1 h, then a 3.6M $K_2CO_3$ solution (305 mL, 2.0 equiv., 1.1 mol) was added and the mixture was stirred at room temp. overnight. The resulting organic layer was concentrated under reduced pressure and the residue treated with EtOAc (2 L). The organic layer was washed with water (2×500 mL), dried ($MgSO_4$) and concentrated under reduced pressure to give a dark oil (160 g). The oil was dissolved in $CH_2Cl_2$ (150 mL) and passed through a silica gel plug (3 g $SiO_2$/1 g crude product) with the aid of a 5% EtOAc/hex solution to afford an oil containing the desired product and some residual isocyanide dichloride (134 g). The oil was dissolved in EtOAc (500 mL) and treated with HCl (1N in $Et_2O$, 500 mL). The resulting (4S)-2-(4-cyano-2-ethylphenylimino)-3,4-diisobutyl-1,3-thiazolidine HCl salt was removed by filtration (147 g, 70%): $^1$H NMR ($CDCl_3$) δ0.96 (d, J=5.9 Hz, 3H), 1.02 (d, J=6.3 Hz, 3H), 1.12 (m, 6H), 1.23 (t, J=7.7 Hz, 3H), 1.46–1.76 (m, 3H), 2.10–2.20 (m, 1H), 2.82 (q, J=7.7 Hz, 2H), 3.06–3.14 (m, 2H), 3.55 (dd, J=11.4 , 7.7 Hz, 1H), 4.18–4.25 (m, 1H), 5.02 (dd, J=14.3, 8.1 Hz, 1H), 7.32 (d, J=8.1 Hz, 1H), 7.51 (dd, J=8.1, 1.8 Hz, 1H), 7.58 (d, J=1.8 Hz, 1H).

C6b. General Method for the Synthesis of 2-imino-1,3-thiazolidines Via Conversion of Chloroethylamines into 2-thioethylamines Followed by Reaction with Isocyanide Dichlorides Synthesis of 1-cyclopentyl-2-(2-methyl4-nitrophenylimino)-3-thia-1-azaspiro[4.4]nonane HCl salt

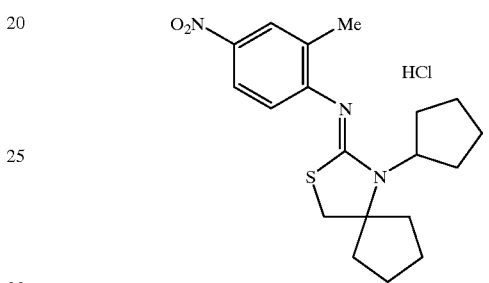

To a solution of sodium hydrogen sulfide (31 g, 0.55 mol, 2.2 equiv.) in water (250mL) was added 1-(chloromethyl)-1-(cyclopentylamino)cyclopentane HCl salt. (Method B7d; 60 g, 0.25 mol, 1.0 equiv.) The reaction mixture was stirred at room temp. for 8 h then 2-methyl-4-nitrophenyl isocyanide dichloride (Method A3b; 125 g, 0.25 mol, 1.0 equiv.) was added followed by isopropyl alcohol (300 mL). The reaction mixture was stirred at room temp. for 1 h, then a 3.6M $K_2CO_3$ solution (305 mL, 2.0 equiv., 0.5 mol) was added. The reaction was stirred at room temp. overnight. The resulting upper aqueous organic layer was separated and concentrated under reduced pressure and the residue was treated with EtOAc (1 L). The resulting organic layer was washed with water (2×200 mL), dried ($MgSO_4$) and concentrated under reduced pressure. The residual oil (86 g) was dissolved in $CH_2Cl_2$ (50 mL) and filtered through a plug of silica gel (3 g $SiO_2$/1 g crude product) with the aid of a 5% EtOAc/hex solution to afford an oil (34 g) containing the desired product and some residual isocyanide dichloride. This oil was dissolved in EtOAc (300 mL) and with HCl (1N in $Et_2O$, 1.5 L). The resulting solids were removed by filtration to give 1-cyclopentyl-2-(2-methyl-4-nitrophenylimino)-3-thia-1-azaspiro[4.4]nonane HCl salt as a white powder (36.8 g); $^1$H NMR ($CD_3OD$) δ1.40–1.55 (m, 2H), 1.55–1.68 (m, 2H) 1.68–1.80 (m, 8H), 1.80–2.00 (m, 4H), 2.16 (s, 3H), 3.16 (s, 2H), 3.60–3.70 (m, 1H) 6.70 (br s, 1H), 6.93 (d, J=8.4 Hz, 1H), 7.96–8.04 (m, 1H), 8.03 (d, J=3 Hz, 1H).

C6c. General Method for the Synthesis of 2-imino-1,3-thiazolidines Via Conversion of Hydroxyethylamines into 2-thioethylamines Followed by Reaction with Isocyanide Dichlorides Synthesis of 1-cyclopentyl-2-(2-methyl-4-nitrophenylimino)-3-thia-1-azaspiro[4.4]nonane

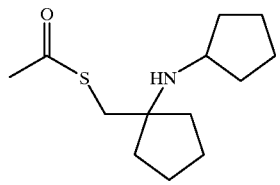

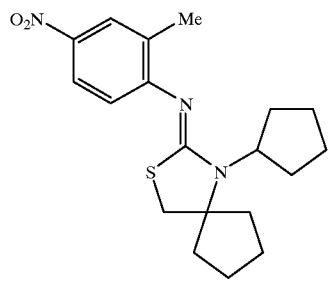

Step 1

To a 0° C. solution of Ph$_3$P (27.9 g, 0.107 mol, 1.3 equiv.) in anh. THF (400 mL) were successively added diisopropyl azodicarboxylate (21.5 g, 0.107 mol, 1.3 equiv.) and 1-cyclopentylamino-1-(hydroxymethyl)cyclopentane (Method B4d; 15.0 g, 0.082 mol). The resulting slurry was stirred for 30 min., then was treated with thiolacetic acid (7.6 mL, 0.107 mol, 1.3 equiv.). The resulting yellow solution was stirred for 15 min. and concentrated under reduced pressure to about 100 mL. The residue was dissolved in EtOAc (200 mL) and the resulting solution was extracted with a 1N HCl solution (5×125 mL). The combined aqueous layers were washed with EtOAc (2×200 mL), neutralized with K$_2$CO$_3$ to pH 7.0–7.5, then extracted with EtOAc (5×200 mL). The organic layers were combined, dried (Na$_2$SO$_4$) and concentrated under reduced pressure. The residue was dried in vacuo to afford 1-cyclopentylamino-1-(thioacetylmethyl)cyclopentane as a yellow oil (19.1 g): TLC (10% EtOAc/hexanes) R$_f$ 0.16; $^1$H NMR (CDCl$_3$) δ1.20–1.87 (m, 16H), 2.34 (s, 3H), 2.92–3.02 (m, 1H), 3.15 (s, 2H); $^{13}$C NMR (CDCl$_3$) δ23.9, 25.2, 29.3, 36.4, 40.1, 55.8, 73.0, 169.8; CI-LRMS m/z (rel abundance) 242 ((M+H)$^+$, 100%).

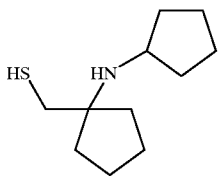

Step 2

A solution of 1-cyclopentylamino-1-(thioacetylmethyl) cyclopentane (19.1 g) in a 0.33 M KOH solution in 9:1 MeOH:H$_2$O (273 mL, 0.090 mol, 1.1 equiv.) was stirred for 30 min. The reaction mixture was concentrated under reduced pressure and the residue was dried in vacuo for to afford crude 1-cyclopentylamino-1-(thiomethyl) cyclopentane as a yellow oil: TLC (10% EtOAc/hexanes) Rf 0.18 (streak); $^1$H NMR (CD$_3$OD) δ1.32–1.71 (m, 14H), 1.87–1.94 (m, 2H), 2.67 (s, 2H), 3.07–3.14 (m, 1H); FAB-LRMS m/z (rel abundance) 200 ((M+H)$^+$, 19%). This material was used immediately in the next step without further purification Step 3

A solution of crude 1-cyclopentylamino-1-(thiomethyl) cyclopentane anh. CH$_2$Cl$_2$ (100 mL) at 0° C. was treated with a slurry of crude 2-methyl-4-nitrophenyl isocyanide dichloride (Method A3b; 19.1 g, 0.082 mol, 1.0 equiv. based on 1-cyclopentylamino-1-(thioacetylmethyl)cyclopentane) in CH$_2$Cl$_2$ (200 mL) followed by Et$_3$N (30 mL, 0.215 mol, 2.6 equiv.), and the reaction mixture was allowed to warm to room temp. and stirred for 2 d. N,N-Dimethylethylenediamine (92 g, 0.023 mol, 0.3 equiv.) was added and the reaction mixture was stirred for 1 h. Silica gel (50 g) was added and the resulting mixture was concentrated under reduced pressure. The residue was dried in vacuo overnight and purified by flash chromatography (11×10 cm SiO$_2$, 5% EtOAc/hex) to afford 1-cyclopentyl-2-(2-methyl-4-nitrophenylimino)-3-thia-1-azaspiro[4.4]nonane as a yellow granular solid (17.8 g, 60% overall): mp 120–121° C.; TLC (10% EtOAc/hexanes) R$_f$ 0.45; $^1$H NMR (CDCl$_3$) δ1.47–1.91 (m, 14H), 2.22 (s, 3H), 2.46–2.55 (m, 2H), 3.03 (s, 2H), 3.66 (pent, J=8.8 Hz, 1H), 6.89 (d, J=8.5 Hz, 1H), 7.95–8.03 (m, 2H); $^{13}$C NMR (CDCl$_3$) δ18.3, 24.3, 25.6, 28.5, 36.0, 40.6, 56.7, 75.3, 120.6, 122.3, 125.3, 132.0, 142.3, 155.1, 157.4; LC-LRMS m/z (rel abundance) 360 ((M+H)$^+$, 100%). Anal. Calcd. For C$_{19}$H$_{25}$N$_3$O$_2$S: C, 63.48; H, 7.01; N, 11.69. Found: C, 63.48; H, 6.89; N, 11.76.

C7a. General Method for the Synthesis of 2-imino-1,3-oxazolidines Via Reaction of Hydroxyethylamines with Aryl Isocyanate Dichlorides Synthesis of 2-(4-cyano-2-ethylphenylimino)-3-cyclopentyl4,4-dimethyl-1,3-oxazolidine

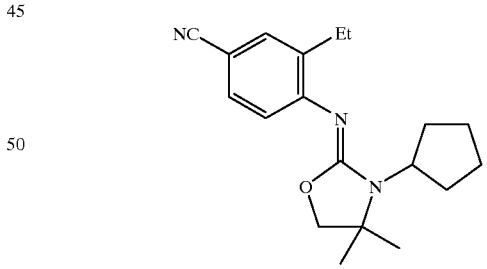

A solution of N-cyclopentyl-(1,1-dimethyl-2-hydroxyethyl)amine (Method B4b; 0.12 g, 0.69 mmol) in THF (2.5 mL) was added dropwise via syringe to a slurry of NaH (95%, 0.05 g, 1.2 mmol) in THF (5 mL) room temp. The reaction mixture was stirred 15 min, then a solution of 4-cyano-2-ethylphenyl isocyanate dichloride (Method A3a; 0.15 g, 0.63 mmol) in THF (2.5 mL) was added dropwise via syringe. The resulting mixture was stirred overnight, then treated with a 5% citric acid solution (10 mL), followed by EtOAc (25 mL). The organic phase was sequentially washed with 5% citric acid solution (20 mL), H$_2$O (20 mL) and a saturated NaCl solution (20 mL), dried (Na$_2$SO$_4$) and concentrated under reduced pressure. The residue was purified by chromatography (SiO$_2$, 5% EtOAc/hex) to give 2-(4-cyano-2-ethylphenylimino)-3-cyclopentyl-4,4-dimethyl-1,3-oxazolidine as a yellow solid (0.09 g, 43%): mp 112–114° C.; TLC (15% EtOAc/hex) R$_f$ 0.60; $^1$H NMR (CDCl$_3$) δ1.16 (t, J=7.5 Hz, 3H), 1.32 (s, 6H), 1.49–1.61 (m, 2H), 1.71–1.81 (m, 2H), 1.82–1.92 (m, 2H), 2.38–2.50 (m, 2H), 2.61 (q, J=7.6 Hz, 2H), 3.52–3.58 (m, 1H), 3.97 (s, 2H), 7.04 (d, J=8.3 Hz, 1H), 7.35 (dd, J=8.1, 1.8 Hz, 1H), 7.40 (d, J=1.8 Hz, 1H); CI-MS m/z (rel abundance) 312 ((M+H)$^+$, 100%). HRMS Cacld for C$_{17}$H$_{23}$N$_3$O$_3$: 311.1998. Found: 311.1991.

C7b. General Method for the Synthesis of 2-imino-1,3-oxazolidines Via Reaction of Hydroxyethylamines with Aryl Isocyanate Dichlorides Synthesis of (4S)-2-(4-cyano-2-ethylphenylimino)-3,4-diisobutyl-1,3-oxazolidine

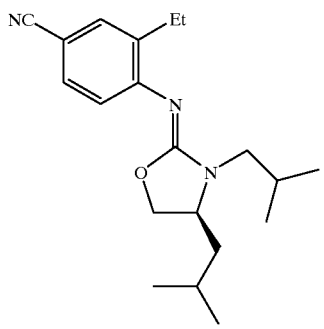

A solution of 4-cyano-2-ethylphenyl isocyanide dichloride (Method A3a; 0.42 g, 1.83 mmol, 1.2 equiv.) and (2S)-4-methyl-2-(isobutylamino)pentan-1-ol (Method B4c; 0.26 g, 1.52 mmol) in THF (5 mL) was added Et$_3$N (0.5 mL). The resulting mixture was stirred at room temp. for 1 h, then was treated with 2-(dimethylamino)ethylamine (0.5 mL). This mixture was stirred at room temp. for 1 h, then concentrated under reduced pressure. The residue was purified by column chromatography (gradient from 5% EtOAc/hex to 10% EtOAc/hex) to give (4S)-2-(4-cyano-2-ethylphenylimino)-3,4-diisobutyl-1,3-oxazolidine as a yellow oil (0.15 g): TLC (10% EtOAc/hex) R$_f$ 0.35; $^1$H NMR (CDCl$_3$) δ0.81–1.00 (m, 12H), 1.14 (t, J=4.8 Hz, 3H), 1.25–1.43 (m, 2H), 1.53–1.70 (m, 2H), 2.57 (sept, J=7.5 Hz, 1H), 2.58 (q, J=7.5 Hz, 2H), 3.01 (dd, J=14.0, 6.3 Hz, 1H), 3.33 (dd, J=13.6, 8.8 Hz, 1H), 3.73–3.83 (m, 1H), 3.94 (app t, J=7.5 Hz, 1H), 4.37 (app t, J=7.9 Hz, 1H), 7.01 (d, J=8.1 Hz, 1H), 7.33 (dd, J=8.1, 1.8 Hz, 1H), 7.38 (d, J=1.8 Hz, 1H); $^{13}$C NMR (CDCl$_3$) δ13.8, 19.9, 20.3, 21.8, 23.6, 24.7, 24.9, 26.7, 40.6, 50.1, 55.3, 70.1, 104.1, 120.2, 123.4, 129.9, 131.8, 138.4, 151.4, 152.9; HPLC ES-MS m/z 328 ((M+H)$^+$, 100%).

C8a. General Method for the Synthesis of 2-inimo-4-oxoheterocycle synthesis Via Reaction of an Isothiocyanate with an Amine, Followed by Reaction with a Haloacid Halide Synthesis of 2-(2-methyl-4-nitrophenylimino)-3-isobutyl-1,3-thiazolidin-4-one

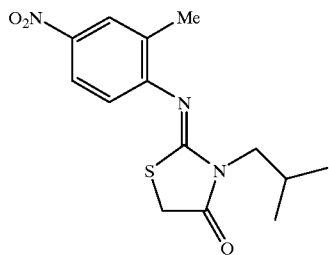

To a solution of 2-methyl-4-nitrophenyl isothiocyanate (0.190 g, 1.0 mmol) in DMF (5.3 mL) was added isobutylamine (0.4 M solution in DMF, 5.3 mL) and the reaction mixture was allowed to stir for 4 h at which time TLC analysis (hexane:EtOAc 3:1) indicated consumption of the isothiocyanate. To the resulting mixture was added chloroacetic acid (0.8 M solution in DMF, 4.0 mL) followed by N-methylmorpholine (0.7 mL, 6.4 mmol). The reaction mixture was stirred at 80° C. for 18 h, then was partitioned between water (10 mL) and EtOAc (25 mL). The aqueous phase was back-extracted with EtOAc (2×10 mL). The combined organic layers were washed with a saturated NaCl solution (25 mL), dried (Na$_2$SO$_4$) and concentrated under reduced pressure. The resulting residue was purified by MPLC (Biotage 40 S silica gel column, gradient from 5% EtOAc/hex to 33% EtOAc/hex) to afford 2-(2-methyl-4-nitrophenylimino)-3-isobutyl-1,3-thiazolidin-4-one as a pale yellow oil (0.52 g, 85%).

C9a. General Method for the Synthesis of 2-imino-1,3-thiazolidines by Reaction of Hydroxyethylamines with Isothiocyanates Followed by Acid Catalyzed Ring Closure Synthesis of 2-(2,6-dichlorophenylimino)-3-cyclohexyl-4,4-dimethyl-1,3-thiazolidine

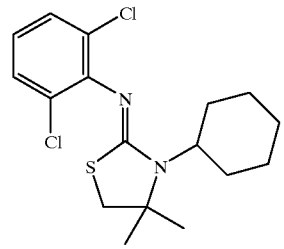

N-Cyclohexyl-1,1-dimethyl-2-hydroxyethanamine was prepared in a manner analogous to Method B4a. A solution of 2,6-dichlorophenyl isothiocyanate (1.2 g, 6.0 mmol) and N-cyclohexyl-1,1-dimethyl-2-hydroxyethanamine (1.0 g, 6.0 mmol) in CH$_2$Cl$_2$ (10 mL) was stirred for 20 h at room temp. The resulting mixture was concentrated under reduced pressure, then treated with a 33% HCl solution (15 mL). The resulting mixture was heated at the reflux temp. for 1 h, cooled to room temp. and neutralized with a 45% NaOH solution. The resulting slurry was filtered, and the resulting solids were washed with water (20 mL), then recrystallized (EtOH) to yield 2-(2,6-dichlorophenylimino)-3-cyclohexyl-4,4-dimethyl-1,3-thiazolidine (0.70 g, 33%/o): mp 134° C. When appropriate, the product was converted into the HCl salt by dissolving the free base (5 mmol) in Et$_2$O (50 mL) and treating this solution with a 2N ethereal HCl solution until no more solid precipitated. The resulting slurry was filtered and the resulting solids were washed with Et$_2$O (25 mL) followed by EtOAc (25 mL).

C10a. General Method for the Reaction of 2-chlorothiazolinium Salts with Anilines Synthesis of 2-(2-(N-phenylcarbamoyl)phenylimino)-3,4-diisobutyl-1,3-thiazolidine

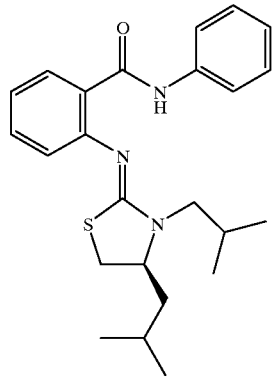

A solution of 2-(N-phenylcarbamoyl)aniline (0.097 g, 0.36 mmol, 1.0 equiv.) and Et₃N (0.5 mL, 3.6 mmol, 10 equiv.) in p-dioxane (5 mL) was added to a solution of (4S)-2-chloro-3,4-diisobutyl-4,5-dihydro-1,3-thiazolinium chloride in dichloroethane (Method B10a: 0.12 M, 0.5 mL, 0.36 mmol). The resulting mixture was heated at 70° C. overnight, then was cooled to room temp., and diluted with EtOAc (25 mL). the EtOAc mixture was sequentially washed with water (2×25 mL) and a saturated NaCl solution (25 mL), dried (Na₂SO₄), and concentrated under reduced pressure. The residue was absorbed onto SiO₂, and purified by MPLC (Biotage 40 S silica gel column; 5% EtOAc/hex) to give 2-(2-(N-phenylcarbamoyl)phenylimino)-3,4-diisobutyl-1,3-thiazolidine (0.090 g, 61%).

C11a. General Method for Synthesis of 2-imino-1,3-thiazolidin-5-ones Via Reaction of Amino Acid Esters with Isothiocyanates Synthesis of 2-(2-methyl-4-nitrophenylimino)-3-isobutyl-1,3-thiazolidin-5-one

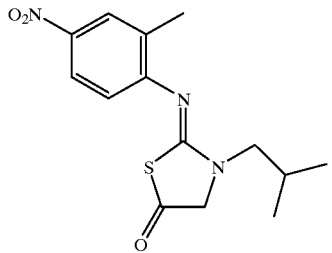

A solution of N-isobutylglycine ethyl ester (0.41 g, 2.57 mmol) in water (5 mL) was treated with Et₃N (0.71 mL, 5.15 mmol), followed by a solution of 2-methyl-4-nitrophenyl isothiocyanate (0.50 g, 2.57 mmol) in acetone (5 mL). The resulting mixture waxs heated at 40° C. for 2 h, then cooled to room temperature and concentrated under reduced pressure. The residue was separated between water (25 mL) and ethyl acetate (25 mL). The organic phase was dried (MgSO₄) and concentrated under reduced pressure to afford 2-(2-methyl-4-nitrophenylimino)-3-isobutyl-1,3-thiazolidin-5-one (0.16 g, 88%): mp 152° C.

D. General Methods for the Interconversion of Iminoheterocycles

D1a. General Method for the Neutralization of Iminoheterocycle Salts

Synthesis of (4S)-2-(4-cyano-2-ethylphenylimino)-3,4-diisobutyl-1,3-thiazolidine

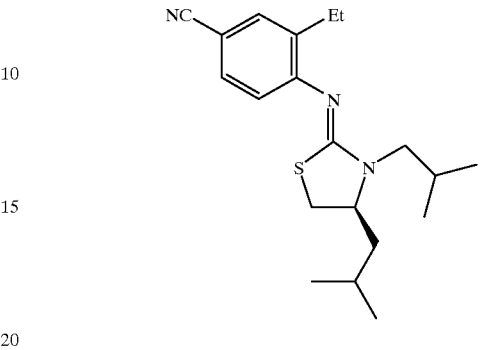

To a mixture of (4S)-2-(4-cyano-2-ethylphenylimino)-3,4-diisobutyl-1,3-thiazolidine HCl salt (Method C6a; 304 g, 0.8 mol), water (1 L) and EtOAc (1.4 L) was added NaHCO₃ (150 g, 1.78 mol, 2.2 equiv.). The resulting mixture was stirred for 1 h. The organic layer was dried (MgSO₄) and concentrated under reduced pressure. The resulting viscous oil was treated with EtOH and concentrated under reduced pressure twice to afford (4S)-2-(4-cyano-2-ethylphenylimino)-3,4-diisobutyl-1,3-thiazolidine as a low melting solid (264 g, 96%): mp 50° C.; $[\alpha]_D$=+2.4, (c 1.0, CH₃OH); ¹H NMR (CDCl₃) 0.92–0.99 (m, 12H), 1.13 (t, J=7.4 Hz, 3H), 1.47–1.52 (m, 1H), 1.58–1.67 (m, 2H), 2.07–2.11 (m, 1H), 2.54 (q, J=7.4 Hz, 2H), 2.84–2.90 (m, 2H), 3.28 (dd, J=10.6, 6.6 Hz, 1H), 3.68 (dd, J=13.6, 8.1, Hz, 1H), 3.81–3.87 (m, 1H), 6.85 (d, J=7.9 Hz, 1H), 7.36–7.42 (m, 2H); CI-MS m/z 344 ((M+H)⁺).

D1b. General Method for the Neutralization of Iminoheterocycle Salts

Synthesis of 1-cyclopentyl-2-(2-methyl-4-nitrophenylimino)-3-thia-1-azaspiro[4.4]nonane

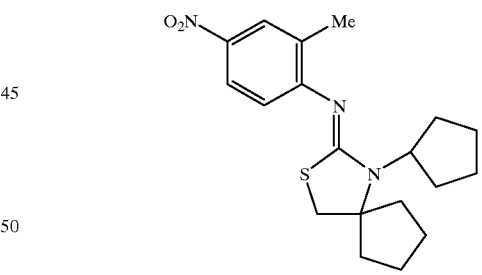

To 1-cyclopentyl-2-(2-methyl-4-nitrophenylimino)-3-thia-1-azaspiro[4.4]nonane HCl salt (Method C6b; 52.4 g, 0.132 mol) dissolved in a mixture of water (300 mL) and EtOAc (500 mL) wag added NaHCO₃ (15 g, 0.178 mol, 1.3 equiv.). The mixture was stirred for 1 h and the resulting organic layer was dried (MgSO₄) concentrated under reduced pressure. The resulting light yellow solid was treated with EtOH (100 mL), and concentrated under reduced pressure twice to give 1-cyclopentyl-2-(2-methyl-4-nitrophenylimino)-3-thia-1-azaspiro[4.4]nonane (46 g, 97%): mp 111–112° C.; ¹H NMR (CDCl₃) δ1.49–1.53 (m, 2H), 1.63–1.80 (m, 8H), 1.81–1.91 (m, 4H), 2.21 (s, 3H), 3.02 (s, 2H), 3.60–3.70 (m, 1H), 6.87 (d J=8.5 Hz, 1H), 8.02 (m, 2H), CI-MS m/z 360 ((M+H)⁺).

D2a. General Method for the Ring-nitrogen Alkylation of 2-imino Heterocycles

Synthesis of (4S)-2-(2-methyl-4-nitrophenylimino)-3,4-diisobutyl-1,3-thiazolidine HCl salt

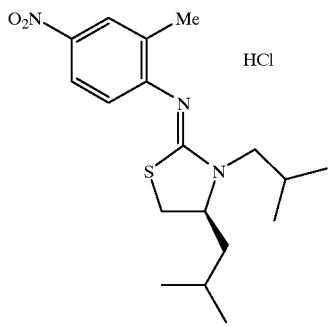

A slurry of (4S)-2-(2-methyl-4-nitrophenylimino)4-isobutyl-1,3-thiazolidine (Method C1a; 0.10 g, 0.34 mmol), isobutyl bromide (0.11 mL, 1.03 mmol) and $Cs_2CO_3$ (0.12 g, 0.38 mmol) in DMF (2 mL) was heated at 90° C. for 18 h, then cooled to 20° C., diluted with EtOAc (50 mL) and washed with water (2×200 mL). The organic phase was dried ($MgSO_4$), concentrated under reduced pressure, and the residue was purified by chromatography ($SiO_2$, gradient from 100% hex to 10% EtOAc/hex). The resulting material was dissolved in $CH_2Cl_2$ (10 mL), treated with an HCl solution (1M in $Et_2O$, 2 mL), then concentrated wider reduced pressure to afford (4S)-2-(2-methyl-4-nitrophenylimino)-3,4-diisobutyl-1,3-thiazolidine HCl salt (0.088 g, 68%): TLC (free base, 20% EtOAc/hex) $R_f$ 0.74.

D2b. General Method for the Ring-nitrogen Alkylation of 2-imino Heterocycles

Synthesis of 1-cyclopentyl-2-(2-methyl-4-nitrophenylimino)-3-thia-1-azaspiro[4.4]nonane

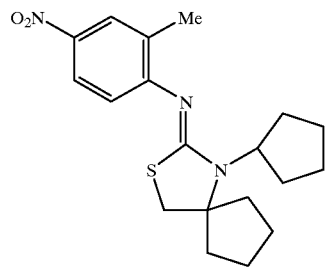

A solution of 2-(2-methyl-4-nitrophenylimino)-3-thia-1-azaspiro[4.4]nonane (Method C2a; 33.2 g, 114 mmol) in DMF (1 L) was treated with NaOH (690 g, 17.3 mol) and cyclopentyl bromide (865 mL, 6.3 mol) and the resulting mixture was stirred at 20–40° C. for 18 h, then cooled to 4° C., and treated with water (1.5 L). A conc. HCl solution was added to adjust the pH to 0, and the mixture was extracted with EtOAc (80 mL). The organic phase was washed with a 1N HCl solution (1 L), dried ($MgSO_4$) and concentrated under reduced pressure. The residue was dissolved in $CH_2Cl_2$ (500 mL) and filtered through a pad of silica gel (9×4 cm). Hexane was added to the resulting solution and volatiles were slowly removed by partial vacuum until crystals formed. The solids were collected to yield 1-cyclopentyl-2-(2-methyl-4-nitrophenylimino)-3-thia-1-azaspiro[4.4]nonane as yellow crystals (10.9 g, 26%): mp 118–9° C.; TLC (5% EtOAc/hex) $R_f$ 0.34.

D2c. General Method for the Ring-nitrogen Alkylation of 2-imino Heterocycles

Synthesis of (4R)-3-isobutyl-4-isopropyl-2-(2-methyl-4-nitrophenylimino)tetrahydro-2H-1,3-thiazine

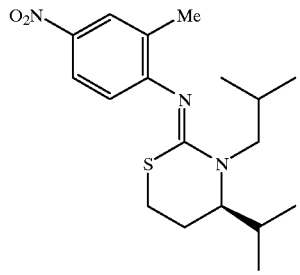

(R)-4-Isopropyl-2-(2-methyl-4-nitrophenylimino)-2,3,4,5-tetrahydro-1,3-thiazine Method C3a) was reacted with isobutyl bromide in a manner analogous to Method D2a to yield (4R)-3-isobutyl-4-isopropyl-2-(2-methyl-4-nitrophenylimino)tetrahydro-2H-1,3-thiazine (0.081 g, 32%). TLC (33% EtOAc/hex) $R_f$ 0.76.

D2d. General Method for the Ring-nitrogen Alkylation of 2-imino Heterocycles 2-(2-Methyl-4-nitrophenylimino)-3-propanoyl-1,3-thiazolidine

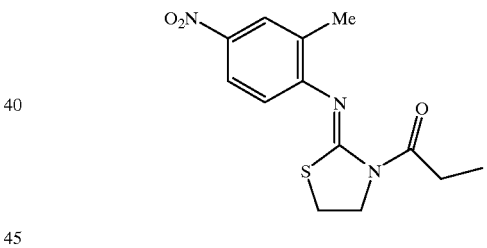

To a solution of 2-(2-methyl-4-nitrophenylimino)-1,3-thiazolidine (prepared in a manner analogous to that described in Method C1a; 0.084 g, 0.35 mmol) in $CH_2Cl_2$ (5 mL) was added propionyl chloride (0.033 g, 0.35 mmol) and $Et_3N$ (0.049 mL, 0.35 mmol). The mixture was allowed to stir at room temp for 1 h, then was diluted with $CH_2Cl_2$ (40 mL). The resulting solution was sequentially washed with $H_2O$ (10 mL) and a saturated NaCl solution (10 mL), dried ($Na_2SO_4$), and concentrated under reduced pressure. The residue was purified by preparative TLC (40% EtOAc/hex) to give 2-(2-methyl-4-nitrophenylimino)-3-propanoyl-1,3-thiazolidine (0.036 g, 35%): FAB-MS m/z 294 ((M+H)$^+$).

D2e. General Method for the Ring-nitrogen Alkylation of 2-imino Heterocycles

Synthesis of 1-(cyclohexylmethyl)-2-(2-methyl-4-nitrophenylimino)-3-thia-1-azaspiro[4.4]nonane

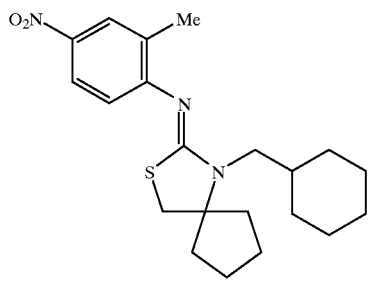

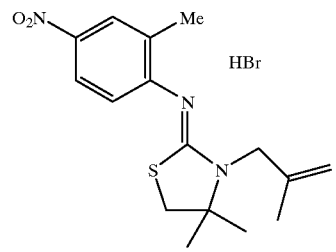

To a solution of 2-(2-methyl-4-nitrophenylimino)-3-thia-1-azaspiro[4.4]nonane (Method C2a; 0.10g, 0.3432 mmol) and bromomethylcyclohexane (1.00 mL) in DMF (1.00 mL) was added NaOH (approx. 0.13 g). The resulting mixture was stirred at 45° C. for 2 d during which it turned from deep red to bright orange. The reaction mixture was then cooled to room temp., filtered and concentrated under reduced pressure. The residual oil was purified by chromatography (SiO$_2$; 5% EtOAc/hex) to afford 1-(cyclohexylmethyl)-2-(2-methyl-4-nitrophenylimino)-3-thia-1-azaspiro[4.4]nonane (0.042 g, 32%) mp 85–7° C.

D2f General Method for the Ring-nitrogen Alkylation of 2-imino Heterocycles

Synthesis of (4S)-2-(2-chloro-4-cyano-6-methylphenylimino)-3,4-diisobutyl-1,3-thiazolidine trifluoroacetate salt

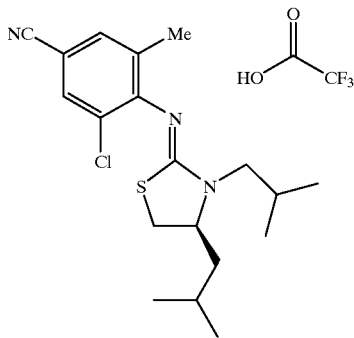

To a solution of (4S)-2-(2-chloro-4-cyano-6-methylphenylimino)-4-isobutyl-1,3-thiazolidine (Method C1c; 0.050 g, 0.16 mmol) in DMF (1.0 mL) was added NaH (0.0045 g, 1.1 equiv.), and the resulting mixture was stirred at room temp. for 5 min. Isobutyl bromide (0.053 mL, 3 equiv.) was then added and the resulting mixture was stirred at 98° C. for 4 h. The reaction mixture was filtered, then concentrated under reduced pressure. The residue was purified by preparative reverse phase HPLC (C-18 column, gradient from 0.1% TFA/20% CH$_3$CN/79.9% water to 0.1% TFA/99.9% CH$_3$CN) to furnish (4S)-2-(2-chloro-4-cyano-6-methylphenylimino)-3,4-diisobutyl-1,3-thiazolidine trifluoroacetate salt (0.030 g, 52% yield).

D2g. General Method for the Ring-nitrogen Alkylation of 2-imino Heterocycles

Synthesis of 2-(2-methyl-4-nitrophenylimino)-3-(2-methyl-prop-2-enyl)-4,4-dimethyl-1,3-thiazolidine HBr Salt 2-(2-methyl-4-nitrophenylimino)-4,4-dimethyl-1,3-thiazolidine was prepared in a manner analogous to that described in Method C1a. To a suspension of 2-(2-methyl-4-nitrophenylimino)-4,4-dimethyl-1,3-thiazolidine (1.5 mmol) in toluene (10 mL) was added 2-methylprop-2-en-1-yl bromide (4.5 mmol) and the reaction mixture was heated at the reflux temp. for 3 h at which time the reaction was judged complete by TLC. The resulting precipitate was filtered at 50 ° C. The collected solids were washed with toluene (20 mL) and CH$_2$Cl$_2$ (20 mL) to yield 2-(2-methyl-4-nitrophenylimino)-3-(2-methyl-prop-2-enyl)-4,4-dimethyl-1,3-thiazolidine HBr salt (1.14 g, 77%): mp 229° C.

D2h. General Method for the Ring-nitrogen Alkylation of 2-imino Heterocycles

Synthesis of 2-(2,4-dimethyl-3-cyano-4-pyridylimino)-1-isobutyl-3-thia-1-azaspiro[4.4]nonane

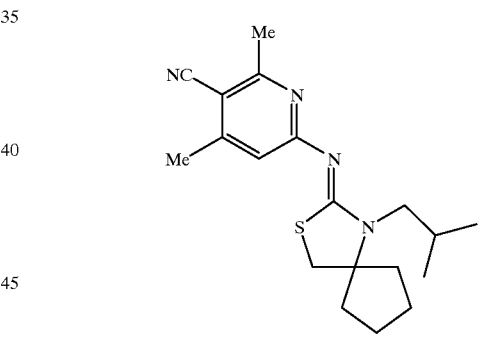

To a solution of 2-(2,4-dimethyl-3-cyano-6-pyridylimino)-3-thia-1-azaspiro[4.4]nonane (Method C1e; 0.192 g, 0.669 mmol) and isobutyl bromide (0.5 mL) in anh. DMF (0.5 mL) was added NaH (95%; 0.62 g, 6.69 mmol) portionwise. The resulting mixture was heated at 50° C. for 3 h, then treated with MeOH (approximately 0.5 mL) and concentrated under reduced pressure. The residue was purified by chromatography (SiO$_2$, gradient from 20% EtOAc/hex to 100% CH$_2$Cl$_2$) to give 2-(2,4-dimethyl-3-cyano-6-pyridylimino)-1-isobutyl-3-thia-1-azaspiro[4.4]nonane (0.04 g, 17%): CI-MS m/z 343 ((M+H)+).

D3a. General Method for the Deprotection of Tert-butylcarbamoyl-protected Alcohols Synthesis of (4S)-4-(1(R)-hydroxyethyl)-3-isobutyl-2-(2-methyl-4-nitrophenylimino)-1,3-thiazolidine

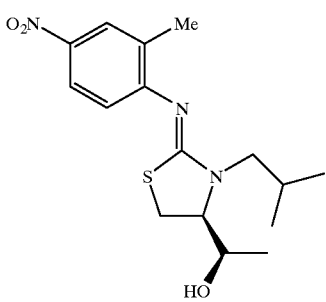

A solution of TFA (8 mL) was cooled to 4° C. and added to solid (4S)-4-(1 (R)-tert-butoxyethyl)-3-isobutyl-2-(2-methyl-4-nitrophenylimino)-1,3-thiazolidine (Method C5b; 0.16 g, 0.42 mmol) via cannula. The resulting solution was warmed to 20° C. and stirred at that temp. for 1.5 h. The reaction mixture was concentrated under reduced pressure and the residue was partitioned between Et2O (100 mL) and a saturated NaHCO$_3$ solution (100 mL). The ether layer was dried (MgSO$_4$) and concentrated under reduced pressure. The residue was purified by chromatography (SiO$_2$; gradient from hexane to 10% EtOAc/hex) to yield (4S)-4-(1(R)-hydroxyethyl)-3-isobutyl-2-(2-methyl-4-nitrophenylimino)-1,3-thiazolidine (0.13 g, 90%): TLC (25% EtOAc/hex) R$_f$ 0.13.

D4a. General Method for the Synthesis of 2-imino-1,3-thiazolidine 3-oxides and 2-imino-1,3-thiazolidine 3,3-dioxides via oxidation of 2-imino-1,3-thiazolidines Synthesis of 1-cyclopentyl-2-(2-methyl-4-nitrophenylimino)-3-thia-1-azaspiro[4.4]nonane 3-oxide and 1-cyclopentyl-2-(2-methyl-4-nitrophenylimino)-3-thia-1-azaspiro[4.4]nonane 3,3-dioxide

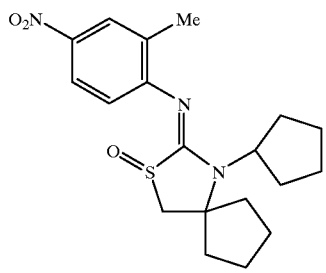

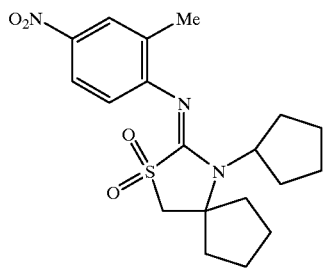

A solution of 1-cyclopentyl-2-(2-methyl-4-nitrophenylimino)-3-thia-1-azaspiro[4.4]nonane (Method D2b; 0.041 g, 0.11 mmol) and m-chloroperbenzoic acid (approximately 80%, 0.040 g, 0.19 mmol) in CH$_2$Cl$_2$ (5 mL) was stirred for 30 min., then washed with a saturated NaHCO$_3$, dried (MgSO$_4$), and concentrated under reduced pressure. The residue was purified by chromatography (SiO$_2$, gradient from hexane to 30% EtOAc/hex) to yield 1-cyclopentyl-2-(2-methyl-4-nitrophenylimino)-3-thia-1-azaspiro[4.4]nonane 3,3-dioxide (0.030 g, 67%) followed by 1-cyclopentyl-2-(2-methyl-4-nitrophenylimino)-3-thia-1-azaspiro[4.4]nonane 3-oxide (0.011 g, 26%). 1-Cyclopentyl-2-(2-methyl-4-nitrophenylimino)-3-thia-1-azaspiro[4.4] nonane 3,3-dioxide; TLC (25% EtOAc/hex) R$_f$ 0.27. 1-Cyclopentyl-2.(2-methyl-4-nitrophenylimino)-3-thia-1-azaspiro[4.4]nonane 3-oxide: TLC (25% EtOAc/hex) R$_f$ 0.10.

D5a. General Method for the Reduction of Heterocycles Containing Ketones or Aldehydes Synthesis of 2-(2-methyl-4-nitrophenylimino)-3-(3,3-dimethyl-2-hydroxybutyl)-1,3-thiazolidine

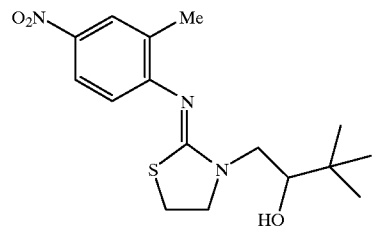

2-(2-Methyl-4-nitrophenylimino)-1,3-thiazolidine was prepared in a manner analogous to that described in method C2a and was alkylated with 1-bromo-3,3-dimethyl-2-butanone in a manner analogous to that described in Method D2a to give 2-(2-methyl-4-nitrophenylimino)-3-(3,3-dimethyl-2-oxobutyl)-1,3-thiazolidine. To a solution of 2-(2-methyl-4-nitrophenylimino)-3-(3,3-dimethyl-2-oxobutyl)-1,3-thiazolidine (0.022 g, 0.065 mmol) in MeOH (2 mL) was added NaBH$_4$ (0.0096 g, 0.26 mmol) in portions. The resulting mixture was stirred at room temp for 4 h, then was separated between EtOAc (10 mL) and H$_2$O (5 mL) and the aqueous layer was extracted with EtOAc (3×10 mL). The combined organic layers were sequentially washed with H$_2$O (15 mL), a saturated NaCl solution (15 mL), dried (Na$_2$SO$_4$), and concentrated under reduced pressure. The residue was purified by preparative TLC (20% EtOAc/hexane) to yield 2-(2-methyl-4-nitrophenylimino)-3-(3,3-dimethyl-2-hydroxybutyl)-1,3-thiazolidine (0.024 g, 92%); FAB-MS m/z 338 ((M+H)$^+$).

D6a. General Method for the Interconversion of Carboxylic Acid Derivatives

Synthesis of (4S)-2-(4-carbamoyl-2-methylphenylimino)-3,4-diisobutyl-1,3-thiazolidine

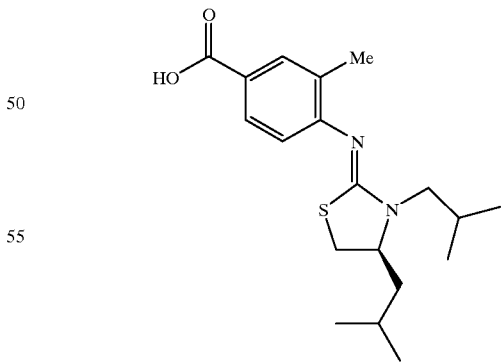

Step 1

To a solution of (4S)-2-(4-methoxycarbonyl-2-methylphenylimino)-3,4-diisobutyl-1,3-thiazolidine (prepared in a manner analogous to that described in Method D2a; 0.035 g, 0.097 mmol) in a mixture of MeOH (1.5 mL) and H$_2$O (1.5 mL) was added LiOH (0.016 g, 0.39 mmol).

The resulting mixture was stirred for 2 d at room temp., then was concentrated under reduced pressure. The residue was adjusted to pH 1 with a 1% HCl solution, then extracted with EtOAc (4×10 mL). The combined organic layers were sequentially washed with H₂O (15 mL), a saturated NaCl solution (15 mL), and dried (Na₂SO₄). Concentration under reduced pressure gave (4S)-2-(4-carboxy-2-methylphenylimino)-3,4-diisobutyl-1,3-thiazolidine (0.034 g, 100%): TLC (40% EtOAc/hex) R$_f$ 0.08. This material was used in the next step without further purification.

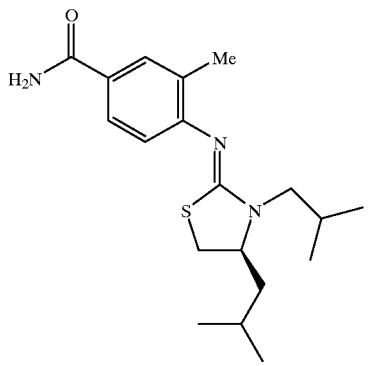

Step 2

To a solution of (4S)-2-(4-carboxy-2-methylphenylimino)-3,4-diisobutyl-1,3-thiazolidine (0.035 g, 0.10 mmol) in CH₂Cl₂ (5 mL) was added carbonyl diimidazole (0.047 g, 0.29 mmol). The mixture was allowed to stir at room temp. for 2 h, then anh NH₃ (approximately 30 drops) was condensed into the solution at −78° C. The resulting mixture was warmed to room temp. overnight, then treated with H₂O (20 mL). The aqueous layer was extracted with CH₂Cl₂ (3×20 mL), sequentially washed with H₂O (20 mL) and a saturated NaCl solution (20 mL), dried Na2SO₄), and concentrated under reduced pressure. The residue was purified by flash chromatography (40% EtOAc/hexane) to give (4S)-2-(4-carbamoyl-2-methylphenylimino)-3,4-diisobutyl-1,3-thiazolidine as a white solid (0.027 g, 73%): mp 130–131° C.

D6b. General Method for the Interconversion of Carboxylic Acid Derivatives

Synthesis of 2-(2ethyl-4-(N-methylcarbamoyl) phenylimino)-1-cyclopentyl-3-thia-1-azaspiro[4.4]nonane

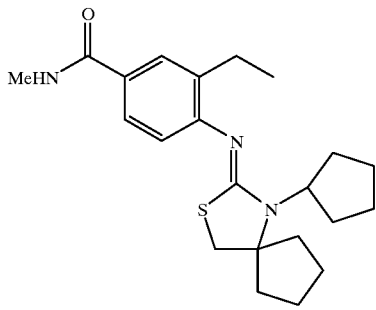

To a solution of 2-(4-carboxy-2-ethylphenylimino)-1-cyclopentyl-3-thia-1-azaspiro[4.4]nonane (Method D9a; 0.58 g, 0.167 mmol) in CHCl₃ (5 mL) was added SOCl₂ (0.06 mL, 0.83 mmol). The reaction mixture was heated at the reflux temp. for 3 h, then concentrated under reduced pressure. The residue was dissolved in CH₂Cl₂ (3 mL) and treated with methylamine (2.0M in THF, 4 mL). The reaction mixture was stirred at room temp. for 2 h, then treated with a 1N NaOH solution (10 mL). The resulting mixture was extracted with CH₂Cl₂ (3×20 mL), and the combined organic layers were washed with a saturated NaCl solution (20 mL), dried (Na₂SO₄) and concentrated under reduced pressure. The residue was purified by preparative TLC (50% EtOAc/hexane) to give 2-(2-ethyl-4-(N-methylcarbamoyl) phenylimino)-1-cyclopentyl-3-thia-1-azaspiro[4.4]nonane (36 g, 56%): TLC (30% EtOAc/hex) Rf 0.44.

D7a. General Method for the Synthesis of Cyanoarylimines from Iodoarylimines

Synthesis of 2-(4cyano-2-propylphenylimino)-3-thia-1-azaspiro[4.4]nonane

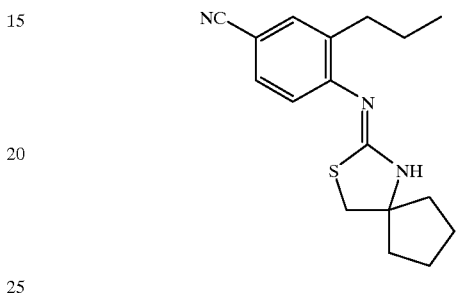

4-Iodo-2-n-propylaniline was converted into 4-iodo-2-n-propylphenyl isothiocyanate in a manner analogous to Method A2b. Concurrently, 1-amino-1-(hydroxymethyl) cyclopentane was converted to the chloromethyl analogue, then reacted with the isothiocyanate in a manner analogous to Method C2a to give 2-(4-iodo-2-propylphenylimino)-3-thia-1-azaspiro[4.4]nonane. A slurry of 2-(4-iodo-2-propylphenylimino)-3-thia-1-azaspiro[4.4]nonane (0.54 g, 1.35 mmol) and CuCN (0.24 g, 2.70 mmol) in DMF (4 mL) was heated at 140° C. overnight. The resulting mixture was cooled to room temp, concentrated under reduced pressure and purified by flash chromatography (10% EtOAc/hex) to give 2-(4-cyano-2 -propylphenylimino)-3-thia-1-azaspiro [4.4]nonane as a white solid (0.26 g, 65%): TLC (30% EtOAc/hex) R$_f$0.37.

D8a. General Method for the Synthesis of Phenylacetylenes
Synthesis of 2-(2,3-dimethyl-4-ethynylphenylimino)-1-isobutyl-3-thia-1-azaspiro[4.4]nonane

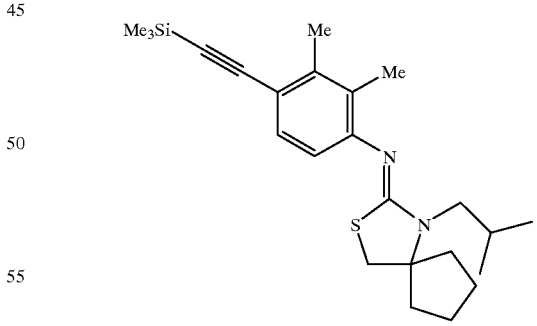

Step 1

4-Iodo-2,3-dimethylaniline was converted into 4-iodo-2, 3-dimethylphenyl isothiocyanate in a manner analogous to Method A2b. 2-(2,3-Dimethyl-4-iodophenylimino)-3-thia-1-azaspiro[4.4]nonane was prepared in a manner analogous to that described in Method C2a, then was alkylated with isobutyl bromide in a manner analogous to that described in Method D2a. A mixture of the iodophenyl compound (0.009 g, 0.021 mmol), (trimethylsilyl)acetylene (30 mL, 0.21 mmol), Pd(PPh₃)₂Cl₂ (0.005 g) and CuI (0.012 g, 0.063 mmol) in Et₃N (2 mL) was stirred at room temp. for 18 h. The resulting slurry was filtered, and the filtrate was concentrated under reduced pressure. The residue was purified by preparative TLC (2% EtOAc/hex) to give 2-(2,3-dimethyl-4-(2-trimethylsilyl-1-ethynyl)phenylimino)-1-isobutyl-3-thia-1-azaspiro[4.4]nonane (0.005 g, 59%).

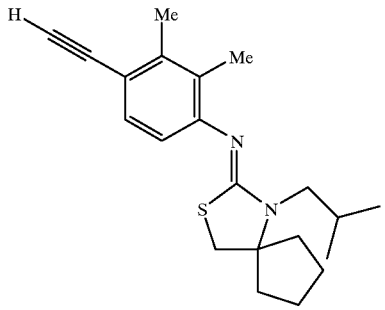

Step 2

A mixture of 2-(2,3-dimethyl-4-(2-trimethylsilyl-1-ethynyl)phenylimino)-1-isobutyl-3-thia-1-azaspiro[4.4]nonane (0.005 g, 0.0125 mmol) and NaOH (0.006 g, 0.15 mmol) in MeOH (2 mL) was stirred overnight at room temp. The reaction mixture was diluted with CH₂Cl₂ (20 mL), filtered, and the filtrate was concentrated under reduced pressure. Thre residue was purified by preparative TLC (2% EtOAc/Hex) to give 2-(2,3-dimethyl-4-ethynylphenylimino)-1-isobutyl-3-thia-1-azaspiro[4.4]nonane (0.003.2 g, 78%): TLC (20% EtOAc/hex) R_f 0.70.

D9a. General Method for the Synthesis of Benzoic Acids Via Hydrolysis of Benzonitriles Synthesis of 2-(4-carboxy-2-ethylphenylimino)-1-cyclopentyl-3-thia-1-azaspiro[4.4]nonane

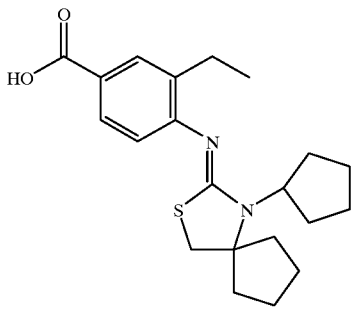

2-(4-Cyano-2-ethylphenylimino)-3-thia-1-azaspiro[4.4]nonane was prepared in a manner analogous to Method C2a and the thiazolidine was alkylated in a manner analogous to Method D2b to give 2-(4-cyano-2-ethylphenylimino)-1-cyclopentyl-3-thia-1-azaspiro[4.4]nonane. A solution of 2-(4-cyano-2-ethylphenylimino)-1-cyclopentyl-3-thia-1-azaspiro[4.4]nonane (0.32 g, 9.42 mmol) in conc. HCl (15 mL) was heated at 100° C. overnight, then was cooled to room temp. to give a white precipitate. The resulting mixture was adjusted to pH 6.5 with a 1N NaOH solution,, then extracted with CH₂Cl₂ (4×40 mL). The combined organic layers were sequentially washed with water (30 mL) and a saturated NaCl solution (30 mL), dried (Na₂SO₄) and concentrated under reduced pressure. to give 2-(4-carboxy-2-ethylphenylimino)-1-cyclopentyl-3-thia-1-azaspiro[4.4]nonane as a white solid (0.34 g, 100%): mp 208–209° C.

D10a. General Method for the Conversion of Carboxylic Acids Into Ketones

Synthesis of 2-(4-acetyl-2-ethylphenylimino)-1-cyclopentyl-3-thia-1-azaspiro[4.4]nonane

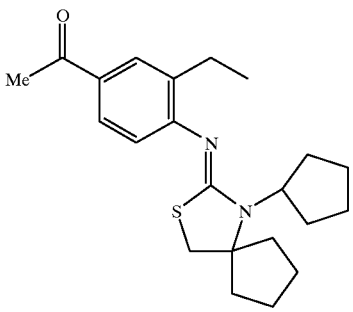

To a solution of the 2-(4-carboxy-2-ethylphenylimino)-1-cyclopentyl-3-thia-1-azaspiro[4.4]nonane (Method D9a; 0.046 g, 0.128 mmol) in THF (10 mL) at −78° C. was added methyllithium (1.4 M in Et₂O, 0.91 mL, 1.28 mmol). The reaction mixture was while allowed to gradually warm to room temp., then was stirred overnight. Trimethylsilyl chloride (0.5 mL) was added and the mixture was stirred at room temp. for 2 h, then a 1N HCl solution (2 mL) was added. The mixture was stirred for 0.5 h, then was treated with a saturated NaHCO₃ solution (10 mL). The resulting mixture was extracted with EtOAc (4×20 mL), and the combined organic layers were washed with a saturated NaCl solution (30 mL), dried (Na₂SO₄) and concentrated under reduced pressure. The residue was purified by preparative TLC (10% EtOAc/hex) to give 2-(4-acetyl-2-ethylphenylimino)-1-cyclopentyl-3-thia-1-azaspiro[4.4]nonane as a white solid (0.032 g, 73%): mp 114–115° C.

D11a. General Method for the Conversion of Nitriles Into Aldehydes

Synthesis of 2-(2-ethyl-4-formylphenylimino)-1-cyclopentyl-3-thia-1-azaspiro[4.4]nonane

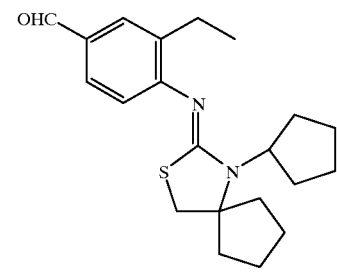

2-(4-Cyano-2-ethylphenylimino)-3-thia-1-azaspiro[4.4]nonane was prepared in a manner analogous to Method C2a and the thiazolidine was alkylated in a manner analogous to Method D2b to give 2-(4-cyano-2-ethylphenylimino)-1-cyclopentyl-3-thia-1-azaspiro[4.4]nonane. To a solution of 2-(4-cyano-2-ethylphenylimino)-1-cyclopentyl-3-thia-1-azaspiro[4.4]nonane (0.21 g, 0.60 mmol) in anh. toluene (20 mL) at −78C. was added DIBAL (1.0M in toluene, 1.20 mL, 1.20 mmol). The reaction mixture was stirred at −78° C. for 3 h, then EtOAc (3 mL) was added at −78° C., stirring was continued for 0.5 h, and wet silica gel (5% water, 2 g) was added. The reaction mixture was warmed to room temp., stirred for 3 h, then filtered through a pad of through Celite®. The filtrate was concentrated under reduced pressure, and the residue was purified by preparative TLC (30% EtOAc/hex) to give 2-(2-ethyl-4-formylphenylimino)-1-cyclopentyl-3-thia-1-azaspiro[4.4]nonane as a white solid (0.16 g, 75%): mp 104–105° C.

D12a. General Methods for the Chain Homologation of Aldehydes or Ketones

Synthesis of 2-(2-ethyl-4-((1E)-2-ethoxycarbonylvinyl)phenylimino)-1-cyclopentyl-3-thia-1-azaspiro[4.4]nonane

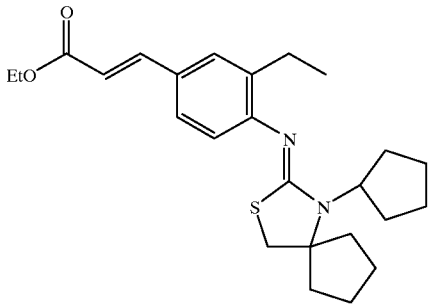

To a solution of 2-(2-ethyl-4-formylphenylimino)-1-cyclopentyl-3-thia-1-azaspiro[4.4]nonane (Method D11a; 0.053 g, 0.149 mmol) in CH$_3$CN was added LiCl (0.0076 g, 0.182 mmol) followed by DBU (0.025 g, 0.167 mmol) and triethyl phosphonoacetate (0.041 g, 0.182 mmol). The reaction mixture was stirred at room temp. for 18 h, then concentrated under reduced pressure. The residue was purified by flash chromatography (3% EtOAc/hex) to give 2-(2-ethyl-4-((1E)-2-ethoxycarbonylvinyl)phenylimino)-1-cyclopentyl-3-thia-1-azaspiro[4.4]nonane as a colorless oil (0.029 g, 48%): TLC (30% EtOAc/hex) R$_f$0.68.

D12b. General Methods for the Chain Homologation of Aldehydes or Ketones

Synthesis of 2-(2-ethyl-4-((1E)-2-nitrovinyl)phenylimino)-1-cyclopentyl-3-thia-1-azaspiro[4.4]nonane

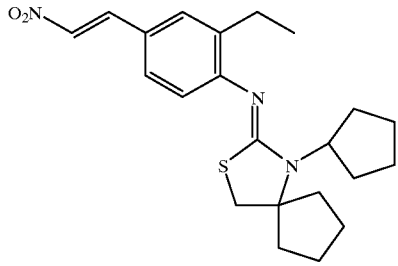

To a solution of 2-(2-ethyl-4-formylphenylimino)-1-cyclopentyl-3-thia-1-azaspiro[4.4]nonane (Method D11a; 0.041 g, 0.115 mmol) in CH$_2$Cl$_2$ (10 mL) was added MeNO$_2$ (2 drops) and piperidine (4 drops). The reaction mixture was heated at the reflux temp. overnight, them cooled to room temp. and concentration under reduced pressure. The residue was purified by flash chromatography (3% EtOAc/hex) to give 2-(2-ethyl-4-((1E)-2-nitrovinyl)phenylimino)-1-cyclopentyl-3-thia-1-azaspiro[4.4]nonane as a red solid (0.022 g, 48%): mp 141–142° C.

D12c. General Methods for the Chain Homologation of Aldehydes or Ketones

Synthesis of 2-(2-ethyl-4-(2,2-dicyanovinyl)phenylimino)-1-cyclopentyl-3-thia-1-azaspiro[4.4]nonane

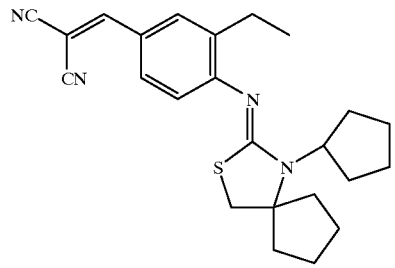

To a solution of 2-(2-ethyl-4-formylphenylimino)-1-cyclopentyl-3-thia-1-azaspiro[4.4]nonane (Method D11a; 0.037 g, 0.104 mmol) in EtOH (10 mL) was added malononitrile (0.007 g, 0.104 mmol) and piperidine (4 drops). The reaction mixture was stirred at room temp. for 2 h, then concentrated under reduced pressure. The residue was purified by preparative TLC (20% EtOAc/hex) to give 2-(2-ethyl-4-(2,2-dicyanovinyl)phenylimino)-1-cyclopentyl-3-thia-1-azaspiro[4.4]nonane as a yellow solid (0.012 g, 28%): mp 135–136° C.

D12d. General Methods for the Chain Homologation of Aldehydes or Ketones

Synthesis of 2-(2-ethyl-4-(2cyanovinyl)phenylimino)-1-cyclopentyl-3-thin-1-azaspiro[4.4]nonane

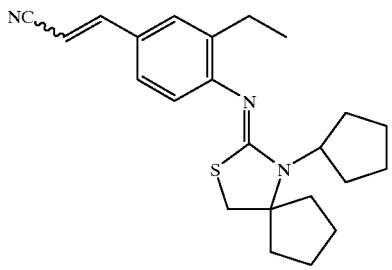

To a solution of KOH (0.024 g, 0.36 mmol) in CH$_3$CN (20 ml) at the reflux temp. was added 2-(2-ethyl-4-formylphenylimino)-1-cyclopentyl-3-thia-1-azaspiro[4.4]nonane (Method D11a; 0.127 g, 0.36 mmol). The reaction mixture was heated at the reflux temp. for 4 h, cooled to room temp., and concentrated under reduced pressure The residue was diluted with water (15 mL) and extracted with CH$_2$Cl$_2$ (3×15 mL). The combined organic layers were washed with a saturated NaCl solution and dried (Na$_2$SO$_4$). The resulting material was purified by preparative TLC (30% EtOAc/hex) to give 2-(2-ethyl-4-(2-cyanovinyl)phenylimino)-1-cyclopentyl-3-thia-1-azaspiro[4.4]nonane as 1:3 cis/trans mixture of isomers (0.050 g): TLC (30% EtOAc/hex) R$_f$0.56.

D13a. General Method for the Alkylation of Chloromethyl Side Chains

Synthesis of 2-(2-methyl-4-nitrophenylimino)-4-(N-methylaminomethyl)-1,3-thiazolidine

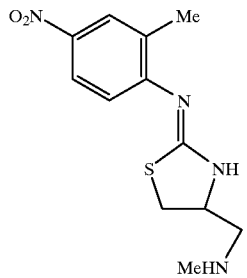

To a solution of methylamine in methanol (2.0M, 5 mL) was added 2-(2-methyl-4-nitrophenylimino)-4-(chloromethyl)-1,3-thiazolidine (prepared in a manner analogous to that described in Method C2a; 0.040 g, 0.140 mmol) and the resulting mixture was stirred at room temp for 72 h. The mixture was concentrated under reduced pressure and the resulting residue was purified by flash chromatography (5% MeOH/CH$_2$Cl$_2$) to give 2-(2-methyl-4-nitrophenylimino)-4-(N-methylaminomethyl)-1,3-thiazolidine as a solid (0.014 g, 35%).

D14a. Acid-catalyzed Rearrangement of Carbon-carbon Double Bonds

Synthesis of 2-(4-nitrophenylimino)-3-(2-methylprop-1-en-1-yl)-1,3-thiazolidine

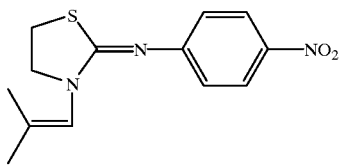

2-Chloroethylammonium chloride (Entry 1) was reacted with 4-nitrophenyl isothiocyanate according to Method C1a to give 2-(4-nitrophenyl)-1,3-thiazolidine. The thiazolidine was reacted with 1-bromo-2-methyl-2-propene according to Method D2a to give 2-(4-nitrophenylimino)-3-(2-methylprop-2-en-1-yl)-1,3-thiazolidine. A mixture of 2-(4-nitrophenylimino)-3-(2-methylprop-2-en-1-yl)-1,3-thiazolidine (0.20 g) in poly(phosphoric acid) (0.4 mL) was heated at 80 °C. for 5 h. The reaction mixture was then dissolved in 0 °C. water (20 mL) with the aid of sonication. The aqueous mixture was adjusted to pH 12 with a 1N NaOH solution, then extracted with EtOAc (3×25 mL). The combined organic phases were dried (K$_2$CO$_3$) and concentrated under reduced pressure. The residue (0.21 g) was purified by preparative HPLC to afford 2-(4-nitrophenylimino)-3-(2-methylprop-1-en-1-yl)-1,3-thiazolidine.

Specific Compound Preparations

Descriptions of the detailed preparative steps used to prepare the specific compounds listed in Tables 1–4 are provided below. Many of the compounds listed in the Tables can be synthesized following a variety of methods. The specific examples below are therefore provided by way of illustration only and should not be construed to limit the scope of the invention in any way.

Entry 1

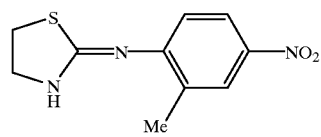

2-Chloroethylamine HCl salt was reacted with 2-methyl-4-nitrophenyl isothiocyanate according to Method C1a to give 2-(2-methyl-4-nitrophenylimino)-1,3-thiazolidine.

Entry 2

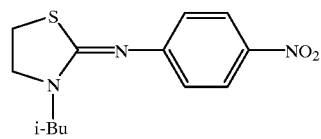

2-Chloroethylammonium chloride (Entry 1) was reacted with 4-nitrophenyl isothiocyanate according to Method C1a to give 2-(4-nitrophenylimino) -1,3-thiazolidine, which was reacted with isobutyl bromide according to Method D2a to give 2-(4-nitrophenylimino)-3-isobutyl-1,3-thiazolidine.

Entry 3

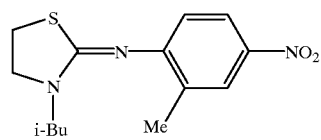

2-Chloroethylammonium chloride (Entry 1) was reacted with 2-methyl-4-nitrophenyl isothiocyanate, which was reacted with isobutyl bromide according to Method D2a to give 2-(2-methyl-4-nitrophenylimino)-3-isobutyl-1,3-thiazolidine.

Entry 4

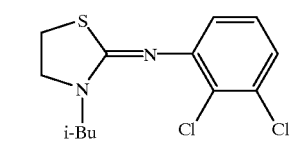

2-Chloroethylammonium chloride (Entry 1) was reacted with 2,3-dichlorophenyl isothiocyanate according to Method C1a to give 2-(2,3-dichlorophenylimino)-1,3-thiazolidine, which was reacted with isobutyl bromide according to Method D2a to give 2-(2,3-dichlorophenylimino)-3-isobutyl-1,3-thiazolidine.

Entry 5

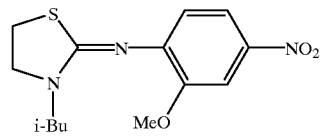

N-Chloroethyl-N'-isobutylammonuim chloride (prepared as described in Method B7c) was reacted with 2-methoxy-4-nitrophenyl isothiocyanate according to method C1d to give 2-(2-methoxy-4-nitrophenylimino)-3-isobutyl-1,3-thiazolidine.

Entry 6

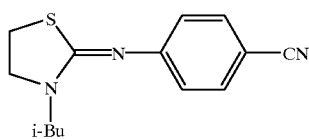

N-Chloroethyl-N'-isobutylammonuimchloride (prepared as described in Method B7c) was reacted with 4-cyanophenyl isothiocyanate according to method C1d to give 2-(4-cyanophenylimino)-3-isobutyl-1,3-thiazolidine.

Entry 7

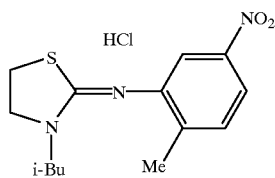

2-Chloroethylammonium chloride (Entry 1) was reacted with 2-methyl-5-nitrophenyl isothiocyanate according to Method C1a to give the thiazolidine, which was reacted with isobutyl bromide according to Method D2a to give 2-(2-methyl-5-nitrophenylimino)-3-isobutyl-1,3-thiazolidine HCl salt.

Entry 8

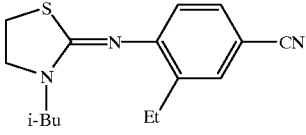

N-Chloroethyl-N'-isobutylammonuimchloride (prepared as described in Method B7c) was reacted with 4-cyano-2-ethylphenyl isothiocyanate according to method C1d to give 2-(4-cyano-2-ethylphenylimino)-3-isobutyl-1,3-thiazolidine.

Entry 9

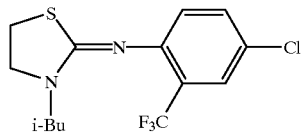

N-Chloroethyl-N'-isobutylammonium chloride (prepared as described in Method B7c) was reacted with 4-chloro-2-(trifluoromethyl)phenyl isothiocyanate according to method C1d to give 2-(4-chloro-2-(trifluoromethyl)phenylimino)-3-isobutyl-1,3-thiazolidine.

Entry 10

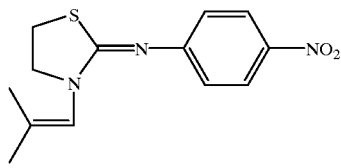

2-Chloroethylammonium chloride (Entry 1) was reacted with 4-nitrophenyl isothiocyanate according to Method C1a to give the thiazolidine, which was reacted with 1-bromo-2-methyl-2-propene according to Method D2a to give 2-(4-nitrophenylimino)-3-(2-methylprop-2-en-1-yl)-1,3-thiazolidine. The 3-allyl-1,3-thiazolidine was rearranged according to Method D14a to give 2-(4-nitrophenylimino)-3-(2-methylprop-1-en-1-yl)-1,3-thiazolidine.

Entry 11

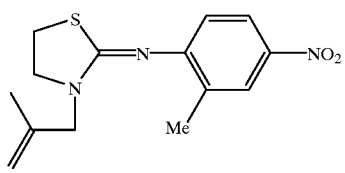

2-Chloroethylammonium chloride (Entry 1) was reacted with 2-methyl-4-nitrophenyl isothiocyanate according to Method C1a to give the thiazolidine, which was reacted with 1-bromo-2-methyl-2-propene according to Method D2a to give 2-(2-methyl-4-nitrophenylimino)-3-(2-methylprop-2-en-1-yl)-1,3-thiazolidine.

Entry 12

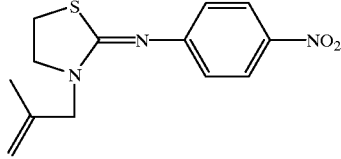

2-Chloroethylammonium chloride (Entry 1) was reacted with 4-nitrophenyl isothiocyanate according to Method C1a to give the thiazolidine, which was reacted with 1-bromo-2-methyl-2-propene according to Method D2a to give 2-(4-nitrophenylimino)-3-(2-methylprop-2-en-1-yl)-1,3-thiazolidine.

Entry 13

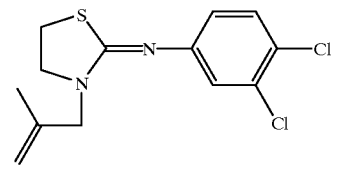

2-Chloroethylammonium chloride (Entry 1) was reacted with 3,4-dichlorophenyl isothiocyanate according to Method C1a to give the thiazolidine, which was reacted with 1-bromo-2-methyl-2-propene according to Method D2a to give 2-(3,4-dichlorophenylimino)-3-(2-methylprop-2-en-1-yl)-1,3-thiazolidine.

Entry 14

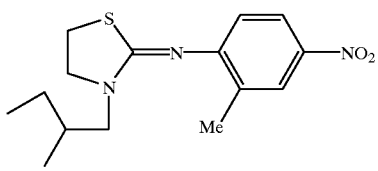

N-(2-Hydroxyethyl)-N-(2-methylbutyl)amine was reacted with SOCl$_2$ according to Method B7a to give N-(2-chloroethyl)-N-(2-methylbutyl)ammonium chloride. The chloroethylamine was reacted with 2-methyl-4-nitrophenyl isothiocyanate according to Method C1a to give to give 2-(2-methyl-4-nitrophenylimino)-3-(2-methyl-1-butyl)-1,3-thiazolidine.

Entry 15

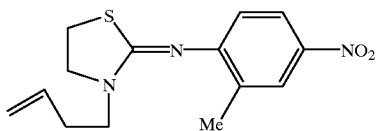

2-Chloroethylammonium chloride (Entry 1) was reacted with 2-methyl-4-nitrophenyl isothiocyanate according to Method C1a to give the thiazolidine, which was reacted with 4-bromobut-1-ene according to Method D2a to give 2-(2-methyl-4-nitrophenylimino)-3-(but-1-en-4-yl)-1,3-thiazolidine.

Entry 16

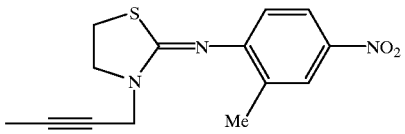

2-Chloroethylammonium chloride (Entry 1) was reacted with 2-methyl-4-nitrophenyl isothiocyanate according to Method C1a to give the thiazolidine, which was reacted with 1-bromobut-2-yne according to Method D2a to give 2-(2-methyl-4-nitrophenylimino)-3-(but-2-yn-1-yl)-1,3-thiazolidine.

Entry 17

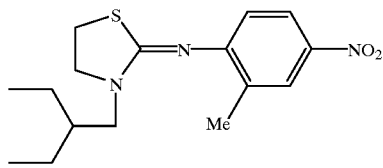

2-Chloroethylammonium chloride (Entry 1) was reacted with 2-methyl-4-nitrophenyl isothiocyanate according to Method C1a to give the thiazolidine, which was reacted with 2-ethylbutyl bromide according to Method D2a to give 2-(2-methyl-4-nitrophenylimino)-3-(2-ethyl-1-butyl)-1,3-thiazolidine.

Entry 18

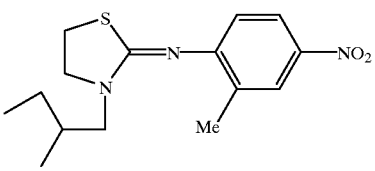

2-Chloroethylammonium chloride (Entry 1) was reacted with 2-methyl-4-nitrophenyl isothiocyanate according to Method C1a to give the thiazolidine, which was reacted with 2-methylbutyl bromide according to Method D2a to give 2-(2-methyl-4-nitrophenylimino)-3-(2-methyl-1-butyl)-1,3-thiazolidine.

Entry 19

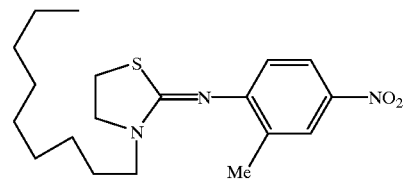

2-Chloroethylammonium chloride (Entry 1) was reacted with 2-methyl-4-nitrophenyl isothiocyanate according to Method C1a to give the thiazolidine, which was reacted with 1-nonyl bromide according to Method D2a to give 2-(2-methyl-4-nitrophenylimino)-3-(1-nonyl)-1,3-thiazolidine.

Entry 20

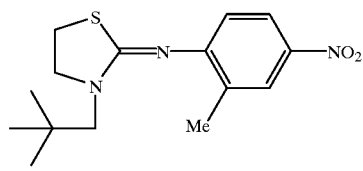

2-Chloroethylammonium chloride (Entry 1) was reacted with 2-methyl-4-nitrophenyl isothiocyanate according to Method C1a to give the thiazolidine, which was reacted with 2,2-dimethylpropyl bromide according to Method D2a to give 2-(2-methyl-4-nitrophenylimino)-3-(2,2-dimethylpropyl)-1,3-thiazolidine.

Entry 21

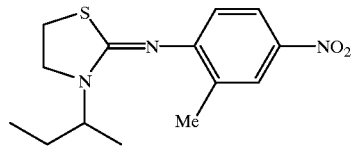

2-Butylamine was converted to N-(2-hydroxyethyl)-N-(2-butyl)amine according to Method B5a. The amine was reacted with SOCl$_2$ according to Method B7a to give N-(2-chloroethyl)-N-(2-butyl)ammonium chloride. The chloroethylamine was reacted with 2-methyl-4-nitrophenyl isothiocyanate according to Method C1a to give to give 2-(2-methyl-4-nitrophenylimino)-3-(2-butyl)-1,3-thiazolidine.

Entry 22

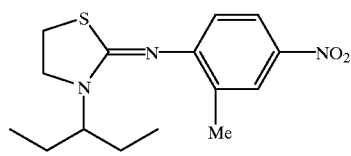

3-Pentylamine was converted to N-(2-hydroxyethyl)-N-(3-pentyl)amine according to Method B5a. The amine was reacted with $SOCl_2$ according to Method B7a to give N-(2-chloroethyl)-N-(3-pentyl)ammonium chloride. The chloroethylamine was reacted with 2-methyl-4-nitrophenyl isothiocyanate according to Method C1a to give to give 2-(2-methyl-4-nitrophenylimino)-3-(3-pentyl)-1,3-thiazolidine.

Entry 23

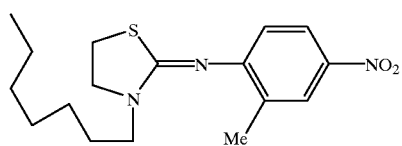

2-Chloroethylammonium chloride (Entry 1) was reacted with 2-methyl-4-nitrophenyl isothiocyanate according to Method C1a to give the thiazolidine, which was reacted with 1-heptyl bromide according to Method D2a to give 2-(2-methyl4-nitrophenylimino)-3-(1-heptyl)-1,3-thiazolidine.

Entry 24

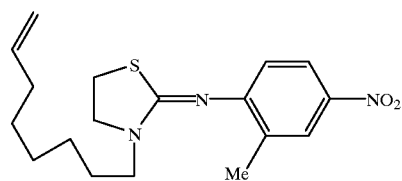

2-Chloroethylammonium chloride (Entry 1) was reacted with 2-methyl-4-nitrophenyl isothiocyanate according to Method C1a to give the thiazolidine, which was reacted with 8-bromo-1-octene according to Method D2a to give 2-(2-methyl-4-nitrophenylimino)-3-(oct-1-en-8-yl)-1,3-thiazolidine.

Entry 25

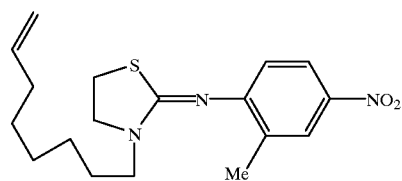

2-Propyl-1-hydroxypentane was converted to 1-bromo-2-propylpentane according to Method B2b, Step 2. 2-Chloroethylammonium chloride (Entry 1) was reacted with 2-methyl-4-nitrophenyl isothiocyanate according to Method C1a to give the thiazolidine, which was reacted with 1-bromo-2-propylpentane according to Method D2a to give 2-(2-methyl-4-nitrophenylimino)-3-(2-propyl-1-pentyl)-1,3-thiazolidine.

Entry 26

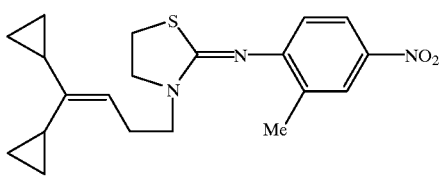

2-Chloroethylammonium chloride (Entry 1) was reacted with 2-methyl-4-nitrophenyl isothiocyanate according to Method C1a to give the thiazolidine, which was reacted with 1,1-dicyclopropylbut-1-en-4-yl bromide according to Method D2a to give 2-(2-methyl-4-nitrophenylimino)-3-(1, 1-dicyclopropylbut-1-en-4-yl)-1,3-thiazolidine.

Entry 27

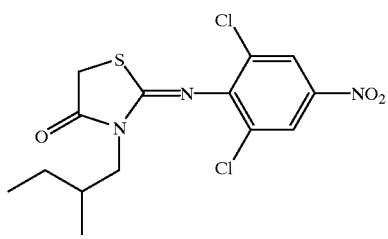

2,6-Dichloro-4-nitrophenyl isothiocyanate was reacted with 2-butylamine followed by chloroacetic acid according to Method C8a to afford 2-(2,6-dichloro-4-nitrophenylimino)-3-(2-butyl)-1,3-thiazolidin-4-one.

Entry 28

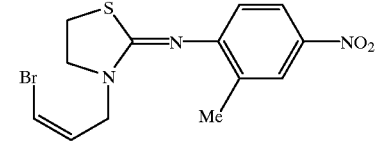

2-Chloroethylammonium chloride (Entry 1) was reacted with 2-methyl-4-nitrophenyl isothiocyanate according to Method C1a to give the thiazolidine, which was reacted with (E/Z)-1,3-dibromopropene according to Method D2a to give 2-(2-methyl-4-nitrophenylimino)-3-(bromoprop-1-en-3-yl)-1,3-thiazolidine as an E-/Z-mixture. The mixture was separated using preparative TLC to afford 2-(2-methyl-4-nitrophenylimino)-3-((2)-bromoprop-1-en-3-yl)-1,3-thiazolidine.

Entry 29

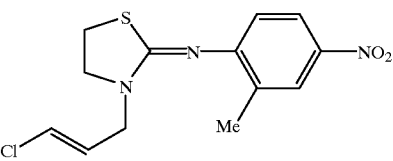

2-Chloroethylammonium chloride (Entry 1) was reacted with 2-methyl-4-nitrophenyl isothiocyanate according to Method C1a to give the thiazolidine, which was reacted with (E)-1,3-dichloropropene according to Method D2a to give 2-(2-methyl-4-nitrophenylimino)-3-((E)-chloroprop-1-en-3-yl)-1,3-thiazolidine.

Entry 30

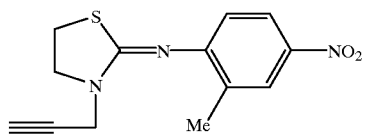

2-Chloroethylammonium chloride (Entry 1) was reacted with 2-methyl-4-nitrophenyl isothiocyanate according to Method C1a to give the thiazolidine, which was reacted with 3-chloro-1-propyne according to Method D2a to give 2-(2-methyl-4-nitrophenylimino)-3-(prop-1-yn-3-yl)-1,3-thiazolidine.

Entry 31

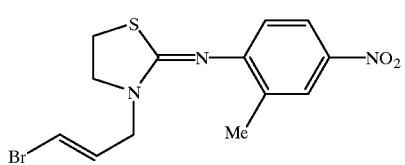

2-Chloroethylammonium chloride (Entry 1) was reacted with 2-methyl-4-nitrophenyl isothiocyanate according to Method C1a to give the thiazolidine, which was reacted with (E/Z)-1,3-dibromopropene according to Method D2a to give 2-(2-methyl-4-nitrophenylimino)-3-(bromoprop-1-en-3-yl)-1,3-thiazolidine as an E-/Z-mixture. The mixture was separated using preparative TLC to afford 2-(2-methyl-4-nitrophenylimino)-3-((E)-bromoprop-1-en-3-yl)-1,3-thiazolidine.

Entry 32

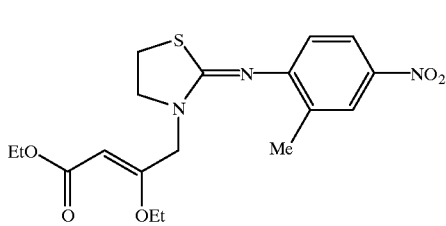

2-Chloroethylammonium chloride (Entry 1) was reacted with 2-methyl-4-nitrophenyl isothiocyanate according to Method C1a to give the thiazolidine, which was reacted with ethyl (Z)-4-chloro-3-ethoxybut-2-enoate according to Method D2a to give 2-(2-methyl-4-nitrophenylimino)-3-(1-ethoxycarbonyl-2-ethoxyprop-1-en-3-yl) -1,3-thiazolidine.

Entry 33

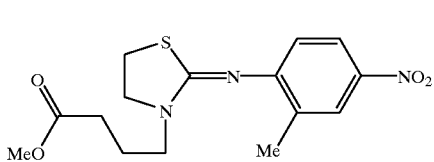

2-Chloroethylammonium chloride (Entry 1) was reacted with 2-methyl-4-nitrophenyl isothiocyanate according to Method C1a to give the thiazolidine, which was reacted with methyl 4-bromobutanoate according to Method D2a to give 2-(2-methyl-4-nitrophenylimino)-3-(1-methoxycarbonyl-3-propyl)-1,3-thiazolidine.

Entry 34

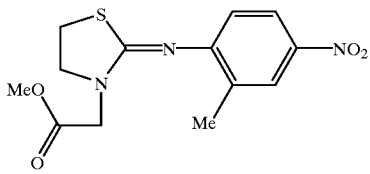

2-Chloroethylammonium chloride (Entry 1) was reacted with 2-methyl-4-nitrophenyl isothiocyanate according to Method C1a to give the thiazolidine, which was reacted with methyl chloroacetate according to Method D2a to give 2-(2-methyl-4-nitrophenylimino)-3-(1-methoxycarbonylmethyl)-1,3-thiazolidine.

Entry 35

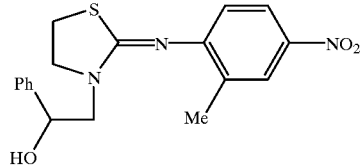

2-Chloroethylammonium chloride (Entry 1) was reacted with 2-methyl-4-nitrophenyl isothiocyanate according to Method C1a to give the thiazolidine, which was reacted with α-chloroacetophenone according to Method D2a to give 2-(2-methyl-4-nitrophenylimino)-3-(1-oxo-1-phenyl-2-ethyl)-1,3-thiazolidine. The ketone was reduced according to Method D5a to give 2-(2-methyl-4-nitrophenylimino)-3-(1-hydroxy-1-phenyl-2-ethyl)-1,3-thiazolidine.

Entry 36

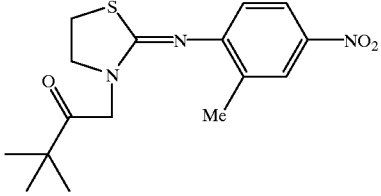

2-Chloroethylammonium chloride (Entry 1) was reacted with 2-methyl-4-nitrophenyl isothiocyanate according to Method C1a to give the thiazolidine, which was reacted with 1-chloro-3,3-dimethyl-2-butanone according to Method D2a to give 2-(2-methyl-4-nitrophenylimino)-3-(2-oxo-3,3-dimethyl-1-butyl)-1,3-thiazolidine.

Method 37

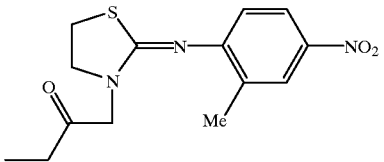

2-Chloroethylammonium chloride (Entry 1) was reacted with 2-methyl-4-nitrophenyl isothiocyanate according to Method C1a to give the thiazolidine, which was reacted with 1-chloro-2-butanone according to Method D2a to give 2-(2-methyl-4-nitrophenylimino)-3-(2-oxo-1-butyl)-1,3-thiazolidine.

Method 38

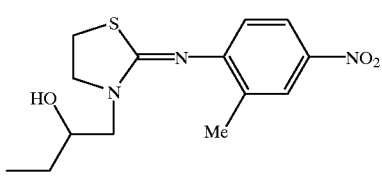

2-Chloroethylammonium chloride (Entry 1) was reacted with 2-methyl-4-nitrophenyl isothiocyanate according to Method C1a to give the thiazolidine, which was reacted with 1-chloro-2-butanone according to Method D2a to give 2-(2-methyl-4-nitrophenylimino)-3-(2-oxo-1-butyl)-1,3-thiazolidine. The ketone was reducded according to Method D5a to give 2-(2-methyl-4-nitrophenylimino)-3-(2-hydroxy-1-butyl)-1,3-thiazolidine.

Method 39

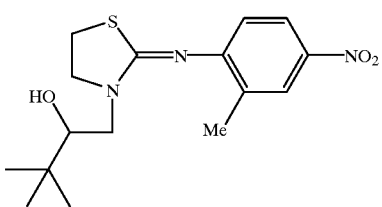

2-Chloroethylammonium chloride (Entry 1) was reacted with 2-methyl-4-nitrophenyl isothiocyanate according to Method C1a to give the thiazolidine, which was reacted with 1-chloro-3,3-dimethyl-2-butanone according to Method D2a to give 2-(2 -methyl-4-nitrophenylimino)-3-(2-oxo-3,3-dimethyl-1-butyl)-1,3 -thiazolidine. The ketone was reduced according to Method D5a to give 2-(2-methyl-4-nitrophenylimino)-3-(2-hydroxy-3,3-dimethyl-1-butyl)-1,3-thiazolidine.

Entry 40

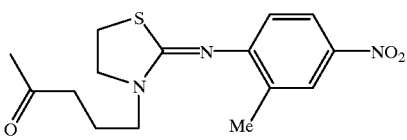

2-Chloroethylammonium chloride (Entry 1) was reacted with 2-methyl-4-nitrophenyl isothiocyanate according to Method C1a to give the thiazolidine, which was reacted with 5-bromo-2-pentanone according to Method D2a to give 2-(2-methyl-4-nitrophenylimino)-3-(2-oxo-5-pentanyl)-1,3-thiazolidine.

Entry 41

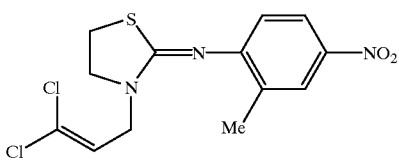

2-Chloroethylammonium chloride (Entry 1) was reacted with 2-methyl-4-nitrophenyl isothiocyanate according to Method C1a to give the thiazolidine, which was reacted with 1,1,3-trichloro-1-propene according to Method D2a to give 2-(2-methyl-4-nitrophenylimino)-3-(1,1-dichloroprop-1-en-3-yl)-1,3-thiazolidine.

Entry 42

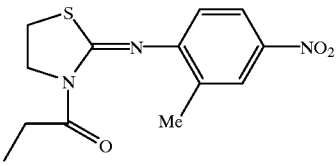

2-Chloroethylammonium chloride (Entry 1) was reacted with 2-methyl-4-nitrophenyl isothiocyanate according to Method C1a to give the thiazolidine, which was reacted with propionyl chloride according to Method D2d to give 2-(2-methyl-4-nitrophenylimino)-3-(1-oxo-1-propyl)-1,3-thiazolidine.

Entry 43

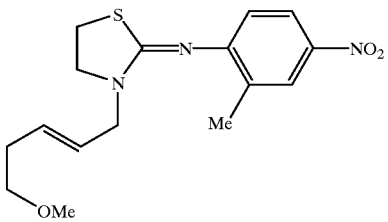

2-Chloroethylammonium chloride (Entry 1) was reacted with 2-methyl-4-nitrophenyl isothiocyanate according to Method C1a to give the thiazolidine, which was reacted with (E)-1-chloro-5-methoxy-2-pentene according to Method D2a to give 2-(2-methyl-4-nitrophenylimino)-3-((E)-5-methoxypent-2-en-1-yl)-1,3-thiazolidine.

Entry 44

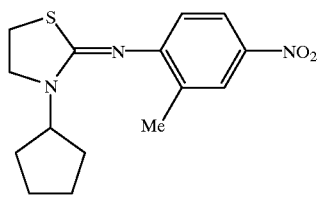

2-Hydroxyethylamine and cyclopentanone were reacted according to Method B4b, Step 1 to afford 4-aza-1-oxaspiro [4.4]nonane. The oxazolidine was reduced according to method B4b, Step 2 to afford N-cyclopentyl-N-(2-hydroxyethyl)amine. The alcohol was reacted with $SOCl_2$ according to Method B7c to afford N-cyclopentyl-N-(2-chloroethyl)amine. The amine was reacted with 2-methyl-4-nitrophenyl isothiocyanate according to Method C1d to afford 2-(2-methyl-4-nitrophenylimino)-3-(cyclopentyl)-1,3-thiazolidine.

Entry 45

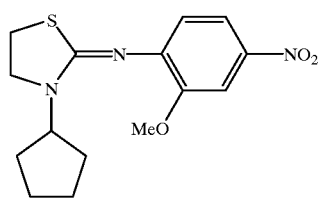

2-Hydroxyethylamine and cyclopentanone were reacted according to Method B4b, Step 1 to afford 4-aza-1-oxaspiro[4.4]nonane. The oxazolidine was reduced according to method B4b, Step 2 to afford N-cyclopentyl-N-(2-hydroxyethyl)amine. The alcohol was reacted with SOCl$_2$ according to Method B7c to afford N-cyclopentyl-N-(2-chloroethyl)amine. The amine was reacted with 2-methoxy-4-nitrophenyl isothiocyanate according to Method C1d to afford 2-(2-methoxy-4-nitrophenylimino)-3-(cyclopentyl)-1,3-thiazolidine.

Entry 46

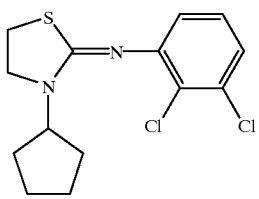

2-Hydroxyethylamine and cyclopentanone were reacted according to Method B4b, Step 1 to afford 4-aza-1-oxaspiro[4.4]nonane. The oxazolidine was reduced according to method B4b, Step 2 to afford N-cyclopentyl-N-(2-hydroxyethyl)amine. The alcohol was reacted with SOCl$_2$ according to Method B7c to afford N-cyclopentyl-N-(2-chloroethyl)amine. The amine was reacted with 2,3-dichlorophenyl isothiocyanate according to Method C1d to afford 2-(2,3-dichlorophenylimino)-3-cyclopentyl-1,3-thiazolidine.

Entry 47

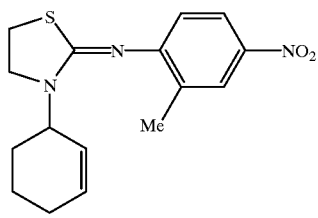

Cyclohex-2-en-1-one was reduced according to Method B2b, Step 1 to afford cyclohex-2-en-1-ol. The alcohol was converted to the 3-bromo-1-cyclohexene according to Method B2b, Step 2. The halide was converted to N-(cyclohex-2-en-1-yl)-N-(2-hydroxyethyl)amine according to Method B2b, Step 3. The alcohol was reacted with SOCl$_2$ according to Method B7a to afford N-(cyclohex-2-en-1-yl)-N-(2-chloroethyl)ammmonium chloride. The chloroethylamine was reacted with 2-methyl-4-nitrophenyl isothiocyanate according to method C1a to afford 2-(2-methyl-4-nitrophenylimino)-3-(cyclohex-2-en-1-yl)-1,3-thiazolidine.

Entry 48

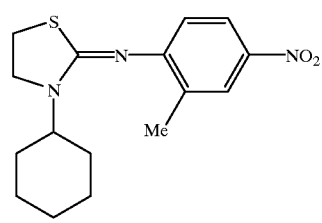

2-Hydroxyethylamine and cyclohexanone were reacted according to Method B4a, Step 1 to afford 4-aza-1-oxaspiro[4.5]decane. The oxazolidine was reduced according to method B4a, Step 2 to afford N-cyclohexyl-N-(2-hydroxyethyl)amine. The alcohol was reacted with SOCl$_2$ according to Method B7c to afford N-cyclohexyl-N-(2-chloroethyl)amine. The amine was reacted with 2-methoxy-4-nitrophenyl isothiocyanate according to Method C1d to afford 2-(2-methyl-4-nitrophenylimino)-3-cyclohexyl-1,3-thiazolidine.

Entry 49

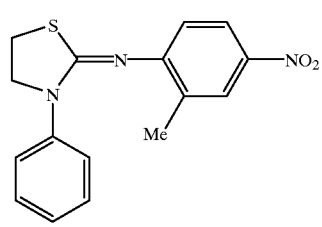

N-(2-Hydroxyethyl)aniline was reacted with SOCl$_2$ according to Method B7a to give N-2-chloroethyl)anilinium chloride. The chloroethylamine was reacted with 2-methyl-4-nitrophenyl isothiocyanate according to Method C1a to afford 2-(2-methyl-4-nitrophenylimino)-3-phenyl-1,3-thiazolidine.

Entry 50

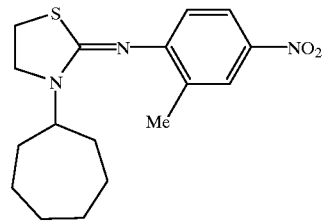

2-Hydroxyethylamine was reacted with cycloheptyl bromide according to Method B2a to give N-cycloheptyl-N-(2-hydroxyethyl)amine. The alcohol was reacted with SOCl$_2$ according to Method B7c to give N-cycloheptyl-N-(2-chloroethyl)ammonium chloride. The chloroethylamine was reacted with 2-methyl-4-nitrophenyl isothiocyanate to give 2-(2-methyl-4-nitrophenylimino)-3-cycloheptyl-1,3-thiazolidine.

Entry 51

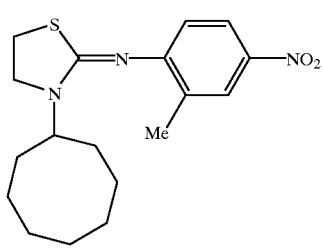

2-Hydroxyethylamine was reacted with cyclooctyl bromide according to Method B2a to give N-cyclooctyl-N-(2-hydroxyethyl)amine. The alcohol was reacted with $SOCl_2$ according to Method B7c to give N-cyclooctyl-N-(2-chloroethyl)ammonium chloride. The chloroethylamine was reacted with 2-methyl-4-nitrophenyl isothiocyanate to give 2-(2-methyl-4-nitrophenylimino)-3-cyclooctyl-1,3-thiazolidine.

Entry 52

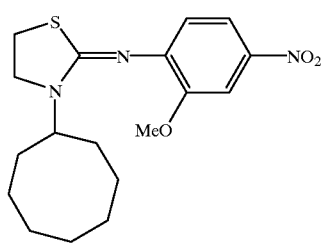

2-Hydroxyethylamine was reacted with cyclooctyl bromide according to Method B2a to give N-cyclooctyl-N-(2-hydroxyethyl)amine. The alcohol was reacted with $SOCl_2$ according to Method B7c to give N-cyclooctyl-N-(2-chloroethyl)ammonium chloride. The chloroethylamine was reacted with 2-methoxy-4-nitrophenyl isothiocyanate to give 2-(2-methoxy-4-nitrophenylimino)-3-cyclooctyl-1,3-thiazolidine.

Entry 53

2-Hydroxyethylamine was reacted with cyclooctyl bromide according to Method B2a to give N-cyclooctyl-N-(2-hydroxyethyl)amine. The alcohol was reacted with $SOCl_2$ according to Method B7c to give N-cyclooctyl-N-(2-chloroethyl)ammonium chloride. The chloroethylamine was reacted with 2,3-dichlorophenyl isothiocyanate to give 2-(2,3-dichlorophenylimino)-3-cyclooctyl-1,3-thiazolidine.

Entry 54

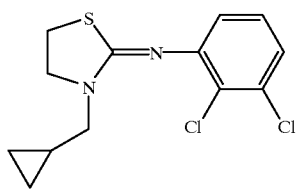

2-Hydroxyethylamine was reacted with cyclopropylmethyl bromide according to Method B2a to give N-cyclopropylmethyl-N-(2-hydroxyethyl)amine. The alcohol was reacted with $SOCl_2$ according to Method B7c to give N-cyclopropylmethyl-N-(2-chloroethyl)ammonium chloride. The chloroethylamine was reacted with 2,3-dichlorophenyl isothiocyanate to give 2-(2,3-dichlorophenylimino)-3-(cyclopropylmethyl)-1,3-thiazolidine.

Entry 55

2-Hydroxyethylamine was reacted with cyclopropylmethyl bromide according to Method B2a to give N-cyclopropylmethyl-N-(2-hydroxyethyl)amine. The alcohol was reacted with $SOCl_2$ according to Method B7c to give N-cyclopropylmethyl-N-(2-chloroethyl)ammonium chloride. The chloroethylamine was reacted with 2-methyl-4-nitrophenyl isothiocyanate to give 2-(2-methyl-4-nitrophenylimino)-3-(cyclopropylmethyl)-1,3-thiazolidine.

Entry 56

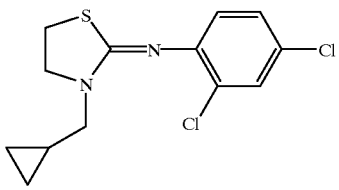

2-Hydroxyethylamine was reacted with cyclopropylmethyl bromide according to Method B2a to give N-cyclopropylmethyl-N-(2-hydroxyethyl)amine. The alcohol was reacted with $SOCl_2$ according to Method B7c to give N-cyclopropylmethyl-N-(2-chloroethyl)ammonium chloride. The chloroethylamine was reacted with 2,4-dichlorophenyl isothiocyanate to give 2-(2,4-dichlorophenylimino)-3-(cyclopropylmethyl)-1,3-thiazolidine.

Entry 57

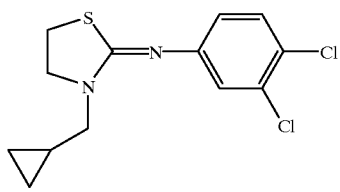

2-Hydroxyethylamine was reacted with cyclopropylmethyl bromide according to Method B2a to give N-cyclopropylmethyl-N-(2-hydroxyethyl)amine. The alcohol was reacted with SOCl$_2$ according to Method B7c to give N-cyclopropylmethyl-N-(2-chloroethyl)ammonium chloride. The chloroethylamine was reacted with 3,4-dichlorophenyl isothiocyanate to give 2-(3,4-dichlorophenylimino)-3-(cyclopropylmethyl)-1,3-thiazolidine.

Entry 58

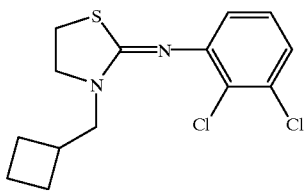

2-Hydroxyethylamine was reacted with cyclobutylmethyl bromide according to Method B2a to give N-cyclobutylmethyl-N-(2-hydroxyethyl)amine. The alcohol was reacted with SOCl$_2$ according to Method B7c to give N-cyclobutylmethyl-N-(2-chloroethyl)ammonium chloride. The chloroethylamine was reacted with 2,2-dichlorophenyl isothiocyanate to give 2-(2,2-dichlorophenylimino)-3-(cyclobutylmethyl)-1,3-thiazolidine.

Entry 59

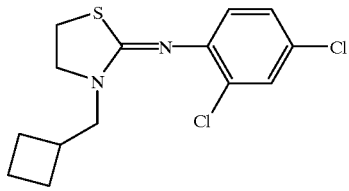

2-Hydroxyethylamine was reacted with cyclobutylmethyl bromide according to Method B2a to give N-cyclobutylmethyl-N-(2-hydroxyethyl)amine. The alcohol was reacted with SOCl$_2$ according to Method B7c to give N-cyclobutylmethyl-N-(2-chloroethyl)ammonium chloride. The chloroethylamine was reacted with 2,4-dichlorophenyl isothiocyanate to give 2-(2,4-dichlorophenylimino)-3-(cyclobutylmethyl)-1,3-thiazolidine.

Entry 60

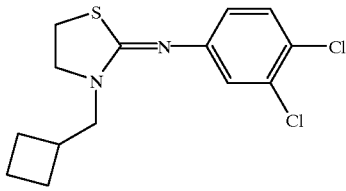

2-Hydroxyethylamine was reacted with cyclobutylmethyl bromide according to Method B2a to give N-cyclobutylmethyl-N-(2-hydroxyethyl)amine. The alcohol was reacted with SOCl$_2$ according to Method B7c to give N-cyclobutylmethyl-N-(2-chloroethyl)ammonium chloride. The chloroethylamine was reacted with 3,4-dichlorophenyl isothiocyanate to give 2-(3,4-dichlorophenylimino)-3-(cyclobutylmethyl)-1,3-thiazolidine.

Entry 61

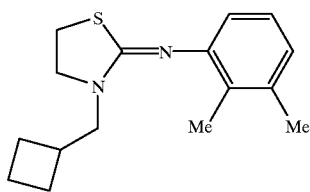

2-Hydroxyethylamine was reacted with cyclobutylmethyl bromide according to Method B2a to give N-cyclobutylmethyl-N-(2-hydroxyethyl)amine. The alcohol was reacted with SOCl$_2$ according to Method B7c to give N-cyclobutylmethyl-N-(2-chloroethyl)ammonium chloride. The chloroethylamine was reacted with 2,3-dimethylphenyl isothiocyanate to give 2-(2,3-dimethylphenylimino)-3-(cyclobutylmethyl)-1,3-thiazolidine.

Entry 62

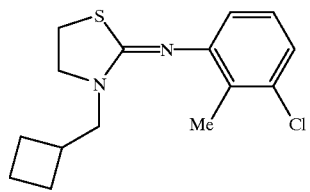

2-Hydroxyethylamine was reacted with cyclobutylmethyl bromide according to Method B2a to give N-cyclobutylmethyl-N-(2-hydroxyethyl)amine. The alcohol was reacted with SOCl$_2$ according to Method B7c to give N-cyclobutylmethyl-N-(2-chloroethyl)ammonium chloride. The chloroethylamine was reacted with 3-chloro-2-methylphenyl isothiocyanate to give 2-(3-chloro-2-methylphenylimino)-3-(cyclobutylmethyl)-1,3-thiazolidine.

Entry 63

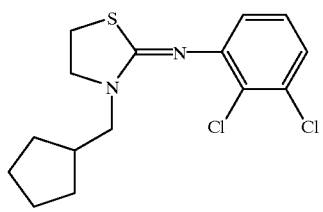

2-Hydroxyethylamine was reacted with cyclopentylmethyl bromide according to Method B2a to give N-cyclopentylmethyl-N-(2-hydroxyethyl)amine. The alcohol was reacted with SOCl$_2$ according to Method B7c to give N-cyclopentylmethyl-N-(2-chloroethyl)ammonium chloride. The chloroethylamine was reacted with 2,3-dichlorophenyl isothiocyanate to give 2-(2,3-dichlorophenylimino)-3-(cyclopentylmethyl)-1,3-thiazolidine.

Entry 64

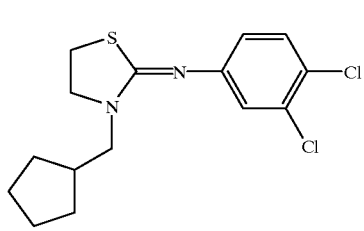

2-Hydroxyethylamine was reacted with cyclopentylmethyl bromide according to Method B2a to give N-cyclopentylmethyl-N-(2-hydroxyethyl)amine. The alcohol was reacted with SOCl$_2$ according to Method B7c to give N-cyclopentylmethyl-N-(2-chloroethyl)ammonium chloride. The chloroethylamine was reacted with 3,4-dichlorophenyl isothiocyanate to give 2-(3,4-dichlorophenylimino)-3-(cyclopentylmethyl)-1,3-thiazolidine.

Entry 65

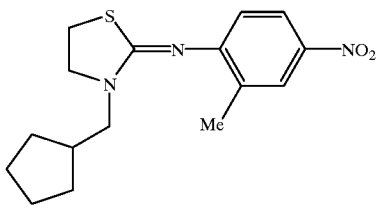

2-Hydroxyethylamine was reacted with cyclopentylmethyl bromide according to Method B2a to give N-cyclopentylmethyl-N-(2-hydroxyethyl)amine. The alcohol was reacted with SOCl$_2$ according to Method B7c to give N-cyclopentylmethyl-N-(2-chloroethyl)ammonium chloride. The chloroethylamine was reacted with 2-methyl-4-nitrophenyl isothiocyanate to give 2-(2-methyl-4-nitrophenylimino)-3-(cyclopentylmethyl)-1,3-thiazolidine.

Entry 66

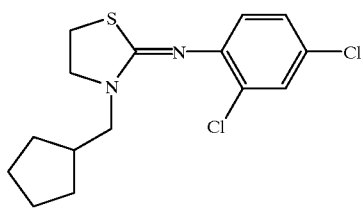

2-Hydroxyethylamine was reacted with cyclopentylmethyl bromide according to Method B2a to give N-cyclopentylmethyl-N-(2-hydroxyethyl)amine. The alcohol was reacted with SOCl$_2$ according to Method B7c to give N-cyclopentylmethyl-N-(2-chloroethyl)ammonium chloride. The chloroethylamine was reacted with 2,4-dichlorophenyl isothiocyanate to give 2-(2,4-dichlorophenylimino)-3-(cyclopentylmethyl)-1,3-thiazolidine.

Entry 67

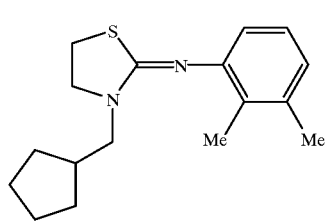

2-Hydroxyethylamine was reacted with cyclopentylmethyl bromide according to Method B2a to give N-cyclopentylmethyl-N-(2-hydroxyethyl)amine. The alcohol was reacted with SOCl$_2$ according to Method B7c to give N-cyclopentylmethyl-N-(2-chloroethyl)ammonium chloride. The chloroethylamine was reacted with 2,3-dimethylphenyl isothiocyanate to give 2-(2,3-dimethylphenylimino)-3-(cyclopentylmethyl)-1,3-thiazolidine.

Entry 68

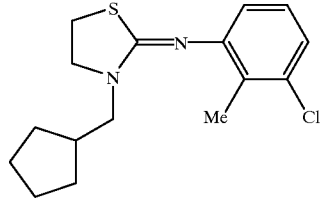

2-Hydroxyethylamine was reacted with cyclopentylmethyl bromide according to Method B2a to give N-cyclopentylmethyl-N-(2-hydroxyethyl)amine. The alcohol was reacted with SOCl$_2$ according to Method B7c to give N-cyclopentylmethyl-N-(2-chloroethyl)ammonium chloride. The chloroethylamine was reacted with 3-chloro-2-methylphenyl isothiocyanate to give 2-(3-chloro-2-methylphenylimino)-3-(cyclopentylmethyl)-1,3-thiazolidine.

Entry 69

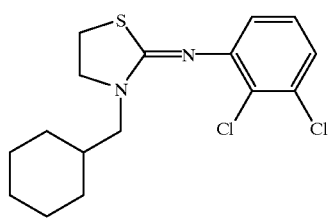

2-Hydroxyethylamine was reacted with cyclohexylmethyl bromide according to Method B2a to give N-cyclohexylmethyl-N-(2-hydroxyethyl)amine. The alcohol was reacted with SOCl₂ according to Method B7c to give N-cyclohexylmethyl-N-(2-chloroethyl)ammonium chloride. The chloroethylamine was reacted with 2,3-dichlorophenyl isothiocyanate to give 2-(2,3-dichlorophenylimino)-3-(cyclohexylmethyl)-1,3-thiazolidine.

Entry 70

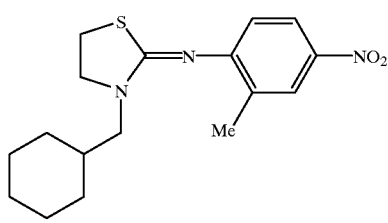

2-Hydroxyethylamine was reacted with cyclohexylmethyl bromide according to Method B2a to give N-cyclohexylmethyl-N-(2-hydroxyethyl)amine. The alcohol was reacted with SOCl₂ according to Method B7c to give N-cyclohexylmethyl-N-(2-chloroethyl)ammonium chloride. The chloroethylamine was reacted with 2-methyl-4-nitrophenyl isothiocyanate to give 2-(2-methyl-4-nitrophenylimino)-3-(cyclohexylmethyl)-1,3-thiazolidine.

Entry 71

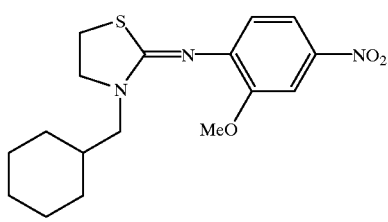

2-Hydroxyethylamine was reacted with cyclohexylmethyl bromide according to Method B2a to give N-cyclohexylmethyl-N-(2-hydroxyethyl)amine. The alcohol was reacted with SOCl₂ according to Method B7c to give N-cyclohexylmethyl-N-(2-chloroethyl)ammonium chloride. The chloroethylamine was reacted with 2-methoxy4-nitrophenyl isothiocyanate to give 2-(2-methoxy-4-nitrophenylimino)-3-(cyclohexylmethyl)-1,3-thiazolidine.

Entry 72

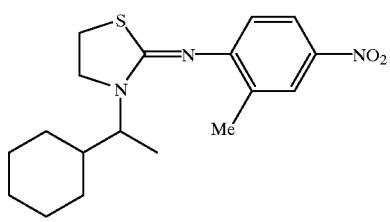

1-Cyclohexyl-1-ethylamine was converted to N-(2-hydroxyethyl)-N-(1-cyclohexyl-1-ethyl)amine according to Method B5a. The alcohol was reacted with SOCl₂ according to Method B7a to give N-(2-chloroethyl)-N-(1-cyclohexyl-1-ethyl)ammonium chloride. The chloroethylamine was reacted with 2-methyl-4-nitrophenyl isothiocyanate according to Method C1a to give 2-(2-methyl-4-nitrophenylimino)-3-(1-cyclohexyl-1-ethyl)-1,3-thiazolidine.

Entry 73

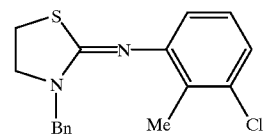

2-Hydroxyethylamine was reacted with benzyl bromide according to Method B2a to give N-benzyl-N-(2-hydroxyethyl)amine. The alcohol was reacted with SOCl₂ according to Method B7c to give N-benzyl-N-(2-chloroethyl)ammonium chloride. The chloroethylamine was reacted with 3-chloro-2-methylphenyl isothiocyanate to give 2-(3-chloro-2-methylphenylimino)-3-benzyl-1,3-thiazolidine.

Entry 74

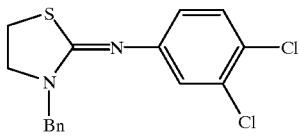

2-Hydroxyethylamine was reacted with benzyl bromide according to Method B2a to give N-benzyl-N-(2-hydroxyethyl)amine. The alcohol was reacted with SOCl₂ according to Method B7c to give N-benzyl-N-(2-chloroethyl)ammonium chloride. The chloroethylamine was reacted with 3,4-dichlorophenyl isothiocyanate to give 2-(3,4-dichlorophenylimino)-3-benzyl-1,3-thiazolidine.

Entry 75

2-Hydroxyethylamine was reacted with benzyl bromide according to Method B2a to give N-benzyl-N-(2-hydroxyethyl)amine. The alcohol was reacted with SOCl₂ according to Method B7c to give N-benzyl-N-(2-chloroethyl)ammonium chloride. The chloroethylamine was reacted with 2,4-dichlorophenyl isothiocyanate to give 2-(2,4-dichlorophenylimino)-3-benzyl-1,3-thiazolidine.

Entry 76

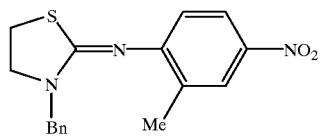

2-Hydroxyethylamine was reacted with benzyl bromide according to Method B2a to give N-benzyl-N-(2-hydroxyethyl)amine. The alcohol was reacted with SOCl$_2$ according to Method B7c to give N-benzyl-N-(2-chloroethyl)ammonium chloride. The chloroethylamine was reacted with 2-methyl-4-nitrophenyl isothiocyanate to give 2-(2-methyl-4-nitrophenylimino)-3-benzyl-1,3-thiazolidine.

Entry 77

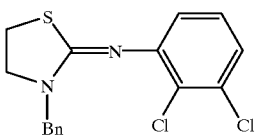

2-Hydroxyethylamine was reacted with benzyl bromide according to Method B2a to give N-benzyl-N-(2-hydroxyethyl)amine. The alcohol was reacted with SOCl$_2$ according to Method B7c to give N-benzyl-N-(2-chloroethyl)ammonium chloride. The chloroethylamine was reacted with 2,3-dichlorophenyl isothiocyanate to give 2-(2,3-dichlorophenylimino)-3-benzyl-1,3-thiazolidine.

Entry 78

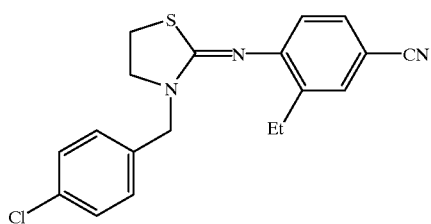

2-Hydroxyethylamine was reacted with 4-chlorobenzyl bromide according to Method B2a to give N-(4-chlorobenzyl)-N-(2-hydroxyethyl)amine. The alcohol was reacted with SOCl$_2$ according to Method B7c to give N-(4-chlorobenzyl)-N-(2-chloroethyl)ammonium chloride. The chloroethylamine was reacted with 4-cyano-2-ethylphenyl isothiocyanate to give 2-(4-cyano-2-ethylphenylimino)-3-(4-chlorobenzyl)-1,3-thiazolidine.

Entry 79

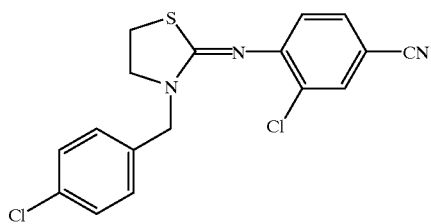

2-Hydroxyethylamine was reacted with 4-chlorobenzyl bromide according to Method B2a to give N-(4-chlorobenzyl)-N-(2-hydroxyethyl)amine. The alcohol was reacted with SOCl$_2$ according to Method B7c to give N-(4-chlorobenzyl)-N-(2-chloroethyl)ammonium chloride. The chloroethylamine was reacted with 2-chloro-4-cyanophenyl isothiocyanate to give 2-(2-chloro-4-cyanophenylimino)-3-(4-chlorobenzyl)-1,3-thiazolidine.

Entry 80

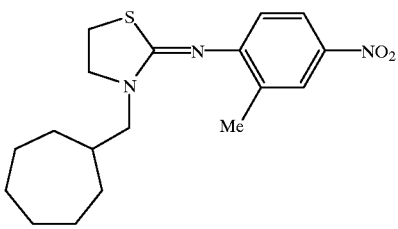

2-Hydroxyethylamine was reacted with cycloheptylmethyl bromide according to Method B2a to give N-cycloheptylmethyl-N-(2-hydroxyethyl)amine. The alcohol was reacted with SOCl$_2$ according to Method B7c to give N-cycloheptylmethyl-N-(2-chloroethyl)ammonium chloride. The chloroethylamine was reacted with 2-methyl-4-nitrophenyl isothiocyanate to give 2-(2-methyl-4-nitrophenylimino)-3-(cycloheptylmethyl)-1,3-thiazolidine.

Entry 81

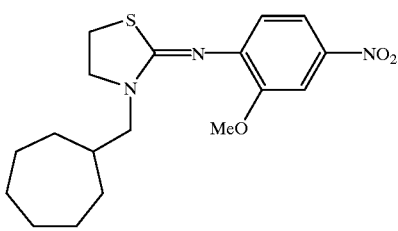

2-Hydroxyethylamine was reacted with cycloheptylmethyl bromide according to Method B2a to give N-cycloheptylmethyl-N-(2-hydroxyethyl)amine. The alcohol was reacted with SOCl$_2$ according to Method B7c to give N-cycloheptylmethyl-N-(2-chloroethyl)ammonium chloride. The chloroethylamine was reacted with 2-methoxy-4-nitrophenyl isothiocyanate to give 2-(2-methoxy-4-nitrophenylimino)-3-(cycloheptylmethyl)-1,3-thiazolidine.

Entry 82

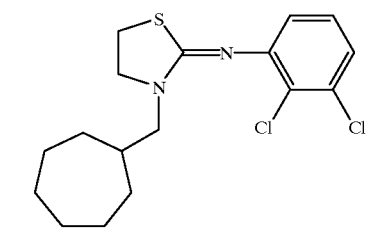

2-Hydroxyethylamine was reacted with cycloheptylmethyl bromide according to Method B2a to give N-cycloheptylmethyl-N-(2-hydroxyethyl)amine. The alcohol was reacted with SOCl$_2$ according to Method B7c to give N-cycloheptylmethyl -N-(2-chloroethyl)ammonium chloride. The chloroethylamine was reacted with 2,3-dichlorophenyl isothiocyanate to give 2-(2,3- dichlorophenylimino)-3-(cycloheptylmethyl)-1,3-thiazolidine.

Entry 83

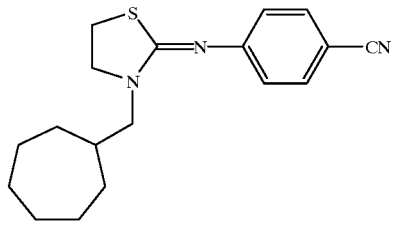

2-Hydroxyethylamine was reacted with cycloheptylmethyl bromide according to Method B2a to give N-cycloheptylmethyl-N-(2-hydroxyethyl)amine. The alcohol was reacted with SOCl$_2$ according to Method B7c to give N-cycloheptylmelthyl-N-(2-chloroethyl)ammonium chloride. The chloroethylamine was reacted with 4-cyanophenyl isothiocyanate to give 2-(4-cyanophenylimino)-3-(cycloheptylmethyl)-1,3-thiazolidine.

Entry 84

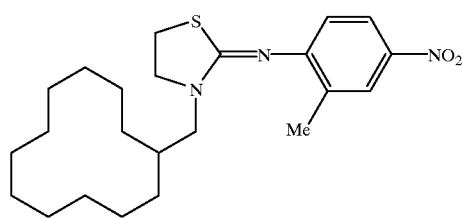

Methyl cyclododecanecarboxylate was reduced according to Method B2b, Step 1 to give cyclododecylmethanol. The alcohol was converted to cyclododecylmethylbromide according to Method B2b, Step 2. The halide was reacted with 2-hydroxyethylamine according to Method B2b, Step 3 to give N-(2-hydroxyethyl)-N-(cyclododecylmethyl)amine. The alcohol was reacted with SOCl$_2$ according to Method B7a to give N-(2-chloroethyl)-N-(cyclododecylmethyl) ammonium chloride. The chloroethylamine was reacted with 2-methyl-4-nitrophenyl isothiocyanate according to Method C1a to give 2-(2-methyl-4-nitrophenylimino)-3-(cyclododecylmethyl)-1,3 -thiazolidine.

Entry 85

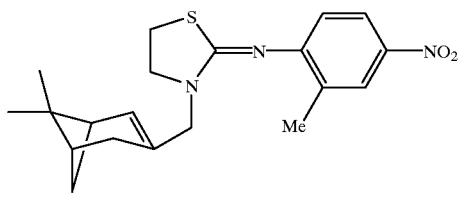

2-Chloroethylammonium chloride (Entry 1) was reacted with 2-methyl-4-nitrophenyl isothiocyanate according to Method C1a to give 2-(2-methyl-4-nitrophenylimino)-1,3-thiazolidine, which was reacted with 3-(chloromethyl)-6,6-dimethylbicyclo[3.1.1]hept-2-ene according to Method D2a to give 2-(4-nitrophenylimino)-3-((6,6-dimethylbicyclo[3.1.1]hept-2-en-3-yl)methyl)-1,3-thiazolidine.

Entry 86

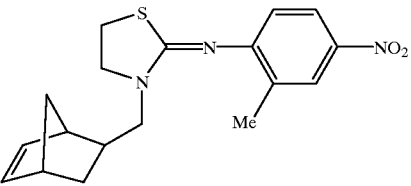

2-Chloroethylammonium chloride (Entry 1) was reacted with 2-methyl-4-nitrophenyl isothiocyanate according to Method C1a to give 2-(2-methyl-4-nitrophenylimino)-1,3-thiazolidine, which was reacted with 5-(bromomethyl)bicyclo[2.2.1]hept-2-ene according to Method D2a to give 2-(4-nitrophenylimino)-3-((bicyclo[2.2.1]hept-2-en-5-yl)methyl)-1,3 -thiazolidine.

Entry 87

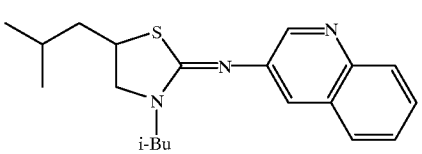

3-Aminoquinoline was converted to 3-quinoline isothiocyanate according to Method A2c. (1S)-1-(Hydroxymethyl)-3-methylbutylamine was made from (L)-leucine methyl ester as described in Method B1b. The 2-hydroxyethylamine was converted to (2S)-4-methyl-2-(isobutylamino)pentanol as described in Method B4c, Steps 1–2. The alcohol was converted to N-(1S)-1-(chloromethyl)-3-methylbutyl)-N-(isobutyl)ammonium chloride as described in Method B7c. 3-Quinoline isothiocyanate was reacted with N-(1S)-1-(chloromethyl)-3-methylbutyl)-N-(isobutyl)ammonium chloride according to Method C1f to give 2-(3-quinolylimino)-3,5-diisobutyl-1,3thiazolidine.

Entry 88

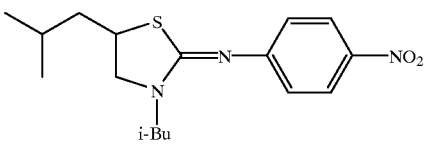

(1S)-1-(Hydroxymethyl)-3-methylbutylamine was made from (L)-leucine methyl ester as described in Method B1b. The 2-hydroxyethylamine was converted to (2S)-4-methyl-2-(isobutylamino)pentanol as described in Method B4c, Steps 1–2. The alcohol was converted to N-(1S)-1-(chloromethyl)-3-methylbutyl)-N-(isobutyl)ammonium chloride as described in Method B7c. 4-Nitrophenyl isothiocyanate was reacted with N-(1S)-1-(chloromethyl)-3-methylbutyl)-N-(isobutyl)ammonium chloride according to Method C1f to give 2-(4-nitrophenylimino)-3,5-diisobutyl-1,3-thiazolidine.

Entry 89

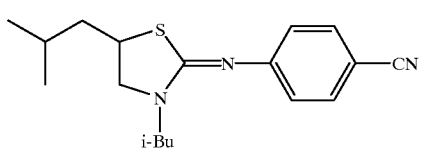

(1S)-1-(Hydroxymethyl)-3-methylbutylamine was made from (L)-leucine methyl ester as described in Method B1b. The 2-hydroxyethylamine was converted to (2S)-4-methyl-2-(isobutylamino)pentanol as described in Method B4c, Steps 1–2. The alcohol was converted to N-(1S)-1-(chloromethyl)-3-methylbutyl)-N-(isobutyl)ammonium chloride as described in Method B7c. 4-Cyanophenyl isothiocyanate was reacted with N-(1S)-1-(chloromethyl)-3-methylbutyl)-N-(isobutyl)ammonium chloride according to Method C1f to give 2-(4-cyanophenylimino)-3,5-diisobutyl-1,3-thiazolidine.

Entry 90

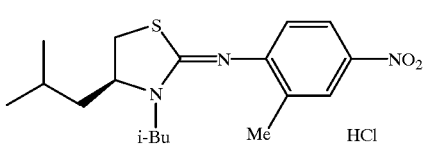

(1S)-1-(Hydroxymethyl)-3-methylbutylamine was converted to (1S)-1-(chloromethyl)-3-methylbutanammonium chloride as described in Method B7a. 2-Methyl-4-nitrophenyl isothiocyanate was reacted with (1S)-1-(chloromethyl)-3-methylbutanammonium chloride according to Method C1a to give (4S)-2-(2-methyl-4-nitrophenylimino)-4-isobutyl-1,3-thiazolidine. The thiazolidine was reacted with isobutyl bromide according to Method D2a to afford (4S)-2-(2-methyl-4-nitrophenylimino)-3,4-diisobutyl-1,3-thiazolidine HCl salt.

Entry 91

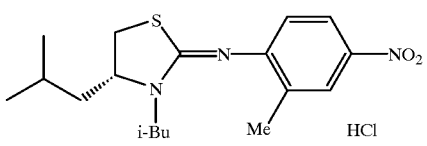

(1S)-1-(Hydroxymethyl)-3-methylbutylamine was converted to (1R)-1-(chloromethyl)-3-methylbutanammonium chloride as described in Method B7a. 2-Methyl-4-nitrophenyl isothiocyanate was reacted with (1R)-1-(chloromethyl)-3-methylbutanammonium chloride according to Method C1a to give (4R)-2-(2-methyl-4-nitrophenylimino)-4-isobutyl-1,3-thiazolidine. The thiazolidine was reacted with isobutyl bromide according to Method D2a to afford (4R)-2-(2-methyl-4-nitrophenylimino)-3,4-diisobutyl-1,3-thiazolidine HCl salt.

Entry 92

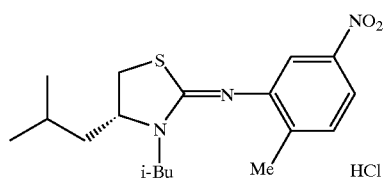

(1S)-1-(Hydroxymethyl)-3-methylbutylamine was converted to (1R)-1-(chloromethyl)-3-methylbutanammonium chloride as described in Method B7a. 2-Methyl-5-nitrophenyl isothiocyanate was reacted with (1R)-1-(chloromethyl)-3-methylbutanammonium chloride according to Method C1a to give (4R)-2-(2-methyl-5-nitrophenylimino)-4-isobutyl-1,3-thiazolidine. The thiazolidine was reacted with isobutyl bromide according to Method D2a to afford (4R)-2-(2-methyl-5-nitrophenylimino)-3,4-diisobutyl-1,3-thiazolidine HCl salt.

Entry 93

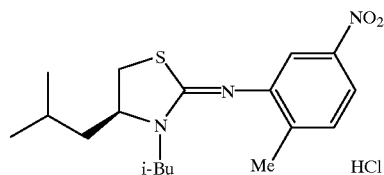

(1S)-1-(Hydroxymethyl)-3-methylbutylamine was converted to (1S)-1-(chloromethyl)-3-methylbutanammonium chloride as described in Method B7a. 2-Methyl-5-nitrophenyl isothiocyanate was reacted with (1S)-1-(chloromethyl)-3-methylbutanammonium chloride according to Method C1a to give (4S)-2-(2-methyl-5-nitrophenylimino)-4-isobutyl-1,3-thiazolidine. The thiazolidine was reacted with isobutyl bromide according to Method D2a to afford (4S)-2-(2-methyl-5-nitrophenylimino)-3,4-diisobutyl-1,3-thiazolidine HCl salt.

Entry 94

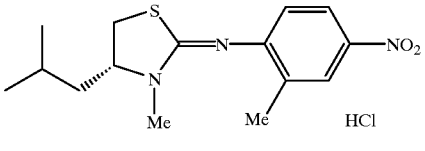

(1S)-1-(Hydroxymethyl)-3-methylbutylamine was converted to (1R)-1-(chloromethyl)-3-methylbutanammonium chloride as described in Method B7a. 2-Methyl-4-nitrophenyl isothiocyanate was reacted with (1R)-1-(chloromethyl)-3-methylbutanammonium chloride according to Method C1a to give (4R)-2-(2-methyl-4-nitrophenylimino)-4-isobutyl-1,3-thiazolidine. The thiazolidine was reacted with methyl iodide according to Method D2a to afford (4R)-2-(2-methyl-4-nitrophenylimino)-4-isobutyl-3-methyl-1,3-thiazolidine HCl salt.

Entry 95

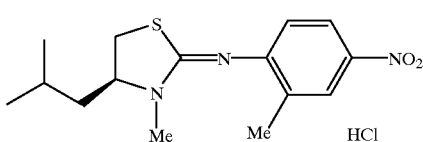

(1S)-1-(Hydroxymethyl)-3-methylbutylamine was converted to (1S)-1-(chloromethyl)-3-methylbutanammonium chloride as described in Method B7a. 2-Methyl-4-nitrophenyl isothiocyanate was reacted with (1S)-1-(chloromethyl)-3-methylbutanammonium chloride according to Method C1a to give (4S)-2-(2-methyl-4-nitrophenylimino)-4-isobutyl-1,3-thiazolidine. The thiazolidine was reacted with methyl iodide according to Method D2a to afford (4S)-2-(2-methyl-4-nitrophenylimino)-4-isobutyl-3-methyl-1,3-thiazolidine HCl salt.

Entry 96

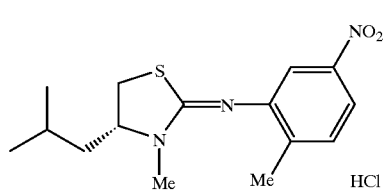

(1S)-1-(Hydroxymethyl)-3-methylbutylamine was converted to (1R)-1-(chloromethyl)-3-methylbutanammonium chloride as described in Method B7a. 2-Methyl-5-nitrophenyl isothiocyanate was reacted with (1R)-1-(chloromethyl)-3-methylbutanammonium chloride according to Method C1a to give (4R)-2-(2-methyl-5-nitrophenylimino)-4-isobutyl-1,3-thiazolidine. The thiazolidine was reacted with methyl iodide according to Method D2a to afford (4R)-2-(2-methyl-5-nitrophenylimino)-4-isobutyl-3-methyl-1,3-thiazolidine HCl salt.

Entry 97

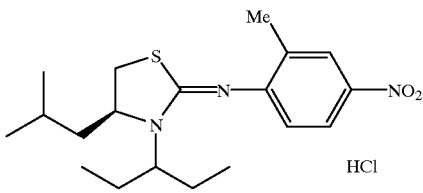

(1S)-1-(Hydroxymethyl)-3-methylbutylamine was converted to (1S)-1-(chloromethyl)-3-methylbutanammonium chloride as described in Method B7a. 2-Methyl-4-nitrophenyl isothiocyanate was reacted with (1S)-1-(chloromethyl)-3-methylbutanammonium chloride according to Method C1a to give (4S)-2-(2-methyl-4-nitrophenylimino)-4-isobutyl-1,3-thiazolidine. The thiazolidine was reacted with 1-bromo-2-ethylbutane according to Method D2a to afford (4S)-2-(2-methyl-4-nitrophenylimino)-4-isobutyl-3-(2-ethyl-1-butyl)-1,3-thiazolidine HCl salt.

Entry 98

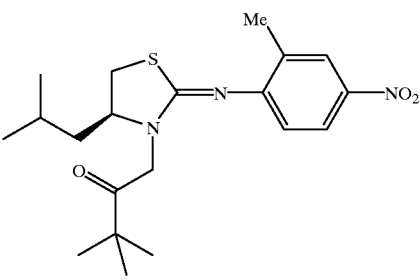

(1S)-1-(Hydroxymethyl)-3-methylbutylamine was made from (L)-leucine methyl ester as described in Method B1b. The 2-hydroxyethylamine was converted to (1S)-1-(chloromethyl)-3-methylbutanammonium chloride as described in Method B7a. 2-Methyl-4-nitrophenyl isothiocyanate was reacted with (1S)-1-(chloromethyl)-3-methylbutanammonium chloride according to Method C1a to give (4S)-2-(2-methyl-4-nitrophenylimino)-4-isobutyl-1,3-thiazolidine. The thiazolidine was reacted with 1-chloro-3,3-dimethyl-2-butanone according to Method D2a to afford (4S)-2-(2-methyl-4-nitrophenylimino)4-isobutyl-3-(2-oxo-3,3-dimethyl-1-butyl)-1,3-thiazolidine.

Entry 99

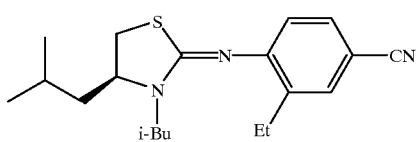

(1S)-1-(Hydroxymethyl)-3-methylbutylamine was made from (L)-leucine methyl ester as described in Method B1b. The 2-hydroxyethylamine was converted to (1S)-1-(chloromethyl)-3-methylbutanammonium chloride as described in Method B7a. 2-Ethyl-4-cyanophenyl isothiocyanate was reacted with (1S)-1-(chloromethyl)-3-methylbutanammonium chloride according to Method C1a to give (4S)-2-(2-methyl-4-nitrophenylimino)-4-isobutyl-1,3-thiazolidine. The thiazolidine was reacted with isobutyl bromide according to Method D2f to afford (4S)-2-(2-ethyl-4-cyanophenylimino)-4-isobutyl-3-(2-oxo-3,3-dimethyl-1-butyl)-1,3-thiazolidine.

Entry 100

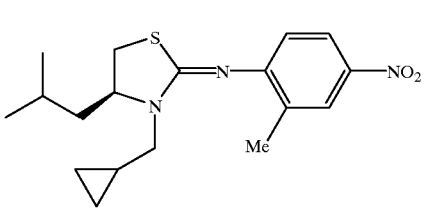

(1S)-1-(Hydroxymethyl)-3-methylbutylamine was made from (L)-leucine methyl ester as described in Method B1b. The 2-hydroxyethylamine was converted to (1S)-1-(chloromethyl)-3-methylbutanammonium chloride as described in Method B7a. 2-Methyl-4-nitrophenyl isothiocyanate was reacted with (1S)-1-(chloromethyl)-3-methylbutanammonium chloride according to Method C1a to give (4S)-2-(2-methyl-4-nitrophenylimino)-4-isobutyl-1,3-thiazolidine. The thiazolidine was reacted with cyclopropylmethyl bromide according to Method D2a to afford (4S)-2-(2-methyl-4-nitrophenylimino)-4-isobutyl-3-(cyclopropylmethyl)-1,3-thiazolidine.

Entry 101

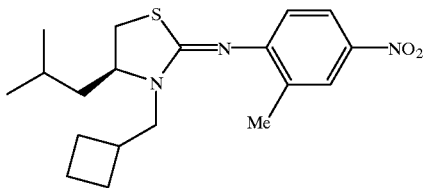

(1S)-1-(Hydroxymethyl)-3-methylbutylamine was made from (L)-leucine methyl ester as described in Method B1b. The 2-hydroxyethylamine was converted to (1S)-1-(chloromethyl)-3-methylbutanammonium chloride as described in Method B7a. 2-Methyl-4-nitrophenyl isothiocyanate was reacted with (1S)-1-(chloromethyl)-3-methylbutanammonium chloride according to Method C1a to give (4S)-2-(2-methyl-4-nitrophenylimino)-4-isobutyl-1,3-thiazolidine. The thiazolidine was reacted with cyclobutylmethyl bromide according to Method D2a to afford (4S)-2-(2-methyl-4-nitrophenylimino)-4-isobutyl-3-(cyclobutylmethyl)-1,3-thiazolidine.

Entry 102

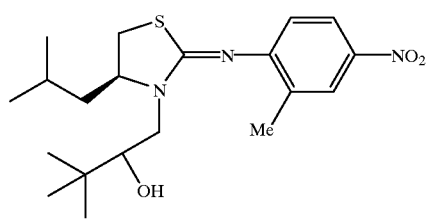

(1S)-1-(Hydroxymethyl)-3-methylbutylamine was made from (L)-leucine methyl ester as described in Method B1b. The 2-hydroxyethylamine was converted to (1S)-1-(chloromethyl)-3-methylbutanammonium chloride as described in Method B7a. 2-Methyl-4-nitrophenyl isothiocyanate was reacted with (1S)-1-(chloromethyl)-3-methylbutanammonium chloride according to Method C1a to give (4S)-2-(2-methyl-4-nitrophenylimino)-4-isobutyl-1,3-thiazolidine. The thiazolidine was reacted with 2-chloro-3,3-dimethyl-2-butanone according to Method D2a to give (4S)-2-(2-methyl-4-nitrophenylimino)-4-isobutyl-3-(2-oxo-3,3-dimethyl-1-butyl)-1,3-thiazolidine. The ketone was reduced according to Method D5a to afford (4S)-2-(2-methyl-4-nitrophenylimino)-4-isobutyl-3-(3,3-dimethyl-2-hydroxy-1-butyl)-1,3-thiazolidine.

Entry 103

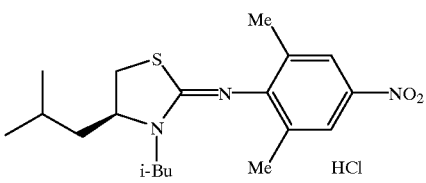

(1S)-1-(Hydroxymethyl)-3-methylbutylamine was converted to (1S)-1-(chloromethyl)-3-methylbutanammonium chloride as described in Method B7a. 2,6-Dimethyl-4-nitroaniline was converted into 2,6-dimethyl-4-nitrophenyl isothiocyanate according to Method A2b. 2,6-Dimethyl-4-nitrophenyl isothiocyanate was reacted with (1S)-1-(chloromethyl)-3-methylbutanammonium chloride according to Method C1a to give (4S)-2-(2-methyl-4-nitrophenylimino)-4-isobutyl-1,3-thiazolidine. The thiazolidine was reacted with isobutyl bromide according to Method D2a to give (4S)-2-(2,6-dimethyl-4-nitrophenylimino)-3,4-diisobutyl-1,3-thiazolidine HCl salt.

Entry 104

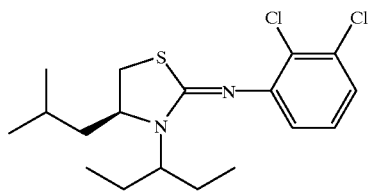

(1S)-1-(Hydroxymethyl)-3-methylbutylamine was made from (L)-leucine methyl ester as described in Method B1b. The 2-hydroxyethylamine was converted to (1S)-1-(chloromethyl)-3-methylbutanammonium chloride as described in Method B7a. 2,3-Dichlorophenyl isothiocyanate was reacted with (1S)-1-(chloromethyl)-3-methylbutanammonium chloride according to Method C1a to give (4S)-2-(2-methyl-4-nitrophenylimino)-4-isobutyl-1,3-thiazolidine. The thiazolidine was reacted with 3-bromopentane according to Method D2a to give (4S)-2-(2,3-dichlorophenylimino)-4-isobutyl-3-(3-pentyl)-1,3-thiazolidine.

Entry 105

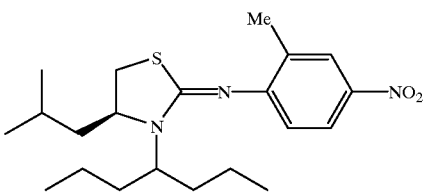

(1S)-(Hydroxymethyl)-3-methylbutylamine was made from (L)-leucine methyl ester as described in Method B1b. The 2-hydroxyethylamine was converted to (1S)-1-(chloromethyl)-1-methylbutanammonium chloride as described in Method B7a. 2-Methyl-4-nitrophenyl isothiocyanate was reacted with (1S)-1-(chloromethyl)-3-methylbutanammonium chloride according to Method C1a to give (4S)-2-(2-methyl-4-nitrophenylimino)-4-isobutyl-1,3-thiazolidine. The thiazolidine was reacted with 5-iodoheptane according to Method D2a to give (4S)-2-(2-methyl-4-nitrophenylimino)-4-isobutyl-3-(5-heptyl)-1,3-thiazolidine.

Entry 106

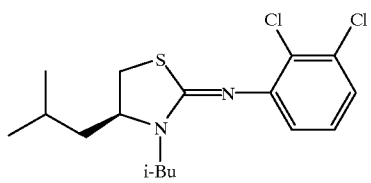

(1S)-1-(Hydroxymethyl)-3-methylbutylamine was made from (L)-leucine methyl ester as described in Method B1b. The 2-hydroxyethylamine was converted to (1S)-1-(chloromethyl)-3-methylbutanammonium chloride as described in Method B7a. 2,3-Dichlorophenyl isothiocyanate was reacted with (1S)-1-(chloromethyl)-3- methylbutanammonium chloride according to Method C1a to give (4S)-2-(2-methyl-4-nitrophenylimino)-4-isobutyl-1,3-thiazolidine. The thiazolidine was reacted with isobutyl bromide according to Method D2a to give (4S)-2-(2,3-dichlorophenylimino)-3,4-diisobutyl-1,3-thiazolidine.

Entry 107

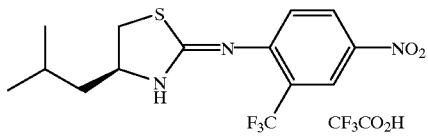

(1S)-1-(Hydroxymethyl)-3-methylbutylamine was made from (L)-leucine methyl ester as described in Method B1b. The 2-hydroxyethylamine was converted to (1S)-1-(chloromethyl)-3-methylbutanammonium chloride as described in Method B7a. 2-(Trifluoromethyl)-4-nitrophenyl isothiocyanate was reacted with (1S)-1-(chloromethyl)-3-methylbutanammonium chloride according to Method C1c to give (4S)-2-(2-(trifluoromethyl)-4-nitrophenylimino)-4-isobutyl-1,3-thiazolidine trifluoroacetate salt.

Entry 108

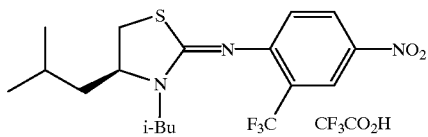

(1S)-1-(Hydroxymethyl)-3-methylbutylamine was made from (L)-leucine methyl ester as described in Method B1b. The 2-hydroxyethylamine was converted to (1S)-1-(chloromethyl)-3-methylbutanammonium chloride as described in Method B7a. 2-(Trifluoromethyl)4-nitrophenyl isothiocyanate was reacted with (1S)-1-(chloromethyl)-3-methylbutanammonium chloride according to Method C1c to give (4S)-2-(2-(trifluoromethyl)-4-nitrophenylimino)-4-isobutyl-1,3-thiazolidine. The thiazolidine was reacted with isobutyl bromide according to Method D2f to afford (4S)-2-(2-(trifluoromethyl)-4-nitrophenylimino)-3,4-diisobutyl-1,3-thiazolidine trifluoroacetate salt.

Entry 109

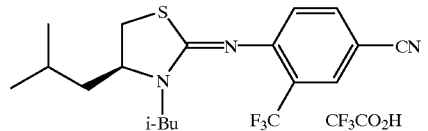

(1S)-1-(Hydroxymethyl)-3-methylbutylamine was made from (L)-leucine methyl ester as described in Method B1b. The 2-hydroxyethylamine was converted to (1S)-1-(chloromethyl)-3-methylbutanammonium chloride as described in Method B7a. 4-Cyano-2-(trifluoromethyl)phenyl isothiocyanate was reacted with (1S)-1-(chloromethyl)-3-methylbutanammonium chloride according to Method C1c to give (4S)-2-(4-cyano-2-(trifluoromethyl)phenylimino)-4-isobutyl-1,3-thiazolidine. The thiazolidine was reacted with isobutyl bromide according to Method D2f to afford (4S)-2-(4-cyano-2-(trifluoromethyl)phenylimino)-3,4-diisobutyl-1,3-thiazolidine trifluoroacetate salt.

Entry 110

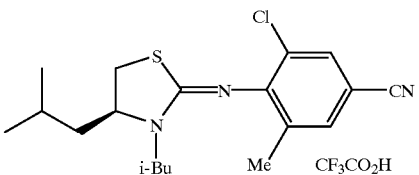

(1S)-1-(Hydroxymethyl)-3-methylbutylamine was made from (L)-leucine methyl ester as described in Method B1b. The 2-hydroxyethylamine was converted to (1S)-1-(chloromethyl)-3-methylbutanammonium chloride as described in Method B7a. 2-Chloro-4-cyano-6-methylphenyl isothiocyanate was reacted with (1S)-1-(chloromethyl)-3-methylbutanammonium chloride according to Method C1c to give (4S)-2-(2-chloro4-cyano-6-methylphenylimino)-4-isobutyl-1,3-thiazolidine. The thiazolidine was reacted with isobutyl bromide according to Method D2f to afford (4S)-2-(2-chloro-4-cyano-6-methylphenylimino)-3,4-diisobutyl-1,3-thiazolidine trifluoroacetate salt.

Entry 111

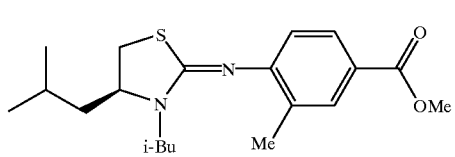

(1S)-1-(Hydroxymethyl)-3-methyl butylamine was made from (L)-leucine methyl ester as described in Method B1b. The 2-hydroxyethylamine was converted to (1S)-1-(chloromethyl)-3-methylbutanammonium chloride as described in Method B7a. 4-(Methoxycarbonyl)-2-methylphenyl isothiocyanate was reacted with (1S)-1-(chloromethyl)-3-methylbutanammonium chloride according to Method C1a to give (4S)-2-(4-(methoxycarbonyl)-2-methylphenylimino)-4-isobutyl-1,3-thiazolidine. The thiazolidine was reacted with isobutyl bromide according to Method D2a to give (4S)-2-(4-(methoxycarbonyl)-2-methylphenylimino)-3,4-diisobutyl-1,3-thiazolidine.

Entry 112

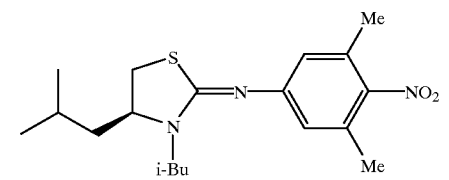

(1S)-1-(Hydroxymethyl)-3-methylbutylamine was made from (L)-leucine methyl ester as described in Method B1b. The 2-hydroxyethylamine was converted to (1S)-1-(chloromethyl)-3-methylbutanammonium chloride as described in Method B7a. 3,5-Dimethyl-4-nitroaniline was converted to 3,5-Dimethyl-4-nitrophenyl isothiocyanate according to Method A2a, Step 3. 3,5-Dimethyl-4-nitrophenyl isothiocyanate was reacted with (1S)-1-(chloromethyl)-3-methylbutanammonium chloride according to Method C1a to give (4S)-2-(3,5-dimethyl-4-nitrophenylimino)-4-isobutyl-1,3-thiazolidine. The thiazolidine was reacted with isobutyl bromide according to Method D2a to give (4S)-2-(3,5-dimethyl-4-nitrophenylimino)-3,4-diisobutyl-1,3-thiazolidine.

Entry 113

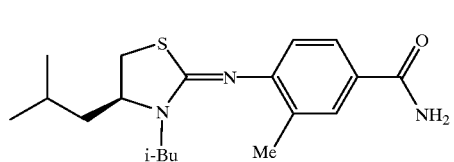

(1S)-1-(Hydroxymethyl)-1-methylbutylamine was made from (L)-leucine methyl ester as described in Method B1b. The 2-hydroxyethylamine was converted to (1S)-1-(chloromethyl)-3-methylbutanammonium chloride as described in Method B7a. 4-(Methoxycarbonyl)-2-methylphenyl isothiocyanate was reacted with (1S)-1-(chloromethyl)-3-methylbutanammonium chloride according to Method C1a to give (4S)-2-(4-(methoxycarbonyl)-2-methylphenylimino)-4-isobutyl-1,3-thiazolidine. The thiazolidine was reacted with isobutyl bromide according to Method D2a to give (4S)-2-(4-(methoxycarbonyl)-2-methylphenylimino)-3,4-diisobutyl-1,3-thiazolidine. The thiazolidine was saponified according to Method D6a, Step 1 to give (4S)-2-(4-carboxy-2-methylphenylimino)-3,4-diisobutyl-1,3-thiazolidine. The acid was coupled with ammonia as described in Method D6a, Step 2 to afford (4S)-2-(4-carbamoyl-2-methylphenylimino)-3,4-diisobutyl-1,3-thiazolidine.

Entry 114

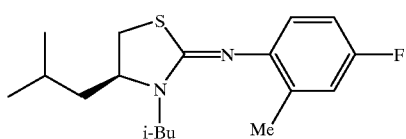

(1S)-1-(Hydroxymethyl)-3-methylbutylamine was made from (L)-leucine methyl ester as described in Method B1b. The 2-hydroxyethylamine was converted to (1S)-1-(chloromethyl)-3-methylbutanammonium chloride as described in Method B7a. 4-Fluoro-2-methylphenyl isothiocyanate was reacted with (1S)-1-(chloromethyl)-3-methylbutanammonium chloride according to Method C1a to give (4S)-2-(4-fluoro -2-methylphenylimino)-4-isobutyl-1,3-thiazolidine. The thiazolidine was reacted with isobutyl bromide according to Method D2a to give (4S)-2-(4-fluoro-2-methylphenylimino)-3,4-diisobutyl-1,3-thiazolidine.

Entry 115

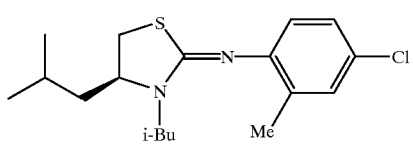

(1S)-1-(Hydroxymethyl)-3-methylbutylamine was made from (L)-leucine methyl ester as described in Method B1b. The 2-hydroxyethylamine was converted to (1S)-1-(chloromethyl)-3-methylbutanammonium chloride as described in Method B7a. 4 -Chloro-2-methylphenyl isothiocyanate was reacted with (1S)-1-(chloromethyl)-3-methylbutanammonium chloride according to Method C1a to give (4S)-2-(4-Chloro-2-methylphenylimino)-4-isobutyl-1,3-thiazolidine. The thiazolidine was reacted with isobutyl bromide according to Method D2a to give (4S)-2-(4-chloro-2-methylphenylimino)-3,4-diisobutyl-1,3-thiazolidine.

Entry 116

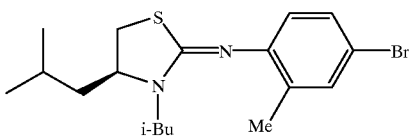

(1S)-1-(Hydroxymethyl)-3-methylbutylamine was made from (L)-leucine methyl ester as described in Method B1b. The 2-hydroxyethylamine was converted to (1S)-1-(chloromethyl)-3-methylbutanammonium chloride as described in Method B7a. 4-Bromo-2-methylphenyl isothiocyanate was reacted with (1S)-1-(chloromethyl)-3-methylbutanammonium chloride according to Method C1a to give (4S)-2-(4-bromo -2-methylphenylimino)-4-isobutyl-1,3-thiazolidine. The thiazolidine was reacted with isobutyl bromide according to Method D2a to give (4S)-2-(4-bromo-2-methylphenylimino)-3,4-diisobutyl-1,3-thiazolidine.

Entry 117

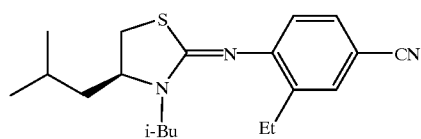

(1S)-1-(Hydroxymethyl)-3-methylbutylamine was reacted with $SOCl_2$ followed by 4-cyano-2-ethylphenyl isothiocyanate according to Method C2a to give (4S)-2-(4-cyano-2-ethylphenylimino)-4-isobutyl-1,3-thiazolidine. The thiazolidine was reacted with isobutyl bromide according to Method D2a to give (4S)-2-(4-cyano-2-ethylphenylimino)-3,4-diisobutyl-1,3-thiazolidine.

Entry 118

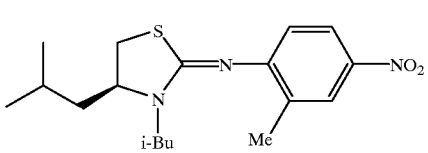

(1S)-1-(Hydroxymethyl)-3-methylbutylamine was made from (L)-leucine methyl ester as described in Method B1b. The 2-hydroxyethylamine was converted to (2S)-4-methyl-2-(isobutylamino)pentan-1-ol as described in Method B4c. The resulting 2-hydroxyethylamine was converted to N-(1S)-1-(chloromethyl)-3-methylbutyl)-N-(isobutyl) ammonium chloride according to Method B7c. 2-Methyl-4-nitrophenyl isothiocyanate was reacted with N-(1S)-1-(chloromethyl)-3-methylbutyl)-N-(isobutyl)ammonium chloride to Method C1b to afford (4S)-2-(2-methyl-4-nitrophenylimino)-3,4-diisobutyl-1,3-thiazolidine.

Entry 119

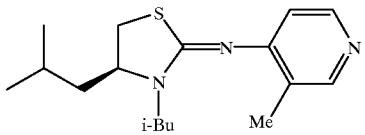

(1S)-1-(Hydroxymethyl)-3-methylbutylamine was made from (L)-leucine methyl ester as described in Method B1b. The 2-hydroxyethylamine was converted to (2S)-4-methyl- 2-(isobutylamino)pentan-1-ol as described in Method B4c. The resulting 2-hydroxyethylamine was converted to N-(1S)-1-(chloromethyl)-3-methylbutyl)-N-(isobutyl) ammonium chloride according to Method B7c. 4-Amino-3methylpyridine was converted to 3-methyl-4-pyridylisocyanate according to Method A2b. 3-Methyl-4-pyridyl isothiocyanate was reacted with N-(1S)-1-(chloromethyl)-3-methylbutyl)-N-(isobutyl)ammonium chloride to Method C1b to afford (4S)-2-(2-methyl-4-nitrophenylimino)-3,4-diisobutyl-1,3-thiazolidine.

Entry 120

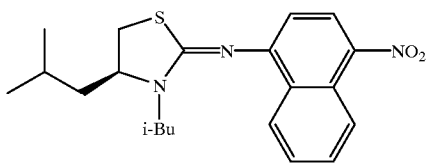

(1S)-1-(Hydroxymethyl)-3-methylbutylamine was made from (L)-leucine methyl ester as described in Method B1b. 4-Nitro-1-naphthylamine was converted to 4-nitro-1-naphthyl isothiocyanate according to Method A2b. 4-Nitro-1-naphthyl isothiocyanate was reacted with (1S)-1-(hydroxymethyl)-3-methylbutylamine to Method C2a to give (4S)-2-(4-nitro-1-naphthylimino)-4-isobutyl-1,3-thiazolidine. The thiazolidine was reacted with isobutyl bromide according to Method D2a to give (4S)-2-(4-nitro-1-naphthylimino)-3,4-diisobutyl-1,3-thiazolidine.

Entry 121

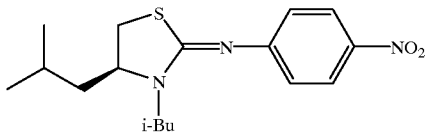

(1S)-1-(Hydroxymethyl)-3-methylbutylamine was made from (L)-leucine methyl ester as described in Method B1b. The 2-hydroxyethylamine was converted to (2S)-4-methyl-2-(isobutylamino)pentan-1-ol as described in Method B4c. The resulting 2-hydroxyethylamine was converted to N-(1S)-1-(chloromethyl)-3-methylbutyl)-N-(isobutyl) ammonium chloride according to Method B7c. 4-Nitrophenyl isothiocyanate was reacted with N-(1S)-1-(chloromethyl)-3-methylbutyl)-N-(isobutyl)ammonium chloride to Method C1f to afford (4S)-2-(4-nitrophenylimino)-3,4-diisobutyl-1,3-thiazolidine.

Entry 122

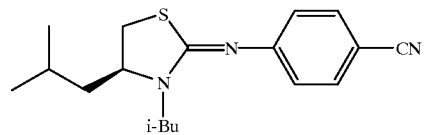

(1S)-1-(Hydroxymethyl)-3-methylbutylamine was made from (L)-leucine methyl ester as described in Method B1b. The 2-hydroxyethylamine was converted to (2S)-4-methyl-2-(isobutylamino)pentan-1-ol as described in Method B4c. The resulting 2-hydroxyethylamine was converted to N-(1S)-1-(chloromethyl)-3-methylbutyl)-N-(isobutyl) ammonium chloride according to Method B7c. 4-Cyanophenyl isothiocyanate was reacted with N-(1S)-1-(chloromethyl)-3methylbutyl)N-(isobutyl)ammonium chloride to Method C1f to afford (4S)-2-(4-cyanophenylimino)-3,4-diisobutyl-1,3-thiazolidine.

Entry 123

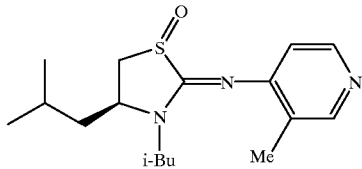

(1S)-1-(Hydroxymethyl)-3-methylbutylamine was made from (L)-leucine methyl ester as described in Method B1b. The 2-hydroxyethylamine was converted to (2S)-4-methyl-2-(isobutylamino)pentan-1-ol as described in Method B4c. The resulting 2-hydroxyethylamine was converted to N-(1S)-1-(chloromethyl)-3-methylbutyl)-N-(isobutyl) ammonium chloride according to Method B7c. 4-Amino-3-methylpyridine was converted to 3-methyl-4-pyridylisocyanate according to Method A2b. 3-Methyl-4-pyridyl isothiocyanate was reacted with N-(1S)-1-(chloromethyl)-3-methylbutyl)-N-(isobutyl)ammonium chloride to Method C1b to afford (4S)-2-(2-methyl-4-nitrophenylimino)-3,4-diisobutyl-1,3-thiazolidine. The thiazolidine was oxidized according to Method D4a to afford (4S)-2-(2-methyl-4nitrophenylimino)-3,4-diisobutyl-1,3-thiazolidine 1-oxide.

Entry 124

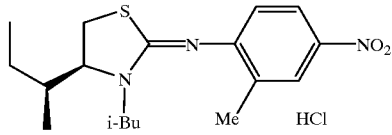

(1S,2S)-1-(Hydroxymethyl)-2-methylbutylamine was converted to (1S,2S)-1-(chloromethyl)-2-methylbutanammonium chloride as described in Method B7a. 2-Methyl-4-nitrophenyl isothiocyanate was reacted with (1S,2S)-1-(chloromethyl)-2-methylbutanammonium chloride according to Method C1a to give (4S)-2-(2-methyl-4-nitrophenylimino)-4-((2S)-2-butyl)-1,3-thiazolidine. The thiazolidine was reacted with isobutyl bromide according to Method D2a to afford (4S)-2-(2-methyl-4-nitrophenylimino)-4-((2S)-2-butyl)-3-isobutyl-1,3-thiazolidine HCl salt.

Entry 125

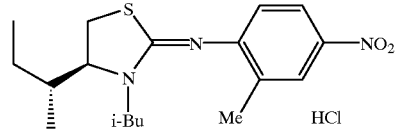

N-(tert-Butoxycarbamoyl)-(1S,2R)-1-(hydroxymethyl)-2methylbutylamine was prepared from N-(tert-butoxycarbamoyl)-(L)-allo-isoleucine as described in Method B1a, Step 2. The carbamate was converted to (1S,2R)-1-(chloromethyl)-2-methylbutanammonium chloride as described in Method B7b. 2-Methyl-4-nitrophenyl isothiocyanate was reacted with (1S,2R)-1-(chloromethyl)-2-methylbutanammonium chloride to Method C1e to give (4S)-2-(2-methyl-4-nitrophenylimino)-4-((2R)-2-butyl)-1,3-thiazolidine. The thiazolidine was reacted with isobutyl bromide according to Method D2a to afford (4S)-2-(2- methyl-4-nitrophenylimino)-4-((2R)-2-butyl)-3-isobutyl-1, 3-thiazolidine HCl salt.

Entry 126

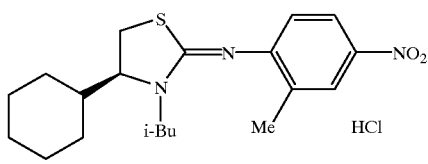

N-(tert-Butoxycarbamoyl)-(1S)-1-cyclohexyl-2-hydroxyethylbutylamine was prepared from N-(tert-Butoxycarbamoyl)-(L)-cyclohexylglycine according to Method B1a, Step 2. The carbamate was reacted with $SOCl_2$ according to Method B1b, and the resulting material was reacted with 2-methyl-4-nitrophenyl isothiocyanate according to Method C1a to give (4S)-2-(2-methyl-4-nitrophenylimino)-4-cyclohexyl-1,3-thiazolidine. The thiazolidine was reacted with isobutyl bromide according to Method D2a to afford (4S)-2-(2-methyl-4-nitrophenylimino)-4-cyclohexyl-3-isobutyl-1,3-thiazolidine HCl salt.

Entry 127

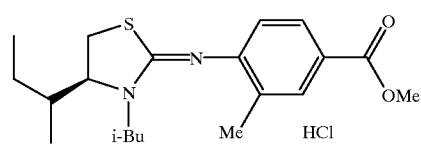

(1S)-1-(Hydroxymethyl)-2-methylbutylamine was made from (L)-isoleucine methyl ester as described in Method B1b. The 2-hydroxyethylamine was converted to (1S)-1-(chloromethyl)-2-methylbutanammonium chloride as described in Method B7a. 4-Methoxycarbonyl-2-methylphenyl isothiocyanate was reacted with (1S)-1-(chloromethyl)-2-methylbutanammonium chloride to Method C1a to give (4S)-2-(4-methoxycarbonyl-2-methylphenylimino)-4-(2-butyl)-1,3-thiazolidine. The thiazolidine was reacted with isobutyl bromide according to Method D2a to afford (4S)-2-(4-methoxycarbonyl-2-methylphenylimino)-4-(2-butyl)-3-isobutyl-1,3-thiazolidine.

Entry 128

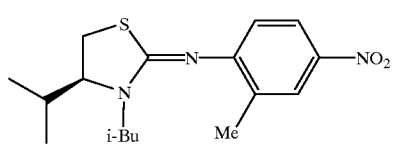

(1S)-1-Isopropyl-2-hydroxyethylamine was converted to (1S)-2-chloro-1-isopropylethylammonium chloride according to Method B7a. 2-Methyl-4-nitrophenyl isothiocyanate was reacted with (1S)-2-chloro-1-isopropylethylammonium chloride according to Method C1a to give (45)-2-(2-methyl-4-nitrophenylimino)-4-isopropyl-1,3-thiazolidine. The thiazolidine was reacted with isobutyl bromide according to Method D2a to afford (4S)-2-(2-methyl-4-nitrophenylimino)-4-isopropyl-3-isobutyl-1,3-thiazolidine HCl salt.

Entry 129

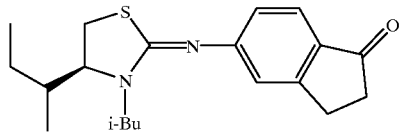

(1S)-1-(Hydroxymethyl)-2-methylbutylamine was made from (L)-isoleucine methyl ester as described in Method B1b. The 2-hydroxyethylamine was converted to (1S)-1-(chloromethyl)-2-methylbutanammonium chloride as described in Method B7a. 5-Aminoindan-1-one was converted to 1-oxo-5-indanyl isothiocyanate according to Method A2a. The isothiocyanate was reacted with (1S)-1-(chloromethyl)-2-methylbutanammonium chloride to Method C1a to give (4S)-2-(1-oxo-5-indanylimino)-4-(2-butyl)-1,3-thiazolidine. The thiazolidine was reacted with isobutyl bromide according to Method D2a to afford (4S)-2-(1-oxo-5-indanylimino)-4-(2-butyl)-3-isobutyl-1,3-thiazolidine.

Entry 130

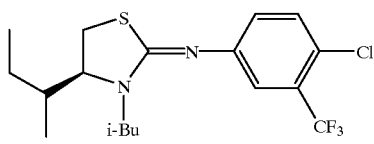

(1S)-1-(Hydroxymethyl)-2-methylbutylamine was made from (L)-isoleucine methyl ester as described in Method B1b. The 2-hydroxyethylamine was converted to (1S)-1-(chloromethyl)-2-methylbutanammonium chloride as described in Method B7a. 4-Chloro-3-(trifluoromethyl) aniline was converted to 4-chloro-3-(trifluoromethyl)phenyl isothiocyanate according to Method A2a, Step 3 4-Chloro-3-(trifluoromethyl)phenyl isothiocyanate was reacted with (1S)-1-(chloromethyl)-2-methylbutanammonium chloride according to Method C1a to give (4S)-2-(4-chloro-3-(trifluoromethyl)phenylimino)-4-(2-butyl)-1,3-thiazolidine. The thiazolidine was reacted with isobutyl bromide according to Method D2a to afford (4S)-2-(4-chloro-3-(trifluoromethyl)phenylimino)-4-(2-butyl)-3-isobutyl-1,3-thiazolidine.

Entry 131

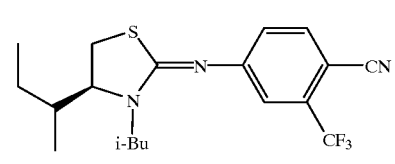

(1S)-1-(Hydroxymethyl)-2-methylbutylamine was made from (L)-isoleucine methyl ester as described in Method B1b. The 2-hydroxyethylamine was converted to (1S)-1-(chloromethyl)-2-methylbutanammonium chloride as described in Method B7a. 4-Cyano-3-(trifluoromethyl) aniline was converted to 4-cyano-3-(trifluoromethyl)phenyl isothiocyanate according to A2a, Step 3. The isothiocyanate was reacted with (1S)-1-(chloromethyl)-2-methylbutanammonium chloride according to Method C1a to give (4S)-2-(4-cyano-3-(trifluoromethyl)phenylimino)-4-(2-butyl)-1,3-thiazolidine. The thiazolidine was reacted with isobutyl bromide according to Method D2a to afford (4S)-2-(4-cyano-3-(trifluoromethyl)phenylimino)-4-(2-butyl)-3-isobutyl-1,3-thiazolidine.

Entry 132

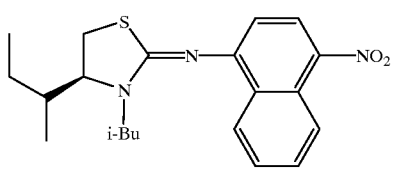

(1S)-1-(Hydroxymethyl)-2-methylbutylamine was made from (L)-isoleucine methyl ester as described in Method B1b. The 2-hydroxyethylamine was converted to (1S)-1-(chloromethyl)-2-methylbutanammonium chloride as described in Method B7a. 4-Nitro-1-naphthylamine was converted to 4-nitro-1-naphthyl isothiocyanate according to Method A2b. 4-Nitro-1-naphthyl isothiocyanate was reacted with (1S)-1-(chloromethyl)-2-methylbutanammonium chloride to Method C1a to give (4S)-2-(4-nitro-1-naphthylimino)-4-(2-butyl)-1,3-thiazolidine. The thiazolidine was reacted with isobutyl bromide according to Method D2a to give (4S)-2-(4-nitro-1-naphthylimino)-4-butyl-3-isobutyl-1,3-thiazolidine.

Entry 133

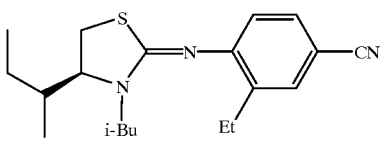

(1S)-1-(Hydroxymethyl)-2-methylbutylamine was made from (L)-isoleucine methyl ester as described in Method B1b. The 2-hydroxyethylamine was converted to (1S)-1-(chloromethyl)-2-methylbutanammonium chloride as described in Method B7a. 4-Cyano-2-ethylphenyl isothiocyanate was reacted with (1S)-1-(chloromethyl)-2-methylbutanammonium chloride to Method C1a to give (4S)-2-(4-cyano-2-ethylphenylimino)-4-(2-butyl)-1,3-thiazolidine. The thiazolidine was reacted with isobutyl bromide according to Method D2a to give (4S)-2-(4-cyano-2-ethylphenylimino)-4-butyl-3-isobutyl-1,3-thiazolidine.

Entry 124

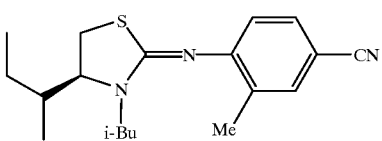

(1S)-1-(Hydroxymethyl)-2-methylbutylamine was made from (L)-isoleucine methyl ester as described in Method B1b. The 2-hydroxyethylamine was converted to (1S)-1-(chloromethyl)-2-methylbutanammonium chloride as described in Method B7a. 4-Cyano-2-methylaniline was synthesized as described in Method A1a. The aniline was converted to 4-cyano-2-methylphenyl isothiocyanate as described in Method A2a, Step 3. 4-Cyano-2-methylphenyl isothiocyanate was reacted with (1S)-1-(chloromethyl)-2-methylbutanammonium chloride to Method C1a to give (4S)-2-(4 -cyano-2-methylphenylimino)-4-(2-butyl)-1,3-thiazolidine. The thiazolidine was reacted with isobutyl bromide according to Method D2a to give (4S)-2-(4-cyano-2-methylphenylimino)-4-butyl-3-isobutyl-1,3-thiazolidine.

Entry 135

(1S)-1-(Hydroxymethyl)-2-methylbutylamine was made from (L)-isoleucine methyl ester as described in Method B1b. The 2-hydroxyethylamine was converted to (1S)-1-(chloromethyl)-2-methylbutanammonium chloride as described in Method B7a. 2,5-Dimethyl-4-nitrobenzonitrile was converted to 4-cyano-2,5-methylaniline according to Method A1a. The aniline was converted to 4-cyano-2,5-dimethylphenyl isothiocyanate as described in Method A2a, Step 3. 4-Cyano-2,5-dimethylphenyl isothiocyanate was reacted with (1S)-1-(chloromethyl)-2-methylbutanammonium chloride to Method C1a to give (4S)-2-(4-cyano-2,5-dimethylphenylimino)-4-(2-butyl)-1,3-thiazolidine. The thiazolidine was reacted with isobutyl bromide according to Method D2a to give (4S)-2-(4-cyano-2,5-dimethylphenylimino)-4-butyl-3-isobutyl-1,3-thiazolidine.

Entry 136

(1S)-1-(Hydroxymethyl)-2-methylbutylamine was made from (L)-isoleucine methyl ester as described in Method B1b. The 2-hydroxyethylamine was converted to (1S)-1-(chloromethyl)-2-methylbutanammonium chloride an described in Method B7a. 2,5-methylaniline was converted to 2,5-dimethyl-4-nitrophenyl isothiocyanate according to Method A2a. 2,5-Dimethyl-4-nitrophenyl isothiocyanate was reacted with (1S)-1-(chloromethyl)-2-methylbutanammonium chloride to Method C1a to give (4S)-2-(2,5-dimethyl-4-nitrophenylimino)-4-(2-butyl)-1,3-thiazolidine. The thiazolidine was reacted with isobutyl bromide according to Method D2a to give (4S)-2-(2,5dimethyl-4-nitrophenylimino)-4-butyl-3-isobutyl-1,3-thiazolidine.

Entry 137

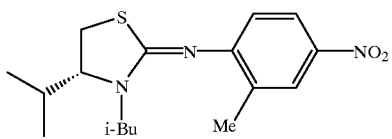

(1R)-1-Isopropyl-2-hydroxyethylamine was reacted with SOCl₂ followed by 2-Methyl-4-nitrophenyl isothiocyanate according to Method C2a to give (4R)-2-(2-methyl-4-nitrophenylimino)-4-isopropyl-1,3-thiazolidine. The thiazolidine was reacted with isobutyl bromide according to Method D2a to afford (4R)-2-(2-methyl -4-nitrophenylimino)-4-isopropyl-3-isobutyl-1,3-thiazolidine.

Entry 138

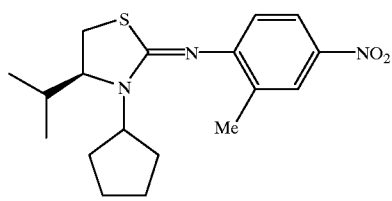

(1S)-1-Isopropyl-2-hydroxyethylamine was reacted with SOCl$_2$ followed by 2-methyl-4-nitrophenyl isothiocyanate according to Method C2a to give (4S)-2-(2-methyl-4-nitrophenylimino)-4-isopropyl-1,3-thiazolidine. The thiazolidine was reacted with cyclopentyl bromide according to Method D2a to afford (4S)-2-(2-methyl-4-nitrophenylimino)-4-isopropyl-3-cyclopentyl-1,3-thiazolidine.

Entry 139

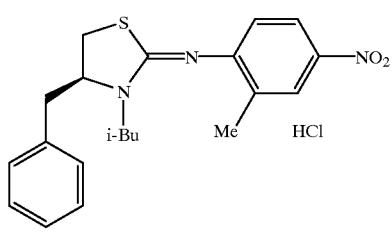

(1S)-1-Benzyl-2-hydroxyethylamine was converted to (1S)-2-chloro-1-benzylethylammonium chloride according to Method B7b. 2-Methyl-4-nitrophenyl isothiocyanate was reacted with (1S)-2-chloro-1-benzylethylammonium chloride according to Method C1a to give (4S)-2-(2-methyl-4-nitrophenylimino)-4-benzyl -1,3-thiazolidine. The thiazolidine was reacted with isobutyl bromide according to Method D2a to afford (4S)-2-(2-methyl-4-nitrophenylimino)-4-benzyl-3-isobutyl-1,3-thiazolidine HCl salt.

Entry 140

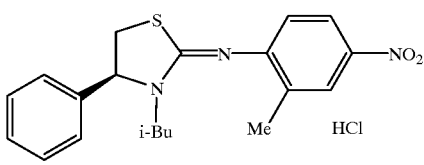

(1S)-1-Phenyl-2-hydroxyethylamine was converted to (1S)-2-chloro-1-phenylethylammonium chloride according to Method B7b. 2-Methyl-4-nitrophenyl isothiocyanate was reacted with (1S)-2-chloro-1-benzylethylammonium chloride according to Method C1a to give (4S)-2-(2-methyl-4-nitrophenylimino)-4-phenyl-1,3-thiazolidine. The thiazolidine was reacted with isobutyl bromide according to Method D2a to afford (4S)-2-(2-methyl-4-nitrophenylimino)-4-phenyl-3-isobutyl-1,3-thiazolidine HCl salt.

Entry 141

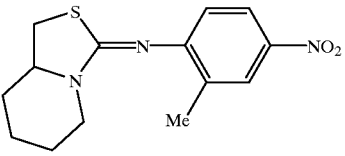

2-Piperidenemethanol was made from methyl pipecolinate as described in Method B1b. The 2-hydroxyethylamine was converted to 2-chloromethylpiperidinium chloride according to Method B7a. 2-Methyl4-nitrophenyl isothiocyanate was reacted with 2-chloromethylpiperidinium chloride according according to Method C1a to give 9-(2-methyl-4-nitrophenylimino)-1-aza-8-thiabicyclo[4.3.0]nonane.

Entry 142

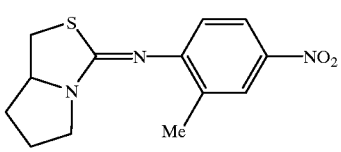

2-Pyrrolidinemethanol was made from proline methyl ester as described in Method B1b. The 2-hydroxyethylamine was converted to 2-chloromethylpyrrolidinium chloride according to Method B7a. 2-Methyl4-nitrophenyl isothiocyanate was reacted with 2-chloromethylpyrrolidinium chloride according according to Method C1a to give 3-(2-methyl-4-nitrophenylimino)-2,5,6,7,7a-pentahydro-2-thiapyrrolizine.

Entry 143

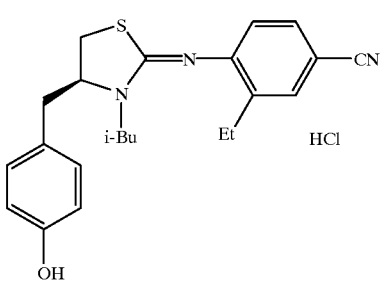

(1S)-1-(4-Hydroxyphenylmethyl)-2-hydroxyethylamine was made from (L)-tyrosine methyl ester as described in Method B1b. The 2-hydroxyethylamine was converted to (4S)-2-isopropyl-4-(4-hydroxyphenylmethyl)-1,3-oxazolidine according to Method B4c, Step 1. The oxazolidine was reduced to N-((1S)-1-(4-hydroxyphenylmethyl)-2-hydroxyethyl)-N-isobutylamine according to Method B4c, Step 2. The resulting 2-hydroxyethylamine was treated with SOCl$_2$ according to Method B7c to give N-((1S)-1-(4-hydroxyphenylmethyl)-2-chloroethyl)-N-isobutylammonium chloride. 2-Ethyl-4-cyanophenyl isothiocyanate was reacted with N-((1S)-1-(4-hydroxyphenylmethyl)-2-chloroethyl)-N-isobutylammonium chloride according to Method C1b to give (4S)-2-(2-ethyl-4-cyanophenylimino)-4-(4-hydroxyphenylmethyl)-3-isobutyl-1,3-thiazolidine HCl salt.

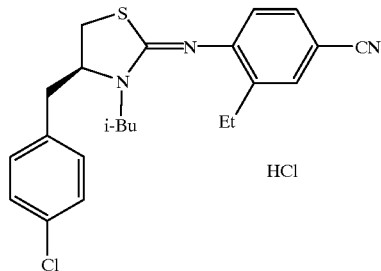

Entry 144

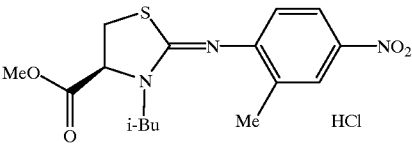

Entry 146

(R)-N-isobutylserine methyl ester HCl salt was made from (D)-serine methyl ester as described in Method B3a. The ester was reacted with SOCl$_2$, followed by 2-methyl-4-nitrophenyl isothiocyanate according to Method C2a to afford (4S)-2-(2-methyl-4-nitrophenylimino)-4-(methoxycarbonyl)-3-isobutyl-1,3-thiazolidine HCl salt.

(1S)-1-(4-Chlorophenylmethyl)-2-hydroxyethylamine was made from (L)-4-chlorophenylalanine methyl ester as described in Method B1b. The 2-hydroxyethylamine was converted to (4S)-2-isopropyl-4-(4-chlorophenylmethyl)-1,3-oxazolidine according to Method B4c, Step 1. The oxazolidine was reduced to N-((1S)-1-(4-chlorophenylmethyl)-2-hydroxyethyl)-N-isobutylamine according to Method B4c, Step 2. The resulting 2-Hydroxyethylamine was treated with SOCl$_2$ according to Method B7c to give N-((1S)-1-(4-chlorophenylmethyl)-2-chloroethyl)-N-isobutylammonium chloride. 2-Ethyl-4-cyanophenyl isothiocyanate was reacted with N-((1S)-1-(4-chlorophenylmethyl)-2-chloroethyl)-N isobutylammonium chloride according to Method C1b to give (4S)-2-(2-ethyl-4-cyanophenylimino)-4-(4-chlorophenylmethyl)-3-isobutyl-1,3-thiazolidine HCl salt.

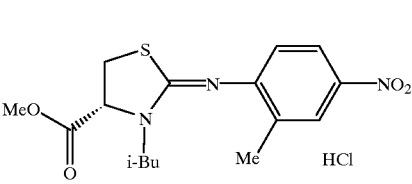

Entry 147

(S)-N-isobutylserine methyl ester HCl salt was made from (L)-serine methyl ester as described in Method B3a. The ester was reacted with SOCl$_2$, followed by 2-methyl-4-nitrophenyl isothiocyanate according to Method C2a to afford (4R)-2-(2-methyl-4-nitrophenylimino)-4-(methoxycarbonyl)-3-isobutyl-1,3-thiazolidine HCl salt.

Entry 145

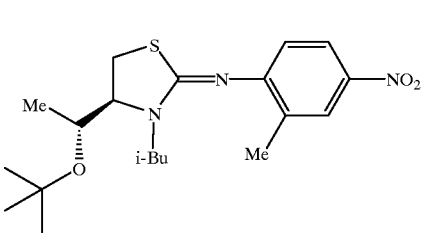

Entry 148

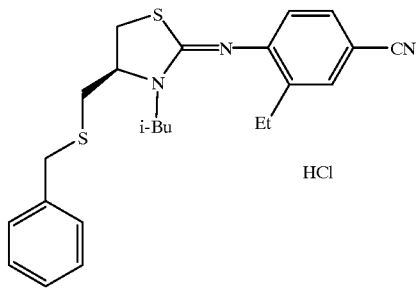

(1R,2R)-1-Methanesulfonyloxymethyl)-2-(tert-butoxy) propanammonium chloride was made from (L)-(1S,2R)-N-(benzyloxycarbonyl)-O-tert-butylthreonine dicyclohexylamine salt as described in Method B8a. (1R,2R)-1-Methanesulfonyloxymethyl)-2-(tert-butoxy) propanammonium chloride was reacted with 2-methyl-4-nitrophenyl isothiocyanate followed by isobutyl bromide according to Method C5b to afford (4R)-2-(2-methyl-4-nitrophenylimino)-4-((1R)-1-tert-butoxyethyl)-3-isobutyl-1,3-thiazolidine.

(1S)-1-(Benzylthiomethyl)-2-hydroxyethylamine was made from (L)-S-benzylcysteine methyl ester as described in Method B1b. The 2-hydroxyethylamine was converted to (4S)-2-isopropyl-4-(benzylthiomethyl)-1,3-oxazolidine according to Method B4c, Step 1. The oxazolidine was reduced to N-((1S)-1-(benzylthiomethyl)-2-hydroxyethyl)-N-isobutylamine according to Method B4c, Step 2. The resulting 2-hydroxyethylamine was treated with SOCl$_2$ according to Method B7c to give N-((1S)-1-(benzylthiomethyl)-2-chloroethyl)-N-isobutylammonium chloride. 2-Ethyl-4-cyanophenyl isothiocyanate was reacted with N-((1S)-1-(benzylthiomethyl)-2-chloroethyl)-N-isobutylammonium chloride according to Method C1b to give (4S)-2-(2-ethyl-4-cyanophenylimino)-4-(benzylthiomethyl)-3-isobutyl-1,3-thiazolidine HCl salt.

Entry 149

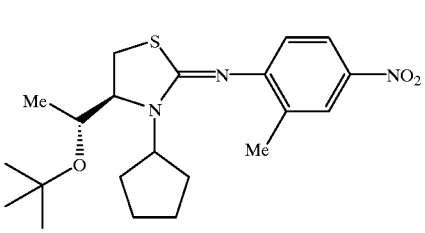

(1R,2R)-1-Methanesulfonyloxymethyl)-2-(tert-butoxy) propanammonium chloride was made from (L)-(1S,2R)-N-(benzyloxycarbonyl)-O-tert-butylthreonine dicyclohexylamine salt as described in Method B8a. (1R,2R)-1-Methanesulfonyloxymethyl)-2-(tert-butoxy) propanammonium chloride was reacted with 2-methyl-4-nitrophenyl isothiocyanate followed by cyclopentyl bromide according to Method C5b to afford (4R)-2-(2-methyl-4-nitrophenylimino)-4-((1R)-1-tert-butoxyethyl)-3-cyclopentyl 1,3-thiazolidine.

Entry 150

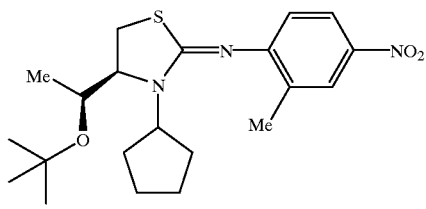

(1R,2S)-1-Methanesulfonyloxymethyl)-2-(tert-butoxy) propanammonium chloride was made from (L)-(1S,2S)-N-(benzyloxycarbonyl)-O-tert-butylthreonine dicyclohexylamine salt as described in Method B8a. (1R,2S)-1-Methanesulfonyloxymethyl)-2-(tert-butoxy) propanammonium chloride was reacted with 2-methyl-4-nitrophenyl isothiocyanate followed by cyclopentyl bromide according to Method C5b to afford (4R)-2-(2-methyl-4-nitrophenylimino)-4-((1S)-1-tert-butoxyethyl)-3-cyclopentyl-1,3-thiazolidine.

Entry 151

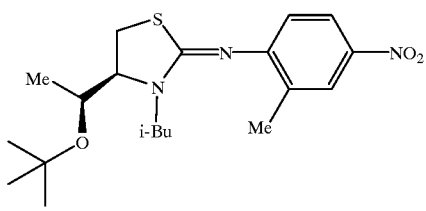

(1R,2S)-1-Methanesulfonyloxymethyl)-2-(tert-butoxy) propanammonium chloride was made from (L)-(1S,2S)-N-(benzyloxycarbonyl)-O-tert-butylthreonine dicyclohexylamine salt as described in Method B8a. (1R,2S)-1-Methanesulfonyloxymethyl)-2-(tert-butoxy) propanammonium chloride was reacted with 2-methyl-4-nitrophenyl isothiocyanate followed by isobutyl bromide according to Method C5b to afford (4R)-2-(2-methyl-4-nitrophenylimino)-4-((1S)-1-tert -butoxyethyl)-3-isobutyl-1,3-thiazolidine.

Entry 152

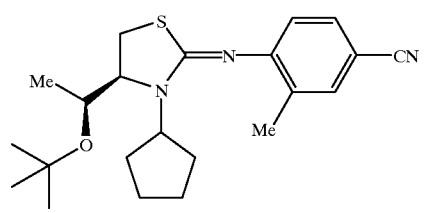

(1R,2S)-1-Methanesulfonyloxymethyl)-2-(tert-butoxy) propanammonium chloride was made from (L)-(1S,2S)-N-(benzyloxycarbonyl)-tert-butylthreonine dicyclohexylamine salt as described in Method B8a. (1R,2S)-1-Methanesulfonyloxymethyl)-2-(tert-butoxy) propanammonium chloride was reacted with 4-cyano-2-methylphenyl isothiocyanate followed by cyclopentyl bromide according to Method C5b to afford (4R)-2-(4-cyano-2-methylphenylimino)-4-((1S)-1-tert-butoxyethyl)-3-cyclopentyl-1,3-thiazolidine.

Entry 153

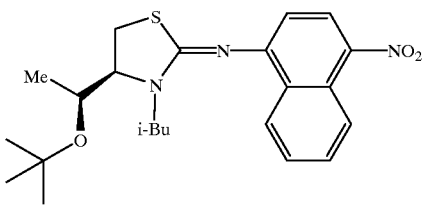

(1R,2S)-1-Methanesulfonyloxymethyl)-2-(tert-butoxy) propanammonium chloride was made from (L)-(1S,2S)-N-(benzyloxycarbonyl)-O-tert-butylthreonine dicyclohexylamine salt as described in Method B8a. 4-Nitro-1-naphthylamine was converted to 4-nitro-1-naphthyl isothiocyanate according to Method A2b. (1R,2S)-1-Methanesulfonyloxymethyl)-2-(tert-butoxy) propanammonium chloride was reacted with 4-nitronaphthyl isothiocyanate followed by isobutyl bromide according to Method C5b to afford (4R)-2-(4-nitro-1-naphthylimino)-4-((1S)-1-tert-butoxyethyl)-3-isobutyl-1,3-thiazolidine.

Entry 154

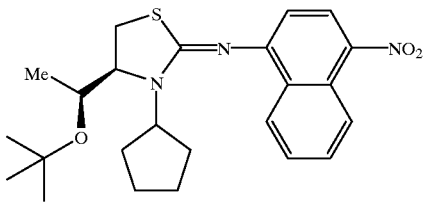

(1R,2S)-1-Methanesulfonyloxymethyl)-2-(tert-butoxy) propanammonium chloride was made from (L)-(1S,2S)-N-(benzyloxycarbonyl)-O-tert-butylthreonine dicyclohexylamine salt as described in Method B8a. 4-Nitro-1-naphthylamine was converted to 4-nitro-1-naphthyl isothiocyanate according to Method A2b. (1R,2S)-1-Methanesulfonyloxymethyl)-2-(tert-butoxy) propanammonium chloride was reacted with 4-nitronaphthyl isothiocyanate followed by cyclopentyl bromide according to Method C5b to afford (4R)-2-(4-nitro-1-naphthylimino)-4-((1S)-1-tert-butoxyethyl)-3-cyclopentyl-1,3-thiazolidine.

Entry 155

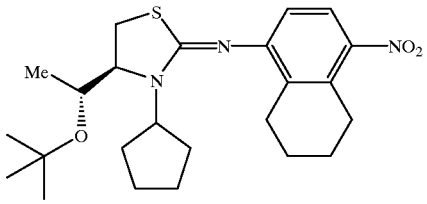

(1R,2R)-1-Methanesulfonyloxymethyl)-2-(tert-butoxy) propanammonium chloride was made from (L)-(1S,2R)-N-(benzyloxycarbonyl)-O-tert-butylthreonine dicyclohexylamine salt as described in Method B8a. 1-Amino-5,6,7,8-tetrahydronaphthalene was converted to 4-nitro-5,6,7,8- tetrahydronaphth-1-yl isothiocyanate according to Method A2a. (1R,2R)-1-Methanesulfonyloxymethyl)-2-(tert-butoxy)propanammonium chloride was reacted with 4-nitro-5,6,7,8-tetrahydronaphth-1-yl isothiocyanate followed by cyclopentyl bromide according to Method C5b to afford (4R)-2-(4-nitro-5,6,7,8-tetrahydronaphth-1-ylimino)-4-((1R)-1-tert-butoxyethyl)-3-cyclopentyl-1,3-thiazolidine.

Entry 156

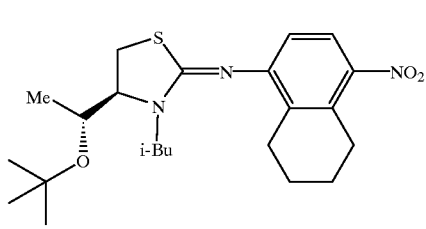

(1R,2R)-1-Methanesulfonyloxymethyl)-2-(tert-butoxy)propanammonium chloride was made from (L)-(1S,2R)-N-(benzyloxycarbonyl)-O-tert-butylthreonine dicyclohexylamine salt as described in Method B8a. 1-Amino-5,6,7,8-tetrahydronaphthalene was converted to <sup>4</sup>-nitro-5,6,7,8-tetrahydronaphth-1-yl isothiocyanate according to Method A2a. (1R,2R)-1-Methanesulfonyloxymethyl)-2-(tert-butoxy)propanammonium chloride was reacted with 4-nitro-5,6,7,8-tetrahydronaphth-1-yl isothiocyanate followed by isobutyl bromide according to Method C5b to afford (4R)-2-(4-nitro-5,6,7,8-tetrahydronaphth-1-ylimino)-4-((1R)-1-tert-butoxyethyl)-3-isobutyl-1,3-thiazolidine.

Entry 157

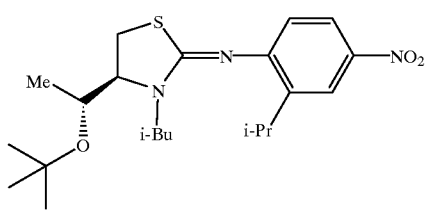

(1R,2R)-1-Methanesulfonyloxymethyl)-2-(tert-butoxy)propanammonium chloride was made from (L)-(1S,2R)-N-(benzyloxycarbonyl)-tert-butylthreonine dicyclohexylamine salt as described in Method B8a. 2-Isopropylaniline was converted to 2-isopropyl-4-nitrophenyl isothiocyanate according to Method A2a. (1R,2R)-1-Methanesulfonyloxymethyl)-2-(tert-butoxy)propanammonium chloride was reacted with 2-isopropyl-4-nitrophenyl isothiocyanate followed by isobutyl bromide according to Method C5b to afford (4R)-2-(2-isopropyl-4-nitrophenylimino)-4-((1R)-1-tert-butoxyethyl)-3-isobutyl-1,3-thiazolidine.

Entry 158

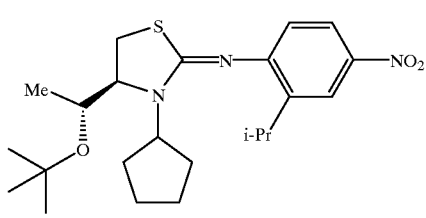

(1R,2R)-1-Methanesulfonyloxymethyl)-2-(tert-butoxy)propanammonium chloride was made from (L)-(1S,2R)-N-(benzyloxycarbonyl)-O-tert-butylthreonine dicyclohexylamine salt as described in Method B8a. 2-Isopropylaniline was converted to 2-isopropyl-4-nitrophenyl isothiocyanate according to Method A2a. (1R,2R)-1-Methanesulfonyloxymethyl)-2-(tert-butoxy)propanammonium chloride was reacted with 2-isopropyl-4-nitrophenyl isothiocyanate followed by cyclopentyl bromide according to Method C5b to afford (4R)-2-(2-isopropyl-4-nitrophenylimino)-4-((1R)-1-tert-butoxyethyl)-3-cyclopentyl-1,3-thiazolidine.

Entry 159

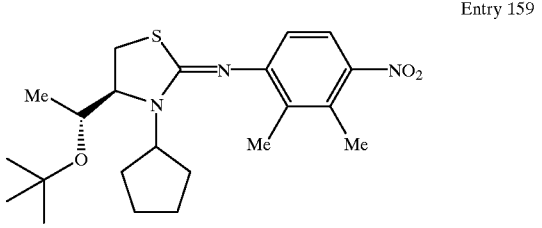

(1R,2R)-1-Methanesulfonyloxymethyl)-2-(tert-butoxy)propanammonium chloride was made from (L)-(1S,2R)-N-(benzyloxycarbonyl)-O-tert-butylthreonine dicyclohexylamine salt as described in Method B8a. 2,3-Dimethyl-4-nitroaniline was converted to 2,3-dimethyl-4-nitrophenyl isothiocyanate according to Method A2b. (1R,2R)-1-Methanesulfonyloxymethyl)-2-(tert-butoxy)propanammonium chloride was reacted with 2,3-dimethyl-4-nitrophenyl isothiocyanate followed by cyclopentyl bromide according to Method C5b to afford (4R)-2-(2,3-dimethyl-4-nitrophenylimino)-4-((1R)-1-tert-butoxyethyl)-3-cyclopentyl-1,3-thiazolidine.

Entry 160

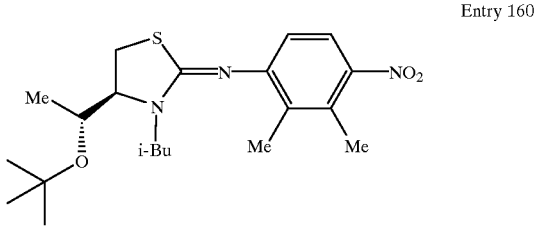

(1R,2R)-1-Methanesulfonyloxymethyl)-2-(tert-butoxy)propanammonium chloride was made from (L)-(1S,2R)-N-(benzyloxycarbonyl)-O-tert-butylthreonine dicyclohexylamine salt as described in Method B8a. 2,3-Dimethyl-4-nitroaniline was converted to 2,3-dimethyl-4-nitrophenyl isothiocyanate according to Method A2b. (1R,2R)-1-Methanesulfonyloxymethyl)-2-(tert-butoxy)propanammonium chloride was reacted with 2,3-dimethyl-4-nitrophenyl isothiocyanate followed by isobutyl bromide according to Method C5b to afford (4R)-2-(2,3-dimethyl-4-nitrophenylimino)-4-((1R)-1-tert-butoxyethyl)-3-isobutyl-1,3-thiazolidine.

Entry 161

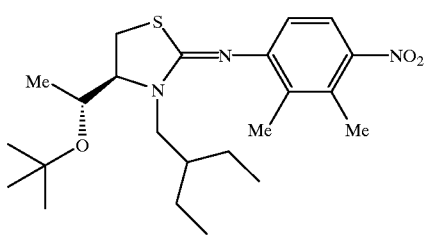

(1R,2R)-1-Methanesulfonyloxymethyl)-2-(tert-butoxy) propanammonium chloride was made from (L)-(1S,2R)-N-(benzyloxycarbonyl)-O-tert-butylthreonine dicyclohexylamine salt as described in Method B8a. 2,3-Dimethyl-4-nitroaniline was converted to 2,3-dimethyl-4-nitrophenyl isothiocyanate according to Method A2b. (1R,2R)-1-Methanesulfonyloxymethyl)-2-(tert-butoxy) propanammonium chloride was reacted with 2,3-dimethyl-4-nitrophenyl isothiocyanate followed by 2-ethyl-1-butyl bromide according to Method C5b to afford (4R)-2-(2,3-dimethyl-4-nitrophenylimino)-4-((1R)-1-tert-butoxyethyl)-3-(2-ethyl-1-butyl)-1,3-thiazolidine.

Entry 162

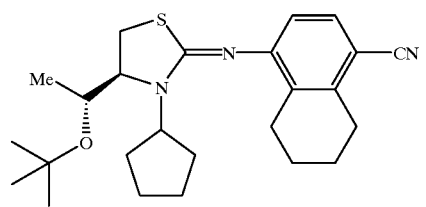

(1R,2R)-1-Methanesulfonyloxymethyl)-2-(tert-butoxy) propanammonium chloride was made from (L)-(1S,2R)-N-(benzyloxycarbonyl)-O-tert-butylthreonine dicyclohexylamine salt as described in Method B8a. 1-amino-4-cyano-5,6,7,8-tetrahydronaphthalene was converted to 4-cyano-5,6,7,8-tetrahydronaphthyl isothiocyanate according to Method A2b. (1R,2R)-1-Methanesulfonyloxymethyl)-2-(tert-butoxy)propanammonium chloride was reacted with 4-cyano-5,6,7,8-tetrahydronaphthyl isothiocyanate followed by cyclopentyl bromide according to Method C5b to afford (4R)-2-(4-cyano-5,6,7,8-tetrahydronaphthylimino)-4-((1R)-1-tert-butoxyethyl)-3-cyclopentyl-1,3-thiazolidine.

Entry 163

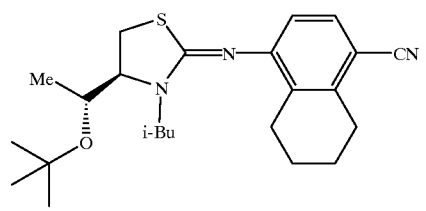

(1R,2R)-1-Methanesulfonyloxymethyl)-2-(tert-butoxy) propanammonium chloride was made from (L)-(1S,2R)-N-(benzyloxycarbonyl)-O-tert-butylthreonine dicyclohexylamine salt as described in Method B8a. 1-amino-4-cyano-5,6,7,8-tetrahydronaphthalene was converted to 4-cyano-5,6,7,8-tetrahydronaphthyl isothiocyanate according to Method A2b. (1R,2R)-1-Methanesulfonyloxymethyl)-2-(tert-butoxy)propanammonium chloride was reacted with 4-cyano-5,6,7,8-tetrahydronaphthyl isothiocyanate followed by isobutyl bromide according to Method C5b to afford (4R)-2-(4-cyano-5,6,7,8-tetrahydronaphthylimino)-4-((1R)-1-tert-butoxyethyl)-3-isobutyl-1,3-thiazolidine.

Entry 164

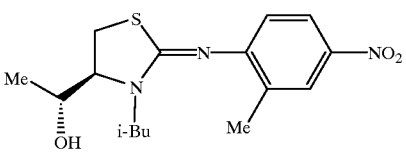

(1R,2R)-1-Methanesulfonyloxymethyl)-2-(tert-butoxy) propanammonium chloride was made from (L)-(1S,2R)-N-(benzyloxycarbonyl)-O-tert-butylthreonine dicyclohexylamine salt as described in Method B8a. (1R,2R)-1-Methanesulfonyloxymethyl)-2-(tert-butoxy) propanammonium chloride was reacted with 2-methyl-4-nitrophenyl isothiocyanate followed by isobutyl bromide according to Method C5b to give (4R)-2-(2-methyl-4-nitrophenylimino)-4-((1R)-1-tert-butoxy)-3-isobutyl-1,3-thiazolidine. The tert-butyl ether was deprotected according to Method D3a to afford (4R)-2-(2-methyl-4-nitrophenylimino)-4-((1R)-1-hydroxyethyl)-3-isobutyl-1,3-thiazolidine.

Entry 165

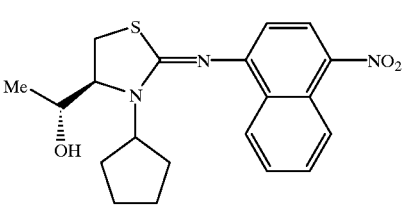

(1R,2S)-1-Methanesulfonyloxymethyl)-2-(tert-butoxy) propanammonium chloride was made from (L)-(1S,2S)-N-(benzyloxycarbonyl)-O-tert-butylthreonine dicyclohexylamine salt as described in Method B8a. 4-Nitro-1-naphthylamine was converted to 4-nitro-1-naphthyl isothiocyanate according to Method A2b. (1R,2S)-1-Methanesulfonyloxymethyl)-2-(tert-butoxy) propanammonium chloride was reacted with 4-nitronaphthyl isothiocyanate followed by cyclopentyl bromide according to Method C5b to afford (4R)-2-(4-nitro-1-naphthylimino)-4-((1S)-1-tert-butoxyethyl)-3-cyclopentyl-1,3-thiazolidine. The tert-butyl ether was deprotected according to Method D3a to afford (4R)-2-(4-nitro-1-naphthylimino)-4-((1S)1-hydroxyethyl)-3-cyclopentyl-1,3-thiazolidine.

Entry 166

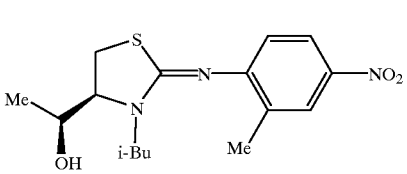

(1R,2S)-1-Methanesulfonyloxymethyl)-2-(tert-butoxy) propanammonium chloride was made from (L)-(1S,2S)-N-(benzyloxycarbonyl)-O-tert-butylthreonine dicyclohexylamine salt as described in Method B8a. (1R,2S)-1-Methanesulfonyloxymethyl)-2-(tert-butoxy) propanammonium chloride was reacted with 2-methyl-4- nitrophenyl isothiocyanate followed by cyclopentyl bromide according to Method C5b to afford (4R)-2-(2-methyl-4-nitrophenylimino)-4-((1S)-1-tert-butoxyethyl)-3-cyclopentyl-1,3-thiazolidine. The tert-butyl ether was deprotected according to Method D3a to afford (4R)-2-(2-methyl-4-nitrophenylimino)-4-((1S)-1-hydroxyethyl)-3-cyclopentyl-1,3-thiazolidine.

Entry 167

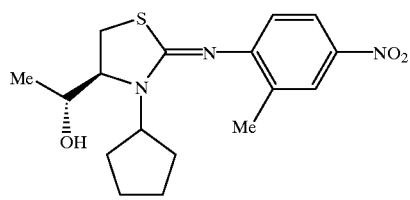

(1R,2R)-1-Methanesulfonyloxymethyl)-2-(tert-butoxy) propanammonium chloride was made from (L)-(1S,2R)-N-(benzyloxycarbonyl)-O-tert-butylthreonine dicyclohexylamine salt as described in Method B8a. (1R,2R)-1-Methanesulfonyloxymethyl)-2-(tert-butoxy) propanammonium chloride was reacted with 2-methyl-4-nitrophenyl isothiocyanate followed by cyclopentyl bromide according to Method C5b to afford (4R)-2-(2-methyl-4-nitrophenylimino)-4-((1R)-1-tert-butoxyethyl)-3-cyclopentyl-1,3-thiazolidine. The tert-butyl ether was deprotected according to Method D3a to afford (4R)-2-(2-methyl-4-nitrophenylimino)-4-((1R)-1-hydroxyethyl)-3-cyclopentyl-1,3-thiazolidine.

Entry 168

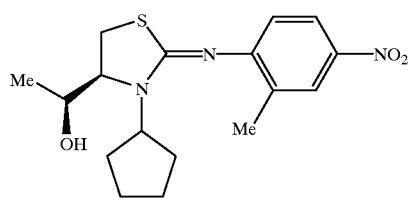

(1R,2S)-1-Methanesulfonyloxymethyl)-2-(tert-butoxy) propanammonium chloride was made from (L)-(1S,2S)-N-(benzyloxycarbonyl)-O-tert-butylthreonine dicyclohexylamine salt as described in Method B8a. (1R,2S)-1-Methanesulfonyloxymethyl)-2-(tert-butoxy) propanammonium chloride was reacted with 2-methyl-4-nitrophenyl isothiocyanate followed by cyclopentyl bromide according to Method C5 b to afford (4R)-2-(2-methyl-4-nitrophenylimino)-4-((1S)-1-tert-butoxyethyl)-3-cyclopentyl-1,3-thiazolidine. The tert-butyl ether was deprotected according to Method D3a to afford (4R)-2-(2-methyl-4-nitrophenylimino)-4-((1S)-1-hydroxyethyl)-3-cyclopentyl-1,3-thiazolidine.

Entry 169

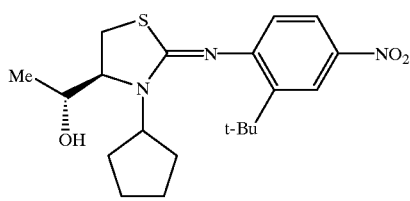

(1R,2R)-1-Methanesulfonyloxymethyl)-2-(tert-butoxy) propanammonium chloride was made from (L)-(1S,2R)-N-(benzyloxycarbonyl)-O-tert-butylthreonine dicyclohexylamine salt as described in Method B8a. 2-tert-Butyl-4-cyanoaniline was converted to 2-tert-butyl-4-cyanophenyl isothiocyanate according to Method A2b. (1R,2R)-1-Methanesulfonyloxymethyl)-2-(tert-butoxy) propanammonium chloride was reacted with 2-tert-butyl-4-cyanophenyl isothiocyanate followed by cyclopentyl bromide according to Method C5b to afford (4R)-2-(2-tert-butyl-4-cyanophenylimino)-4-((1R)-1-tert-butoxyethyl)-3-cyclopentyl-1,3-thiazolidine. The tert-butyl ether was deprotected according to Method D3a to afford (4R)-2-(2-tert-butyl-4-cyanophenylimino)-4-((1R)-1-hydroxyethyl)-3-cyclopentyl-1,3-thiazolidine.

Entry 170

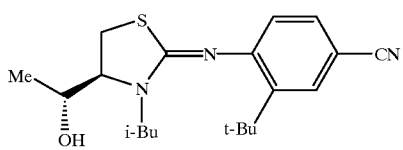

(1R,2R)-1-Methanesulfonyloxymethyl)-2-(tert-butoxy) propanammonium chloride was made from (L)-(1S,2R)-N-(benzyloxycarbonyl)-O-tert-butylthreonine dicyclohexylamine salt as described in Method B8a. 2-tert-Butyl-4-cyanoaniline was converted to 2-tert-butyl-4-cyanophenyl isothiocyanate according to Method bA2a. (1R,2R)-1-Methanesulfonyloxymethyl)-2-(tert-butoxy) propanammonium chloride was reacted with 2-tert-butyl-4-cyanophenyl isothiocyanate followed by isobutyl bromide according to Method C5b to afford (4R)-2-(2-tert-butyl-4-cyanophenylimino)-4-((1R)-1-tert-butoxyethyl)-3- isobutyl-1,3-thiazolidine. The tert-butyl ether was deprotected according to Method D3a to afford (4R)-2-(2-tert-butyl-4-cyanophenylimino)-4-((1R)-1-hydroxyethyl)-3-isobutyl-1, 3-thiazolidine.

Entry 171

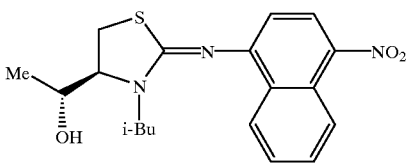

(1R,2R)-1-Methanesulfonyloxymethyl)-2-(tert-butoxy) propanammonium chloride was made from (L)-(1S,2R)-N-(benzyloxycarbonyl)-O-tert-butylthreonine dicyclohexylamine salt as described in Method B8a. 4-Nitro-1-naphthylamine was converted to 4-nitro-1-naphthyl isothiocyanate according to Method A2b. (1R,2R)-1-Methanesulfonyloxymethyl)-2-(tert-butoxy) propanammonium chloride was reacted with 4-nitronaphthyl isothiocyanate followed by cyclopentyl bromide according to Method C5b to afford (4R)-2-(4-nitro-1-naphthylimino)-4-((1R)-1-tert-butoxyethyl)-3-cyclopentyl-1,3-thiazolidine. The tert-butyl ether was deprotected according to Method D3a to afford (4R)-2-(4-nitro-1-naphthylimino)-4-((1R)-1-hydroxyethyl)-3-cyclopentyl-1, 3-thiazolidine.

Entry 172

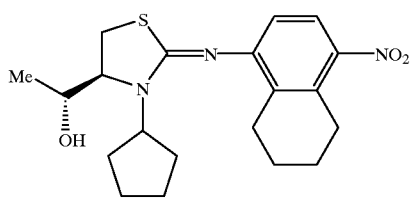

(1R,2R)-1-Methanesulfonyloxymethyl)-2-(tert-butoxy) propanammonium chloride was made from (L)-(1S,2R)-N-(benzyloxycarbonyl)-O-tert-butylthreonine dicyclohexylamine salt as described in Method B8a. 1-Amino-5,6,7,8-tetrahydronaphthalene was converted to 4-nitro-5,6,7,8-tetrahydronaphth-1-yl isothiocyanate according to Method A2a. (1R,2R)-1-Methanesulfonyloxymethyl)-2-(tert-butoxy)propanammonium chloride was reacted with 4-nitro-5,6,7,8-tetrahydronaphth-1-yl isothiocyanate followed by cyclopentyl bromide according to Method C5b to afford (4R)-2-(4-nitro-5,6,7,8-tetrahydronaphth-1-ylimino)-4-((1R)-1-tert-butoxyethyl)-3-cyclopentyl-1,3-thiazolidine. The tert-butyl ether was deprotected according to Method D3a to afford (4R)-2-(4-nitro-5,6,7,8-tetrahydronaphth-1-ylimino)-4-((1R)-1-hydroxyethyl)-3-cyclopentyl-1,3-thiazolidine.

Entry 173

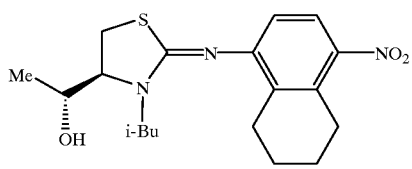

(1R,2R)-1-Methanesulfonyloxymethyl)-2-(tert-butoxy) propanammonium chloride was made from (L)-(1S,2R)-N-(benzyloxycarbonyl)-O-tert-butylthreonine dicyclohexylamine salt as described in Method B8a. 1-Amino-5,6,7,8-tetrahydronaphthalene was converted to 4-nitro-5,6,7,8-tetrahydronaphth-1-yl isothiocyanate according to Method A2a. (1R,2R)-1-Methanesulfonyloxymethyl)-2-(tert-butoxy)propanammonium chloride was reacted with 4-nitro-5,6,7,8-tetrahydronaphth-1-yl isothiocyanate followed by isobutyl bromide according to Method C5b to afford (4R)-2-(4-nitro-5,6,7,8-tetrahydronaphth-1-ylimino)-4-((1R)-1-tert-butoxyethyl)-3-isobutyl-1,3-thiazolidine. The tert-butyl ether was deprotected according to Method D3a to afford (4R)-2-(4-nitro-5,6,7,8-tetrahydronaphth-1-ylimino)-4-((1R)-1-hydroxyethyl)-3-isobutyl-1,3-thiazolidine.

Entry 174

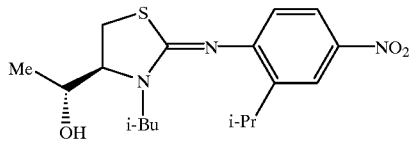

(1R,2R)-1-Methanesulfonyloxymethyl)-2-(tert-butoxy) propanammonium chloride was made from (L)-(1S,2R)-N-(benzyloxycarbonyl)-O-tert-butylthreonine dicyclohexylamine salt as described in Method B8a. 2-Isopropylaniline was converted to 2-isopropyl-4-nitrophenyl isothiocyanate according to Method A2a. (1R,2R)-1-Methanesulfonyloxymethyl)-2-(tert-butoxy) propanammonium chloride was reacted with 2-isopropyl-4-nitrophenyl isothiocyanate followed by isobutyl bromide according to Method C5b to afford (4R)-2-(2-isopropyl-4-nitrophenylimino)-4-((1R)-1-tert-butoxyethyl)-3-isobutyl-1,3-thiazolidine. The tert-butyl ether was deprotected according to Method D3a to afford (4R)-2-(2-isopropyl-4-nitrophenylimino)-4-((1R)-1-hydroxyethyl)-3-isobutyl-1,3-thiazolidine.

Entry 175

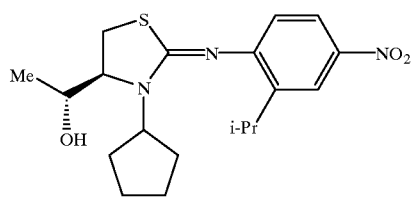

(1R,2R)-1-Methanesulfonyloxymethyl)-2-(tert-butoxy) propanammonium chloride was made from (L)-(1S,2R)-N-(benzyloxycarbonyl)-O-tert-butylthreonine dicyclohexylamine salt as described in Method B8a. 2-Isopropylaniline was converted to 2-isopropyl-4-nitrophenyl isothiocyanate according to Method A2a. (1R,2R)-1-Methanesulfonyloxymethyl)-2-(tert-butoxy) propanammonium chloride was reacted with 2-isopropyl-4-nitrophenyl isothiocyanate followed by cyclopentyl bromide according to Method C5b to afford (4R)-2-(2-isopropyl-4-nitrophenylimino)-4-((1R)-1-tert-butoxyethyl)-3-cyclopentyl-1,3-thiazolidine. The tert-butyl ether was deprotected according to Method D3a to afford (4R)-2-(2-isopropyl-4-nitrophenylimino)-4-((1R)-1-hydroxyethyl)-3-cyclopentyl-1,3-thiazolidine.

Entry 176

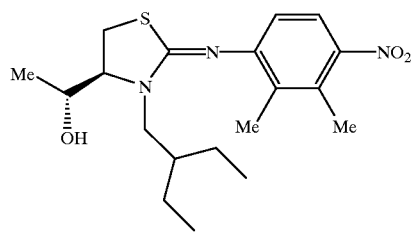

(1R,2R)-1-Methanesulfonyloxymethyl)-2-(tert-butoxy) propanammonium chloride was made from (L)-(1S,2R)-N-(benzyloxycarbonyl)-O-tert-butylthreonine dicyclohexylamine salt as described in Method B8a. 2,3-Dimethyl-4-nitroaniline was converted to 2,3-dimethyl-4-nitrophenyl isothiocyanate according to Method A2b. (1R,2R)-1-Methanesulfonyloxymethyl)-2-(tert-butoxy) propanammonium chloride was reacted with 2,3-dimethyl-4-nitrophenyl isothiocyanate followed by 2-ethyl-1-butyl bromide according to Method C5b to afford (4R)-2-(2,3-dimethyl-4-nitrophenylimino)-4-((1R)-1-tert-butoxyethyl)-3-(2-ethyl-1-butyl)-1,3-thiazolidine. The tert-butyl ether was deprotected according to Method D3a to afford (4R)-2-(2,3-dimethyl-4-nitrophenylimino)-4-((1R)-1-hydroxyethyl)-3-(2-ethyl-1-butyl)-1,3-thiazolidine.

Entry 177

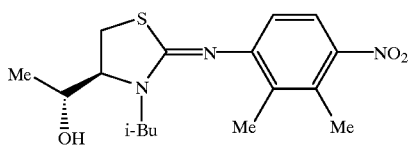

(1R,2R)-1-Methanesulfonyloxymethyl)-2-(tert-butoxy) propanammonium chloride was made from (L)-(1S,2R)-N-(benzyloxycarbonyl)-O-tert-butylthreonine dicyclohexylamine salt as described in Method B8a. 2,3-Dimethyl-4-nitroaniline was converted to 2,3-dimethyl-4-nitrophenyl isothiocyanate according to Method A2b. (1R,2R)-1-Methanesulfonyloxymethyl)-2-(tert-butoxy) propanammonium chloride was reacted with 2,3-dimethyl-4-nitrophenyl isothiocyanate followed by isobutyl bromide according to Method C5b to afford (4R)-2-(2,3-dimethyl-4-nitrophenylimino)-4-((1R)-1-tert-butoxyethyl)-3-isobutyl-1,3-thiazolidine. The tert-butyl ether was deprotected according to Method D3a to afford (4R)-2-(2,3-dimethyl-4-nitrophenylimino)-4-((1R)-1-hydroxyethyl)-3-isobutyl-1,3-thiazolidine.

Entry 178

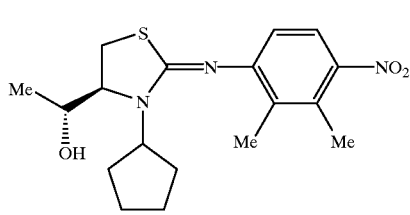

(1R,2R)-1-Methanesulfonyloxymethyl)-2-(tert-butoxy) propanammonium chloride was made from (L)-(1S,2R)-N-(benzyloxycarbonyl)-O-tert-butylthreonine dicyclohexylamine salt as described in Method B8a. 2,3-Dimethyl-4-nitroaniline was converted to 2,3-dimethyl-4-nitrophenyl isothiocyanate according to Method A2b. (1R,2R)-1-Methanesulfonyloxymethyl)-2-(tert-butoxy) propanammonium chloride was reacted with 2,3-dimethyl-4-nitrophenyl isothiocyanate followed by cyclopentyl bromide according to Method C5b to afford (4R)-2-(2,3-dimethyl-4-nitrophenylimino)-4-((1R)-1-tert-butoxyethyl)-3-cyclopentyl-1,3-thiazolidine. The tert-butyl ether was deprotected according to Method D3a to afford (4R)-2-(2,3-dimethyl-4-nitrophenylimino)-4-((1R)-1-hydroxyethyl)-3-cyclopentyl-1,3-thiazolidine.

Entry 179

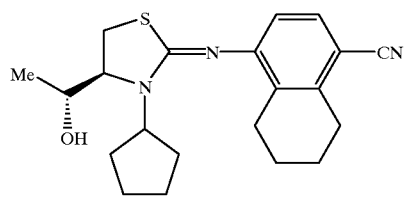

(1R,2R)-1-Methanesulfonyloxymethyl)-2-(tert-butoxy) propanammonium chloride was made from (L)-(1S,2R)-N-(benzyloxycarbonyl)-O-tert-butylthreonine dicyclohexylamine salt as described in Method B8a. 1-amino-4-cyano-5,6,7,8-tetrahydronaphthalene was converted to 4-cyano-5,6,7,8-tetrahydronaphthyl isothiocyanate according to Method A2b. (1R,2R)-1-Methanesulfonyloxymethyl)-2-(tert-butoxy)propanammonium chloride was reacted with 4-cyano-5,6,7,8-tetrahydronaphthyl isothiocyanate followed by cyclopentyl bromide according to Method C5b to afford (4R)-2-(4-cyano-5,6,7,8-tetrahydronaphthylimino)-4-((1R)-1-tert-butoxyethyl)-3-cyclopentyl-1,3-thiazolidine. The tert-butyl ether was deprotected according to Method D3a to afford (4R)-2-(4-cyano-5,6,7,8-tetrahydronaphthylimino)-4-((1R)-1-hydroxyethyl)-3-cyclopentyl-1,3-thiazolidine.

Entry 180

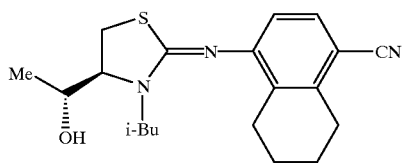

(1R,2R)-1-Methanesulfonyloxymethyl)-2-(tert-butoxy) propanammonium chloride was made from (L)-(1S,2R)-N-(benzyloxycarbonyl)-O-tert-butylthreonine dicyclohexylamine salt as described in Method B8a. 1-amino-4-cyano-5,6,7,8-tetrahydronaphthalene was converted to 4-cyano-5,6,7,8-tetrahydronaphthyl isothiocyanate according to Method A2b. (1R,2R)-1-Methanesulfonyloxymethyl)-2-(tert-butoxy)propanammonium chloride was reacted with 4-cyano-5,6,7,8-tetrahydronaphthyl isothiocyanate followed by isobutyl bromide according to Method C5b to afford (4R)-2-(4-cyano-5,6,7,8-tetrahydronaphthylimino)-4-((1R)-1-tert-butoxyethyl)-3-isobutyl-1,3-thiazolidine. The tert-butyl ether was deprotected according to Method D3a to afford (4R)-2-(4-cyano-5,6,7,8-tetrahydronaphthylimino)-4-((1R)-1-hydroxyethyl)-3-isobutyl-1,3-thiazolidine.

Entry 181

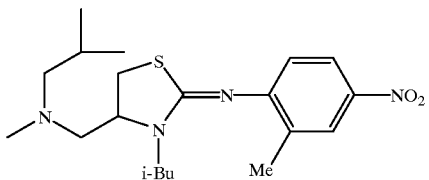

2-Amino-1,3-propanediol was reacted with excess $SOCl_2$ followed by 2-methyl-4-nitrophenyl isothiocyanate according to Method C2a to give 2-(2-methyl-4-nitrophenylimino)-4-(chloromethyl)-1,3-thiazolidine. The thiazolidine was reacted with N-methylamine according to Method D13a to give 2-(2-methyl-4-nitrophenylimino)-4-(N-methylaminomethyl)-1,3-thiazolidine, which was reacted with isobutyl bromide according to Method D2a to afford 2-(2-methyl-4-nitrophenylimino)-3-isobutyl-4-(N-isobutyl-N-methylaminomethyl)-1,3-thiazolidine.

Entry 182

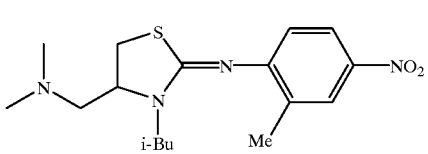

2-Amino-1,3-propanediol was reacted with excess $SOCl_2$ followed by 2-methyl-4-nitrophenyl isothiocyanate according to Method C2a to give 2-(2-methyl-4-nitrophenylimino)-4-(chloromethyl)-1,3-thiazolidine. The thiazolidine was reacted with dimethylamine according to Method D13a to give 2-(2-methyl-4-nitrophenylimino)-4-(N-isobutyl-N-methylaminomethyl)-1,3-thiazolidine, which was reacted with isobutyl bromide according to Method D2a to afford 2-(2-methyl-4-nitrophenylimino)-3-isobutyl-4-(N,N-dimethylaminomethyl)-1,3-thiazolidine.

Entry 183

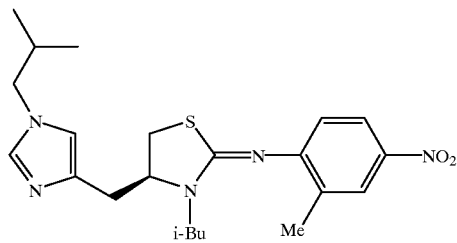

(L)-Histidinol was reacted with SOCl$_2$ followed by 2-methyl-4-nitrophenyl isothiocyanate according to Method C2a to give (4S)-2-(2-methyl-4-nitrophenylimino)-4-(1-(isobutylimidazoly)methyl)-1,3-thiazolidine. The thiazolidine was reacted with isobutyl bromide according to Method D2a to afford (4S)-2-(2-methyl-4-nitrophenylimino)-3-isobutyl-4-(1-(isobutylimidazolyl)methyl)-1,3-thiazolidine.

Entry 184

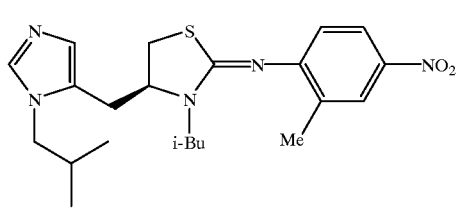

(L)-Histidinol was reacted with SOCl$_2$ followed by 2-methyl-4-nitrophenyl isothiocyanate according to Method C2a to give (4S)-2-(2-methyl-4-nitrophenylimino)-4-(1-(isobutylimidazoly)methyl)-1,3-thiazolidine. The thiazolidine was reacted with isobutyl bromide according to Method D2a to afford (4S)-2-(2-methyl-4-nitrophenylimino)-3-isobutyl-4-(3-(isobutylimidazolyl)methyl)-1,3-thiazolidine.

Entry 185

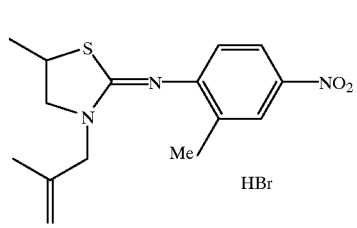

2-Hydroxypropylamine was converted to 2-chloropropylammonium chloride according to Method B7a. 2-Methyl-4-nitrophenyl isothiocyanate was reacted with 2-chloropropylammonium chloride according to Method C1a to give 2-(2-methyl-4-nitrophenylimino)-5-methyl-1,3-thiazolidine. The thiazolidine was reacted with 2-methylprop-2-en-1-yl bromide according to Method D2g to afford 2-(2-methyl-4-nitrophenylimino)-3-(2-methylprop-2-en-1-yl)-5-methyl-1,3-thiazolidine HBr salt.

Entry 186

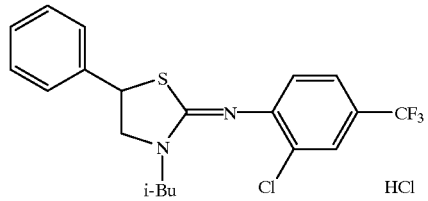

2-Phenyl-2-hydroxyethylamine was reacted with isobutyraldehyde according to Method B4c, Step 1 to give 2isopropyl-5-phenyl-1,3-oxazolidine. The oxazolidine was reduced according to Method B4c, Step 2 to give N-isobutyl-2-phenyl-2-hydroxyethylamine. The ethanolamine was reacted with SOCl$_2$ followed by 2-chloro-4-(trifluoromethyl)phenyl isothiocyanate according to Method C2f to afford 2-(2-chloro-4-(trifluoromethyl)phenylimino)-3-isobutyl-5-phenyl-1,3-thiazolidine HCl salt.

Entry 187

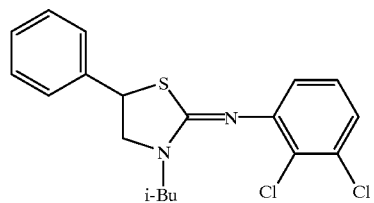

2-Phenyl-2-hydroxyethylamine was reacted with isobutyraldehyde according to Method B4c, Step 1 to give 2-isopropyl-5-phenyl-1,3-oxazolidine. The oxazolidine was reduced according to Method B4c, Step 2 to give N-isobutyl-2-phenyl-2-hydroxyethylamine. The ethanolamine was reacted with SOCl$_2$ followed by 2,3-dichlorophenyl isothiocyanate according to Method C2f to afford 2-(2,3-dichlorophenylimino)-3-isobutyl-5-phenyl-1,3-thiazolidine.

Entry 188

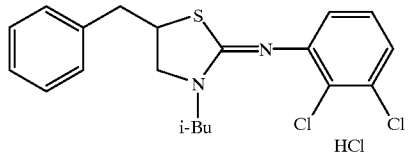

3-Phenyl-2-hydroxypropylamine was reacted with isobutyraldehyde according to Method B4c, Step 1 to give 2-isopropyl-5-benzyl-1,3-oxazolidine. The oxazolidine was reduced according to Method B4c, Step 2 to give N-isobutyl-3-phenyl-2-hydroxypropylamine. The propanolamine was reacted with SOCl$_2$ followed by 2,3-dichlorophenyl isothiocyanate according to Method C2f to afford 2-(2,3-dichlorophenylimino)-3-isobutyl-5-benzyl-1,3-thiazolidine HCl salt.

Entry 189

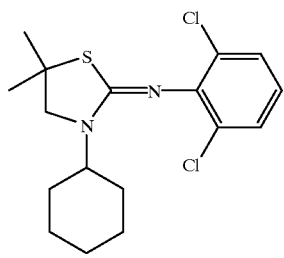

2-Methyl-2-hydroxypropylamine was reacted with cyclohexanecarboxaldehyde according to Method B4c, Step 1 to give 2-cyclohexyl-5,5-dimethyl-1,3-oxazolidine. The oxazolidine was reduced according to Method B4c, Step 2 to give N-cyclohexyl-2-methyl-2-hydroxypropylamine. The propanolamine was reacted with SOCl₂ followed by 2,6-dichlorophenyl isothiocyanate according to Method C2f to afford 2-(2,6-dichlorophenylimino)-3-cyclohexyl-5,5-dimethyl-1,3-thiazolidine.

Entry 190

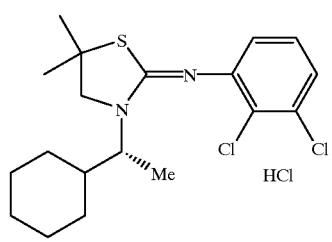

(1R)-1-Cyclohexyl-1-ethylamine was reacted with 1,2-epoxy-2-methylpropane according to Method B5b to give N-((1R)-1-cyclohexyl-1-ethyl)-N-(2,2-dimethyl-2-hydroxyethyl)amine. N-((1R)-1-Cyclohexyl-1-ethyl)-N-(2, 2dimethyl-2-hydroxyethyl)amine was reacted with SOCl₂ followed by 2,3-dichlorophenyl isothiocyanate according to Method C2f to afford 2-(2,3-dichlorophenylimino)-3-((1R)-1-cyclohexyl-1-ethyl)-5,5-dimethyl-1,3-thiazolidine HCl salt.

Entry 191

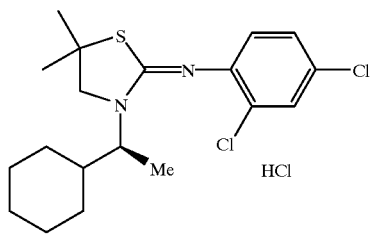

(1S)-1-Cyclohexyl-1-ethylamine was reacted with 1,2-epoxy-2-methylpropane according to Method B5b to give N-((1S)-1-cyclohexyl-1-ethyl)-N-(2,2-dimethyl-2-hydroxyethyl)amine. N-((1S)-1-Cyclohexyl-1-ethyl)-N-(2, 2-dimethyl-2-hydroxyethyl)amine was reacted with SOCl₂ followed by 2,4-dichlorophenyl isothiocyanate according to Method C2f to afford 2-(2,4-dichlorophenylimino)-3-((1S)-1-cyclohexyl-1-ethyl)-5,5-dimethyl-1,3-thiazolidine HCl salt.

Entry 192

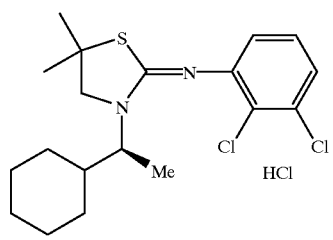

(1S)-1-Cyclohexyl-1-ethylamine was reacted with 1,2-epoxy-2-methylpropane according to Method B5b to give N-((1S)-1-cyclohexyl-1-ethyl)-N-(2,2-dimethyl-2-hydroxyethyl)amine. N-((1S)-1-Cyclohexyl-1-ethyl)-N-(2, 2-dimethyl-2-hydroxyethyl)amine was reacted with SOCl₂ followed by 2,3-dichlorophenyl isothiocyanate according to Method C2f to afford 2-(2,3-dichlorophenylimino)-3-((1S)-1-cyclohexyl-1-ethyl)-5,5-dimethyl-1,3-thiazolidine HCl salt.

Entry 193

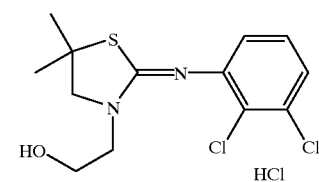

2-Methyl-2-hydroxypropylamine was reacted with SOCl₂ followed by 2,3-dichlorophenyl isothiocyanate according to Method C2f to afford 2-(2,3-dichlorophenylimino)-5,5-dimethyl-1,3-thiazolidine. 2-(2,3-Dichlorophenylimino)-5,5-dimethyl-1,3-thiazolidine was reacted with ethylene oxide according to Method B5b to afford 2-(2,3-dichlorophenylimino)-5,5-dimethyl-1,3-thiazolidine HCl salt.

Entry 194

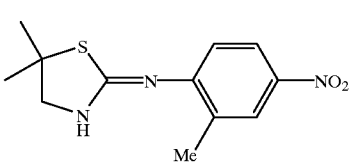

2-Methyl-2-hydroxypropylamine was reacted with SOCl₂ followed by 2-methyl-4-nitrophenyl isothiocyanate according to Method C1a to afford 2-(2-methyl-4-nitrophenylimino)-5,5-dimethyl-1,3-thiazolidine.

Entry 195

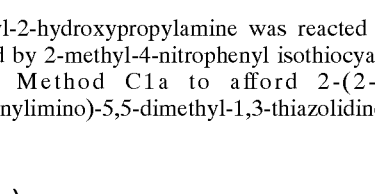

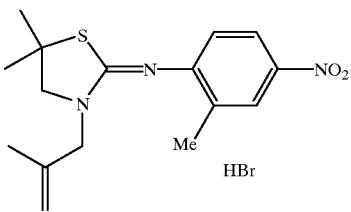

2-Methyl-2-hydroxypropylamine was reacted with SOCl₂ followed by 2-methyl-4-nitrophenyl isothiocyanate according to Method C1a to afford 2-(2-methyl-4-nitrophenylimino)-5,5-dimethyl-1,3-thiazolidine. The thiazolidine was reacted with 2-methylprop-2-en-1-yl bromide according to Method D2g to afford 2-(2-methyl-4-nitrophenylimino)-3-(2-methylprop-2-en-1-yl)-5,5-dimethyl-1,3-thiazolidine HBr salt.

Entry 196

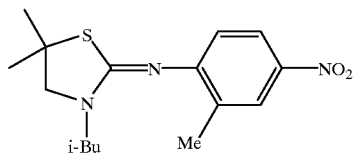

2-Methyl-2-hydroxypropylamine was reacted with SOCl₂ followed by 2-methyl-4-nitrophenyl isothiocyanate according to Method C1a to afford 2-(2-methyl-4-nitrophenylimino)-5,5-dimethyl-1,3-thiazolidine. The thiazolidine was reacted with isobutyl bromide according to Method D2g to afford 2-(2-methyl-4-nitrophenylimino)-3-isobutyl-5,5-dimethyl-1,3-thiazolidine.

Entry 197

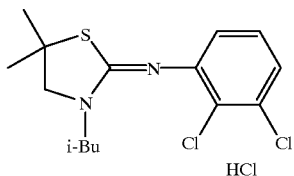

2-Methyl-2-hydroxypropylamine was reacted with SOCl₂ followed by 2,3-dichlorophenyl isothiocyanate according to Method C1a to afford 2-(2,3-dichlorophenylimino)-5,5dimethyl-1,3-thiazolidine. The thiazolidine was reacted with isobutyl bromide according to Method D2g to afford 2-(2,3-dichlorophenylimino)-3-isobutyl-5,5-dimethyl-1,3-thiazolidine.

Entry 198

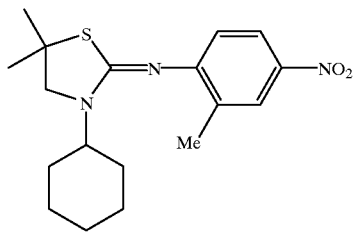

2-Methyl-2-hydroxypropylamine was reacted with cyclohexanecarboxaldehyde according to Method B4c, Step 1 to give 2-cyclohexyl-5,5-dimethyl-1,3-oxazolidine. The oxazolidine was reduced according to Method B4c, Step 2 to give N-cyclohexyl-2-methyl-2-hydroxypropylamine. The propanolamine was reacted with SOCl₂ followed by 2-methyl-4-nitrophenyl isothiocyanate according to Method C2f to afford 2-(2-methyl-4-nitrophenylimino)-3-cyclohexyl-5,5-dimethyl-1,3-thiazolidine.

Entry 199

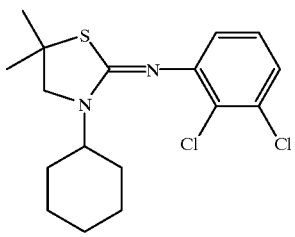

2-Methyl-2-hydroxypropylamine was reacted with cyclohexanecarboxaldehyde according to Method B4c, Step 1 to give 2-cyclohexyl-5,5-dimethyl-1,3-oxazolidine. The oxazolidine was reduced according to Method B4c, Step 2 to give N-cyclohexyl-2-methyl-2-hydroxypropylamine. The propanolamine was reacted with SOCl₂ followed by 2,3-dichlorophenyl isothiocyanate according to Method C2f to afford 2-(2dichlorophenylimino)-3-cyclohexyl-5,5-dimethyl-1,3-thiazolidine.

Entry 200

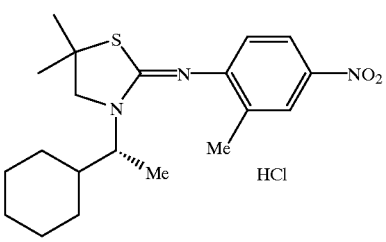

(1R)-1-Cyclohexyl-1-ethylamine was reacted with 1,2-epoxy-2-methylpropane according to Method B5b to give N-((1R)-1-cyclohexyl-1-ethyl)-N-(2,2-dimethyl-2-hydroxyethyl)amine. N-((1R)-1-Cyclohexyl-1-ethyl)-N-(2,2-dimethyl-2-hydroxyethyl)amine was reacted with SOCl₂ followed by 2-methyl-4-nitrophenyl isothiocyanate according to Method C2f to afford 2-(2-methyl-4-nitrophenylimino)-3-((1R)-1-cyclohexyl-1-ethyl)-5,5-dimethyl-1,3-thiazolidine HCl salt.

Entry 201

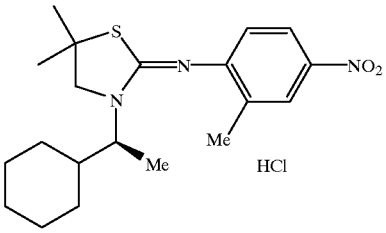

(1S)-1-Cyclohexyl-1-ethylamine was reacted with 1,2-epoxy-2-methylpropane according to Method B5b to give N-((1S)-1-cyclohexyl-1-ethyl)-N-(2,2-dimethyl-2-hydroxyethyl)amine. N-((1S)-1-Cyclohexyl-1-ethyl)-N-(2,2-dimethyl-2-hydroxyethyl)amine was reacted with SOCl₂ followed by 2-methyl-4-nitrophenyl isothiocyanate according to Method C2f to afford 2-(2-methyl-4-nitrophenylimino)-3-((1S)-1-cyclohexyl-1-ethyl)-5,5-dimethyl-1,3-thiazolidine HCl salt.

Entry 202

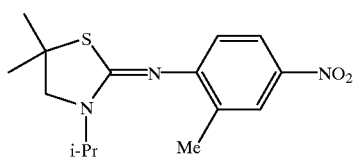

Isopropylamine was reacted with 1,2-epoxy-2-methylpropane according to Method B5b to give N-isopropyl-N-(2,2-dimethyl-2-hydroxyethyl)amine. N-Isopropyl-N-(2,2-dimethyl-2-hydroxyethyl)amine was reacted with SOCl$_2$ followed by 2-methyl-4-nitrophenyl isothiocyanate according to Method C2f to afford 2-(2-methyl-4-nitrophenylimino)-3-isopropyl-5,5-dimethyl-1,3-thiazolidine.

Entry 203

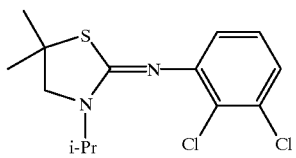

Isopropylamine was reacted with 1,2-epoxy-2-methylpropane according to Method B5b to give N-isopropyl-N-(2,2-dimethyl-2-hydroxyethyl)amine. N-Isopropyl-N-(2,2-dimethyl-2-hydroxyethyl)amine was reacted with SOCl$_2$ followed by 2,3-dichlorophenyl isothiocyanate according to Method C2f to afford 2-(2,3-dichlorophenylimino)-3-isopropyl-5,5-dimethyl-1,3-thiazolidine.

Entry 204

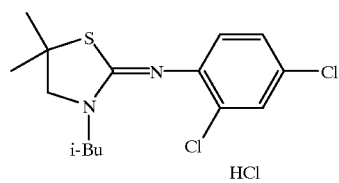

Isobutylamine was reacted with 1,2-epoxy-2-methylpropane according to Method B5b to give N-isobutyl-N-(2,2-dimethyl-2-hydroxyethyl)amine. N-Isobutyl-N-(2,2-dimethyl-2-hydroxyethyl)amine was reacted with SOCl$_2$ followed by 2,4-dichlorophenyl isothiocyanate according to Method C2f to afford 2-(2,4-1-dichlorophenylimino)-3-isobutyl-5,5-dimethyl-1,3-thiazolidine HCl salt.

Entry 205

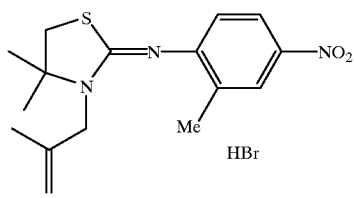

1,1-Dimethyl-2-hydroxyamine was converted to 1,1-dimethyl-2-chloroethylammonium chloride according to Method B7a. 2-Methyl-4-nitrophenyl isothiocyanate was reacted with 1,1-dimethyl-2-chloroethylammonium chloride according to Method C1a to give 2-(2-methyl-4-nitrophenylimino)-4,4-dimethyl-1,3-thiazolidine. The thiazolidine was reacted with 2-methylprop-2-en-1-yl bromide according to Method D2g to afford 2-(2-methyl-4-nitrophenylimino)-4,4-dimethyl-3-(2-methylprop-2-en-1-yl)-1,3-thiazolidine HBr salt.

Entry 206

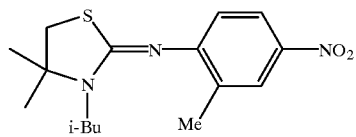

Methyl aminoisobutyric acid was converted to methyl aminoisobutyrate HCl salt according to method B1c, Step 1. The ester was reduced to 3-hydroxy-2-methyl-2-propylamine according to Method B1c, Step 2. The 2-hydroxyethylamine was treated with SOCl$_2$ according to Method B7b, followed by 2-methyl-3-nitrophenyl isothiocyanate according to Method C1a to give 2-(2-methyl-4-nitrophenylimino)-4,4-dimethyl-1,3-thiazolidine. The thiazolidine was reacted with isobutyl bromide according to Method D2a to afford 2-(2-methyl-4-nitrophenylimino)-4,4-dimethyl-3-isobutyl-1,3-thiazolidine.

Entry 207

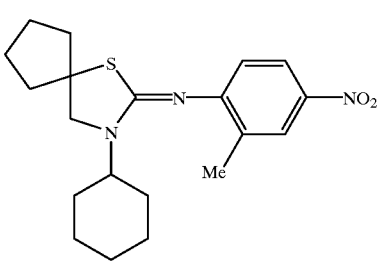

1-Amino-1-(hydroxymethyl)cyclopentane was synthesized as described in Method B1c. 1-(Cyclohexylamino)-1-hydroxymethylcyclopentane was synthesized as described in Method B4a. The 2-hydroxyethylamine was treated with SOCl$_2$ followed by 2-methyl-4-nitrophenyl isothiocyanate according to Method C2a to afford 3-cyclohexyl-2-(2-methyl-4-nitrophenylimino)-1-thia-3-azaspiro[4.4]nonane.

Entry 208

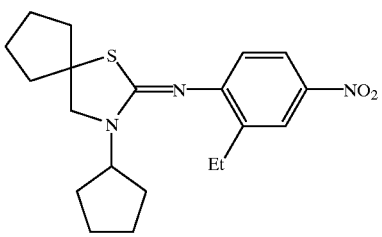

2-Ethylaniline was converted to 2-ethylacetanilide according to Method A2a, Step 1. The acetanilide was converted to 2-ethyl-4-nitroacetanilide according to Method A2a, Step 2. The acetanilide was deprotected according to Method A2a, Step 3 to give 2-ethyl-4-nitroaniline. The aniline was converted to 2-ethyl-4-nitrophenyl isothiocyanate according to Method A2a, Step 3. 1-Amino-1-(hydroxymethyl)cyclopentane was synthesized as described in Method B1c. The 2-hydroxyethylamine was reacted with with SOCl$_2$ according to Method B7a to give 1-amino-1-(chloromethyl) cyclopentane HCl salt. The 2-chloroethylamine was reacted with 2-ethyl-4-nitrophenyl isothiocyanate according to Method C1a to give 2-(2-ethyl-4-nitrophenylimino)-1-thia-3-azaspiro[4.4]nonane. The thiazolidine was reacted with cyclopentyl bromide according to Method D2b to afford 3-cyclopentyl-2-(2-ethyl-4-nitrophenylimino)-1-thia-3-azaspiro[4.4]nonane.

Entry 209

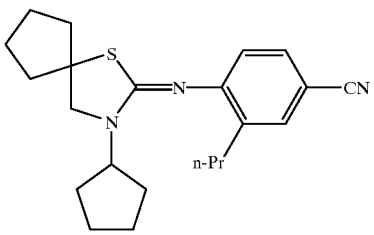

2-n-Propylaniline was converted to 4-iodo-2-n-propylaniline according to Method A5a. The aniline was converted to 4-iodo-2-n-propylphenyl isothiocyanate according to Method A2b. 1-Amino-1-(hydroxymethyl) cyclopentane was synthesized as described in Method B1c. The 2-hydroxyethylamine was reacted with SOCl₂ according to Method B7a to give 1-amino-1-(chloromethyl) cyclopentane HCl salt. The 2-chloroethylamine was reacted with 4-iodo-2-n-propylphenyl isothiocyanate according to Method C1a to give 2-(4-iodo-2-n-propylphenylimino)-1-thia-3-azaspiro[4.4]nonane. The thiazolidine was reacted with cyclopentyl bromide according to Method D2b to give 3-cyclopentyl-2-(4-iodo-2-n-propylphenylimino)-1-thia-3-azaspiro[4.4]nonane. The phenyl iodide was reacted with CuCN according to Method D7a to afford 3-cyclopentyl-2-(4-cyano-2-n-propylphenylimino)-1-thia-3-azaspiro[4.4]nonane.

Entry 210

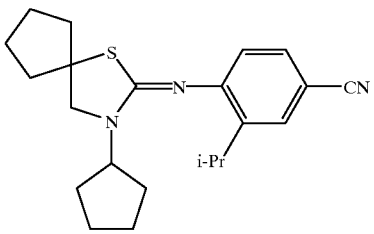

2-Isopropylaniline was converted to 4-iodo-2-isopropylaniline according to Method A5a. The aniline was converted to 4-iodo-2-isopropylphenyl isothiocyanate according to Method A2b. 1-Amino-1-(hydroxymethyl) cyclopentane was synthesized as described in Method B1c. The 2-hydroxyethylamine was reacted with SOCl₂ according to Method B7a to give 1-amino-1-(chloromethyl) cyclopentane HCl salt. The 2-chloroethylamine was reacted with 4-iodo-2-isopropylphenyl isothiocyanate according to Method C1a to give 2-(4-iodo-2-isopropylphenylimino)-1-thia-3-azaspiro[4.4]nonane. The thiazolidine was reacted with cyclopentyl bromide according to Method D2b to give 3-cyclopentyl-2-(4-iodo-2-isopropylphenylimino)-1-thia-3-azaspiro[4.4]nonane. The phenyl iodide was reacted with CuCN according to Method D7a to afford 3-cyclopentyl-2-(4-cyano-2-isopropylphenylimino)-1-thia-3-azaspiro[4.4]nonane.

Entry 211

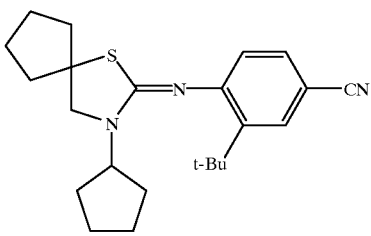

2-tert-Butylaniline was converted to 4-iodo-2-tert-butylaniline according to Method A5a. The aniline was converted to 4-iodo-2-tert-butylphenyl isothiocyanate according to Method A2b. 1-Amino-1-(hydroxymethyl) cyclopentane was synthesized as described in Method B1c. The 2-hydroxyethylamine was reacted with SOCl₂ according to Method B7a to give 1-amino-1-(chloromethyl) cyclopentane HCl salt. The 2-chloroethylamine was reacted with 4-iodo-2-tert-butylphenyl isothiocyanate according to Method C1a to give 2-(4-iodo-2-tert-butylphenylimino)-1-thia-3-azaspiro[4.4]nonane. The thiazolidine was reacted with cyclopentyl bromide according to Method D2b to give 3-cyclopentyl-2-(4-iodo-2-tert-butylphenylimino)-1-thia-3-azaspiro[4.4]nonane. The phenyl iodide was reacted with CuCN according to Method D7a to afford 3-cyclopentyl-2-(4-cyano-2-tert-butylphenylimino)-1-thia-3-azaspiro[4.4]nonane.

Entry 212

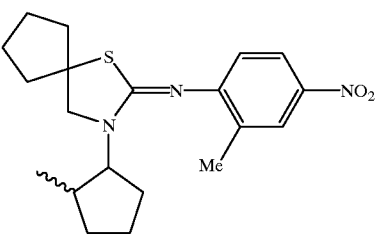

1-Amino-1-(hydroxymethyl)cyclopentane was synthesized as described in Method B1c. The amino alcohol was reacted with 2-methylcyclopentanone according to Method B4a, Step 1 to give 13-aza-1-methyl-6-oxodispiro[4.2.4.1] tridecane, which was reduced with NaBH₄ according to Method B4a, Step 2 to afford 1-(2-methylcyclopentyl) amino-1-(hydroxymethyl)cyclopentane. The 2-hydroxyethylamine was reacted with SOCl₂ followed by 2-methyl-4-nitrophenyl isothiocyanate according to Method C2a to afford 3-(2-methylcyclopentyl)-2-(2-methyl-4-nitrophenylimino)-1-thia-3-azaspiro[4.4]nonane.

Entry 213

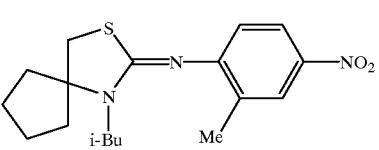

1-Amino-1-(hydroxymethyl)cyclopentane was synthesized as described in Method B1c. The 2-hydroxyethylamine was reacted with SOCl₂ according to Method B7a to give 1-amino-1-(chloromethyl)cyclopentane HCl salt. The 2-chloroethylamine was reacted with 2-methyl-4- nitrophenyl isothiocyanate according to Method C1e to give 2-(2-methyl-4-nitrophenylimino)-3-thia-1-azaspiro[4.4]nonane. The thiazolidine was reacted with isobutyl bromide according to Method D2a to afford 1-isobutyl-2-(2-methyl-4-nitrophenylimino)-3-thia-1-azaspiro[4.4]nonane.

Entry 214

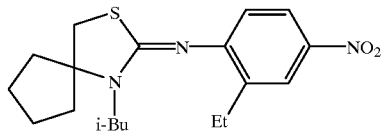

2-Ethylaniline was converted to 2-ethylacetanilide according to Method A2a, Step 1. The acetanilide was converted to 2-ethyl-4-nitroacetanilide according to Method A2a, Step 2. The acetanilide was deprotected according to Method A2a, Step 3 to give 2-ethyl-4-nitroaniline. The aniline was converted to 2-ethyl-4-nitrophenyl isothiocyanate according to Method A2a, Step 3. 1-Amino-1-(hydroxymethyl)cyclopentane was synthesized as described in Method B1c. The 2-hydroxyethylamine was reacted with SOCl$_2$ according to Method B7a to give 1-amino-1-(chloromethyl)cyclopentane HCl salt. The 2-chloroethylamine was reacted with 2-ethyl-4-nitrophenyl isothiocyanate according to Method C1a to give 2-(2-ethyl-4-nitrophenylimino)-3-thia-1-azaspiro[4.4]nonane. The thiazolidine was reacted with isobutyl bromide according to Method D2a to afford 1-isobutyl-2-(2-ethyl-4-nitrophenylimino)-3-thia-1-azaspiro[4.4]nonane.

Entry 215

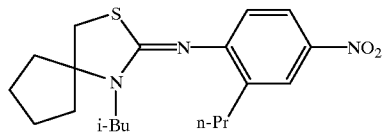

2-n-Propylaniline was converted to 2-n-propylacetanilide according to Method A2a, Step 1. The acetanilide was converted to 2-n-propyl-4-nitroacetanilide according to Method A2a, Step 2. The acetanilide was deprotected according to Method A2a, Step 3 to give 2-n-propyl-4-nitroaniline. The aniline was converted to 2-n-propyl-4-nitrophenyl isothiocyanate according to Method A2a, Step 3. 1-Amino-1-(hydroxymethyl)cyclopentane was synthesized as described in Method B1c. The 2-hydroxyethylamine was reacted with SOCl$_2$ according to Method B7a to give 1-amino-1-(chloromethyl)cyclopentane HCl salt. The 2-chloroethylamine was reacted with 2-n-propyl-4-nitrophenyl isothiocyanate according to Method C1a to give 2-(2-n-propyl-4-nitrophenylimino)-3-thia-1-azaspiro[4.4]nonane. The thiazolidine was reacted with isobutyl bromide according to Method D2a to afford 1-isobutyl-2-(2-n-propyl-14-nitrophenylimino)-3-thia-1-azaspiro[4.4]nonane.

Entry 216

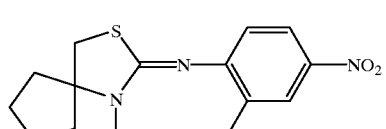

2-Isopropylaniline was converted to 2-isopropylacetanilide according to Method A2a, Step 1. The acetanilide was converted to 2-isopropyl-4-nitroacetanilide according to Method A2a, Step 2. The acetanilide was deprotected according to Method A2a, Step 3 to give 2-isopropyl-4-nitroaniline. The aniline was converted to 2-isopropyl-4-nitrophenyl isothiocyanate according to Method A2a, Step 3. 1-Amino-1-(hydroxymethyl)cyclopentane was synthesized as described in Method B1c. The 2-hydroxyethylamine was reacted with SOCl$_2$ according to Method B7a to give 1-amino-1-(chloromethyl)cyclopentane HCl salt. The 2-chloroethylamine was reacted with 2-isopropyl-4-nitrophenyl isothiocyanate according to Method C1a to give 2-(2-isopropyl-4-nitrophenylimino)-3-thia-1-azaspiro[4.4]nonane. The thiazolidine was reacted with isobutyl bromide according to Method D2a to afford 1-isobutyl-2-(2-isopropyl-4-nitrophenylimino)-3-thia-1-azaspiro[4.4]nonane.

Entry 217

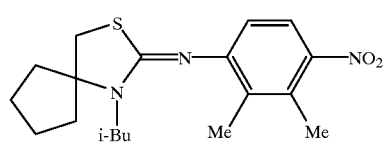

2,3-Dimethyl-4-nitroaniline was synthesized as described in Method A4a. The aniline was converted into 2,3-dimethyl-4-nitrophenyl isothiocyanate as described in method A2d. 1-Amino-1-(hydroxymethyl)cyclopentane was synthesized as described in Method B1c. The 2-hydroxyethylamine was reacted with SOCl$_2$ according to Method B7e to give 1-amino-1-(chloromethyl)cyclopentane HCl salt. The 2-chloroethylamine was reacted with 2,3-dimethyl-4-nitrophenyl isothiocyanate according to Method C1c to give 2-(2,3-dimethyl-4-nitrophenylimino)-3-thia-1-azaspiro[4.4]nonane. The thiazolidine was reacted with isobutyl bromide according to Method D2a to afford 1-isobutyl-2-(2-isopropyl-4-nitrophenylimino)-3-thia-1-azaspiro[4.4]nonane.

Entry 218

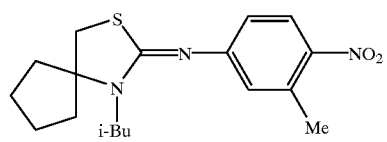

3-Methyl-4-nitroaniline was converted to 3-methyl-4-nitrophenyl isothiocyanate according to Method A2a, Step 3. 1-Amino-1-(hydroxymethyl)cyclopentane was synthesized as described in Method B1c. The 2-hydroxyethylamine was reacted with SOCl$_2$ according to Method B7a to give 1-amino-1-(chloromethyl)cyclopentane HCl salt. The 2-chloroethylamine was reacted with 3-methyl-4-nitrophenyl isothiocyanate according to Method C1a to give 2-(3-methyl-4-nitrophenylimino)-3-thia-1-azaspiro[4.4]nonane. The thiazolidine was reacted with isobutyl bromide according to Method D2a to afford 1-isobutyl-2-(3-methyl-4-nitrophenylimino)-3-thia-1-azaspiro[4.4]nonane.

Entry 219

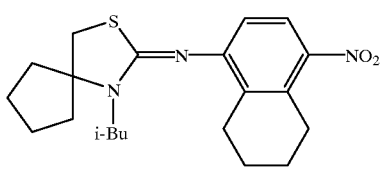

1-Amino-5,6,7,8-tetrahydronaphthaline was converted to 1-acetamino-5,6,7,8-tetrahydronaphthaline according to Method A2a, Step 1. The acetanilide was converted to 1-acetamino-4-nitro-5,6,7,8-tetrahydronaphthaline according according to Method A2a, Step 2. The acetanilide was deprotected according to Method A2a, Step 3 to give 1-amino-4-nitro-5,6,7,8-tetrahydronaphthaline. The aniline was converted to 4-nitro-5,6,7,8-tetrahydro-1-naphthyl isothiocyanate according to Method A2a, Step 3. 1-Amino-1-(hydroxymethyl)cyclopentane was synthesized as described in Method B1c. The 2-hydroxyethylamine was reacted with SOCl₂ according to Method B7a to give 1-amino-1-(chloromethyl)cyclopentane HCl salt. The 2-chloroethylamine was reacted with 4-nitro-5,6,7,8-tetrahydro-1-naphthyl isothiocyanate according to Method C1a to give 2-(4-nitro-5,6,7,8-tetrahydro-1-naphthylimino)-3-thia-1-azaspiro[4.4]nonane. The thiazolidine was reacted with isobutyl bromide according to Method D2a to afford 1-isobutyl-2-(4-nitro-5,6,7,8-tetrahydro-1-naphthylimino)-3-thia-1-azaspiro[4.4]nonane.

Entry 220

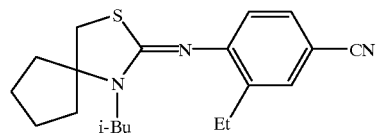

1-Amino-1-(hydroxymethyl)cyclopentane was synthesized as described in Method B1c. The 2-hydroxyethylamine was reacted with SOCl₂ according to Method B7e to give 1-amino-1-(chloromethyl)cyclopentane HCl salt. The 2-chloroethylamine was reacted with 4-cyanophenyl isothiocyanate according to Method C1a to give 2-(4-cyanophenylimino)-3-thia-1-azaspiro[4.4]nonane. The thiazolidine was reacted with isobutyl bromide according to Method D2a to afford 1-isobutyl-2-(4-cyanophenylimino)-3-thia-1-azaspiro[4.4]nonane.

Entry 221

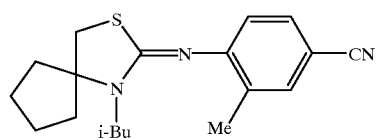

4-Cyano-2-methylaniline was synthesized as described in Method A1a. The aniline was converted to 4-cyano-2-methylphenyl isothiocyanate according to Method A2a, Step 3. 1-Amino-1-(hydroxymethyl)cyclopentane was synthesized as described in Method B1c. The 2-hydroxyethylamine was reacted with SOCl₂ according to Method B7a to give 1-amino-1-(chloromethyl)cyclopentane HCl salt. The 2-chloroethylamine was reacted with 4-cyano-2-methylphenyl isothiocyanate according to Method C1a to give 2-(4-cyano-2-methylphenylimino)-1-thia-3-azaspiro[4.4]nonane. The thiazolidine was reacted with isobutyl bromide according to Method D2b to give 3-isobutyl-2-(4-iodo-2-methylphenylimino)-1-thia-3-azaspiro[4.4]nonane.

Entry 222

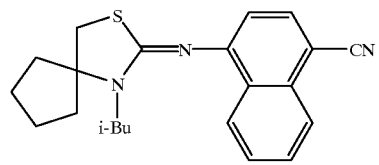

1-Amino-1-(hydroxymethyl)cyclopentane was synthesized as described in Method B1c. The 2-hydroxyethylamine was reacted with SOCl₂ according to Method B7a to give 1-amino-1-(chloromethyl)cyclopentane HCl salt. The 2-chloroethylamine was reacted with 4-cyano-2-ethylphenyl isothiocyanate according to Method C1a to give 2-(4-cyano-2-methylphenylimino)-1-thia-3-azaspiro[4.4]nonane. The thiazolidine was reacted with isobutyl bromide according to Method D2b to give 3-isobutyl-2-(4-cyano-2-methylphenylimino)-1-thia-3-azaspiro[4.4]nonane.

Entry 223

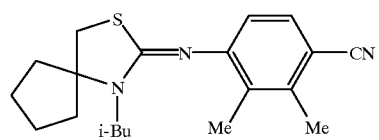

1-Amino-1-(hydroxymethyl)cyclopentane was synthesized as described in Method B1c. The 2-hydroxyethylamine was reacted with SOCl₂ according to Method B7a to give 1-amino-1-(chloromethyl)cyclopentane HCl salt. 1-Amino-4-cyanonaphthalene was converted into 4-cyano-1-naphthyl isothiocyanate according to Method A2a, Step 3. The 2-chloroethylamine was reacted with 4-cyano-1-naphthyl isothiocyanate to Method C1a to give 2-(4-cyano-1-naphthylimino)-1-thia-3-azaspiro[4.4]nonane. The thiazolidine was reacted with isobutyl bromide according to Method D2b to give 3-isobutyl-2-(4-cyano-1-naphthylimino)-1-thia-3-azaspiro[4.4]nonane.

Entry 224

2,3-Dimethylaniline was converted to 2,3-dimethyl-4-iodoaniline according to Method A5a. The aniline was converted to 2,3-dimethyl-4-iodophenyl isothiocyanate according to Method A2a, Step 3. 1-Amino-1-(hydroxymethyl)cyclopentane was synthesized as described in Method B1c. The 2-hydroxyethylamine was reacted with SOCl₂ according to Method B7e to give 1-amino-1-(chloromethyl)cyclopentane HCl salt. The 2-chloroethylamine was reacted with 2,3-dimethyl-4-iodophenyl isothiocyanate according to Method C1e to give 2-(2,3-dimethyl-4-iodophenylimino)-1-thia-3-azaspiro[4.4]nonane. The thiazolidine was reacted with isobutyl bromide according to Method D2h to give 3-isobutyl-2-(4-iodo-2-n-propylphenylimino)-1-thia-3-azaspiro[4.4]nonane. The phenyl iodide was reacted with CuCN according to Method D7a to afford 3-isobutyl-2-(2,3-dimethyl-4-cyanophenylimino)-1-thia-3-azaspiro[4.4]nonane.

Entry 225

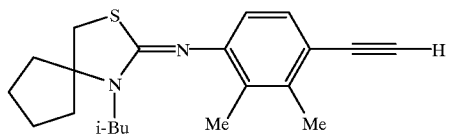

2,3-Dimethylaniline was converted to 2,3-dimethyl-4-iodoaniline according to Method A5a. The aniline was converted to 2,3-dimethyl-4-iodophenyl isothiocyanate according to Method A2a, Step 3. 1-Amino-1-(hydroxymethyl)cyclopentane was synthesized as described in Method B1c. The 2-hydroxyethylamine was reacted with $SOCl_2$ followed by 2,3-dimethyl-4-iodophenyl isothiocyanate according to Method C2a to give 2-(2,3-dimethyl-4-iodophenylimino)-1-thia-3-azaspiro[4.4]nonane. The thiazolidine was reacted with isobutyl bromide according to Method D2a to give 3-isobutyl-2-(4-iodo-2-n-propylphenylimino)-1-thia-3-azaspiro[4.4]nonane. The phenyl iodide was reacted with trimethylsilylacetylene according to Method D8a, Step 1 to give 3-isobutyl-2-(2,3-dimethyl-4-(2-trimethylsilylethynyl)phenylimino)-1-thia-3-azaspiro[4.4]nonane. The silylacetylene was deprotected according to Method D8a, Step 2 to afford 3-isobutyl-2-(2,3-dimethyl-4-ethynylphenylimino)-1-thia-3-azaspiro[4.4]nonane.

Entry 226

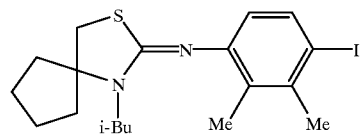

2,3-Dimethylaniline was converted to 2,3-dimethyl-4-iodoaniline according to Method A5a. The aniline was converted to 2,3-dimethyl-4-iodophenyl isothiocyanate according to Method A2a, Step 3. 1-Amino-1-(hydroxymethyl)cyclopentane was synthesized as described in Method B1c. The 2-hydroxyethylamine was reacted with $SOCl_2$ according to Method B7e to give 1-amino-1-(chloromethyl)cyclopentane HCl salt. The 2-chloroethylamine was reacted with 2,3-dimethyl-4-iodophenyl isothiocyanate according to Method C1e to give 2-(2,3-dimethyl-4-iodophenylimino)-1-thia-3-azaspiro[4.4]nonane. The thiazolidine was reacted with isobutyl bromide according to Method D2h to give 3-isobutyl-2-(4-iodo-2-n-propylphenylimino)-1-thia-3-azaspiro[4.4]nonane.

Entry 227

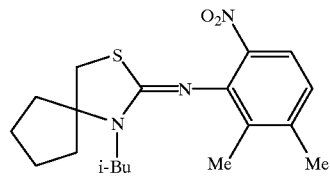

2,3-Dimethylaniline was converted to 2,3-dimethyl-6-nitroaniline according to Method A4a. The aniline was converted to 2,3-dimethyl-6-nitrophenyl isothiocyanate according to Method A2d. 1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 2,3-dimethyl-6-nitrophenyl isothiocyanate according to Method C1e to give 2-(2,3-dimethyl-6-nitrophenylimino)-3-thia-1-azaspiro[4.4]nonane. The thiazolidine was reacted with isobutyl bromide according to Method D2b to afford 2-(2,3-dimethyl-6-nitrophenylimino)-1-isobutyl-3-thia-1-azaspiro[4.4]nonane.

Entry 228

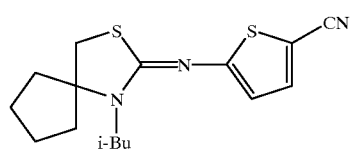

2-Cyano-5-nitrothiophene was reduced to 2-amino-5-cyanothiophene according to Method A1a. The aminothiophene was converted to 5-cyano-1-thiophene isothiocyanate according to Method A2b. 1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 5-cyano-1-thiophene isothiocyanate according to Method C1e to give 2-(5-cyanothienylimino)-3-thia-1-azaspiro[4.4]nonane. The thiazolidine was reacted with isobutyl bromide according to Method D2a to give 2-(5-cyanothienylimino)-1-isobutyl-3-thia-1-azaspiro[4.4]nonane.

Entry 229

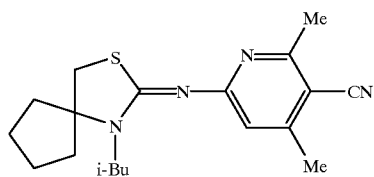

6-Amino-3-cyano-2,3-dimethylpyridine was converted to 3-cyano-2,3-dimethyl-6-pyridyl isothiocyanate according to Method A2c. 1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 3-cyano-2,3-dimethyl-6-pyridyl isothiocyanate according to Method C1e to give 2-(3-cyano-2,3-dimethyl-6-pyridylimino)-3-thia-1-azaspiro[4.4]nonane. The thiazolidine was reacted with isobutyl bromide according to Method D2h to give 2-(5-bromothienylimino)-1-isobutyl-3-thia-1-azaspiro[4.4]nonane.

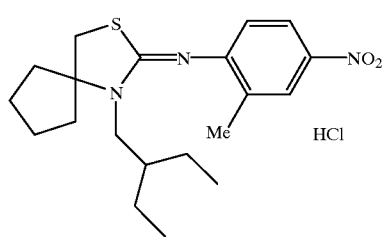

Entry 230

1-(Hydroxymethyl)cyclopentanamine was prepared according to Method B1c. The 2-hydroxyethylamine was sequentially reacted with SOCl₂ and 2-methyl-4-nitrophenyl isothiocyanate according to Method C2a to give 2-(2-methyl-4-nitrophenylimino)-3-thia-1-azaspiro[4.4]nonane. The thiazolidine was reacted with 1-bromo-2-ethylbutane according to Method D2a to afford 2-(2-methyl-4-nitrophenylimino)-1-(2-ethyl-1-butyl)-3-thia-1-azaspiro[4.4]nonane.

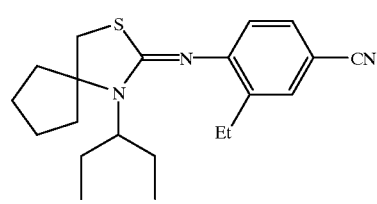

Entry 231

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 4-cyano-2-ethylphenyl isothiocyanate according to Method C1e to give 2-(4-cyano-2-ethylphenylimino)-3-thia-1-azaspiro[4.4]nonane. The thiazolidine was reacted with 3-bromopentane according to Method D2b to give 2-(4-cyano-2-ethylphenylimino)-1-(3-pentyl)-3-thia-1-azaspiro[4.4]nonane.

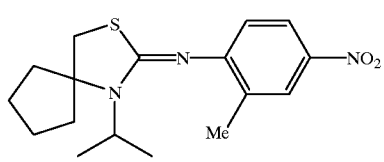

Entry 232

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 2-methyl-4-nitrophenyl isothiocyanate according to Method C1e to give 2-(2-methyl-4-nitrophenylimino)-3-thia-1-azaspiro[4.4]nonane. The thiazolidine was reacted with isopropyl bromide according to Method D2e to give 2-(2-methyl-4-nitrophenylimino)-1-(2-propyl)-3-thia-1-azaspiro[4.4]nonane.

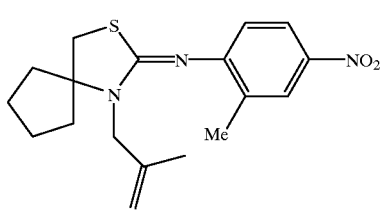

Entry 233

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 2-methyl-4-nitrophenyl isothiocyanate according to Method C1e to give 2-(2-methyl-4-nitrophenylimino)-3-thia-1-azaspiro[4.4]nonane. The thiazolidine was reacted with 3-bromo-2-methylpropene according to Method D2e to give 2-(2-methyl-4-nitrophenylimino)-1-(2-methylprop-1-en-3-yl)-3-thia-1-azaspiro[4.4]nonane.

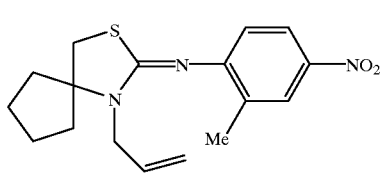

Entry 234

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 2-methyl-4-nitrophenyl isothiocyanate according to Method C1e to give 2-(2-methyl-4-nitrophenylimino)-3-thia-1-azaspiro[4.4]nonane. The thiazolidine was reacted with allyl bromide according to Method D2e to give 2-(2-methyl-4-nitrophenylimino)-1-(prop-1-en-3-yl)-3-thia-1-azaspiro[4.4]nonane.

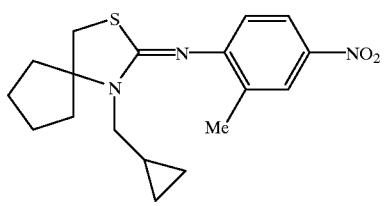

Entry 235

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 2-methyl-4-nitrophenyl isothiocyanate according to Method C1e to give 2-(2-methyl-4-nitrophenylimino)-3-thia-1-azaspiro[4.4]nonane. The thiazolidine was reacted with cyclopropylmethyl bromide according to Method D2e to give 2-(2-methyl-4-nitrophenylimino)-1-(cyclopropylmethyl)-3-thia-1-azaspiro[4.4]nonane.

Entry 236

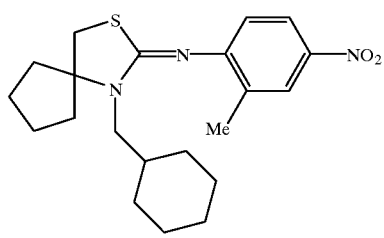

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 2-methyl-4-nitrophenyl isothiocyanate according to Method C1e to give 2-(2-methyl-4-nitrophenylimino)-3-thia-1-azaspiro[4.4]nonane. The thiazolidine was reacted with cyclohexylmethyl bromide according to Method D2e to give 2-(2-methyl-4-nitrophenylimino)-1-(cyclohexylmethyl)-3-thia-1-azaspiro[4.4]nonane.

Entry 237

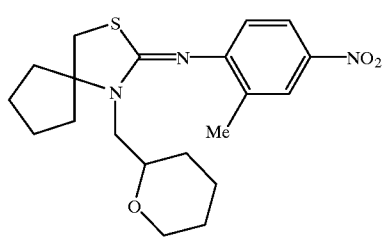

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 2-methyl-4-nitrophenyl isothiocyanate according to Method C1e to give 2-(2-methyl-4-nitrophenylimino)-3-thia-1-azaspiro[4.4]nonane. The thiazolidine was reacted with 2-(bromomethyl)tetrahydro-2H-pyran according to Method D2e to give 2-(2-methyl-4-nitrophenylimino)-1-(tetrahydro-2H-pyran-2-ylmethyl)-3-thia-1-azaspiro[4.4]nonane.

Entry 238

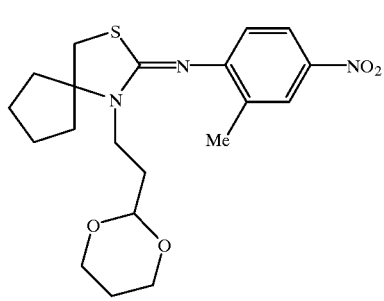

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 2-methyl-4-nitrophenyl isothiocyanate according to Method C1e to give 2-(2-methyl-4-nitrophenylimino)-3-thia-1-azaspiro[4.4]nonane. The thiazolidine was reacted with 2-(2-bromoethyl)-1,3-dioxane according to Method D2e to give 2-(2-methyl-4-nitrophenylimino)-1-(2-(1,3-dioxan-2-yl)ethyl)-3-thia-1-azaspiro[4.4]nonane.

Entry 239

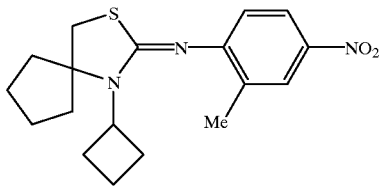

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 2-methyl-4-nitrophenyl isothiocyanate according to Method C1e to give 2-(2-methyl-4-nitrophenylphenylimino)-3-thia-1-azaspiro[4.4]nonane. The thiazolidine was reacted with cyclobutyl bromide according to Method D2e to give 2-(2-methyl-4-nitrophenylimino)-1-cyclobutyl-3-thia-1-azaspiro[4.4]nonane.

Entry 240

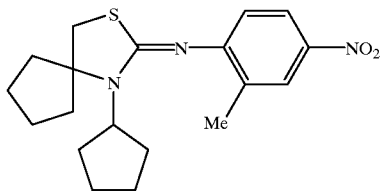

1-(Hydroxymethyl)cyclopentanamine was prepared according to Method B1c. The 2-hydroxyethylamine was treated with SOCl$_2$ followed by 2-methyl-4-nitrophenyl isothiocyanate according to Method C2a to give 2-(2-methyl-4-nitrophenylphenylimino)-3-thia-1-azaspiro[4.4]nonane. The thiazolidine was reacted with cyclopentyl bromide according to Method D2b to give 2-(2-methyl-4-nitrophenylimino)-1-cyclopentyl-3-thia-1-azaspiro[4.4]nonane.

Entry 241

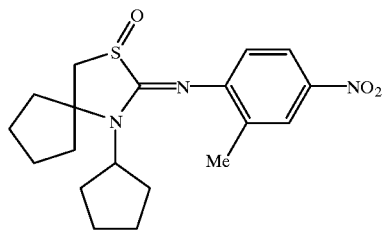

1-Hydroxymethylcyclopentanamine was prepared according to Method B1c. The 2-hydroxyethylamine was reacted with SOCl$_2$ followed by with 2-methyl-4-nitrophenyl isothiocyanate according to Method C2a to give 2-(2-methyl-4-nitrophenylphenylimino)-3-thia-1-azaspiro[4.4]nonane. The thiazolidine was reacted with cyclopentyl bromide according to Method D2b to give 2-(2-methyl-4-nitrophenylimino)-1-2-cyclopentyl-3-thia-1-azaspiro[4.4]nonane. The thiazolidine was oxidized with m-CPBA according to Method D4a to afford 2-(2-methyl-4-nitrophenylimino)-1-cyclopentyl-3-thia-1-azaspiro[4.4]nonane 3-oxide.

Entry 242

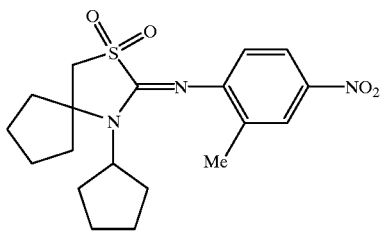

1-Hydroxymethylcyclopentanamine was prepared according to Method B1c. The 2-hydroxyethylamine was reacted with SOCl$_2$ followed by with 2-methyl-4-nitrophenyl isothiocyanate according to Method C2a to give 2-(2-methyl-4-nitrophenylphenylimino)-3-thia-1-azaspiro[4.4]nonane. The thiazolidine was reacted with cyclopentyl bromide according to Method D2b to give 2-(2-methyl-4-nitrophenylimino)-1-2-cyclopentyl-3-thia-1-azaspiro[4.4]nonane. The thiazolidine was oxidized with m-CPBA according to Method D4a to afford 2-(2-methyl-4-nitrophenylimino)-1-cyclopentyl-3-thia-1-azaspiro[4.4]nonane 3,3-dioxide.

Entry 243

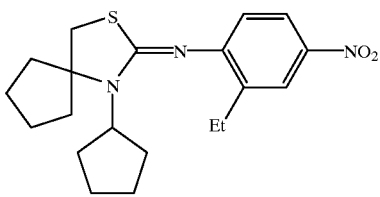

2-Ethylaniline was protected as 2-ethylacetanilide according to Method A2a, Step 1. The acetamide was converted to 2-ethyl-4-nitroaniline, then deprotected according to Method A2a, Step 2. The aniline was converted to 2-ethyl-4-nitrophenyl isothiocyanate according to Method A2a, Step 3. 1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 2-ethyl-4-nitrophenyl isothiocyanate according to Method C1e to give 2-(2-ethyl-4-nitrophenylphenylimino)-3-thia-1-azaspiro[4.4]nonane. The thiazolidine was reacted with cyclopentyl bromide according to Method D2b to give 2-(2-ethyl-4-nitrophenylphenylimino)-1-cyclopentyl-3-thia-1-azaspiro[4.4]nonane.

Entry 244

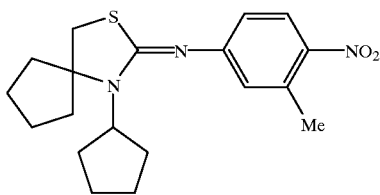

3-Methyl-4-nitroaniline was converted to 3-methyl-4-nitrophenyl isothiocyanate according to Method A2a, Step 3. 1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 3-methyl-4-nitrophenyl isothiocyanate according to Method C1e to give 2-(3-methyl-4-nitrophenylimino)-3-thia-1-azaspiro[4.4]nonane. The thiazolidine was reacted with cyclopentyl bromide according to Method D2b to give 2-(3-methyl-4-nitrophenylimino)-1-cyclopentyl-3-thia-1-azaspiro[4.4]nonane.

Entry 245

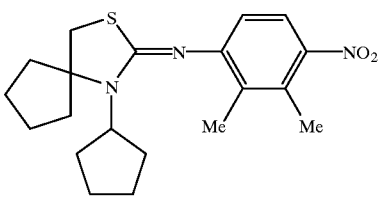

2,3-Dimethylaniline was protected as 2,3-dimethylacetanilide according to Method A2a, Step 1. The acetamide was converted to 2,3-dimethyl-4-nitroaniline, then deprotected according to Method A2a, Step 2. The aniline was converted to 2,-dimethyl-4-nitrophenyl isothiocyanate according to Method A2a, Step 3. 1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 2,3-dimethyl-4-nitrophenyl isothiocyanate according to Method C1e to give 2-(2,3dimethyl-4-nitrophenylimino)-3-thia-1-azaspiro[4.4]nonane. The thiazolidine was reacted with cyclopentyl bromide according to Method D2b to give 2-(2,3-dimethyl-4-nitrophenylimino)-1-cyclopentyl-3-thia-1-azaspiro[4.4]nonane.

Entry 246

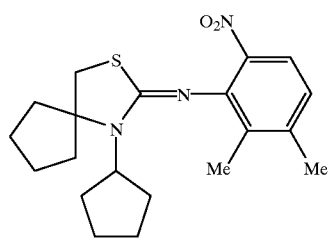

2,3-Dimethylaniline was protected as 2,3-dimethylacetanilide according to Method A2a, step 1. The acetamide was converted to 2,3-dimethyl-6-nitroaniline, then deprotected according to Method A2a, step 2. The aniline was converted to 2,-dimethyl-6-nitrophenyl isothiocyanate according to Method A2a, step 3. 1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 2,3-dimethyl-6-nitrophenyl isothiocyanate according to Method C1e to give 2-(2,3-dimethyl-6-nitrophenylimino)-3-thia-1-azaspiro[4.4]nonane. The thiazolidine was reacted with cyclopentyl bromide according to Method D2b to give 2-(2,3-dimethyl-6-nitrophenylimino)-1-cyclopentyl-3-thia-1-azaspiro[4.4]nonane.

Entry 247

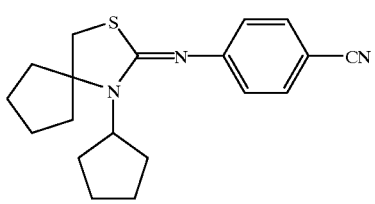

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 4-iodophenyl isothiocyanate according to Method C1e to give 2-(4-iodophenylimino)-3-thia-1-azaspiro[4.4]nonane. The thiazolidine was reacted with cyclopentyl bromide according to Method D2b to give 2-(4-iodophenylimino)-1-2-cyclopentyl-3-thia-1-azaspiro[4.4]nonane. The phenyl iodide was reacted with CuCN according to Method D2h to afford 2-(4-cyanophenylimino)-1-cyclopentyl-3-thia-1-azaspiro[4.4]nonane.

Entry 248

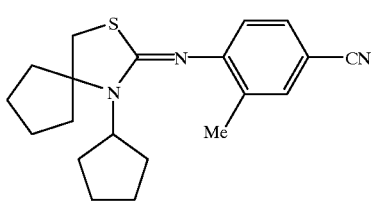

4-Cyano-2-methylaniline was prepared according to Method A1a. The aniline was converted to 4-cyano-2-methylphenyl isothiocyanate according to Method A2b. 1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 4-cyano-2-methylphenyl isothiocyanate according to Method C1e to give 2-(4-cyanophenylphenylimino)-3-thia-1-azaspiro[4.4]nonane. The thiazolidine was reacted with cyclopentyl bromide according to Method D2b to give 2-(4-cyano-2-methylphenylimino)-1-cyclopentyl-3-thia-1-azaspiro[4.4]nonane.

Entry 249

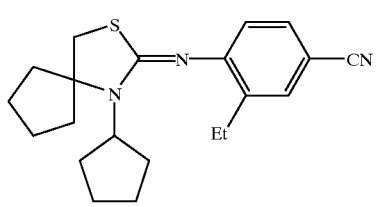

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 4-cyano-2-ethylphenyl isothiocyanate according to Method C1e to give 2-(4-cyano-2-ethylphenylimino)-3-thia-1-azaspiro[4.4]nonane. The thiazolidine was reacted with cyclopentyl bromide according to Method D2b to give 2-(4-cyano-2-ethylphenylimino)-1-cyclopentyl-3-thia-1-azaspiro[4.4]nonane.

Entry 250

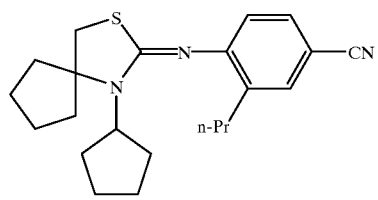

4-Iodo-2-n-propylaniline was converted to 4-iodo-2-n-propylphenyl isothiocyanate according to Method A2b. 1-Hydroxymethylcyclopentanamine was prepared according to Method B1c. The 2-hydroxyethylamine was sequentially reacted with $SOCl_2$ and 4-iodo-2-n-propylphenyl isothiocyanate according to Method C2a to give 2-(4-iodo-2-n-propylphenylimino)-3-thia-1-azaspiro[4.4]nonane. The thiazolidine was reacted with cyclopentyl bromide according to Method D2b to give 2-(4-iodo-2-n-propylphenylimino)-1-cyclopentyl-3-thia-1-azaspiro[4.4]nonane. The phenyl iodide was reacted with CuCN according to Method D7a to afford 2-(4-cyano-2-n-propylphenylimino)-1-cyclopentyl-3-thia-1-azaspiro[4.4]nonane.

Entry 251

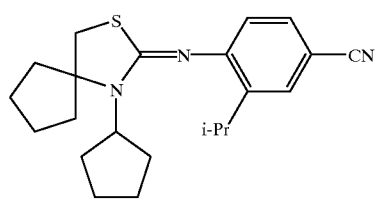

4-Iodo-2-isopropylaniline was converted to 4-iodo-2-isopropylphenyl isothiocyanate according to Method A2b. 1-Hydroxymethylcyclopentanamine was prepared according to Method B1c. The 2-hydroxyethylamine was sequentially reacted with $SOCl_2$ and 4-iodo-2-isopropylphenyl isothiocyanate according to Method C2a to give 2-(4-iodo-2-isopropylphenylimino)-3-thia-1-azaspiro[4.4]nonane. The thiazolidine was reacted with cyclopentyl bromide according to Method D2b to give 2-(4-iodo-2-isopropylphenylimino)-1-cyclopentyl-3-thia-1-azaspiro[4.4]nonane. The phenyl iodide was reacted with CuCN according to Method D7a to afford 2-(4-cyano-2-isopropylphenylimino)-1-cyclopentyl-3-thia-1-azaspiro[4.4]nonane.

Entry 252

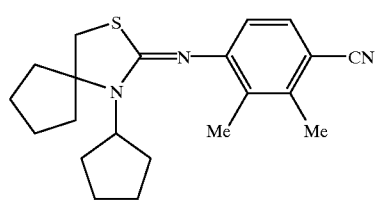

4-Iodo-2,3-dimethylaniline was converted to 4-iodo-2,3-dimethylphenyl isothiocyanate according to Method A2b. 1-Hydroxymethylcyclopentanamine was prepared according to Method B1c. The 2-hydroxyethylamine was sequentially reacted with SOCl₂ and 4-iodo-2,3-dimethylphenyl isothiocyanate according to Method C2a to give 2-(4-iodo-2,3-dimethylphenylimino)-3-thia-1-azaspiro[4.4]nonane. The thiazolidine was reacted with cyclopentyl bromide according to Method D2b to give 2-(4-iodo-2,3-dimethylphenylimino)-1-cyclopentyl-3-thia-1-azaspiro[4.4]nonane. The phenyl iodide was reacted with CuCN according to Method D7a to afford 2-(4-cyano-2,3-dimethylphenylimino)-1-cyclopentyl-3-thia-1-azaspiro[4.4]nonane.

Entry 253

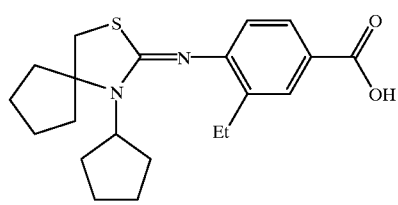

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 4-cyano-2-ethylphenyl isothiocyanate according to Method C1e to give 2-(4-cyano-2-ethylphenylimino)-3-thia-1-azaspiro[4.4]nonane. The thiazolidine was reacted with cyclopentyl bromide according to Method D2b to give 2-(4-cyano-2-ethylphenylimino)-1-cyclopentyl-3-thia-1-azaspiro[4.4]nonane. The nitrile was hydrolyzed according to Method D9a to afford 2-(4-carboxy-2-ethylphenylimino)-1-cyclopentyl-3-thia-1-azaspiro[4.4]nonane.

Entry 254

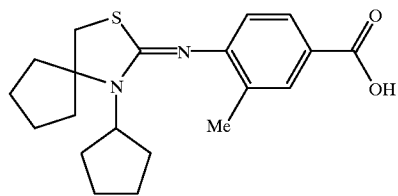

4-Cyano-2-methylaniline was prepared according to Method A1a. The aniline was converted to 4-cyano-2-methylphenyl isothiocyanate according to Method A2b. 1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 4-cyano-2-methylphenyl isothiocyanate according to Method C1e to give 2-(4-cyanophenylphenylimino)-3-thia-1-azaspiro[4.4]nonane. The thiazolidine was reacted with cyclopentyl bromide according to Method D2b to give 2-(4-cyano-2-methylphenylimino)-1-cyclopentyl-3-thia-1-azaspiro[4.4]nonane. The nitrile was hydrolyzed according to Method D9a to afford 2-(4-carboxy-2-methylphenylimino)-1-cyclopentyl-3-thia-1-azaspiro[4.4]nonane.

Entry 255

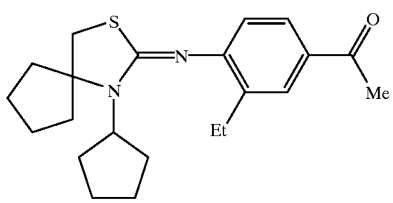

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 4-cyano-2-ethylphenyl isothiocyanate according to Method C1e to give 2-(4-cyano-2-ethylphenylimino)-3-thia-1-azaspiro[4.4]nonane. The thiazolidine was reacted with cyclopentyl bromide according to Method D2b to give 2-(4cyano-2-ethylphenylimino)-1-cyclopentyl-3-thia-1-azaspiro[4.4]nonane. The nitrile was hydrolyzed according to Method D9a to give 2-(4-carboxy-2-ethylphenylimino)-1-2-cyclopentyl-3-thia-1-azaspiro[4.4]nonane. The benzoic acid was converted to 2-(4-acetyl-2-ethylphenylimino)-1-cyclopentyl-3-thia-1-azaspiro[4.4]nonane according to Method D10a.

Entry 256

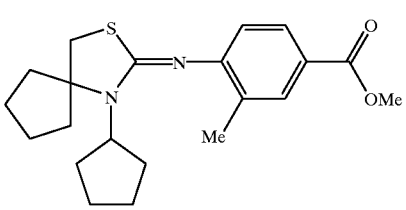

Methyl 4-amino-3-methylbenzoate was converted to 4-methoxycarbonyl-2-methylphenyl isothiocyanate according to Method A2b. 1-Hydroxymethylcyclopentanamine was prepared according to Method B1c. The 2-hydroxyethylamine was sequentially reacted with SOCl₂ and 4-methoxycarbonyl-2-methylphenyl isothiocyanate according to Method C2a to give 2-(4-methoxycarbonyl-2-methylphenylimino)-3-thia-1-azaspiro[4.4]nonane. The thiazolidine was reacted with cyclopentyl bromide according to Method D2h to give 2-(4-methoxycarbonyl-2-methylphenylimino)-1-cyclopentyl-3-thia-1-azaspiro[4.4]nonane.

Entry 257

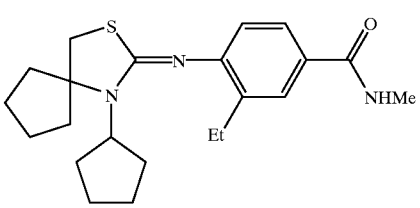

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 4-cyano-2-ethylphenyl isothiocyanate according to Method C1e to give 2-(4-cyano-2-ethylphenylimino)-3-thia-1-azaspiro[4.4]nonane. The thiazolidine was reacted with cyclopentyl bromide according to Method D2b to give 2-(4-cyano-2-ethylphenylimino)-1-cyclopentyl-1-thia-1-azaspiro[4.4]nonane. The nitrile was hydrolyzed according to Method D9a to give 2-(4-carboxy-2-ethylphenylimino)-1-2-cyclopentyl-3-thia-1-azaspiro[4.4] nonane. The benzoic acid was reacted with methylamine according to Method D6b to afford 2-(4-(N-methylcarbamoly)-2-ethylphenylimino)-1-cyclopentyl-3-thia-1-azaspiro[4.4]nonane.

Entry 258

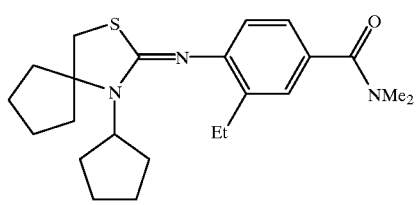

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 4-cyano-2-ethylphenyl isothiocyanate according to Method C1e to give 2-(4-cyano-2-ethylphenylimino)-3-thia-1-azaspiro[4.4]nonane. The thiazolidine was reacted with cyclopentyl bromide according to Method D2b to give 2-(4-cyano-2-ethylphenylimino)-1-cyclopentyl-3-thia-1-azaspiro[4.4]nonane. The nitrile was hydrolyzed according to Method D9a to give 2-(4-carboxy-2-ethylphenylimino)-1-2-cyclopentyl-3-thia-1-azaspiro[4.4] nonane. The benzoic acid was reacted with dimethylamine according to Method D6b to afford 2-(4-(N,N-dimethylcarbamoly)-2-ethylphenylimino)-1-cyclopentyl-3-thia-1-azaspiro[4.4]nonane.

Entry 259

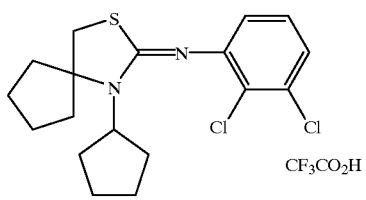

CF₃CO₂H 2,3-Dichloroaniline was converted to the 2,3-dichloroformanilide according to Method A3a, Step 1. The formanilide was converted to 2,3-dichlorophenyl isocyanide dichloride according to Method A3a, Step 2. 1-Hydroxymethylcyclopentanamine HCl salt was synthesized according to Method B1c. The 2-hydroxyethylamine was converted to 13-aza-6-oxadispiro[4.2.4.1]tridecane according to Method B4d, Step 1. The oxazolidine was reductively opened according to Method B4d, Step 2 to give 1-(cyclopentylamino)-1-(hydroxymethyl)cyclopentane. The substituted 2-hydroxyethylamine was converted to 1-(cyclopentylamino)-1-(acetylthiomethyl)cyclopentane according to Method C6c, Step 1. The thioacetate was hydrolyzed according to Method C6c, Step 2 to give 1-(cyclopentylamino)-1-(thiomethyl)cyclopentane. The 2-thioethylamine was reacted with 2,3-dichlorophenyl isocyanide dichloride according to Method C6c to afford 2-(2,3-dichlorophenylimino)-1-cyclopentyl-3-thia-1-azaspiro[4.4]nonane.

Entry 260

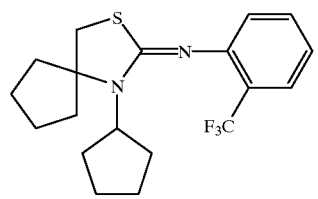

2-(Trifluoromethyl)aniline was converted to the 2-(trifluoromethyl)formanilide according to Method A3a, Step 1. The formanilide was converted to 2-(trifluoromethyl)phenyl isocyanide dichloride according to Method A3a, Step 2. 1-Hydroxymethylcyclopentanamine HCl salt was synthesized according to Method B1c. The 2-hydroxyethylamine was converted to 13-aza-6-oxadispiro [4.2.4.1]tridecane according to Method B4d, Step 1. The oxazolidine was reductively opened according to Method B4d, Step 2 to give 1-(cyclopentylamino)-1-(hydroxymethyl)cyclopentane. The substituted 2-hydroxyethylamine was converted to 1-(cyclopentylamino)-1-(thioacetylmethyl)cyclopentane according to Method C6c, Step 1. The thioacetate was hydrolyzed according to Method C6c, Step 2 to give 1-(cyclopentylamino)-1-(thiomethyl)cyclopentane. The 2-thioethylamine was reacted with 2-(trifluoromethyl) phenyl isocyanide dichloride according to Method C6c to afford 2-(2-(trifluoromethyl)phenylimino)-1-cyclopentyl-3-thia-1-azaspiro[4.4]nonane.

Entry 261

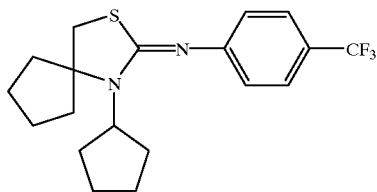

4-(Trifluoromethyl)aniline was converted to the 4-(trifluoromethyl)formanilide according to Method A3a, Step 1. The formanilide was converted to 4-(trifluoromethyl)phenyl isocyanide dichloride according to Method A3a, Step 2. 1-Hydroxymethylcyclopentanamine HCl salt was synthesized according to Method B1c. The 2-hydroxyethylamine was converted to 13-aza-6-oxadispiro [4.2.4. 1]tridecane according to Method B4d, Step 1. The oxazolidine was reductively opened according to Method B4d, Step 2 to give 1-(cyclopentylamino)-1-(hydroxymethyl)cyclopentane. The substituted 2-hydroxyethylamine was converted to 1-(cyclopentylamino)-1-(thioacetylmethyl)cyclopentane according to Method C6c, Step 1. The thioacetate was hydrolyzed according to Method C6c, Step 2 to give 1-(cyclopentylamino)-1-(thiomethyl)cyclopentane. The 2-thioethylamine was reacted with 4-(trifluoromethyl) phenyl isocyanide dichloride according to Method C6c to afford 2-(4-(trifluoromethyl)phenylimino)-1-cyclopentyl-3-thia-1-azaspiro[4.4]nonane.

Entry 262

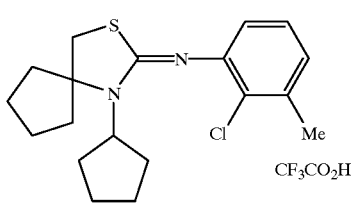

2-Chloro-3-methylaniline was converted to the 2-chloro-3-methylformanilide according to Method A3a, Step 1. The formanilide was converted to 2-chloro-3-methylphenyl isocyanide dichloride according to Method A3a, Step 2. 1-Hydroxymethylcyclopentanamine HCl salt was synthesized according to Method B1c. The 2-hydroxyethylamine was converted to 13-aza-6-oxadispiro[4.2.4.I]tridecane according to Method B4d, Step 1. The oxazolidine was reductively opened according to Method B4d, Step 2 to give 1-(cyclopentylamino)-1-(hydroxymethyl)cyclopentane. The substituted 2-hydroxyethylamine was converted to 1-(cyclopentylamino)-1-(thioacetylmethyl)cyclopentane according to Method C6c, Step 1. The thioacetate was hydrolyzed according to Method C6c, Step 2 to give 1-(cyclopentylamino)-1-(thiomethyl)cyclopentane. The 2-thioethylamine was reacted with 2-chloro-3-methylphenyl isocyanide dichloride according to Method C6c to afford 2-(2-chloro-3-methylphenylimino)-1-cyclopentyl-3-thia-1-azaspiro[4.4]nonane.

Entry 263

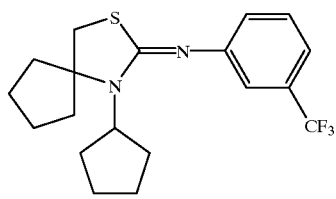

3-(Trifluoromethyl)aniline was converted to the 3-(trifluoromethyl)formanilide according to Method A3a, Step 1. The formanilide was converted to 3-(trifluoromethyl)phenyl isocyanide dichloride according to Method A3a, Step 2. 1-Hydroxymethylcyclopentanamine HCl salt was synthesized according to Method B1c. The 2-hydroxyethylamine was converted to 13-aza-6-oxadispiro[4.2.4.I]tridecane according to Method B4d, Step 1. The oxazolidine was reductively opened according to Method B4d, Step 2 to give 1-(cyclopentylamino)-1-(hydroxymethyl)cyclopentane. The substituted 2-hydroxyethylamine was converted to 1-(cyclopentylamino)-1-(thioacetylmethyl)cyclopentane according to Method C6c, Step 1. The thioacetate was hydrolyzed according to Method C6c, Step 2 to give 1-(cyclopentylamino)-1-(thiomethyl)cyclopentane. The 2-thioethylamine was reacted with 3-(trifluoromethyl)phenyl isocyanide dichloride according to Method C6c to afford 2-(3-(trifluoromethyl)phenylimino)-1-cyclopentyl-3-thia-1-azaspiro[4.4]nonane.

Entry 265

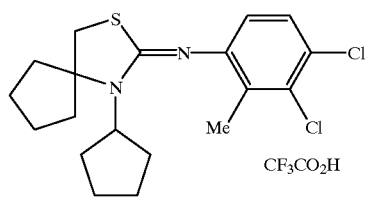

3-Chloro-2-methylaniline was converted to the 3-chloro-2-methylformanilide according to Method A3a, Step 1. The formanilide was converted to 3-chloro-2-methylphenyl isocyanide dichloride according to Method A3a, Step 2. 1-Hydroxymethylcyclopentanamine HCl salt was synthesized according to Method B1c. The 2-hydroxyethylamine was converted to 13-aza-6-oxadispiro[4.2.4. 1]tridecane according to Method B4d, Step 1. The oxazolidine was reductively opened according to Method B4d, Step 2 to give 1-(cyclopentylamino)-1-(hydroxymethyl)cyclopentane. The substituted 2-hydroxyethylamine was converted to 1-(cyclopentylamino)-1-(thioacetylmethyl)cyclopentane according to Method C6c, Step 1. The thioacetate was hydrolyzed according to Method C6c, Step 2 to give 1-(cyclopentylamino)-1-(thiomethyl)cyclopentane. The 2-thioethylamine was reacted with 3-chloro-2-methylphenyl isocyanide dichloride according to Method C6c to afford 2-(3-chloro-2-methylphenylimino)-1-cyclopentyl-3-thia-1-azaspiro[4.4]nonane.

Entry 265

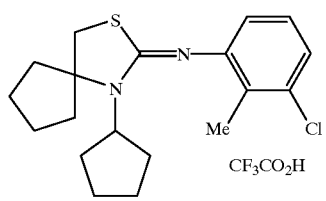

2,3-Dichloro-4-methylaniline was converted to the 2,3-dichloro-4-methylformanilide according to Method A3a, Step 1. The formanilide was converted to 2,3-dichloro-4-methylphenyl isocyanide dichloride according to Method A3a, Step 2. 1-Hydroxymethylcyclopentanamine HCl salt was synthesized according to Method B1c. The 2-hydroxyethylamine was converted to 13-aza-6-oxadispiro [4.2.4.1]tridecane according to Method B4d, Step 1. The oxazolidine was reductively opened according to Method B4d, Step 2 to give 1-(cyclopentylamino)-1-(hydroxymethyl)cyclopentane. The substituted 2-hydroxyethylamine was converted to 1-(cyclopentylamino)-1-(thioacetylmethyl)cyclopentane according to Method C6c, Step 1. The thioacetate was hydrolyzed according to Method C6c, Step 2 to give 1-(cyclopentylamino)-1-(thiomethyl)cyclopentane. The 2-thioethylamine was reacted with 2,3-dichloro-4-methylphenyl isocyanide dichloride according to Method C6c to afford 2-(2,3-dichloro-4-methylphenylimino)-1-cyclopentyl-3-thia-1-azaspiro[4.4]nonane.

Entry 266

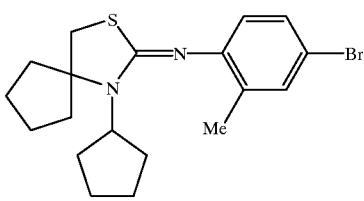

1-Hydroxymethylcyclopentanamine was prepared according to Method B1c. The 2-hydroxyethylamine was sequentially reacted with SOCl$_2$ and 4-bromo-2-methylphenyl isothiocyanate according to Method C2a to give 2-(4-bromo-2-methylphenylimino)-3-thia-1-azaspiro[4.4]nonane. The thiazolidine was reacted with cyclopentyl bromide according to Method1 D2b to give 2-(4-bromo-2-methylphenylimino)-1-cyclopentyl-3-thia-1-azaspiro[4.4]nonane.

Entry 267

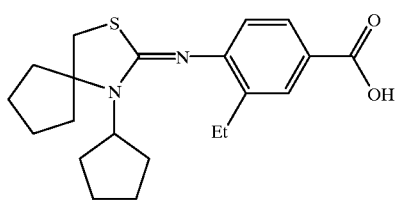

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 4-cyano-2-ethylphenyl isothiocyanate according to Method C1e to give 2-(4-cyano-2-ethylphenylimino)-3-thia-1-azaspiro[4.4]nonane. The thiazolidine was reacted with cyclopentyl bromide according to Method D2b to give 2-(4-cyano-2-ethylphenylimino)-1-cyclopentyl-3-thia-1-azaspiro[4.4]nonane. The nitrile was reduced according to Method D11a to give 2-(4-formyl-2-ethylphenylimino)-1-cyclopentyl-3-thia-1-azaspiro[4.4]nonane.

Entry 268

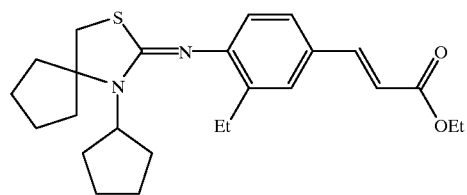

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 4-cyano-2-ethylphenyl isothiocyanate according to Method C1e to give 2-(4-cyano-2-ethylphenylimino)-3-thia-1-azaspiro[4.4]nonane. The thiazolidine was reacted with cyclopentyl bromide according to Method D2b to give 2-(4-cyano-2-ethylphenylimino)-1-cyclopentyl-3-thia-1-azaspiro[4.4]nonane. The nitrile was reduced according to Method D11a to give 2-(4-formyl-2-ethylphenylimino)-1-cyclopentyl-3-thia-1-azaspiro[4.4]nonane. The aldehyde was reacted with triethyl phosphonoacetate according to Method D12a according to afford 2-(2-ethyl-4-((1E)-2-ethoxycarbonylvinyl)phenylimino)-1-cyclopentyl-3-thia-1-azaspiro[4.4]nonane.

Entry 269

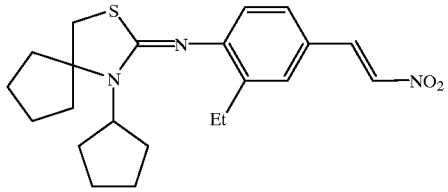

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 4-cyano-2-ethylphenyl isothiocyanate according to Method C1e to give 2-(4-cyano-2-ethylphenylimino)-3-thia-1-azaspiro[4.4]nonane. The thiazolidine was reacted with cyclopentyl bromide according to Method D2b to give 2-(4-cyano-2-ethylphenylimino)-1-cyclopentyl-3-thia-1-azaspiro[4.4]nonane. The nitrile was reduced according to Method D11a to give 2-(4-formyl-2-ethylphenylimino)-1-cyclopentyl-3-thia-1-azaspiro[4.4]nonane. The aldehyde was reacted with nitromethane according to Method D12b according to afford 2-(2-ethyl-4-((1E)-2-nitrovinyl)phenylimino)-1-cyclopentyl-3-thia-1-azaspiro[4.4]nonane.

Entry 270

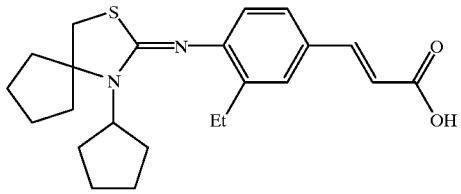

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 4-cyano-2-ethylphenyl isothiocyanate according to Method C1e to give 2-(4-cyano-2-ethylphenylimino)-3-thia-1-azaspiro[4.4]nonane. The thiazolidine was reacted with cyclopentyl bromide according to Method D2b to give 2-(4-cyano-2-ethylphenylimino)-1-cyclopentyl-3-thia-1-azaspiro[4.4]nonane. The nitrile was reduced according to Method D11a to give 2-(4-formyl-2-ethylphenylimino)-1-cyclopentyl-3-thia-1-azaspiro[4.4]nonane. The aldehyde was reacted with triethyl phosphonoacetate according to Method D12a according to afford 2-(2-ethyl-4-((1E)-2-ethoxycarbonylvinyl)phenylimino)-1-cyclopentyl-3-thia-1-azaspiro[4.4]nonane. The ester was saponified according to Method D6a to afford 2-(2-ethyl-4-((1E)-2-carboxyvinyl)phenylimino)-1-cyclopentyl-3-thia-1-azaspiro[4.4]nonane.

Entry 271

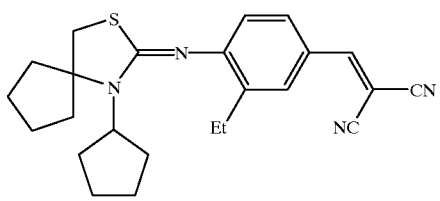

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 4-cyano-2-ethylphenyl isothiocyanate according to Method C1e to give 2-(4-cyano-2-ethylphenylimino)-3-thia-1-azaspiro[4.4]nonane. The thiazolidine was reacted with cyclopentyl bromide according to Method D2b to give 2-(4-cyano-2-ethylphenylimino)-1-cyclopentyl-3-thia-1-azaspiro[4.4]nonane. The nitrile was reduced according to Method D11a to give 2-(4-formyl-2-ethylphenylimino)-1-cyclopentyl-3-thia-1-azaspiro[4.4]nonane. The aldehyde was reacted with malononitrile according to Method D12c according to afford 2-(2-ethyl-4-(2,2-dicyanovinyl)phenylimino)-1-cyclopentyl-3-thia-1-azaspiro[4.4]nonane.

Entry 272

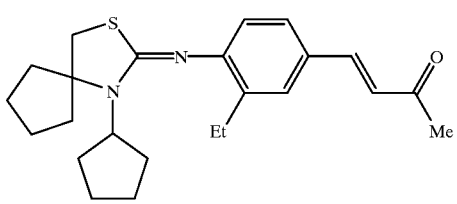

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 4-cyano-2-ethylphenyl isothiocyanate according to Method C1e to give 2-(4-cyano-2-ethylphenylimino)-3-thia-1-azaspiro[4.4]nonane. The thiazolidine was reacted with cyclopentyl bromide according to Method D2b to give 2-(4-cyano-2-ethylphenylimino)-1-cyclopentyl-3-thia-1-azaspiro[4.4]nonane. The nitrile was reduced according to Method D11a to give 2-(4-formyl-2-ethylphenylimino)-1-cyclopentyl-3-thia-1-azaspiro[4.4]nonane. The aldehyde was reacted with diethyl (2-oxopropyl)phosphonate according to Method D12a according to afford 2-(2-ethyl-4-((1E)-2-acetylvinyl)phenylimino)-1-cyclopentyl-3-thia-1-azaspiro[4.4]nonane.

Entry 273

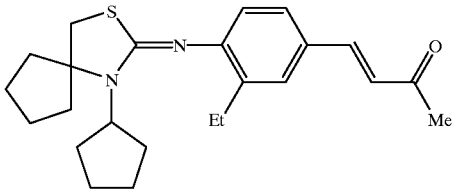

1-Hydroxymethylcyclopentanamine was prepared according to Method B1c. The 2-hydroxyethylamine was converted to 1-chloromethylcyclopentanamine HCl salt according to Method B7e. 1-Chloromethylcyclopentanamine HCl salt was reacted with 4-cyano-2-ethylphenyl isothiocyanate according to Method C1e to give 2-(4-cyano-2-ethylphenylimino)-3-thia-1-azaspiro[4.4]nonane. The thiazolidine was reacted with cyclopentyl bromide according to Method D2b to give 2-(4-cyano-2-ethylphenylimino)-1-cyclopentyl-3-thia-1-azaspiro[4.4]nonane. The nitrile was reduced according to Method D11a to give 2-(4-formyl-2-ethylphenylimino)-1-cyclopentyl-3-thia-1-azaspiro[4.4]nonane. The aldehyde was reacted with acetonitrile according to Method D12d according to afford 2-(2-ethyl-4-((1E)-2-cyanovinyl)phenylimino)-1-cyclopentyl-3-thia-1-azaspiro[4.4]nonane.

Entry 274

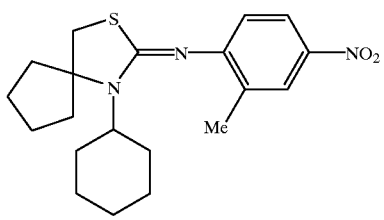

1-Hydroxymethylcyclopentanamine was prepared according to Method B1c. The 2-hydroxyethylamine was sequentially reacted with $SOCl_2$ and 2-methyl-4-nitrophenyl isothiocyanate according to Method C2a to give 2-(2-methyl-4-nitrophenylimino)-3-thia-1-azaspiro[4.4]nonane. The thiazolidine was reacted with cyclohexyl bromide according to Method D2e to give 2-(2-methyl-4-nitrophenylimino)-1-cyclohexyl-3-thia-1-azaspiro[4.4]nonane.

Entry 275

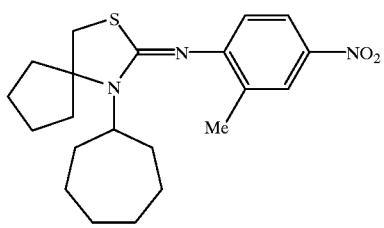

1-Hydroxymethylcyclopentanamine was prepared according to Method B1c. The 2-hydroxyethylamine was sequentially reacted with $SOCl_2$ and 2-methyl-4-nitrophenyl isothiocyanate according to Method C2a to give 2-(2-methyl-4-nitrophenylimino)-3-thia-1-azaspiro[4.4]nonane. The thiazolidine was reacted with cycloheptyl bromide according to Method D2e to give 2-(2-methyl-4-nitrophenylimino)-1-cycloheptyl-3-thia-1-azaspiro [4.4] nonane.

Entry 276

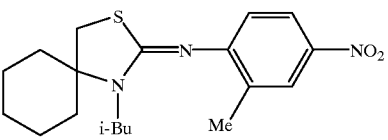

1-Amninocyclohexane-1-carboxylic acid was protected as the benzyloxycarbonylamine according to Method B1a, Step 1. 1-(Benzyloxycarbonylamino)cyclohexane-1-carboxylic acid was reduced to 1-(benzyloxycarbonylamino)-1-(hydroxymethyl)cyclohexane according to Method B1a, Step 2. The carbamate was deprotected according to Method B1a, Step 3 to give 1-amino-1-(hydroxymethyl)cyclohexane. The 2-hydroxyethylamine was sequentially treated with SOCl$_2$ and 2-methyl-4-nitrophenyl isothiocyanate according to Method C2a to give 2-(2-methyl-4-nitrophenylimino)-3-thia-1-azaspiro[4.5]decane. The thiazolidine was alkylated with isobutyl bromide according to Method D2b to afford 2-(2-methyl-4-nitrophenylimino)-1-isobutyl-3-thia-1-azaspiro[4.5]decane.

Entry 277

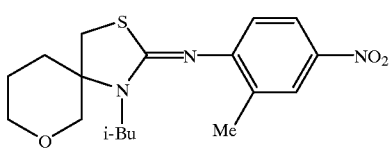

2-Methyl-4-nitroaniline was converted to the 2-methyl-4-nitroformanilide according to Method A3a, Step 1. The formanilide was converted to 2-methyl-4-nitrophenyl isocyanide dichloride according to Method A3a, Step 2. 3-Aminotetrahydro-2H-pyran-3-carboxylic acid was converted to the methyl ester according to Method B1b, Step 1. Methyl 3-aminotetrahydro-2H-pyran-3-carboxylate was reduced to 3-amino-3-(hydroxymethyl)tetrahydro-2H-pyran according to Method B1b, Step 2. The 2-hydroxyethylamine was reacted with isobutyraldehyde according to Method B4c, Step 1 to afford 2-isopropyl-1-aza-3,7-dioxaspiro[4.5]decane. The oxazolidine was reduced to 3-isobutylamino-3-(hydroxymethyl)tetrahydro-2H-pyran. The substituted 2-hydroxyethylamine was converted to 3-isobutylamino-3-(acetylthiomethyl)tetrahydro-2H-pyran according to Method C6c, Step 1. The thioacetate was saponified according to Method C6c, Step 2 to give 3-isobutylamino-3-(thiomethyl)tetrahydro-2H-pyran. The 2-thioethylamine was reacted with 2-methyl-4-nitrophenyl isocyanide dichloride to afford 2-(2-methyl-4-nitrophenylimino-1-isobutyl-1-aza-7-oxa-3-thiaspiro[4.5]decane.

Entry 278

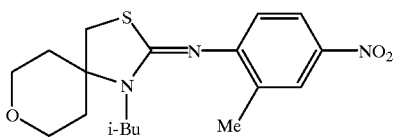

2-Methyl-4-nitroaniline was converted to the 2-methyl-4-nitroformanilide according to Method A3a, Step 1. The formanilide was converted to 2-methyl-4-nitrophenyl isocyanide dichloride according to Method A3a, Step 2. 4-Aminotetrahydro-2H-pyran4-carboxylic acid was converted to the methyl ester according to Method B1b, Step 1. Methyl 4-aminotetrahydro-2H-pyran-4-carboxylate was reduced to 4-amino-4-(hydroxymethyl)tetrahydro-2H-pyran according to Method B1b, Step 2. The 2-hydroxyethylamine was reacted with isobutyraldehyde according to Method B4c, Step 1 to afford 2-isopropyl-1-aza-3,8-dioxaspiro[4.5]decane. The oxazolidine was reduced to 4-isobutylamino-4-(hydroxymethyl)tetrahydro-2H-pyran. The substituted 2-hydroxyethylamine was converted to 4-isobutylamino-4-(acetylthiomethyl)tetrahydro-2H-pyran according to Method C6c, Step 1. The thioacetate was saponified according to Method C6c, Step 2 to give 4-isobutylamino-4-(thiomethyl)tetrahydro-2H-pyran. The 2-thioethylamine was reacted with 2-methyl-4-nitrophenyl isocyanide dichloride to afford 2-(2-methyl-4-nitrophenylimino-1-isobutyl-1-aza-8-oxa-3-thiaspiro[4.5]decane.

Entry 279

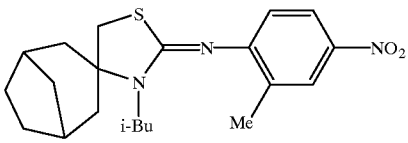

2-Amino-2-norbornane-1-carboxylic acid as a mixture of isomers was converted to the N-benzyloxycarbonyl analogue according to Method B1a, Step 1. 1-(Benzyloxycarbonylamino)-2-norbornane-1-carboxylic acid was reduced to 1-(benzyloxycarbonylamino)-1-(hydroxymethyl)-2-norbornane according to Method B1a, Step 2. The carbamate was deprotected according to Method B1a, Step 3 to give 1-amino-1-(hydroxymethyl)-2-norbornane. The 2-hydroxyethylamine was alkylated with isobutyl bromide according to Method B2a to give N-isobutyl-1-amino-1-(hydroxymethyl)-2-norbornane. The alkylated 2-hydroxyethylamine was treated with SOCl$_2$ according to Method B7a to give N-isobutyl-2-chloroethylamine HCl salt. The chloroethylamine was treated with 2-methyl-4-nitrophenyl isothyiocyanate according to Method C1a to afford 2-(2-methyl-4-nitrophenylimino)-3-isobutylspiro[1,3-thiazolidine-4,3'-bicyclo[3.2.1]octane].

Entry 280

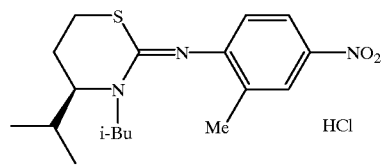

N-(tert-Butoxycarbonyl)-(L)-valine was converted to (S)-3-(tert-butoxycarbonylamino)-1-diazo-4-methylpentan-2-one according to Method B6a, Step 1. The diazo compound was converted to methyl (R)-3-(tert-butoxycarbonylamino)-4-methylpentanoate according to Method B6a, Step 2. The ester was reduced according to Method B6a, Step 3 to give (R)-3-(tert- butoxycarbonylamino)-4-methylpentan-1-ol. The carbamate was deprotected and converted to (R)-3-amino-1-chloro-4-methylpentane according to Method B7e. The 3-chloropropylamine was treated with 2-methyl-4-nitrophenyl isothiocyanate according to Method C2a to give (4R)-2-(2-methyl-4-nitrophenylimino)-4-isopropyl-1,3-thiazine. The thiazine was alkylated with isobutyl bromide according to Method D2a to afford (4R)-2-(2-methyl-4-nitrophenylimino)-3-isobutyl-4-isopropyl-1,3-thiazine HCl salt.

Entry 281

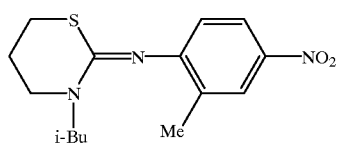

3-Aminopropanol was reacted with butyraldehyde according to Method B9a, Step 1 to afford 2-isopropyltetrahydro,1,3-oxazine. The oxazine was reduced according to Method B9a, Step 2 to give N-isobutyl-3-hydroxypropylamine. The 3-hydroxypropylamine was reacted with SOCl₂ according to Method B9a, Step 3 to give N-isobutyl-3-chloropropylamine HCl salt. The 3-chloropropylamine was reacted with 2-methyl-4-nitrophenyl isothiocyanate according to Method C1a to afford 2-(2-methyl-4-nitrophenylimino)-3-isobutyltetrahydro-1,3-thiazine.

Entry 282

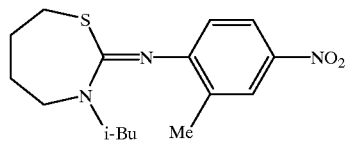

4-Aminobutanol was reacted with butyraldehyde according to Method B9a, Step 1 to afford 2-isopropyltetrahydro,1,3-oxazepine. The 1,3-oxazepine was reduced according to Method B9a, Step 2 to give N-isobutyl-3-hydroxybutylamine. The 3-hydroxybutylamine was reacted with SOCl₂ according to Method B9a, Step 3 to give N-isobutyl-3-chlorobutylamine HCl salt. The 3-chlorobutylamine was reacted with 2-methyl-4-nitrophenyl isothiocyanate according to Method C1a to afford 2-(2-methyl-4-nitrophenylimino)-3-isobutyltetrahydro-1,3-thiazepine.

Entry 283

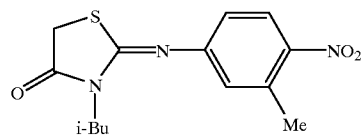

3-Methyl-4-nitrophenyl isothiocyanate was reacted with isobutylamine followed by chloroacetic acid according to Method C8a to afford 2-(1-methyl-4-nitrophenylimino)-3-isobutyl-1,3-thiazolidin-4-one.

Entry 284

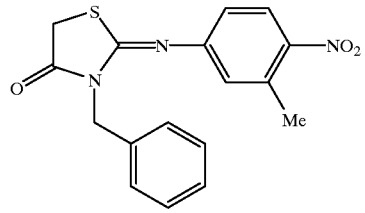

3-Methyl-4-nitrophenyl isothiocyanate was reacted with benzylamine followed by chloroacetic acid according to Method C8a to afford 2-(3-methyl-4-nitrophenylimino)-3-(phenylmethyl)-1,3-thiazolidin-4-one.

Entry 285

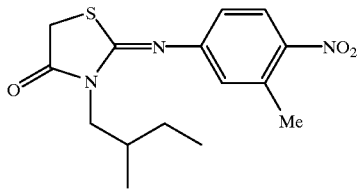

3-Methyl-4-nitrophenyl isothiocyanate was reacted with 2-methyl-1-butylamine followed by chloroacetic acid according to Method C8a to afford 2-(3-methyl-4-nitrophenylimino)-3-(2-methylbutyl)-1,3-thiazolidin-4-one.

Entry 286

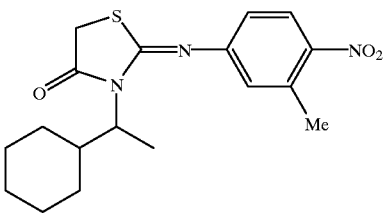

3-Methyl-4-nitrophenyl isothiocyanate was reacted with 1-amino-1-cyclohexylethane followed by chloroacetic acid according to Method C8a to afford 2-(1-methyl-4-nitrophenylimino)-3-(1-cyclohexylethyl)-1,3-thiazolidin4-one.

Entry 287

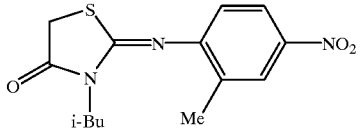

2-Methyl-4-nitrophenyl isothiocyanate was reacted with isobutylamine followed by chloroacetic acid according to Method C8a to afford 2-(2-methyl-4-nitrophenylimino)-3-isobutyl-1,3-thiazolidin4-one.

Entry 288

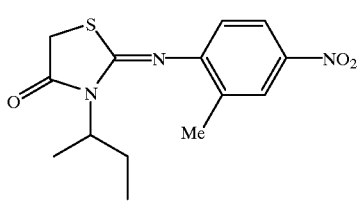

2-Methyl-4-nitrophenyl isothiocyanate was reacted with 2-methyl-1-butylamine followed by chloroacetic acid according to Method C8a to afford 2-(2-methyl-4-nitrophenylimino)-3-(2-methylbutyl)-1,3-thiazolidin4-one.

Entry 289

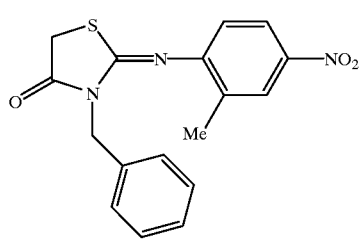

2-Methyl-4-nitrophenyl isothiocyanate was reacted with benzylamine followed by chloroacetic acid according to Method C8a to afford 2-(2-methyl-4-nitrophenylimino)-3-(phenylmethyl)-1,3-thiazolidin-4-one.

Entry 290

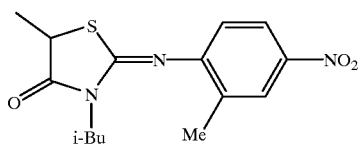

2-Methyl-4-nitrophenyl isothiocyanate was reacted with isobutylamine followed by α-chloropropionic acid according to Method C8a to afford 2-(2-methyl-4-nitrophenylimino)-3-isobutyl-5-methyl-1,3-thiazolidin4-one.

Entry 291

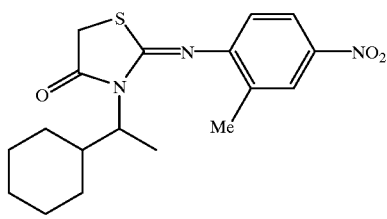

2-Methyl-4-nitrophenyl isothiocyanate was reacted with I-amino-1-cyclohexylethane followed by chloroacetic acid according to Method C8a to afford 2-(2-methyl-4-nitrophenylimino)-3-(1-cyclohexylethyl)-1,3-thiazolidin4-one.

Entry 292

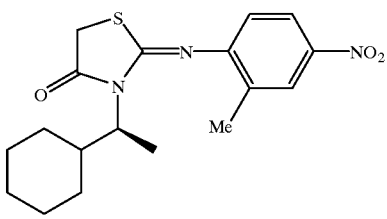

2-Methyl-4-nitrophenyl isothiocyanate was reacted with (1S)-1-amino-1-cyclohexylethane followed by chloroacetic acid according to Method C8a to afford 2-(2-methyl-4-nitrophenylimino)-3-((1S)-1-cyclohexylethyl)-1,3-thiazolidin4-one.

Entry 293

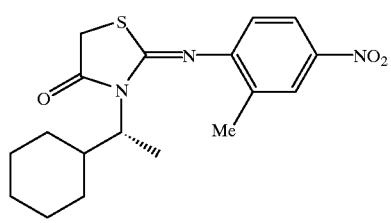

2-Methyl-4-nitrophenyl isothiocyanate was reacted with (1R)-1-amino-1-cyclohexylethane followed by chloroacetic acid according to Method C8a to afford 2-(2-methyl-4-nitrophenylimino)-3-((1R)-1-cyclohexylethyl)-1,3-thiazolidin4-one.

Entry 294

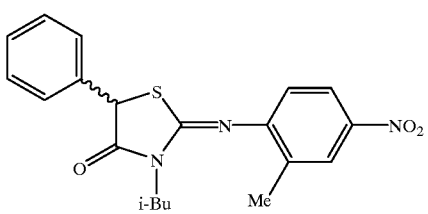

2-Methyl-4-nitrophenyl isothiocyanate was reacted with isobutylamine followed by α-chloro-α-phenylacetic acid according to Method C8a to afford 2-(2-methyl-4-nitrophenylimino)-3-isobutyl-5-phenyl-1,3-thiazolidin4-one.

Entry 295

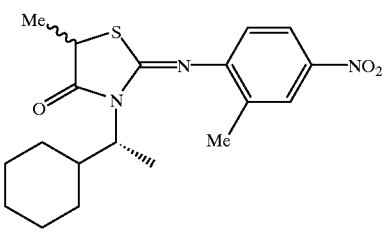

2-Methyl-4-nitrophenyl isothiocyanate was reacted with (1R)-1-amino-1-cyclohexylethane followed by α-chloropropionic acid according to Method C8a to afford 2-(2-methyl-4-nitrophenylimino)-3-((1R)-1-cyclohexylethyl)-5-methyl-1,3-thiazolidin4-one.

Entry 296

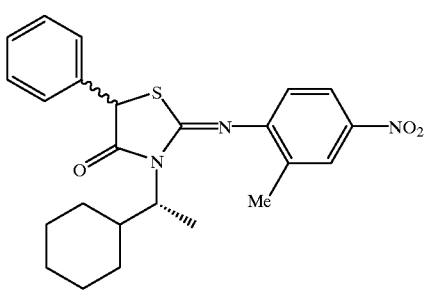

2-Methyl-4-nitrophenyl isothiocyanate was reacted with (1R)-1-amino-1-cyclohexylethane followed by α-chloro-α-phenylacetic acid according to Method C8a to afford 2-(2-methyl-4-nitrophenylimino)-3-((1R)-1-cyclohexylethyl)-5-phenyl-1,3-thiazolidin4-one.

Entry 297

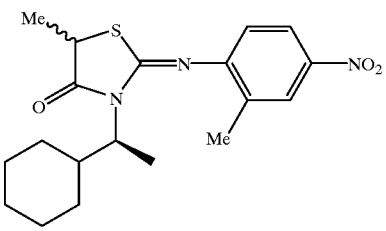

2-Methyl-4-nitrophenyl isothiocyanate was reacted with (1S)-1-amino-1-cyclohexylethane followed by α-chloropropionic acid according to Method C8a to afford 2-(2-methyl-4-nitrophenylimino)-3-((1S)-1-cyclohexylethyl)-5-methyl-1,3-thiazolidin4-one.

Entry 298

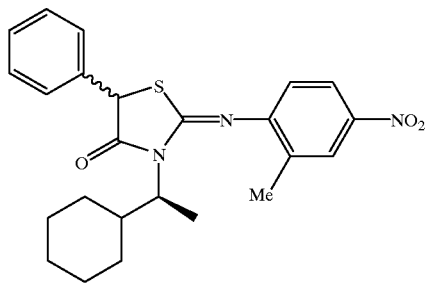

2-Methyl-4-nitrophenyl isothiocyanate was reacted with (1S)-1-amino-1-cyclohexylethane followed by α-chloro-α-phenylacetic acid according to Method C8a to afford 2-(2-methyl-4-nitrophenylimino)-3-((]S)-1-cyclohexylethyl)-5-phenyl-1,3-thiazolidin4-one.

Entry 299

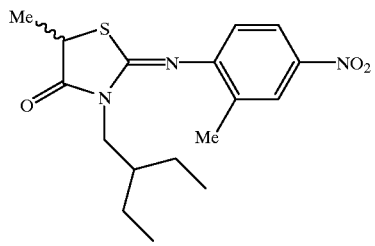

2-Methyl-4-nitrophenyl isothiocyanate was reacted with 2-ethyl-1-butylamine followed by α-chloropropionic acid according to Method C8a to afford 2-(2-methyl-4-nitrophenylimino)-3-(2-ethyl-1-butyl)-5-methyl-1,3-thiazolidin-4-one.

Entry 300

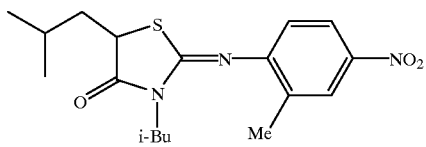

2-Methyl-4-nitrophenyl isothiocyanate was reacted with isobutylamine followed by 2-chloro-4-methylpentanoic acid according to Method C8a to afford 2-(2-methyl-4-nitrophenylimino)-3-isobutyl-5-isobutyl-1,3-thiazolidin-4-one.

Entry 301

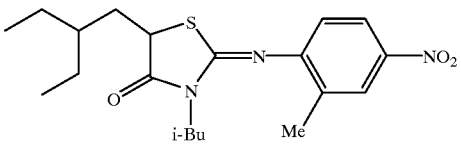

2-Methyl-4-nitrophenyl isothiocyanate was reacted with 2-ethyl-1-butylamine followed by 2-chloro-4-methylpentanoic acid according to Method C8a to afford 2-(2-methyl-4-nitrophenylimino)-3-isobutyl-5-(2-ethyl-1-butyl)-1,3-thiazolidin4-one.

Entry 302

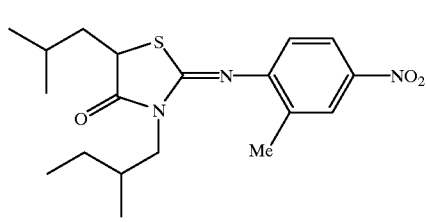

2-Methyl-4-nitrophenyl isothiocyanate was reacted with 2-methylbutylamine followed by 2-chloro-4-methylpentanoic acid according to Method C8a to afford 2-(2-methyl-4-nitrophenylimino)-3-(2-butyl)-5-isobutyl-1,3-thiazolidin4-one.

Entry 303

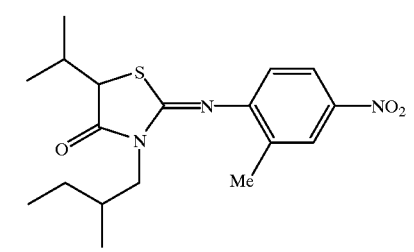

2-Methyl-4-nitrophenyl isothiocyanate was reacted with 2-methylbutylamine followed by 2-chloro-3-methylbutanoic acid according to Method C8a to afford 2-(2-methyl-4-nitrophenylimino)-3-(2-butyl)-5-isopropyl-1,3-thiazolidin-4-one.

Entry 304

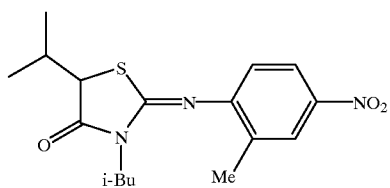

2-Methyl-4-nitrophenyl isothiocyanate was reacted with isobutylamine followed by 2-chloro-3-methylbutanoic acid according to Method C8a to afford 2-(2-methyl-4-nitrophenylimino)-3-isobutyl-5-isopropyl-1,3-thiazolidin-4-one.

Entry 305

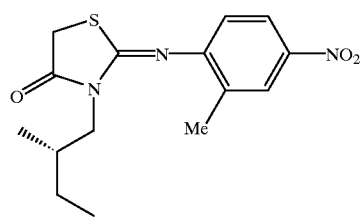

2-Methyl-4-nitrophenyl isothiocyanate was reacted with (2S)-2-methyl-1-butylamine followed by chloroacetic acid according to Method C8a to afford 2-(2-methyl-4-nitrophenylimino)-3-((2S)-2-methyl-1-butyl)-1,3-thiazolidin4-one.

Entry 306

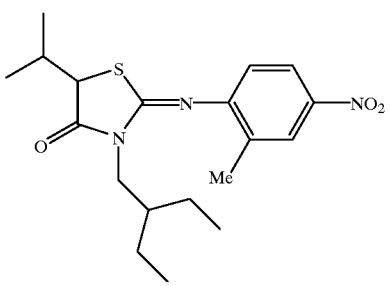

2Methyl-4-nitrophenyl isothiocyanate was reacted with 2-ethyl-1-butylamine followed by 2chloro-3-methylbutanoic acid according to Method C8a to afford 2-(2-methyl-4-nitrophenylimino)-3-(2-ethyl-1-butyl)-5-isopropyl-1,3-thiazolidin-4-one.

Entry 307

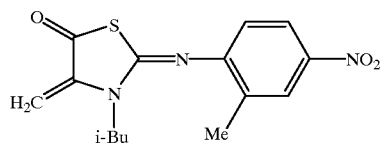

(R)-N-isobutylserine methyl ester HCl salt was prepared from (D)-serine methyl ester as described in Method B3a. The alcohol was reacted with SOCl$_2$ according to Method B7b, followed reaction with 2-methyl-4-nitrophenyl isothiocyanate according to Method C1a to afford 2-(2-methyl-4-nitrophenylimino)-3isobutyl-4-methylene-1-1,3-thiazolidin-5-one.

Entry 308

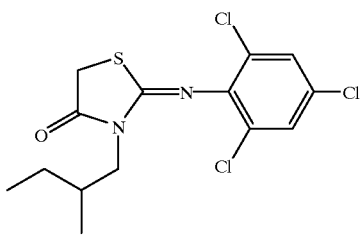

2,4,6-Trichlorophenyl isothiocyanate was reacted with 2-butylamine followed by chloroacetic acid according to Method C8a to afford 2-(2,4,6-trichlorophenylimino)-3-(2-butyl)-1,3-thiazolidin-4-one.

Entry 309

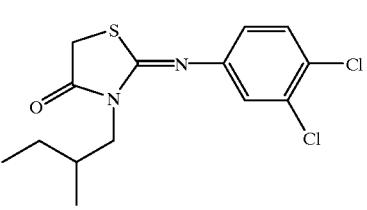

3,4-Dichlorophenyl isothiocyanate was reacted with 2-methylbutylamine followed by chloroacetic acid according to Method C8a to afford 2-(3,4-dichlorophenylimino)-3-(2-butyl)-1,3-thiazolidin4one.

Entry 310

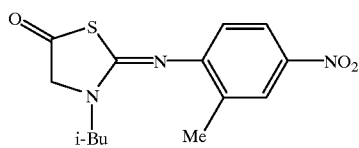

N-Isobutylglycine ethyl ester was reacted with 2-methyl-4-nitrophenyl isothiocyanate according to Method C11a to afford 2-(2-methyl-4-nitrophenylimino)-3-isobutyl-1,3-thiazolidin-5-one.

Entry 311

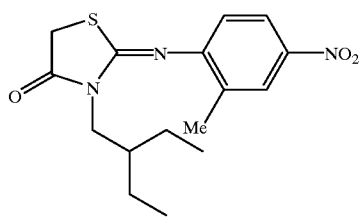

2-Methyl-4-nitrophenyl isothiocyanate was reacted with 2-ethyl-1-butylamine followed by chloroacetic acid according to Method C8a to afford 2-(2-methyl-4-nitrophenylimino)-3-(2-ethyl-1-butyl)-1,3-thiazolidin4-one.

Entry 312

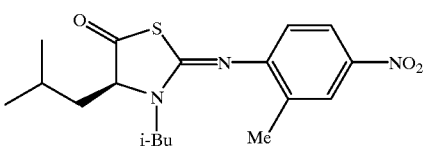

N-Isobutylleucine ethyl ester was reacted with 2-methyl-4-nitrophenyl isothiocyanate according to Method C11a to afford (4S)-2-(2-methyl-4-nitrophenylimino)-3,4-diisobutyl-1,3-thiazolidin-5-one.

Entry 313

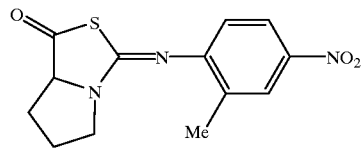

N-Isobutylproline ethyl ester was reacted with 2-methyl-4-nitrophenyl isothiocyanate according to Method C11a to afford 4-(2-methyl-4-nitrophenylimino)-1-oxoperhydro-2-thiapyrrolizine.

Entry 314

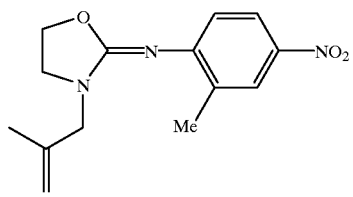

N-(tert-Butoxycarbonyl)glycine tert-butyl ester was reacted with 3-bromo-2-methylpropene according to Method B8b, Step 1 to give N-(tert-butoxycarbonyl)-N-(2-methylprop-2-enyl)glycine tert-butyl ester. The ester was reduced according to Method B8b, Step 2 to give N-(tert-butoxycarbonyl)-N-(2-hydroxyethyl)-1-amino-2-methylprop-2-ene. The alcohol was treated with p-toluenesulfonyl chloride according to Method B8b, Step 3 to give N-(tert-butoxycarbonyl)-N-(2-tosyloxyethyl)-1-amino-2-methylprop-2-ene. The carbamate was deprotected according to Method B8b, Step 4 to give N-(2-tosyloxyethyl)-2-methylprop-2-en-1-ammonium trifluoroacetate. The tosylate was reacted with 2-methyl-4-nitrophenyl isocyanate according to Method C5a to afford 2-(2-methyl-4-nitrophenylimino)-3-(2methylprop-2-enyl)-1,3-oxazolidine.

Entry 312

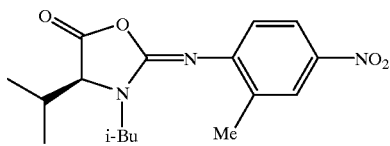

(L)-Valine methyl ester was reduced to (1S)-1-(hydroxymethyl)-2-methylpropylamine according to Method B1b, Step 2. The 2-hydroxyethylamine was reacted with isobutyraldehyde according to Method B4c, Step 1 to afford (4S)-2,4diisopropyl-1,3-oxazolidine. The oxazolidine was reduced according to Method B4c, Step 2 to give (1S)-1-(hydroxymethyl)-N-isobutyl-2-methylpropylamine. The substituted 2-hydroxyethylamine was reacted with SOCl$_2$ according to Method B7b to give (1S)-1-(chloromethyl)-N-isobutyl-2-methylpropylamine. The chloroethylamine was reacted with 2-methyl-4-nitrophenyl isocyanate according to Method C4a to afford (4S)-2-(2-methyl-4-nitrophenylimino)-3-isobutyl-4-isopropyl-1,3-oxazolidine.

Entry 316

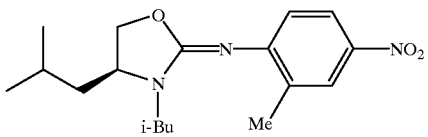

(L)-Leucine methyl ester was reduced to (1S)-1-(hydroxymethyl)-3-methylbutylamine according to Method B1b, Step 2. The 2-hydroxyethylamine was reacted with isobutyraldehyde according to Method B4c, Step 1 to afford (4S)-2-isopropyl-4-isobutyl-1,3-oxazolidine. The oxazolidine was reduced according to Method B4c, Step 2 to give (1S)-1-(hydroxymethyl)-N-isobutyl-3-methylbutylamine. The substituted 2-hydroxyethylamine was reacted with SOCl$_2$ according to Method B7b to give (1S)-1-(chloromethyl)-N-isobutyl-3-methylbutylamine. The chloroethylamine was reacted with 2-methyl-4-nitrophenyl isocyanate according to Method C4a to afford (4S)-2-(2-methyl-4-nitrophenylimino)-3,4-diisobutyl-1,3-oxazolidine.

Entry 317

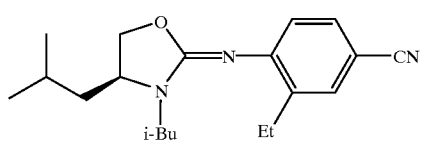

(L)-Leucine methyl ester was reduced to (1S)-1-(hydroxymethyl)-3-methylbutylamine according to Method B1b, Step 2. The 2-hydroxyethylamine was reacted with isobutyraldehyde according to Method B4c, Step 1 to afford (4S)-2-isopropyl-4-isobutyl-1,3-oxazolidine. The oxazolidine was reduced according to Method B4c, Step 2 to give (1S)-1-(hydroxymethyl)-N-isobutyl-3-methylbutylamine. 4-Amino-3-ethylbenzonitrile was converted to 4-cyano-2-ethylformanilide according to Method A3a, Step 1. The formanilide was reacted with SOCl$_2$ and SO$_2$Cl$_2$ according to Method A3a, Step 2 to give 4-cyano-2-ethylphenyl isocyanide dichloride. The substituted 2-hydroxyethylamine was reacted with 4-cyano-2-ethylphenyl isocyanide dichloride according to Method C7b to afford (4S)-2-(4-cyano-2-ethylphenylimino)-3,4-diisobutyl-1,3-oxazolidine.

Entry 318

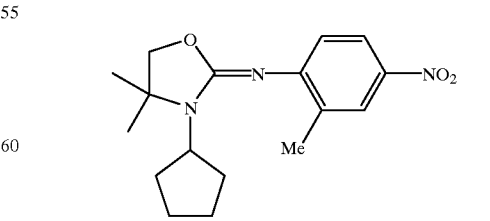

2-Amino-2-methyl-1-propanol was reacted with cyclopentanone according to Method B4b, Step 1 to afford 4-aza-3,3-dimethyl-1-oxaspiro[4.4]nonane. The oxazolidine was reduced according to Method B4b, Step 2 to give N-cyclopentyl-(1,1-dimethyl-2-hydroxyethyl)amine. 2-Methyl-4-nitroaniline was converted to 2-methyl-4-nitroformanilide according to Method A3a, Step 1. The formanilide was reacted with $SOCl_2$ and $SO_2Cl_2$ according to Method A3a, Step 2 to give 2-methyl-4-nitrophenyl isocyanide dichloride. The substituted 2-hydroxyethylamine was reacted with 2-methyl-4-nitrophenyl isocyanide dichloride according to Method C7a to afford 2-(2-methyl-4-nitrophenylimino)-3-cyclopentyl-4,4-dimethyl-1,3-oxazolidine.

Entry 319

2-Amino-2-methyl-1-propanol was reacted with cyclopentanone according to Method B4b, Step 1 to afford 4-aza-3,3-dimethyl-1-oxaspiro[4.4]nonane. The oxazolidine was reduced according to Method B4b, Step 2 to give N-cyclopentyl-(1,1-dimethyl-2-hydroxyethyl)amine. 4-Amino-3-ethylbenzonitrile was converted to 4-cyano-2-ethylformanilide according to Method A3a, Step 1. The formanilide was reacted with $SOCl_2$ and $SO_2Cl_2$ according to Method A3a, Step 2 to give 4-cyano-2-ethylphenyl isocyanide dichloride. The substituted 2-hydroxyethylamine was reacted with 4-cyano-2-ethylphenyl isocyanide dichloride according to Method C7a to afford 2-(4-cyano-2-ethylphenylimino)-3-cyclopentyl-4,4-dimethyl-1,3-oxazolidine.

Entry 320

1-Aminocyclopentanecarboxylic acid was converted to the methyl ester according to Method B1c, Step 1. The ester reduced to 1-hydroxymethylcyclopentanamine according to Method B1c, Step 2. The hydroxyethylamine was reacted with cyclopentanone according to Method B4d, Step 1 to give 6-aza-12-oxadispiro[4.1.4.2]tridecane. The oxazolidine was reduced according to Method B4d, Step 2 to give 1-(cyclopentylamino)-1-(hydroxymethyl)cyclopentane. The substituted 2-hydroxyethylamine was reacted with $SOCl_2$ according to Method B7b to 1-(cyclopentylamino)-1-(chloromethyl)cyclopentane. The 2-chloroethylamine was reacted with 2-methyl-4-nitrophenyl isocyanate according to Method C4a to afford 1-cyclopentyl-2-(2-methyl-4-nitrophenylimino)-3-oxa-1-1-azaspiro[4.4]nonane.

Entry 321

1-Aminocyclopentanecarboxylic acid was converted to the methyl ester according to Method B1c, Step 1. The ester reduced to 1-hydroxymethylcyclopentanamine according to Method B1c, Step 2. The 2-hydroxyethylamine was reacted with cyclobutanone according to Method B4a, Step 1 to give 5-aza-12-oxadispiro[3.1.4.2]dodecane. The oxazolidine was reduced according to Method B4a, Step 2 to give 1-(cyclobutylamino)-1-(hydroxymethyl)cyclopentane. The substituted 2-hydroxyethylamine was reacted with $SOCl_2$ according to Method B7b to 1-(cyclobutylamino)-1-(chloromethyl)cyclopentane. The 2-chloroethylamine was reacted with 2-methyl-4-nitrophenyl isocyanate according to Method C4a to afford 1-cyclobutyl-2-(2-methyl-4-nitrophenylimino)-3-oxa-1-azaspiro[4.4]nonane.

Entry 322

1-Aminocyclopentanecarboxylic acid was converted to the methyl ester according to Method B1c, Step 1. The ester reduced to 1-hydroxymethylcyclopentanamine according to Method B1c, Step 2. The hydroxyethylamine was reacted with cyclohexanone according to Method B4a, Step 1 to give 6-aza-13-oxadispiro[4.1.5.2]tetradecane. The oxazolidine was reduced according to Method B4a, Step 2 to give 1-(cyclohexylamino)-1-(hydroxymethyl)cyclopentane. The substituted 2-hydroxyethylamine was reacted with $SOCl_2$ according to Method B7b to 1-(cyclohexylamino)-1-(chloromethyl)cyclopentane. The 2-chloroethylamine was reacted with 2-methyl-4-nitrophenyl isocyanate according to Method C4a to afford 1-cyclohexyl-2-(2-methyl-4-nitrophenylimino)-3-oxa-1-azaspiro[4.4]nonane.

Entry 323

1-Aminocyclopentanecarboxylic acid was converted to the methyl ester according to Method B1c, Step 1. The ester reduced to 1-hydroxymethylcyclopentanamine according to Method B1c, Step 2. The hydroxyethylamine was reacted with cyclopentanone according to Method B4d, Step 1 to give 6-aza-12-oxadispiro[4.1.4.2]tridecane. The oxazolidine was reduced according to Method B4d, Step 2 to give 1-(cyclopentylamino)-1-(hydroxymethyl)cyclopentane. 4-Amino-3-ethylbenzonitrile was converted to 4-cyano-2-ethylformanilide according to Method A3a, Step 1. The formanilide was reacted with SOCl$_2$ and SO$_2$Cl$_2$ according to Method A3a, Step 2 to give 4-cyano-2-ethylphenyl isocyanide dichloride. The substituted 2-hydroxyethylamine was reacted with 2-methyl-4-nitrophenyl isocyanide dichloride according to Method C7a to afford 1-cyclopentyl-2-(2-methyl-4-nitrophenylimino)-3-oxa-1-azaspiro[4.4]nonane.

Entry 324

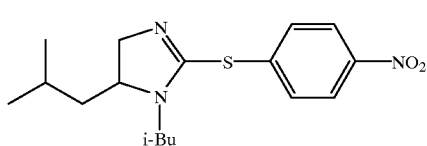

(1S)-1-(Hydroxymethyl)-3-methylbutylamine was made from (L)-leucine methyl ester as described in Method B1b. The 2-hydroxyethylamine was converted to (2S)-4-methyl-2-(isobutylamino)pentanol as described in Method B4c, Steps 1–2. The alcohol was converted to N-(1S)-1-(chloromethyl)-3-methylbutyl)-N-(isobutyl)ammonium chloride as described in Method B7c. 4-Nitrophenyl isothiocyanate was reacted with N-(1S)-1-(chloromethyl)-3-methylbutyl)-N-(isobutyl)ammonium chloride according to Method C1f to give 2-(4-nitrophenylthio)-1,5-diisobutylimidazoline.

Entry 325

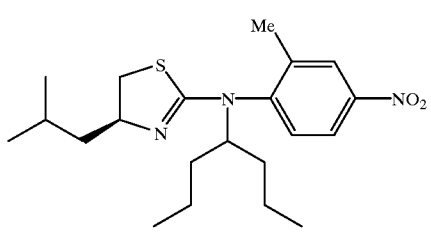

(1S)-1-(Hydroxymethyl)-3-methylbutylamine was made from (L)-leucine methyl ester as described in Method B1b. The 2-hydroxyethylamine was converted to (1S)-1-(chloromethyl)-3-methylbutanammonium chloride as described in Method B7a. 2-Methyl-4-nitrophenyl isothiocyanate was reacted with (1S)-1-(chloromethyl)-3-methylbutanammonium chloride according to Method C1a to give (4S)-2-(2-methyl-4-nitrophenylimino)-4-isobutyl-1,3-thiazolidine. The thiazolidine was reacted with 5-iodoheptane according to Method D2a to give (4S)-2-(N-(4-heptyl)-N-(2-methyl-5-nitrophenyl)amino)-4-isobutyl-1,3-thiazoline.

Entry 326

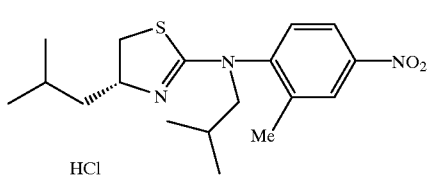

(1R)-1-(Hydroxymethyl)-3-methylbutylamine was made from (D)-leucine methyl ester according to B1b. The 2-hydroxyethylamine was converted to (1R)-1-(chloromethyl)-3-methylbutanammonium chloride as described in Method B7a. 2-Methyl-5-nitrophenyl isothiocyanate was reacted with (1R)-1-(chloromethyl)-3-methylbutanammonium chloride according to Method C1a to give (4R)-2-(2-methyl-5-nitrophenylimino)-4-isobutyl-1,3-thiazolidine. The thiazolidine was reacted with isobutyl bromide according to Method D2a to afford (4R)-2-(N-isobutyl-N-(2-methyl-5-nitrophenyl)amino)-4-isobutyl-1,3-thiazoline HCl salt.

Entry 327

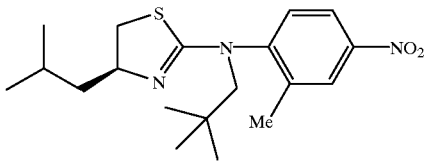

(1S)-1-(Hydroxymethyl)-3-methylbutylamine was made from (L)-leucine methyl ester as described in Method B1b. The 2-hydroxyethylamine was converted to (1S)-1-(chloromethyl)-3-methylbutanammonium chloride as described in Method B7a. 2-Methyl-4-nitrophenyl isothiocyanate was reacted with (1S)-1-(chloromethyl)-3-methylbutanammonium chloride according to Method C1a to give (4S)-2-(2-methyl-4nitrophenylimino)-4-isobutyl-1,3-thiazolidine. The thiazolidine was reacted with neopentyl bromide according to Method D2a to afford (4S)-2-(N-(2,2-dimethylpropyl)-2-methyl-4-nitrophenylamino)-4-isobutyl-1,3-thiazoline.

Entry 328

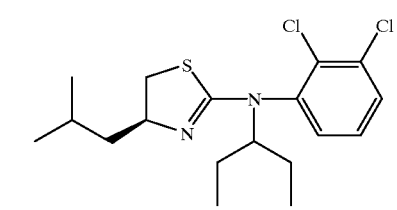

(1S)-1-(Hydroxymethyl)-3-methylbutylamine was made from (L)-leucine methyl ester as described in Method B1b. The 2-hydroxyethylamine was converted to (1S)-1-(chloromethyl)-3-methylbutanammonium chloride as described in Method B7a. 2,3-Dichlorophenyl isothiocyanate was reacted with (1S)-1-(chloromethyl)-3-methylbutanammonium chloride according to Method C1a to give (4S)-2-(2,3-dichlorophenylimino)-4-isobutyl-1,3-thiazolidine. The thiazolidine was reacted with 3-bromopentane according to Method D2a to afford (4S)-2-(N-(3-pentyl)-2-methyl-4-nitrophenylamino)-4-isobutyl-1,3-thiazoline.

TABLES

The compounds listed in Tables 14 below were synthesized according to the methods described above.

TABLE 1

2-Imino-1,3-thiazolidines and Ring Expanded Homologues

| Entry | Compound | mp (° C.) | HPLC (min.) | TLC $R_f$ | TLC Solvent System | Mass Spec. [Source] | Synth. Method |
|---|---|---|---|---|---|---|---|
| 1 | (thiazolidine-NH, =N-2-Me-4-NO$_2$-phenyl) | 90–92 | | 0.36 | 30% EtOAc/hex | 238 (M + H) + [FAB] | C1a |
| 2 | (thiazolidine-N-iBu, =N-4-NO$_2$-phenyl) | | | 0.49 | 20% EtOAc/pentane | 280 (M + H) + [CI] | C1a, D2a |
| 3 | (thiazolidine-N-iBu, =N-2-Me-4-NO$_2$-phenyl) | | | 0.52 | 20% EtOAc/pentane | 294 (M + H) + [CI] | C1a, D2a |
| 4 | (thiazolidine-N-iBu, =N-2,3-diCl-phenyl) | | | 0.78 | 20% EtOAc/pentane | 303 (M + H) + [CI] | C1a, D2a |
| 5 | (thiazolidine-N-iBu, =N-2-MeO-4-NO$_2$-phenyl) | | 11.9 (h) | | | 310 (M + H) + [HPLC ES-MS] | C1d |
| 6 | (thiazolidine-N-iBu, =N-4-CN-phenyl) | | 9.9 (h) | | | 260 (M + H) + [HPLC ES-MS] | C1d |
| 7 | (thiazolidine-N-iBu, =N-2-Me-5-NO$_2$-phenyl, HCl) | | | 0.50 | 20% EtOAc/hex | | C1a, D2a |
| 8 | (thiazolidine-N-iBu, =N-3-Et-4-CN-phenyl) | | 25.0 (h) | | | 288 (M + H) + [HPLC ES-MS] | C1d |
| 9 | (thiazolidine-N-iBu, =N-2-CF$_3$-4-Cl-phenyl) | | 32.0 (h) | | | 337 (M + H) + [HPLC ES-MS] | C1d |

TABLE 1-continued

2-Imino-1,3-thiazolidines and Ring Expanded Homologues

| Entry | Compound | mp (° C.) | HPLC (min.) | TLC $R_f$ | TLC Solvent System | Mass Spec. [Source] | Synth. Method |
|---|---|---|---|---|---|---|---|
| 10 | 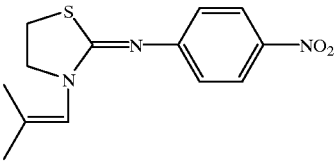 | | | 0.23 | 20% EtOAc/ pentane | 278 (M + H) + [CI] | C1a, D2a, D14a |
| 11 | 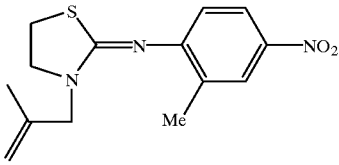 | | | 0.49 | 20% EtOAc/ pentane | 292 (M + H) + [CI] | C1a, D2a |
| 12 | 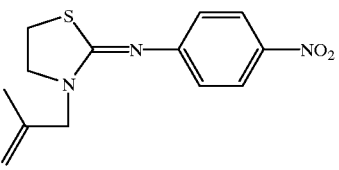 | | | 0.33 | 20% EtOAc/ pentane | 278 (M + H) + [CI] | C1a, D2a |
| 13 | 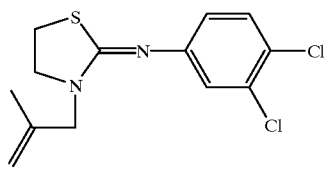 | | | 0.43 | 11% EtOAc/ pentane | 301 (M + H) + [CI] | C1a, D2a |
| 14 | 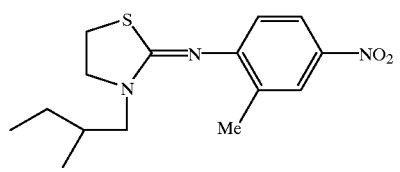 | | | 0.77 | 30% EtOAc/ hex | 308 (M + H) + [FAB] | B2b steps 1–3, B7a, C1a |
| 15 | 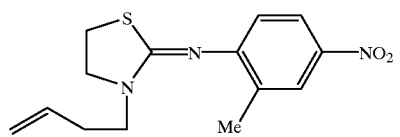 | 69–70 | | 0.78 | 30% EtOAc/ hex | 292 (M + H) + [FAB] | C1a, D2a |
| 16 | 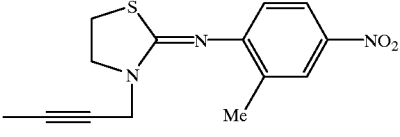 | 108–109 | | 0.78 | 30% EtOAc/ hex | 290 (M + H) + [FAB] | C1a, D2a |
| 17 | 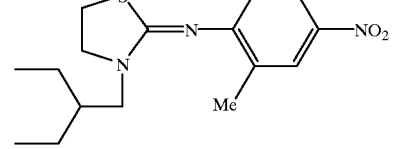 | | | 0.77 | 30% EtOAc/ hex | 322 (M + H) + [FAB] | C1a, D2a |

TABLE 1-continued

2-Imino-1,3-thiazolidines and Ring Expanded Homologues

| Entry | Compound | mp (° C.) | HPLC (min.) | TLC R$_f$ | TLC Solvent System | Mass Spec. [Source] | Synth. Method |
|---|---|---|---|---|---|---|---|
| 18 | | | | 0.77 | 30% EtOAc/hex | 308 (M + H) + [FAB] | C1a, D2a |
| 19 | | | | 0.72 | 40% EtOAc/hex | 364 (M + H) + [FAB] | C1a, D2a |
| 20 | | | | 0.67 | 30% EtOAc/hex | 308 (M + H) + [FAB] | C1a, D2a |
| 21 | | | | 0.71 | 40% EtOAc/hex | 294 (M + H) + [FAB] | B5a, B7a, C1a |
| 22 | | | | 0.71 | 40% EtOAc/hex | 308 (M + H) + [FAB] | B5a, B7a, C1a |
| 23 | | | | 0.72 | 40% EtOAc/hex | 336 (M + H) + [FAB] | C1a, D2a |
| 24 | | | | 0.71 | 40% EtOAc/hex | 348 (M + H) + [FAB] | C1a, D2a |
| 25 | | | | 0.71 | 40% EtOAc/hex | 350 (M + H) + [FAB] | B2b, step 2, C1a, D2a |

TABLE 1-continued

2-Imino-1,3-thiazolidines and Ring Expanded Homologues

| Entry | Compound | mp (° C.) | HPLC (min.) | TLC $R_f$ | TLC Solvent System | Mass Spec. [Source] | Synth. Method |
|---|---|---|---|---|---|---|---|
| 26 | | | | 0.68 | 30% EtOAc/hex | 372 (M + H) + [FAB] | C1a, D2a |
| 28 | | | | 0.74 | 40% EtOAc/hex | 356 (M + H) + [FAB] | C1a, D2a |
| 29 | | | | 0.74 | 40% EtOAc/hex | 312 (M + H) + [FAB] | C1a, D2a |
| 30 | | 129–131 | | | | 276 (M + H) + [FAB] | C1a, D2a |
| 31 | | 112–113 | | | | 356 (M + H) + [FAB] | C1a, D2a |
| 32 | | | | | | 394 (M + H) + [FAB] | C1a, D2a |
| 33 | | | | 0.40 | 40% EtOAc/hex | 238 (M + H) + [FAB] | C1a, D2a |
| 34 | | | | 0.63 | 40% EtOAc/hex | 309 (M+) [EI] | C1a, D2a |

TABLE 1-continued

2-Imino-1,3-thiazolidines and Ring Expanded Homologues

| Entry | Compound | mp (° C.) | HPLC (min.) | TLC $R_f$ | TLC Solvent System | Mass Spec. [Source] | Synth. Method |
|---|---|---|---|---|---|---|---|
| 35 | | | | | | 358 (M + H) + [FAB] | C1a, D2a, D5a |
| 36 | | | | 0.65 | 40% EtOAc/ hex | 336 (M + H) + [FAB] | C1a, D2a |
| 37 | | | | 0.63 | 40% EtOAc/ hex | 308 (M + H) + [FAB] | C1a, D2a |
| 38 | | | | | | 310 (M + H) + [FAB] | C1a, D2a, D5a |
| 39 | | | | | | 338 (M + H) + [FAB] | C1a, D2a, D5a |
| 40 | | | | 0.65 | 40% EtOAc/ hex | 321 (M + H) + [FAB] | C1a, D2a |
| 41 | | | | 0.74 | 40% EtOAc/ hex | 346 (M + H) + [FAB] | C1a, D2a |

TABLE 1-continued
2-Imino-1,3-thiazolidines and Ring Expanded Homologues
| Entry | Compound | mp (° C.) | HPLC (min.) | TLC $R_f$ | TLC Solvent System | Mass Spec. [Source] | Synth. Method |
|---|---|---|---|---|---|---|---|
| 42 | 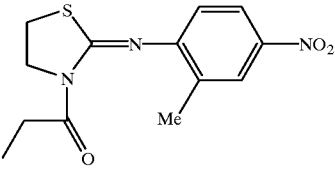 | | | 0.63 | 40% EtOAc/hex | 394 (M + H) + [FAB] | C1a, D2d |
| 43 | 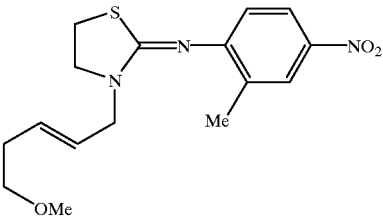 | | | 0.40 | 40% EtOAc/hex | 335 (M + H) + [FAB] | C1a, D2a |
| 44 | 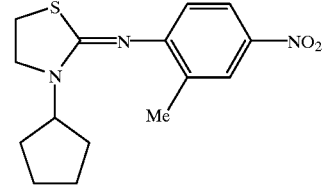 | | 14.9 (f) | | | 306 (M + H) + [HPLC ES-MS] | B4b, B7c, C1d |
| 45 | 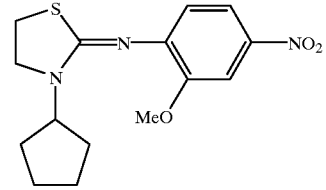 | | 14.4 (h) | | | 322 (M + H) + [HPLC ES-MS] | B4b, B7c, C1d |
| 46 | 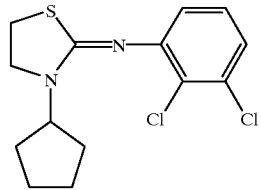 | | 15.6 (f) | | | 315 (M + H) + [HPLC ES-MS] | B4b, B7c, C1d |
| 47 | 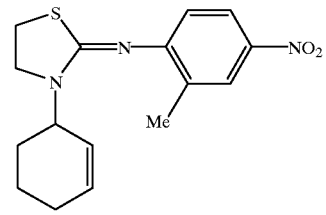 | | | 0.77 | 30% EtOAc/hex | 318 (M + H) + [FAB] | B2b steps 1–3, B7a, C1a |

TABLE 1-continued
2-Imino-1,3-thiazolidines and Ring Expanded Homologues
| Entry | Compound | mp (° C.) | HPLC (min.) | TLC $R_f$ | TLC Solvent System | Mass Spec. [Source] | Synth. Method |
|---|---|---|---|---|---|---|---|
| 48 | 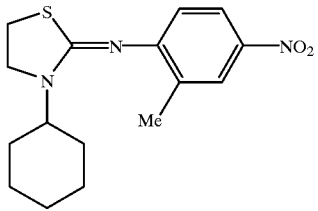 | | | | | 320 (M + H) + [HPLC ES-MS] | B4a, B7c, C1d |
| 49 | 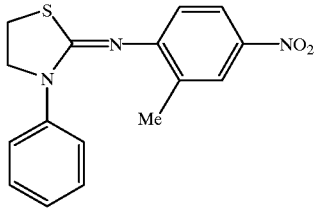 | 119–121 | | 0.37 | 20% EtOAc/ hex | 314 (M + H) + [HPLC ES-MS] | B7a, C1a |
| 50 | 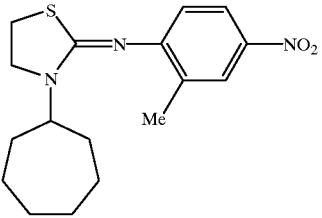 | | 15.4 (h) | | | 334 (M + H) + [HPLC ES-MS] | B2a, B7c, C1d |
| 51 | 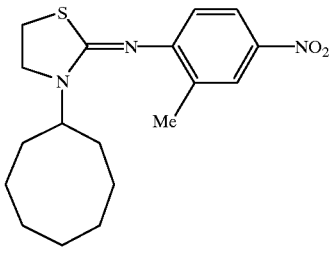 | | 19.1 (h) | | | 348 (M + H) + [HPLC ES-MS] | B2a, B7c, C1d |
| 52 | 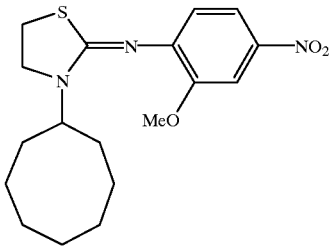 | | 16.9 (h) | | | 364 (M + H) + [HPLC ES-MS] | B2a, B7c, C1d |

TABLE 1-continued

2-Imino-1,3-thiazolidines and Ring Expanded Homologues

| Entry | Compound | mp (° C.) | HPLC (min.) | TLC R$_f$ | TLC Solvent System | Mass Spec. [Source] | Synth. Method |
|---|---|---|---|---|---|---|---|
| 53 | | | 22.1 (h) | | | 357 (M + H) + [HPLC ES-MS] | B2a, B7c, C1d |
| 54 | | | 2.63 (i) | | | 301 (M + H) + [HPLC ES-MS] | B2a, B7c, C1d |
| 55 | | | 2.31 (i) | | | 292 (M + H) + [HPLC ES-MS] | B2a, B7c, C1d |
| 56 | | | 2.78 (i) | | | 301 (M + H) + [HPLC ES-MS] | B2a, B7c, C1d |
| 57 | | | 2.95 (i) | | | 301 (M + H) + [HPLC ES-MS] | B2a, B7c, C1d |
| 58 | | | 3.18 (i) | | | 315 (M + H) + [HPLC ES-MS] | B2a, B7c, C1d |

TABLE 1-continued
2-Imino-1,3-thiazolidines and Ring Expanded Homologues
| Entry | Compound | mp (° C.) | HPLC (min.) | TLC $R_f$ | TLC Solvent System | Mass Spec. [Source] | Synth. Method |
|---|---|---|---|---|---|---|---|
| 59 | 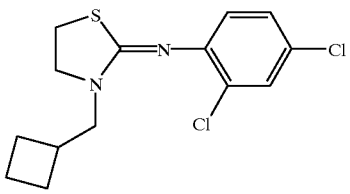 | | 3.29 (i) | | | 315 (M + H) + [HPLC ES-MS] | B2a, B7c, C1d |
| 60 | 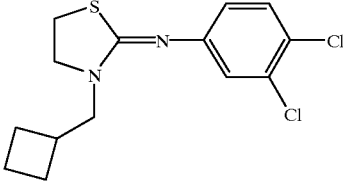 | | 3.48 (i) | | | 315 (M + H) + [HPLC ES-MS] | B2a, B7c, C1d |
| 61 | 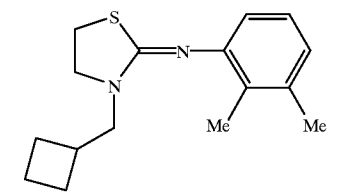 | | 3.18 (i) | | | 275 (M + H) + [HPLC ES-MS] | B2a, B7c, C1d |
| 62 | 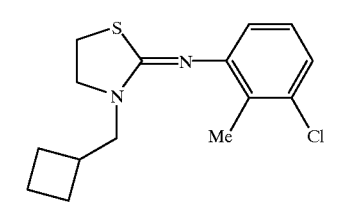 | | 3.23 (i) | | | 295 (M + H) + [HPLC ES-MS] | B2a, B7c, C1d |
| 63 | 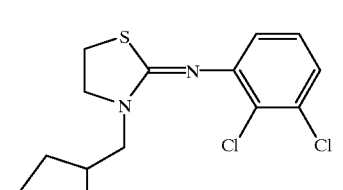 | | 3.99 (i) | | | 329 (M + H) + [HPLC ES-MS] | B2a, B7c, C1d |
| 64 | 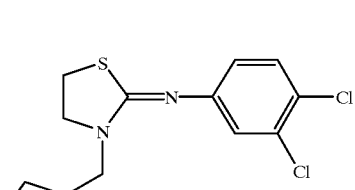 | | 4.13 (i) | | | 329 (M + H) + [HPLC ES-MS] | B2a, B7c, C1d |

TABLE 1-continued
2-Imino-1,3-thiazolidines and Ring Expanded Homologues
| Entry | Compound | mp (° C.) | HPLC (min.) | TLC $R_f$ | TLC Solvent System | Mass Spec. [Source] | Synth. Method |
|---|---|---|---|---|---|---|---|
| 65 | 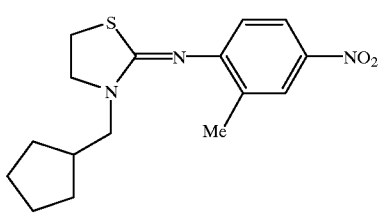 | | 3.60 (i) | | | 320 (M + H) + [HPLC ES-MS] | B2a, B7c, C1d |
| 66 | 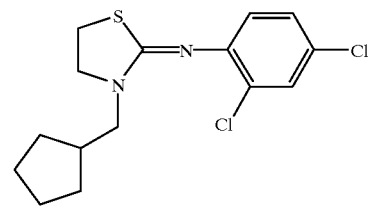 | | 4.08 (i) | | | 329 (M + H) + [HPLC ES-MS] | B2a, B7c, C1d |
| 67 | 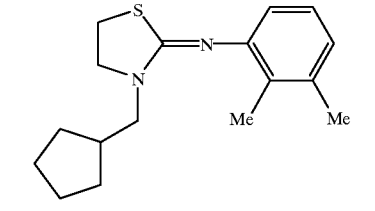 | | 3.99 (i) | | | 289 (M + H) + [HPLC ES-MS] | B2a, B7c, C1d |
| 68 | 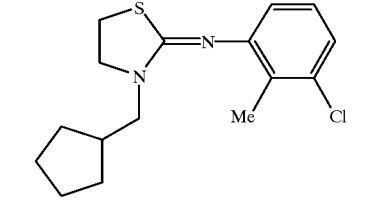 | | 4.05 (i) | | | 309 (M + H) + [HPLC ES-MS] | B2a, B7c, C1d |
| 69 | 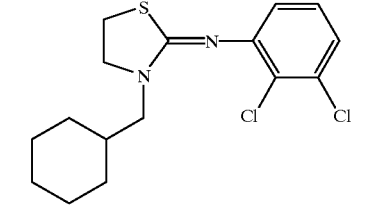 | | 17.0 (f) | | | 343 (M + H) + [HPLC ES-MS] | B2a, B7c, C1d |
| 70 | 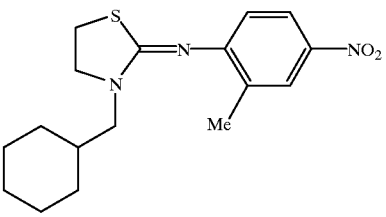 | | 16.7 (f) | | | 334 (M + H) + [HPLC ES-MS] | B2a, B7c, C1d |

TABLE 1-continued

2-Imino-1,3-thiazolidines and Ring Expanded Homologues

| Entry | Compound | mp (° C.) | HPLC (min.) | TLC $R_f$ | TLC Solvent System | Mass Spec. [Source] | Synth. Method |
|---|---|---|---|---|---|---|---|
| 71 | | | 16.3 (f) | | | 350 (M + H) + [HPLC ES-MS] | B2a, B7c, C1d |
| 72 | | 125–126 | | 0.77 | 30% EtOAc/ hex | 348 (M + H) + [FAB] | B5a, B7a, C1a |
| 73 | | | 3.40 (i) | | | 317 (M + H) + [HPLC ES-MS] | B2a, B7c, C1d |
| 74 | | | 3.63 (i) | | | 337 (M + H) + [HPLC ES-MS] | B2a, B7c, C1d |
| 75 | | | 3.68 (i) | | | 337 (M + H) + [HPLC ES-MS] | B2a, B7c, C1d |
| 76 | | | 3.45 (i) | | | 328 (M + H) + [HPLC ES-MS] | B2a, B7c, C1d |
| 77 | | | 3.66 (i) | | | 337 (M + H) + [HPLC ES-MS] | B2a, B7c, C1d |
| 78 | | | 13.9 (g) | | | 356 (M + H) + [HPLC ES-MS] | B2a, B7c, C1d |

TABLE 1-continued

2-Imino-1,3-thiazolidines and Ring Expanded Homologues

| Entry | Compound | mp (° C.) | HPLC (min.) | TLC R_f | TLC Solvent System | Mass Spec. [Source] | Synth. Method |
|---|---|---|---|---|---|---|---|
| 79 | | | 15.3 (g) | | | 362 (M + H) + [HPLC ES-MS] | B2a, B7c, C1d |
| 80 | | | 19.6 (h) | | | 348 (M + H) + [HPLC ES-MS] | B2a, B7c, C1d |
| 81 | | | 18.1 (h) | | | 364 (M + H) + [HPLC ES-MS] | B2a, B7c, C1d |
| 82 | | | 18.7 (h) | | | 357 (M + H) + [HPLC ES-MS] | B2a, B7c, C1d |
| 83 | | | 15.4 (f) | | | 314 (M + H) + [HPLC ES-MS] | B2a, B7c, C1d |
| 84 | | | | 0.68 | 30% EtOAc/ hex | 404 (M + H) + [FAB] | B2b steps 1–3, B7a, C1a |

TABLE 1-continued

2-Imino-1,3-thiazolidines and Ring Expanded Homologues

| Entry | Compound | mp (° C.) | HPLC (min.) | TLC $R_f$ | TLC Solvent System | Mass Spec. [Source] | Synth. Method |
|---|---|---|---|---|---|---|---|
| 85 | | | | 0.68 | 30% EtOAc/ hex | 372 (M + H) + [FAB] | C1a, D2a |
| 86 | | | | 0.71 | 40% EtOAc/ hex | 344 (M + H) + [FAB] | C1a, D2a |
| 87 | | | | 0.38 | 30% EtOAc/ hex | 342 (M + H) + [HPLC ES-MS] | A2c, B1b, B4c, B7c, C1f |
| 88 | | | | 0.78 | 30% EtOAc/ hex | 336 (M + H) + [HPLC ES-MS] | B1b, B4c, B7c, C1f |
| 89 | | | | 0.79 | 30% EtOAc/ hex | 316 (M + H) + [HPLC ES-MS] | B1b, B4c, B7c, C1f |
| 90 | | | | 0.74 | 20% EtOAc/ hex | | B7a, C1a, D2a |
| 91 | | | 7.85 (b) | 0.74 | 20% EtOAc/ hex | 350 (M + H) + [FAB] | B7a, C1a, D2a |
| 92 | | | | 0.77 | 20% EtOAc/ hex | | B7a, C1a, D2a |

TABLE 1-continued

2-Imino-1,3-thiazolidines and Ring Expanded Homologues

| Entry | Compound | mp (° C.) | HPLC (min.) | TLC $R_f$ | TLC Solvent System | Mass Spec. [Source] | Synth. Method |
|---|---|---|---|---|---|---|---|
| 93 | | | | 0.76 | 20% EtOAc/ hex | | B7a, C1a, D2a |
| 94 | | | | 0.50 | 20% EtOAc/ hex | | B7a, C1a, D2a |
| 95 | | | | 0.50 | 20% EtOAc/ hex | | B7a, C1a, D2a |
| 96 | | | | 0.52 | 20% EtOAc/ hex | | B7a, C1a, D2a |
| 97 | | | | 0.79 | 20% EtOAc/ hex | | B7a, C1a, D2a |
| 98 | | | | 0.70 | 30% EtOAc/ hex | 391 (M+) [EI] | B1b, B7a, C1a, D2a |
| 99 | | 46–49 | | 0.65 | 10% EtOAc/ hex | 344 (M + H) + [HPLC ES-MS] | B1b, B7a, C1a, D2f |

TABLE 1-continued

2-Imino-1,3-thiazolidines and Ring Expanded Homologues

| Entry | Compound | mp (° C.) | HPLC (min.) | TLC R_f | TLC Solvent System | Mass Spec. [Source] | Synth. Method |
|---|---|---|---|---|---|---|---|
| 100 | | | | | | 347 (M+) [EI] | B1b, B7a, C1a, D2a |
| 101 | | | | 0.63 | 30% EtOAc/ hex | 361 (M+) [FAB] | B1b, B7a, C1a, D2a |
| 102 | | | | 0.63 | 30% EtOAc/ hex | 394 (M + H) + [FAB] | B1b, B7a, C1a, D2a, D5a |
| 103 | | | 7.67 (b) | | | 363 (M+) [EI] | A2b, B7a, C1a, D2a |
| 104 | | | | 0.74 | 30% EtOAc/ hex | 387 (M + H) + [FAB] | B1b, B7a, C1a, D2a |
| 105 | | | | 0.81 | 30% EtOAc/ hex | 392 (M + H) + [FAB] | B1b, B7a, C1a, D2a |
| 106 | | 53–55 | | | | 360 (M + H) + [FAB] | B1b, B7a, C1a, D2a |

TABLE 1-continued

2-Imino-1,3-thiazolidines and Ring Expanded Homologues

| Entry | Compound | mp (° C.) | HPLC (min.) | TLC $R_f$ | TLC Solvent System | Mass Spec. [Source] | Synth. Method |
|---|---|---|---|---|---|---|---|
| 107 | | | 17.5 (d) | | | 348 (M + H) + [HPLC ES-MS] | B1b, B7a, C1c |
| 108 | | | 28.9 (d) | | | 404 (M + H) + [HPLC ES-MS] | B1b, B7a, C1c, D2f |
| 109 | | | 23.7 (e) | | | 383 (M + H) + [HPLC ES-MS] | B1b, B7a, C1c, D2f |
| 110 | | | 23.8 (d) | | | 364 (M + H) + [HPLC ES-MS] | B1b, B7a, C1c, D2f |
| 111 | | | | 0.36 | 30% EtOAc/ hex | 363 (M + H) + [FAB] | B1b, B7a, C1a, D2a |
| 112 | | | | 0.79 | 30% EtOAc/ hex | 364 (M + H) + [CI] | A2a, step 3, B1b, B7a, C1a, D2a |
| 113 | | 130–131 | | | | 348 (M + H) + [CI] | B1b, B7a, C1a, D2a, D6a |
| 114 | | | | 0.74 | 30% EtOAc/ hex | 323 (M + H) + [FAB] | B1b, B7a, C1a, D2a |
| 115 | | | | 0.74 | 30% EtOAc/ hex | 338 (M+) [EI] | B1b, B7a, C1a, D2a |

TABLE 1-continued

2-Imino-1,3-thiazolidines and Ring Expanded Homologues

| Entry | Compound | mp (° C.) | HPLC (min.) | TLC $R_f$ | TLC Solvent System | Mass Spec. [Source] | Synth. Method |
|---|---|---|---|---|---|---|---|
| 116 | | | | 0.74 | 30% EtOAc/ hex | 383 (M + H) + [FAB] | B1b, B7a, C1a, D2a |
| 117 | | | | 0.54 | 50% EtOAc/ hex | | C2a, D2a |
| 118 | | | | 0.44 | 5% EtOAc/ hex | 350 (M + H) + [CI] | B1b, B4c, B7c, C1b |
| 119 | | | | 0.50 | 80% EtOAc/ hex | 306 (M + H) + [CI] | A2b, B1b, B4c, B7c, C1b |
| 120 | | 124–126 | | 0.43 | 10% EtOAc/ hex | | A2b, B1b, C2a, D2a |
| 121 | | | | 0.80 | 30% EtOAc/ hex | 336 (M + H) + [HPLC ES-MS] | B1b, B4c, B7c, C1f |
| 122 | | | | 0.85 | 30% EtOAc/ hex | 316 (M + H) + [HPLC ES-MS] | B1b, B4c, B7c, C1f |
| 123 | | | | 0.26 | 100% EtOAc | 322 (M + H) + [HPLC ES-MS] | A2b, B1b, B4c, B7c, C1b, D4a |
| 124 | | | | 0.51 | 10% EtOAc/ hex | | B7a, C1a, D2a |

TABLE 1-continued

2-Imino-1,3-thiazolidines and Ring Expanded Homologues

| Entry | Compound | mp (° C.) | HPLC (min.) | TLC R$_f$ | TLC Solvent System | Mass Spec. [Source] | Synth. Method |
|---|---|---|---|---|---|---|---|
| 125 | | | 8.83 (b) | | | 350 (M + H) + [CI] | B1a step 2, B7b, C1e, D2a |
| 126 | | | | 0.50 | 10% EtOAc/ hex | | B1a step 2, B1b, C1a, D2a |
| 127 | | | | 0.36 | 30% EtOAc/ hex | 362 (M + H) + [EI] | B1b, B7a, C1a, D2a |
| 128 | | | | 0.80 | 25% EtOAc/ hex | | B7a, C1a, D2a |
| 129 | | 62–64 | | | | 345 (M + H) + [FAB] | A2a, B7a, C1a, D2a |
| 130 | | | | 0.91 | 30% EtOAc/ hex | 393 (M + H) + [FAB] | A2a, step 3, B1b, B7a, C1a, D2a |
| 131 | | | | 0.70 | 30% EtOAc/ hex | 384 (M + H) + [FAB] | A2a step 3, B1b, B7a, C1a, D2a |
| 132 | | | | | | 386 (M + H) + [FAB] | A2b, B1b, B7a, C1a, D2a |
| 133 | | | | 0.72 | 20% EtOAc/ hex | 343 (M+) [EI] | B1b, B7a, C1a, D2a |

TABLE 1-continued

2-Imino-1,3-thiazolidines and Ring Expanded Homologues

| Entry | Compound | mp (° C.) | HPLC (min.) | TLC $R_f$ | TLC Solvent System | Mass Spec. [Source] | Synth. Method |
|---|---|---|---|---|---|---|---|
| 134 | | | | 0.70 | 30% EtOAc/ hex | 330 (M + H) + [FAB] | A1a, A2a step 3, B1a, B7a, D2a |
| 135 | | | | 0.70 | 30% EtOAc/ hex | 344 (M + H) + [FAB] | A1a, A2a step 3, B1a, B7a, D2a |
| 136 | | | | 0.74 | 30% EtOAc/ hex | 364 (M + H) + [FAB] | A2a, B1b, B7a, C1a, D2a |
| 137 | | | 8.18 (b) | | | 336 (M + H) + [FAB] | C2a, D2a |
| 138 | | | 7.91 (b) | 0.73 | 25% EtOAc/ hex | | C2a, D2a |
| 139 | | | | 0.82 | 33% EtOAc/ hex | | B7b, C1a, D2a |
| 140 | | | | 0.80 | 33% EtOAc/ hex | | B7b, C1a, D2a |

TABLE 1-continued

2-Imino-1,3-thiazolidines and Ring Expanded Homologues

| Entry | Compound | mp (° C.) | HPLC (min.) | TLC $R_f$ | TLC Solvent System | Mass Spec. [Source] | Synth. Method |
|---|---|---|---|---|---|---|---|
| 141 | | | | 0.59 | 50% EtOAc/ hex | 292 (M + H) + [CI] | B1b, B7a, C1a |
| 142 | | | | 0.49 | 50% EtOAc/ hex | 278 (M + H) + [FAB] | B1b, B7a, C1a |
| 143 | | | | 0.24 | 20% EtOAc/ hex | 394 (M + H) + [HPLC ES-MS] | B1b, B4c, B7c, C1b |
| 144 | | | | 0.43 | 10% EtOAc/ hex | 412 (M + H) + [HPLC ES-MS] | B1b, B4c, B7c, C1b |
| 145 | | 88–90 | | 0.20 | 10% EtOAc/ hex | 424 (M + H) + [HPLC ES-MS] | B1b, B4c, B7c, C1b |
| 146 | | | | 0.40 | 25% EtOAc/ hex | | B3a, C2a |

TABLE 1-continued
2-Imino-1,3-thiazolidines and Ring Expanded Homologues
| Entry | Compound | mp (° C.) | HPLC (min.) | TLC $R_f$ | TLC Solvent System | Mass Spec. [Source] | Synth. Method |
|---|---|---|---|---|---|---|---|
| 147 | 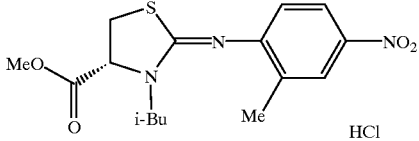 | | | 0.40 | 25% EtOAc/ hex | | B3a, C2a |
| 148 | 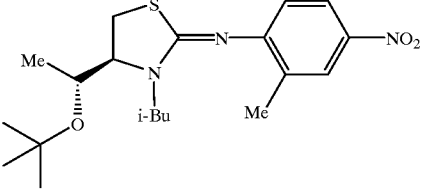 | | 8.79 (b) | | | | B8a, C5b |
| 149 | 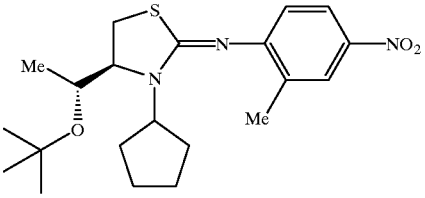 | | 9.11 (b) | | | 406 (M + H) + [CI] | B8a, C5b |
| 150 | 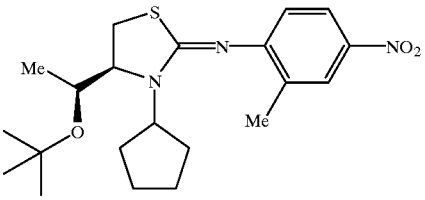 | | 8.84 (b) | | | 406 (M + H) + [CI] | B8a, C5b |
| 151 | 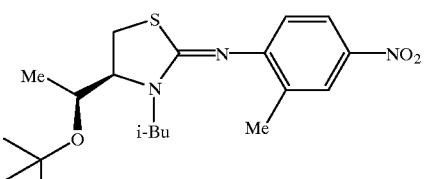 | | 8.63 (b) | | | 394 (M + H) + [CI] | B8a, C5b |
| 152 | 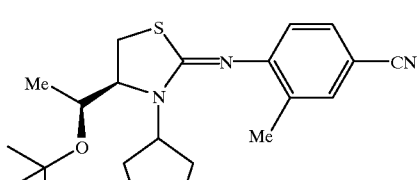 | | 4.05 (a) | | | 385 (M + H) + [HPLC ES-MS] | B8a, C5b |
| 153 | 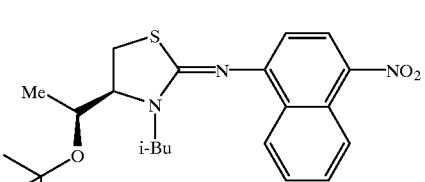 | | 5.26 (a) | | | 430 (M + H) + [HPLC ES-MS] | A2b, B8a, C5b |

TABLE 1-continued
2-Imino-1,3-thiazolidines and Ring Expanded Homologues
| Entry | Compound | mp (° C.) | HPLC (min.) | TLC $R_f$ | TLC Solvent System | Mass Spec. [Source] | Synth. Method |
|---|---|---|---|---|---|---|---|
| 154 | 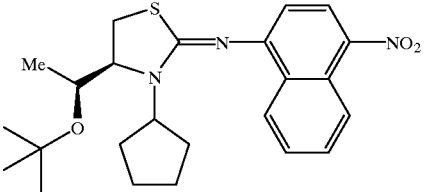 | | 5.44 (a) | | | 442 (M + H) + [HPLC ES-MS] | A2b, B8a, C5b |
| 155 | 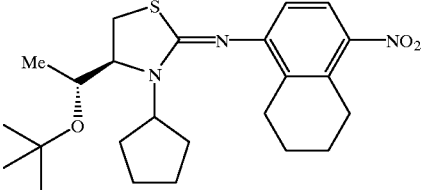 | | 4.19 (a) | | | 446 (M + H) + [HPLC ES-MS] | A2a, B8a, C5b |
| 156 | 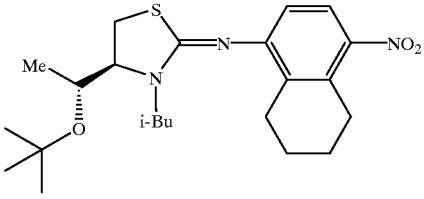 | | 4.80 (a) | | | 434 (M + H) + [HPLC ES-MS] | A2a, B8a, C5b |
| 157 | 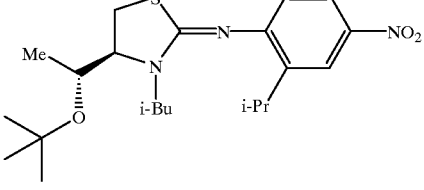 | | 3.98 (a) | | | 422 (M + H) + [HPLC ES-MS] | A2a, B8a, C5b |
| 158 | 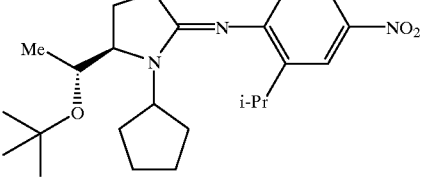 | | 6.12 (a) | | | 434 (M + H) + [HPLC ES-MS] | A2a, B8a, C5b |
| 159 | 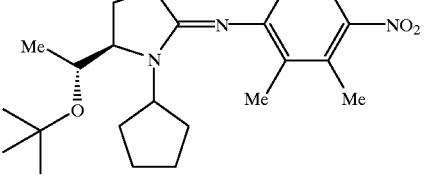 | | 5.74 (a) | | | 420 (M + H) + [HPLC ES-MS] | A2b, B8a, C5b |

TABLE 1-continued
2-Imino-1,3-thiazolidines and Ring Expanded Homologues
| Entry | Compound | mp (° C.) | HPLC (min.) | TLC $R_f$ | TLC Solvent System | Mass Spec. [Source] | Synth. Method |
|---|---|---|---|---|---|---|---|
| 160 | 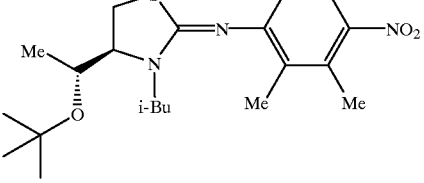 | | 5.40 (a) | | | 408 (M + H) + [HPLC ES-MS] | A2b, B8a, C5b |
| 161 | 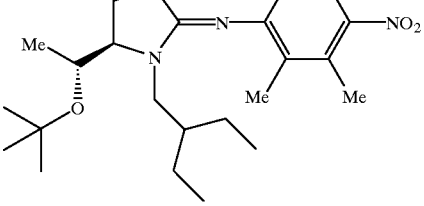 | | 3.65 (a) | | | 436 (M + H) + [HPLC ES-MS] | A2b, B8a, C5b |
| 162 | 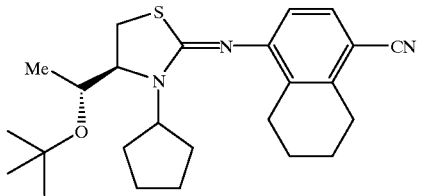 | | 5.07 (a) | | | 426 (M + H) + [HPLC ES-MS] | A2b, B8a, C5b |
| 163 | 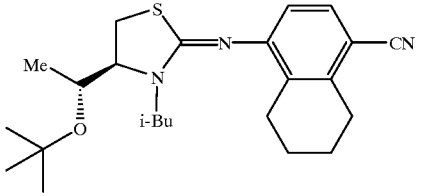 | | 5.00 (a) | | | 414 (M + H) + [HPLC ES-MS] | A2b, B8a, C5b |
| 164 | 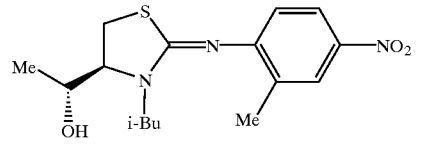 | | | 0.13 | 25% EtOAc/ hex | | B8a, C5b, D3a |
| 165 | 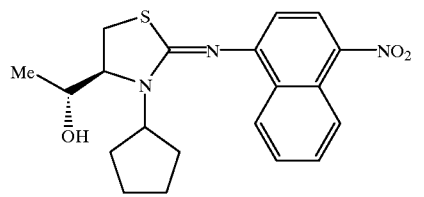 | | 4.75 (a) | | | 386 (M + H) + [HPLC ES-MS] | A2b, B8a, C5b, D3a |
| 166 | 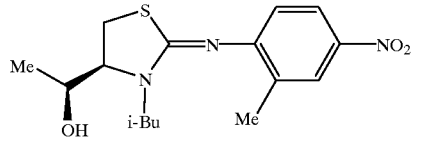 | | 7.29 (b) | | | 338 (M + H) + [CI] | B8a, C5b, D3a |

TABLE 1-continued
2-Imino-1,3-thiazolidines and Ring Expanded Homologues
| Entry | Compound | mp (° C.) | HPLC (min.) | TLC $R_f$ | TLC Solvent System | Mass Spec. [Source] | Synth. Method |
|---|---|---|---|---|---|---|---|
| 167 | 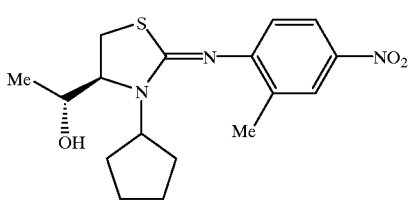 | | | 0.16 | 25% EtOAc/ hex | | B8a, C5b, D3a |
| 168 | 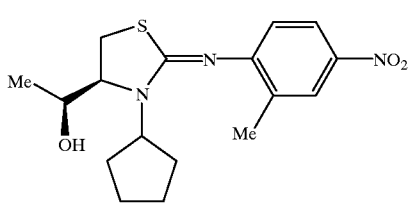 | | 7.18 (b) | | | 350 (M + H) + [CI] | B8a, C5b, D3a |
| 169 | 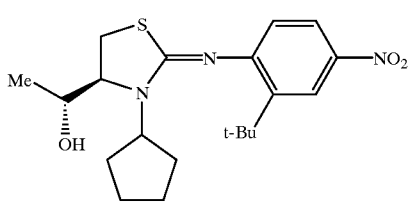 | | 5.07 (a) | | | 372 (M + H) + [HPLC ES-MS] | A2b, B8a, C5b, D3b |
| 170 | 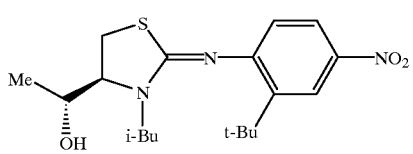 | | 4.75 (a) | | | 360 (M + H) + [HPLC ES-MS] | A2b, B8a, C5b, D3b |
| 171 | 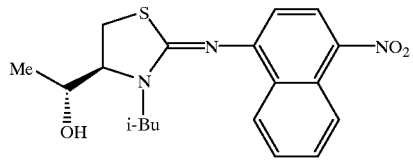 | | 4.68 (a) | | | 374 (M + H) + [HPLC ES-MS] | A2b, B8a, C5b, D3b |
| 172 | 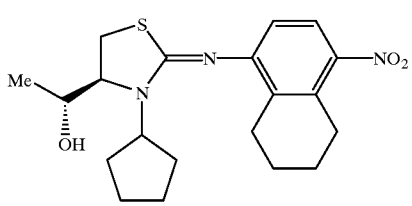 | | 5.02 (a) | | | 390 (M + H) + [HPLC ES-MS] | A2a, B8a, C5b, D3b |
| 173 | 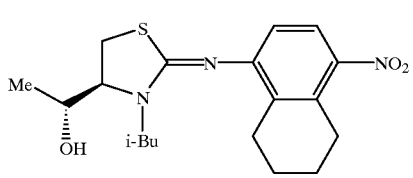 | | 4.55 (a) | | | 378 (M + H) + [HPLC ES-MS] | A2a, B8a, C5b, D3b |

TABLE 1-continued
2-Imino-1,3-thiazolidines and Ring Expanded Homologues
| Entry | Compound | mp (° C.) | HPLC (min.) | TLC R$_f$ | TLC Solvent System | Mass Spec. [Source] | Synth. Method |
|---|---|---|---|---|---|---|---|
| 174 | 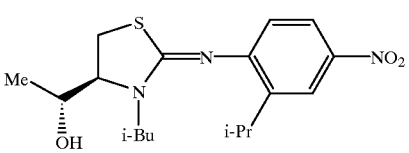 | | 5.86 (a) | | | 366 (M + H) + [HPLC ES-MS] | A2a, B8a, C5b, D3b |
| 175 | 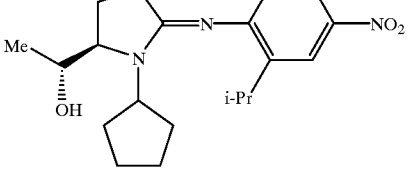 | | 6.00 (a) | | | 378 (M + H) + [HPLC ES-MS] | A2a, B8a, C5b, D3b |
| 176 | 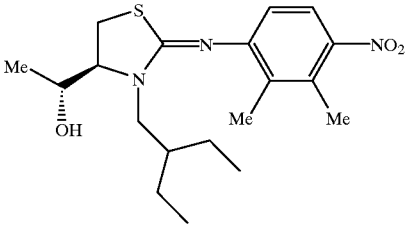 | | 0.89 (a) | | | 380 (M + H) + [HPLC ES-MS] | A2b, B8a, C5b, D3b |
| 177 | 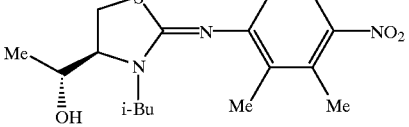 | | 5.42 (a) | | | 352 (M + H) + [HPLC ES-MS] | A2b, B8a, C5b, D3b |
| 178 | 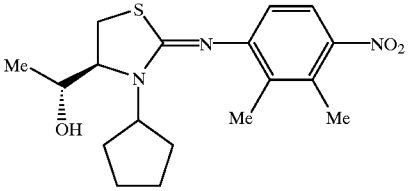 | | 5.64 (a) | | | 364 (M + H) + [HPLC ES-MS] | A2b, B8a, C5b, D3b |
| 179 | 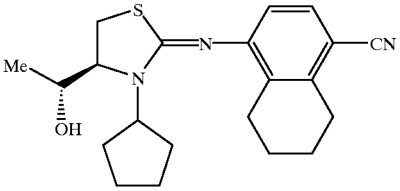 | | 4.26 (a) | | | 370 (M + H) + [HPLC ES-MS] | A2b, B8a, C5b, D3b |
| 180 | 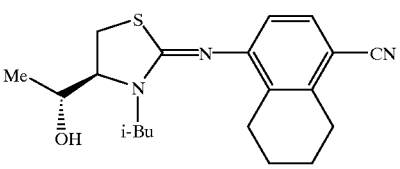 | | 3.94 (a) | | | 358 (M + H) + [HPLC ES-MS] | A2b, B8a, C5b, D3b |

TABLE 1-continued

2-Imino-1,3-thiazolidines and Ring Expanded Homologues

| Entry | Compound | mp (° C.) | HPLC (min.) | TLC R$_f$ | TLC Solvent System | Mass Spec. [Source] | Synth. Method |
|---|---|---|---|---|---|---|---|
| 181 | | | 8.46 (b) | | | | C2a, D13a, D2a |
| 182 | | | | 0.82 | 5% MeOH/ CH2Cl2 | | C2a, D13a, D2a |
| 183 | | | | 0.15 | 25% EtOAc/ CH2Cl2 | | C2a, D2a |
| 184 | | | | 0.04 | 25% EtOAc/ CH2Cl2 | | C2a, D2a |
| 185 | | 211 | | 0.78 | 10% MeOH/ 90% CH2Cl2 | | B7a, C1a, D2g |
| 186 | | 159 | | 0.28 | 10% EtOAc/ 90% pet. ether | | B4c, C2f |
| 187 | | | | 0.26 | 10% EtOAc/ 90% pet. ether | | B4c, C2f |

TABLE 1-continued
2-Imino-1,3-thiazolidines and Ring Expanded Homologues
| Entry | Compound | mp (° C.) | HPLC (min.) | TLC $R_f$ | TLC Solvent System | Mass Spec. [Source] | Synth. Method |
|---|---|---|---|---|---|---|---|
| 188 | 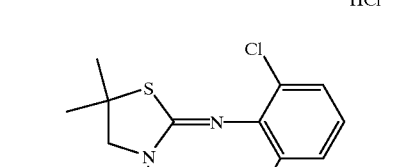 | 177 | | 0.24 | 10% EtOAc/ 90% pet. ether | | B4c, C2f |
| 189 | 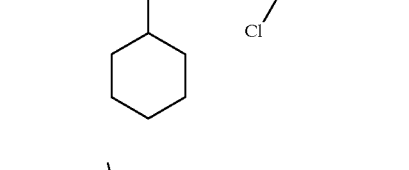 | 134 | | | | | C2f |
| 190 | 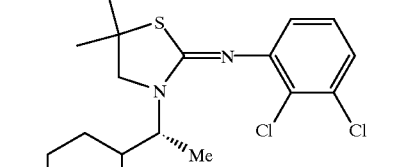 | 209 | | | | | B5b, C2f |
| 191 | 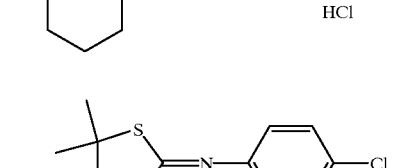 | 162 | | | | | B5b, C2f |
| 192 | 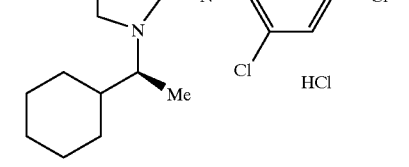 | 209 | | | | | B5b, C2f |
| 193 | 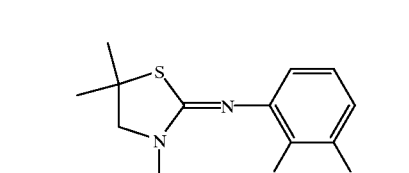 | 164 | | | | | C2f, B5b |

TABLE 1-continued

2-Imino-1,3-thiazolidines and Ring Expanded Homologues

| Entry | Compound | mp (° C.) | HPLC (min.) | TLC R_f | TLC Solvent System | Mass Spec. [Source] | Synth. Method |
|---|---|---|---|---|---|---|---|
| 194 | | 178 | | 0.80 | 10% MeOH/ 90% CH2Cl2 | | C2f |
| 195 | | 181 | | | | | C1a, D2g |
| 196 | | 97 | | | | | C1a, D2g |
| 197 | | 154 | | | | | C1a, D2g |
| 198 | | 156 | | | | | B4c, C2f |
| 199 | | 154 | | | | | B4c, C2f |

TABLE 1-continued

2-Imino-1,3-thiazolidines and Ring Expanded Homologues

| Entry | Compound | mp (° C.) | HPLC (min.) | TLC R_f | TLC Solvent System | Mass Spec. [Source] | Synth. Method |
|---|---|---|---|---|---|---|---|
| 200 | | 196 | | | | | B5b, C2f |
| 201 | | 188–190 | | 0.28 | 10% EtOAc/ 90% pet. ether | | B5b, C2f |
| 202 | | 108 | | 0.16 | 10% EtOAc/ 90% pet. ether | | B5b, C2f |
| 203 | | 63 | | 0.26 | 10% EtOAc/ 90% pet. ether | | B5b, C2f |
| 204 | | 95–97 | | 0.34 | 10% EtOAc/ 90% pet. ether | | B5b, C2f |
| 205 | | 229 | | | | | B7a, C1a, D2g |
| 206 | | | 7.83 (b) | | | 321 (M + H) + [EI] | B1c, B7b, C1a, D2a |

TABLE 1-continued
2-Imino-1,3-thiazolidines and Ring Expanded Homologues
| Entry | Compound | mp (° C.) | HPLC (min.) | TLC $R_f$ | TLC Solvent System | Mass Spec. [Source] | Synth. Method |
|---|---|---|---|---|---|---|---|
| 207 | 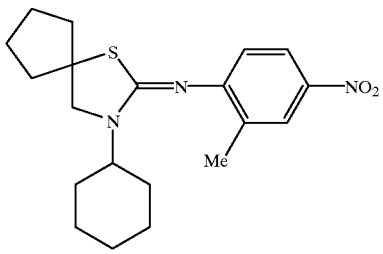 | | 8.59 (b) | | | 374 (M + H) + [CI] | B1c, B4a, C2a |
| 208 | 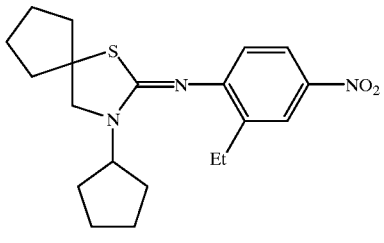 | | | 0.64 | 30% EtOAc/ hex | 374 (M + H) + [CI] | A2a, B1c, B7a, C1a, D2b |
| 209 | 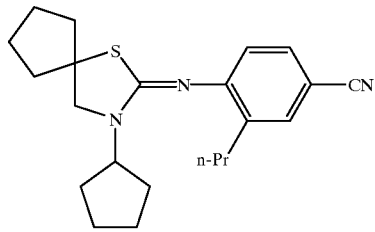 | | | 0.74 | 20% EtOAc/ hex | 368 (M + H) + [CI] | A5a, A2b, B1c, B7a, C1a, D2b, D7a |
| 210 | 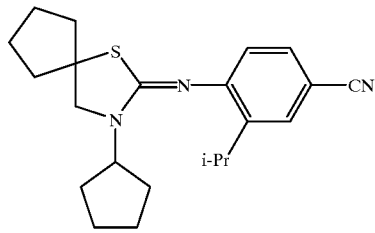 | | | 0.74 | 20% EtOAc/ hex | 368 (M + H) + [CI] | A5a, A2b, B1c, B7a, C1a, D2b, D7a |
| 211 | 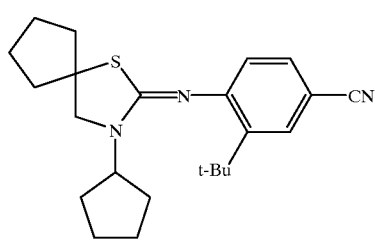 | 200–201 | | 0.74 | 20% EtOAc/ hex | 382 (M + H) + [CI] | A5a, A2b, B1c, B7a, C1a, D2b, D7a |

TABLE 1-continued

2-Imino-1,3-thiazolidines and Ring Expanded Homologues

| Entry | Compound | mp (° C.) | HPLC (min.) | TLC R$_f$ | TLC Solvent System | Mass Spec. [Source] | Synth. Method |
|---|---|---|---|---|---|---|---|
| 212 | | | 8.65 (b) | | | 374 (M + H) + [CI] | B1c, B4a, C2a |
| 213 | | | | 0.82 | 25% EtOAc/ hex | | B1c, B7a, C1e, D2a |
| 214 | | | | 0.86 | 30% EtOAc/ hex | 362 (M + H) + [FAB] | A2a, B1c, B7a, C1a, D2a |
| 215 | | | | 0.80 | 30% EtOAc/ hex | 376 (M + H) + [FAB] | A2a, B1c, B7a, C1a, D2a |
| 216 | | | | 0.86 | 30% EtOAc/ hex | 376 (M + H) + [FAB] | A2a, B1c, B7a, C1a, D2a |
| 217 | | | | 0.83 | 30% EtOAc/ hex | 362 (M + H) + [CI] | A4a, A2d, B1c, B7e, C1c, D2a |
| 218 | | 68–70 | | | | 348 (M + H) + [CI] | A2a, B1c, B7a, C1a, D2a |
| 219 | | | | 0.64 | 30% EtOAc/ hex | 383 (M+) [EI] | A2a, B1c, B7a, C1a, D2a |

TABLE 1-continued

2-Imino-1,3-thiazolidines and Ring Expanded Homologues

| Entry | Compound | mp (° C.) | HPLC (min.) | TLC $R_f$ | TLC Solvent System | Mass Spec. [Source] | Synth. Method |
|---|---|---|---|---|---|---|---|
| 220 | | 71–72 | | | | | B1c, B7e, C1a, D2a |
| 221 | | 98–100 | | | | 327 (M+) [EI] | A1a, A2a, step 3, B1c, B7a, C1a, D2b |
| 222 | | | 26.5 (j) | | | 342 (M + H) + [HPLC ES-MS] | B1c, B7a, C1a, D2b |
| 223 | | | | 0.73 | 20% EtOAc/ hex | 364 (M + H) + [FAB] | A2a step 3, B1c, B7a, C1a, D2b |
| 224 | | | | 0.16 | 50% CH2Cl2/ hex | 342 (M + H) + [CI] | A5a, A2a step 3, B1c, B7e, C1e, D2h, D7a |
| 225 | | | | 0.70 | 20% EtOAc/ hex | | A5a, A2a step 3, B1c, C2a, D2a, D8a |
| 226 | | | | 0.39 | 50% CH2Cl2/ hex | 443 (M + H) + [CI] | A5a, A2a step 3, B1c, B7e, C1e, D2h |
| 227 | | | | | | 362 (M + H) + [CI] | A4a, A2d, B1c, B7e, C1e, D2b |
| 228 | | 58–60 | | | | 320 (M + H) + [CI] | A1a, A2b, B1c, B7e, C1e, D2a |

TABLE 1-continued

2-Imino-1,3-thiazolidines and Ring Expanded Homologues

| Entry | Compound | mp (° C.) | HPLC (min.) | TLC R_f | TLC Solvent System | Mass Spec. [Source] | Synth. Method |
|---|---|---|---|---|---|---|---|
| 229 | | 140–143 | | 0.68 | 30% EtOAc/ hex | 343 (M + H) + [CI-MS] | A2c, B1c, B7e, C1e, D2h |
| 230 | | | | 0.83 | 25% EtOAc/ hex | | B1c, C2a, D2a |
| 231 | | 86–88 | | 0.74 | 20% EtOAc/ hex | 356 (M + H) + [CI] | B1c, B7e, C1e, D2b |
| 232 | | 135–137 | | | | | B1c, B7e, C1e, D2e |
| 233 | | 95–97 | | | | | B1c, B7e, C1e, D2e |
| 234 | | | | 0.28 | 40% EtOAc/ hex | | B1c, B7e, C1e, D2h |
| 235 | | 100–102 | | | | | B1c, B7e, C1e, D2e |

TABLE 1-continued
2-Imino-1,3-thiazolidines and Ring Expanded Homologues
| Entry | Compound | mp (° C.) | HPLC (min.) | TLC R_f | TLC Solvent System | Mass Spec. [Source] | Synth. Method |
|---|---|---|---|---|---|---|---|
| 236 | 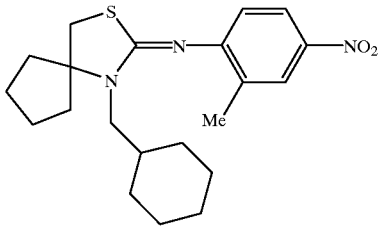 | 85–87 | | | | | B1c, B7e, C1e, D2e |
| 237 | 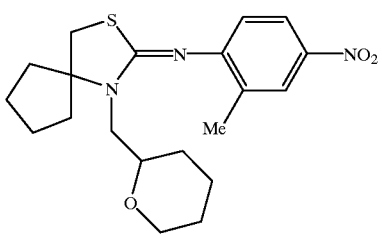 | 96–98 | | | | | B1c, B7e, C1e, D2e |
| 238 | 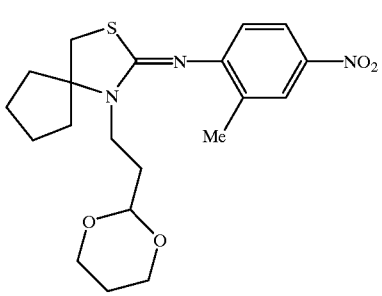 | | 4.81 (a) | | | 406 (M + H) + [HPLC ES-MS] | B1c, B7e, C1e, D2e |
| 239 | 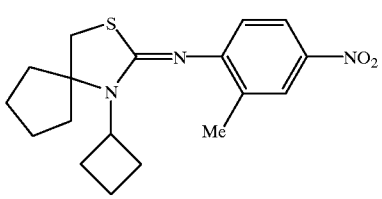 | | 5.29 (a) | | | 346 (M + H) + [HPLC-ES-MS] | B1c, B7e, C1e, D2e |
| 240 | 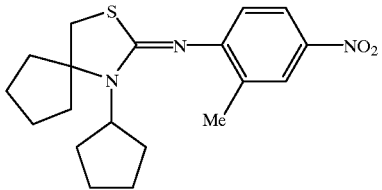 | 120–121 | | 0.45 | 10% EtOAc/hex | | B1c, C2a, D2b |
| 241 | 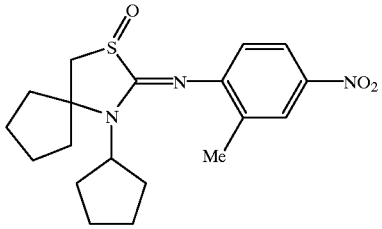 | 126–128 | | 0.10 | 25% EtOAc/hex | | B1c, C2a, D2b, D4a |

TABLE 1-continued
2-Imino-1,3-thiazolidines and Ring Expanded Homologues
| Entry | Compound | mp (° C.) | HPLC (min.) | TLC $R_f$ | TLC Solvent System | Mass Spec. [Source] | Synth. Method |
|---|---|---|---|---|---|---|---|
| 242 | 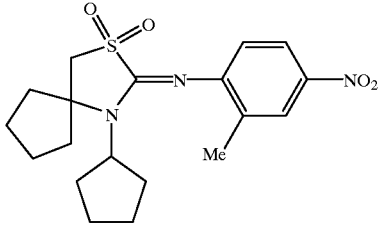 | 181 DEC | | 0.27 | 25% EtOAc/ hex | | B1c, C2a, D2b, D4a |
| 243 | 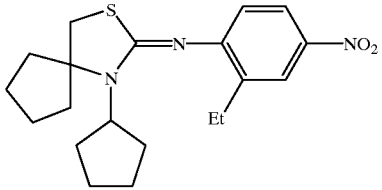 | | | 0.86 | 30% EtOAc/ hex | 374 (M + H) + [CI] | A2a, B1c, B7e, C1e, D2b |
| 244 | 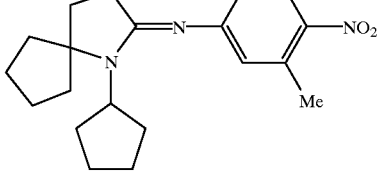 | 136–137 | | | | 360 (M + H) + [FAB] | A2a step 3, B1c, B7e, C1e, D2b |
| 245 | 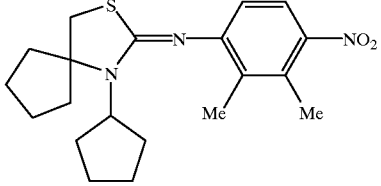 | 83–84 | | | | 374 (M + H) + [CI] | A2a, B1c, B7e, C1e, D2b |
| 246 | 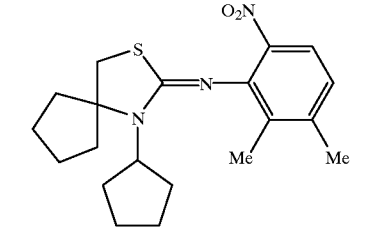 | | | | | 374 (M + H) + [CI] | A2a, B1c, B7e, C1e, D2b |
| 247 | 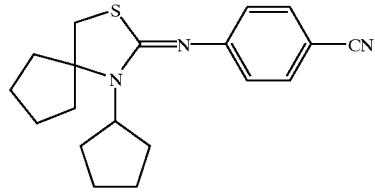 | 158–159 | | | | | B1c, B7e, C1e, D2b, D2h |

TABLE 1-continued
2-Imino-1,3-thiazolidines and Ring Expanded Homologues
| Entry | Compound | mp (° C.) | HPLC (min.) | TLC $R_f$ | TLC Solvent System | Mass Spec. [Source] | Synth. Method |
|---|---|---|---|---|---|---|---|
| 248 | 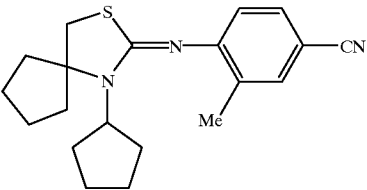 | 106–107 | | 0.73 | 30% EtOAc/hex | 340 (M + H) + [CI] | A1a, A2b, B1c, B7e, C1e, D2b |
| 249 | 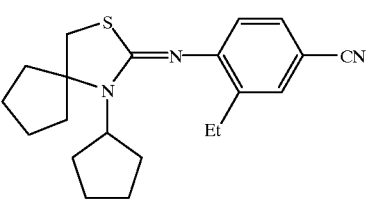 | | 18.1 (j) | 0.66 | 20% EtOAc/hex | 354 (M + H) + [HPLC ES-MS] | A1a, A2b, B7a, D2f |
| 250 | 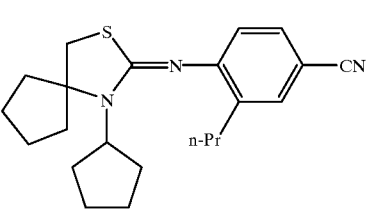 | | | 0.74 | 20% EtOAc/hex | 368 (M + H) + [CI] | B1c, B7e, C1e, D2b |
| 251 | 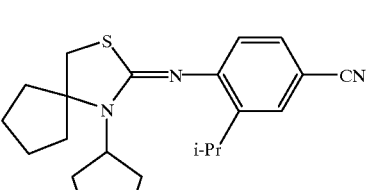 | | | 0.74 | 20% EtOAc/hex | 368 (M + H) + [CI] | A2b, B1c, C2a, D2b, D7a |
| 252 | 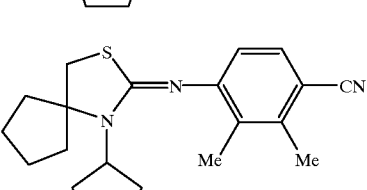 | | | 0.18 | 50% CH2Cl2/hex | 354 (M + H) + [CI] | A2b, B1c, C2a, D2b, D7a |
| 253 | 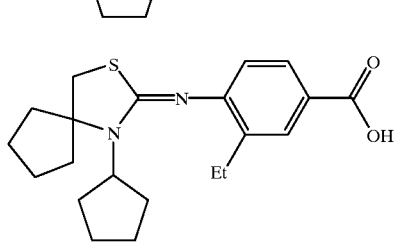 | 208–209 | | | | | B1c, B7e, C2e, D2b, D9a |
| 254 | 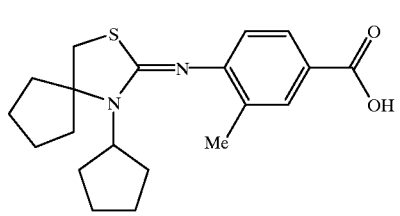 | 228–229 | | | | | A1a, A2b, B1c, B7e, C1e, D2b, D9a |

TABLE 1-continued

2-Imino-1,3-thiazolidines and Ring Expanded Homologues

| Entry | Compound | mp (° C.) | HPLC (min.) | TLC $R_f$ | TLC Solvent System | Mass Spec. [Source] | Synth. Method |
|---|---|---|---|---|---|---|---|
| 255 | | 114–115 | | | | | B1c, B7e, C2e, D2b, D9a, D10a |
| 256 | | | | 0.63 | 30% EtOAc/hex | | A2b, B1c, C2a, D2h |
| 257 | | | | 0.44 | 30% EtOAc/hex | | B1c, B7e, C1e, D2b, D9a, D6b |
| 258 | | | | 0.44 | 30% EtOAc/hex | | B1c, B7e, C1e, D2b, D9a, D6b |
| 259 | | | | 0.71 | 10% EtOAc/hex | 369 (M + H) + [CI] | A3a, B1c, B4d, C6c |
| 260 | | | | 0.62 | 10% EtOAc/hex | 369 (M + H) + [CI] | A3a, B1c, B4d, C6c |
| 261 | | | | 0.78 | 10% EtOAc/hex | 369 (M + H) + [CI] | A3a, B1c, B4d, C6c |

TABLE 1-continued

2-Imino-1,3-thiazolidines and Ring Expanded Homologues

| Entry | Compound | mp (° C.) | HPLC (min.) | TLC $R_f$ | TLC Solvent System | Mass Spec. [Source] | Synth. Method |
|---|---|---|---|---|---|---|---|
| 262 | (structure with Cl, Me, CF₃CO₂H) | | | 0.84 | 10% EtOAc/ hex | 349 (M + H) + [CI] | A3a, B1c, B4d, C6c |
| 263 | (structure with CF₃) | | | 0.80 | 10% EtOAc/ hex | 369 (M + H) + [CI] | A3a, B1c, B4d, C6c |
| 264 | (structure with Me, Cl, Cl, CF₃CO₂H) | | | 0.44 | 2% EtOAc/ hex | 383 (M + H) + [CI] | A3a, B1c, B4d, C6c |
| 265 | (structure with Me, Cl, CF₃CO₂H) | | | 0.65 | 2% EtOAc/ hex | 349 (M + H) + [CI] | A3a, B1c, B4d, C6c |
| 266 | (structure with Me, Br) | | | 0.71 | 20% EtOAc/ hex | | C2a, D2a |
| 267 | (structure with Et, CHO) | 104–105 | | 0.16 | 10% EtOAc/ hex | | B1c, B7e, C1e, D2b, D11a |
| 268 | (structure with Et, CO₂Et) | | | 0.68 | 30% EtOAc/ hex | | B1c, B7e, C1e, D2b, D11a, D12a |

TABLE 1-continued
2-Imino-1,3-thiazolidines and Ring Expanded Homologues
| Entry | Compound | mp (° C.) | HPLC (min.) | TLC $R_f$ | TLC Solvent System | Mass Spec. [Source] | Synth. Method |
|---|---|---|---|---|---|---|---|
| 269 | 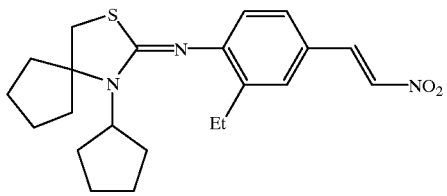 | 141–142 | | 0.61 | 20% EtOAc/ hex | | B1c, B7e, C1e, D2b, D11a D12b |
| 270 | 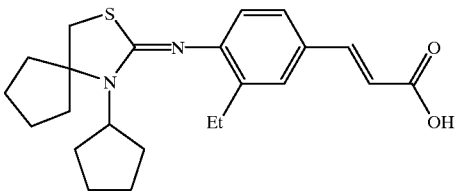 | 182–183 | | | | | B1c, B7e, C1e, D2b, D11a D12a D6a |
| 271 | 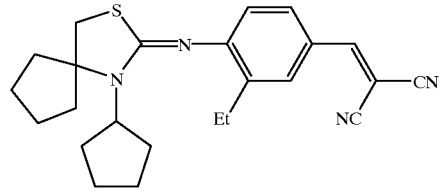 | 135–136 | | 0.52 | 20% EtOAc/ hex | | B1c, B7e, C1e, D2b, D11a D12c |
| 272 | 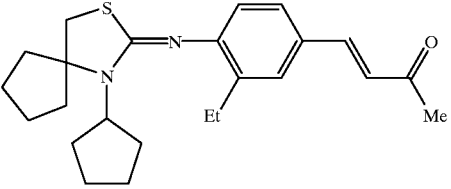 | | | 0.68 | 30% EtOAc/ hex | | B1c, B7e, C1e, D2b, D11a D12a |
| 273 | 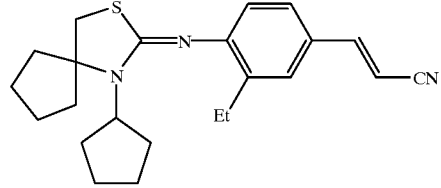 | | | 0.56 | 30% EtOAc/ hex | | B1c, B7e, C1e, D2b, D11a D12d |
| 274 | 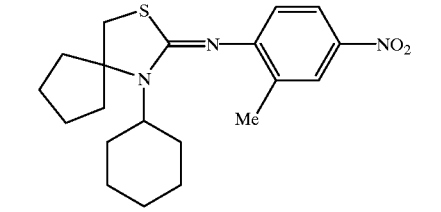 | 155–157 | | | | | B1c, C2a, D2e |

TABLE 1-continued
2-Imino-1,3-thiazolidines and Ring Expanded Homologues
| Entry | Compound | mp (° C.) | HPLC (min.) | TLC $R_f$ | TLC Solvent System | Mass Spec. [Source] | Synth. Method |
|---|---|---|---|---|---|---|---|
| 275 | 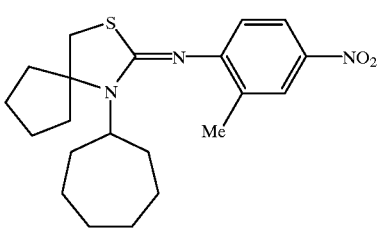 | 159–162 | | | | | B1c, C2a, D2e |
| 276 | 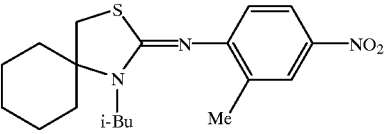 | | | 0.69 | 20% EtOAc/ hex | | B1a, C2a, D2b |
| 277 | 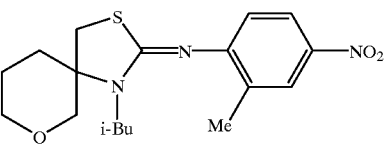 | 101–104 | | 0.15 | 10% EtOAc/ hex | 364 (M + H) + [HPLC ES-MS] | A3a, B1b, B4c, C6c |
| 278 | 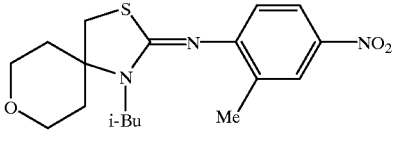 | 102–105 | | 0.29 | 10% EtOAc/ hex | 364 (M + H) + [HPLC ES-MS] | A3a, B1b, B4c, C6c |
| 279 | 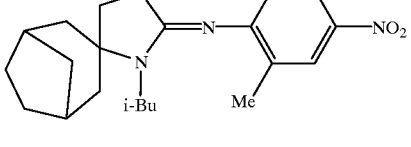 | | | 0.72 | 25% EtOAc/ hex | | B1a, B2a, B7a, C1a |
| 280 | 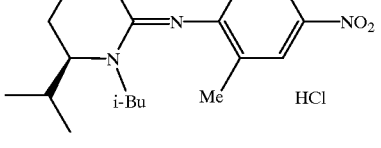 | | | 0.76 | 33% EtOAc/ hex | | B6a, B7e, C2a, D2a |
| 281 | 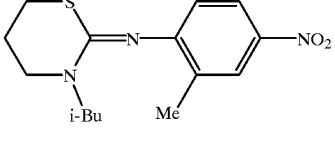 | | | 0.53 | 20% EtOAc/ hex | 308 (M + H) + [HPLC ES-MS] | B9a, C1a |

TABLE 1-continued

2-Imino-1,3-thiazolidines and Ring Expanded Homologues

| Entry | Compound | mp (° C.) | HPLC (min.) | TLC $R_f$ | TLC Solvent System | Mass Spec. [Source] | Synth. Method |
|---|---|---|---|---|---|---|---|
| 282 | [structure: 7-membered ring with S, N-i-Bu, =N-aryl(Me, NO₂)] | | | 0.51 | 20% EtOAc/ hex | 322 (M + H) + [HPLC ES-MS] | B9a, C1a |

(a)Hewlett Packard 1100 HPLC equipped with a Finnigan LCQ MS detector and a 2 × 300 mm Phenomenex 3 uM C-18 column; flow rate 1.0 mL/min.; Buffer A: 0.02% TFA/2% CH₃CN/water, Buffer B: 0.018% TFA/98% CH₃CN/water; hold at 100% Buffer A for 1 min., gradient from 100% Buffer A to 100% Buffer B over 3 min., hold at 100% Buffer B 1 min., gradient from 100% Buffer B to 100% Buffer A over 0.5 min., hold at 100% Buffer A 1.5 min.
(b)Ranin Dynamax HPLC equipped with UV-DII dual wavelength detector (254 and 220 nm) and a 4 × 100 mm Dynamax 3 uM C-18 column; flow rate 1.5 mL/min.; Buffer A: 0.5% TFA/water, Buffer B: 0.5% TFA/CH₃CN; gradient from 100% Buffer A to 100% Buffer B over 10 min, hold at 100% Buffer B 5 min.
(c)Hewlett Packard 1090 HPLC equipped with UV detector (210 nM) and a 4 × 125 mm Nucleosil 3 uM C-18 column; flow rate 2.0 mL/min.; Buffer A: 0.01 mol % H₃PO₄/water, Buffer B: 0.01 mol % H₃PO₄/CH₃CN; 10% Buffer B for 1 min., gradient from 10 Buffer B to 90% Buffer B over 8 min., gradient from 90% Buffer B to 10% Buffer B over 4 min.
(d)Ranin Dynamax HPLC equipped with UV-DII dual wavelength detector (254 and 220 nm) and a 2500 mm Dynamax 8 uM C-18 column; flow rate 18 mL/min.; Buffer A: 0.1% TFA/99.9% water, Buffer B: 0.1% TFA/99.9% CH₃CN; gradient from 30% Buffer B to 100% Buffer B over 25 min., hold at 100% Buffer B 30 min.
(e)Ranin Dynamax HPLC equipped with UV-DII dual wavelength detector (254 and 220 nm) and a 2500 mm Dynamax 8 uM C-18 column; flow rate 18 mL/min.; Buffer A: 0.1% TFA/99.9% water, Buffer B: 0.1% TFA/99.9% CH₃CN; gradient from 50% Buffer B to 60% Buffer B over 25 min., gradient from 60% to 100% over 32 min.
(f)Ranin Dynamax HPLC equipped with UV-DII dual wavelength detector (254 and 220 nm) and a 21 × 2500 mm Microsorb 5 uM C-18 column; flow rate 20 mL/min.; Buffer A: 0.1% TFA/99.9% water, Buffer B: 0.1% TFA/99.9% CH₃CN; gradient from 30% Buffer B to 100% Buffer B over 25 min., hold at 100% B 100% for 30 min.
(g)Ranin Dynamax HPLC equipped with UV-DII dual wavelength detector (254 and 220 nm) and a 21 × 2500 mm Microsorb 5 uM C-18 column; flow rate 20 mL/min.; Buffer A: 0.1% TFA/99.9% water, Buffer B: 0.1% TFA/99.9% CH₃CN; gradient from 50% Buffer B to 100% Buffer B over 25 min., hold at 100% B 100% for 7 min.
(h)Ranin Dynamax HPLC equipped with UV-DII dual wavelength detector (254 and 220 nm) and a 21 × 2500 mm Microsorb 5 uM C-18 column; flow rate 20 mL/min.; Buffer A: 0.1% TFA/99.9% water, Buffer B: 0.1% TFA/99.9% CH₃CN; gradient from 10% Buffer B to 100% Buffer B over 30 min., hold at 100% B 100% for 7 min.
(i)Ranin Dynamax HPLC equipped with UV-DII dual wavelength detector (254 and 220 nm) and a 4.6 × 100 mm Microsorb 5 uM C-8 column; flow rate 20 mL/min.; Buffer A: 0.1% TFA/99.9% water, Buffer B: 0.1% TFA/99.9% CH₃CN; gradient from 10% Buffer B to 100% Buffer B over 5 min., hold at 100% B 100% for 1.5 min.
(j)Ranin Dynamax HPLC equipped with UV-DII dual wavelength detector (254 and 220 nm) and a 21 × 2500 mm Microsorb 5 uM C-18 column; flow rate 20 mL/min.; Buffer A: 0.1% TFA/99.9% water, Buffer B: 0.1% TFA/99.9% CH₃CN; gradient from 20% Buffer B to 100% Buffer B over 30 min., hold at 100% B 100% for 7 min.

TABLE 2

2-Imino-1,3-thiazolidin-4-ones and 2-Imino-1,3-thiazolidin-5-ones

| Entry | Compound | mp (° C.) | HPL (min.) | TLC $R_f$ | TLC Solvent System | Mass Spec. [Source] | Synth. Method |
|---|---|---|---|---|---|---|---|
| 283 | [structure: thiazolidin-4-one with N-i-Bu, =N-aryl(Me, NO₂)] | | 8.03 (c) | 0.44 | 100% CH2Cl2 | 307 (M+) [EI] | C8a |
| 284 | [structure: thiazolidin-4-one with N-benzyl, =N-aryl(Me, NO₂)] | | 7.98 (c) | 0.20 | 100% CH2Cl2 | 341 (M+) [EI] | C8a |

TABLE 2-continued

2-Imino-1,3-thiazolidin-4-ones and 2-Imino-1,3-thiazolidin-5-ones

| Entry | Compound | mp (° C.) | HPL (min.) | TLC $R_f$ | TLC Solvent System | Mass Spec. [Source] | Synth. Method |
|---|---|---|---|---|---|---|---|
| 285 | | | 8.46 (c) | 0.26 | 100% CH2Cl2 | 321 (M+) [EI] | C8a |
| 286 | | | 9.46 (c) | 0.30 | 100% CH2Cl2 | 361 (M+) [EI] | C8a |
| 287 | | | 8.03 (c) | 0.58 | 100% CH2Cl2 | 307 (M+) [EI] | C8a |
| 288 | | | 8.45 (c) | 0.62 | 100% CH2Cl2 | 321 (M+) [EI] | C8a |
| 289 | | | 8.02 (c) | 0.61 | 100% CH2Cl2 | 341 (M+) [EI] | C8a |
| 290 | | | 8.53 (c) | 0.67 | 100% CH2Cl2 | 321 (M+) [EI] | C8a |
| 291 | | | 9.37 (c) | 0.62 | 100% CH2Cl2 | 361 (M+) [EI] | C8a |

TABLE 2-continued

2-Imino-1,3-thiazolidin-4-ones and 2-Imino-1,3-thiazolidin-5-ones

| Entry | Compound | mp (° C.) | HPL (min.) | TLC $R_f$ | TLC Solvent System | Mass Spec. [Source] | Synth. Method |
|---|---|---|---|---|---|---|---|
| 292 | | | 9.35 (c) | 0.76 | 100% CH2Cl2 | 361 (M+) [EI] | C8a |
| 293 | | 98 | 9.36 (c) | 0.76 | 100% CH2Cl2 | 361 (M+) [EI] | C8a |
| 294 | | | 9.01 (c) | 0.78 | 100% CH2Cl2 | 383 (M+) [EI] | C8a |
| 295 | | 63–67 | 9.78 (c) | 0.73 | 100% CH2Cl2 | 375 (M+) [EI] | C8a |
| 296 | | 62–63 | 10.11 (c) | 0.86 | 100% CH2Cl2 | 437 (M+) [EI] | C8a |
| 297 | | 68–71 | 9.77 (c) | 0.74 | 100% CH2Cl2 | 375 (M+) [EI] | C8a |

TABLE 2-continued

2-Imino-1,3-thiazolidin-4-ones and 2-Imino-1,3-thiazolidin-5-ones

| Entry | Compound | mp (° C.) | HPL (min.) | TLC R$_f$ | TLC Solvent System | Mass Spec. [Source] | Synth. Method |
|---|---|---|---|---|---|---|---|
| 298 | | 69–71 | 10.00 (c) | 0.91 | 100% CH2Cl2 | 437 (M+) [EI] | C8a |
| 299 | | | 9.23 (c) | 0.70 | 100% CH2Cl2 | 349 (M+) [EI] | C8a |
| 300 | | | 9.47 (c) | 0.79 | 100% CH2Cl2 | 363 (M+) [EI] | C8a |
| 301 | | | 10.20 (c) | 0.86 | 100% CH2Cl2 | 391 (M+) [EI] | C8a |
| 302 | | | 9.83 (c) | 0.82 | 100% CH2Cl2 | 377 (M+) [EI] | C8a |
| 303 | | | 9.61 (c) | 0.34 | 50% CH2Cl2/ cyclohex | 363 (M+) [EI] | C8a |

TABLE 2-continued
2-Imino-1,3-thiazolidin-4-ones and 2-Imino-1,3-thiazolidin-5-ones
| Entry | Compound | mp (° C.) | HPL (min.) | TLC $R_f$ | TLC Solvent System | Mass Spec. [Source] | Synth. Method |
|---|---|---|---|---|---|---|---|
| 304 | 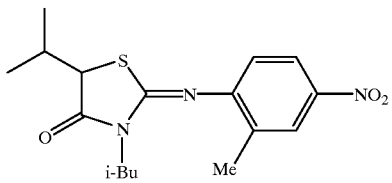 | | 9.23 (c) | 0.32 | 50% CH2Cl2/ cyclohex | 349 (M+) [EI] | C8a |
| 305 | 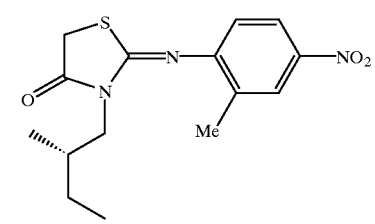 | | 8.37 (c) | 0.55 | 100% CH2Cl2 | 321 (M+) [EI] | C8a |
| 306 | 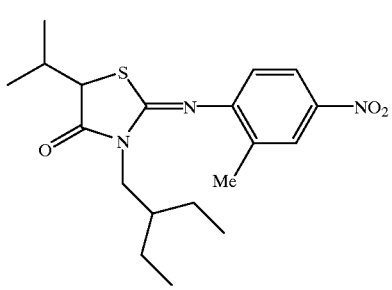 | | 9.90 (c) | 0.78 | 100% CH2Cl2 | 377 (M+) [EI] | C8a |
| 307 | 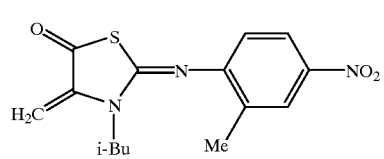 | | | 0.50 | 25% EtOAc/hex | | B3a, B7b, C2a |
| 27 | 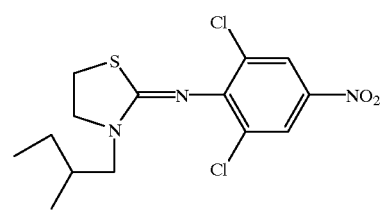 | | 8.97 (c) | 0.40 | 30% EtOAc/hex | 362 (M + H) + [FAB] | C8a |
| 308 | 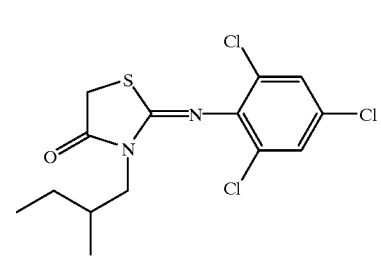 | | 7.95 (c) | 0.35 | 10% EtOAc/hex | 365 (M + H) + [FAB] | C8a |

TABLE 2-continued

2-Imino-1,3-thiazolidin-4-ones and 2-Imino-1,3-thiazolidin-5-ones

| Entry | Compound | mp (° C.) | HPL (min.) | TLC $R_f$ | TLC Solvent System | Mass Spec. [Source] | Synth. Method |
|---|---|---|---|---|---|---|---|
| 309 | | | 7.95 (c) | 0.35 | 10% EtOAc/hex | 635 (M + H) + [FAB] | C8a |
| 310 | | 152 | 7.28 (c) | | | 307 (M+) [EI] | C11a |
| 311 | | | 8.79 (c) | 0.66 | 100% CH2Cl2 | 335 (M+) [EI] | C8a |
| 312 | | | 8.66 (c) | 0.17 | 100% CH2Cl2 | 363 (M+) [EI] | C11a |
| 313 | | 138 | 5.88 (c) | 0.57 | 2% MeOH/ CH2Cl2 | 291 (M+) [EI] | C11a |

(a) Hewlett Packard 1100 HPLC equipped with a Finnigan LCQ MS detector and a 2 × 300 mm Phenomenex 3 uM C-18 colu[001b]mn; flow rate 1.0 mL/min.; Buffer A: 0.02% TFA/2% CH$_3$CN/water, Buffer B: 0.018% TFA/98% CH$_3$CN/water; hold at 100% Buffer A for 1 min., gradient from 100% Buffer A to 100% Buffer B over 3 min., hold at 100% Buffer B 1 min., gradient from 100% Buffer B to 100% Buffer A over 0.5 min., hold at 100% Buffer A 1.5 min.
(b) Ranin Dynamax HPLC equipped with UV-DII dual wavelength detector (254 and 220 nm) and a 4 × 100 mm Dynamax 3 uM C-18 column; flow rate 1.5 mL/min.; Buffer A: 0.5% TFA/water, Buffer B: 0.5% TFA/CH$_3$CN; gradient from 100% Buffer A to 100% Buffer B over 10 min, hold at 100% Buffer B 5 min.
(c) Hewlett Packard 1090 HPLC equipped with UV detector (210 nM) and a 4 × 125 mm Nucleosil 3 uM C-18 column; flow rate 2.0 mL/min.; Buffer A: 0.01 mol % H$_3$PO$_4$/water, Buffer B: 0.01 mol % H$_3$PO$_4$/CH$_3$CN; 10% Buffer B for 1 min., gradient from 10 Buffer B to 90% Buffer B over 8 min., gradient from 90% Buffer B to 10% Buffer B over 4 min.
(d) Ranin Dynamax HPLC equipped with UV-DII dual wavelength detector (254 and 220 nm) and a 2500 mm Dynamax 8 uM C-18 column; flow rate 18 mL/min.; Buffer A: 0.1% TFA/99.9% water, Buffer B: 0.1% TFA/99.9% CH$_3$CN; gradient from 30% Buffer B to 100% Buffer B over 25 min., hold at 100% Buffer B 30 min.
(e) Ranin Dynamax HPLC equipped with UV-DII dual wavelength detector (254 and 220 nm) and a 2500 mm Dynamax 8 uM C-18 column; flow rate 18 mL/min.; Buffer A: 0.1% TFA/99.9% water, Buffer B: 0.1% TFA/99.9% CH$_3$CN; gradient from 50% Buffer B to 60% Buffer B over 25 min., gradient from 60% to 100% over 32 min.
(f) Ranin Dynamax HPLC equipped with UV-DII dual wavelength detector (254 and 220 nm) and a 21 × 2500 mm Microsorb 5 uM C-18 column; flow rate 20 mL/min.; Buffer A: 0.1% TFA/99.9% water, Buffer B: 0.1% TFA/99.9% CH$_3$CN; gradient from 30% Buffer B to 100% Buffer B over 25 min., hold at 100% B 100% for 30 min.
(g) Ranin Dynamax HPLC equipped with UV-DII dual wavelength detector (254 and 220 nm) and a 21 × 2500 mm Microsorb 5 uM C-18 column; flow rate 20 mL/min.; Buffer A: 0.1% TFA/99.9% water, Buffer B: 0.1% TFA/99.9% CH$_3$CN; gradient from 50% Buffer B to 100% Buffer B over 25 min., hold at 100% B 100% for 7 min.
(h) Ranin Dynamax HPLC equipped with UV-DII dual wavelength detector (254 and 220 nm) and a 21 × 2500 mm Microsorb 5 uM C-18 column; flow rate 20 mL/min.; Buffer A: 0.1% TFA/99.9% water, Buffer B: 0.1% TFA/99.9% CH$_3$CN; gradient from 10% Buffer B to 100% Buffer B over 30 min., hold at 100% B 100% for 7 min.
(i) Ranin Dynamax HPLC equipped with UV-DII dual wavelength detector (254 and 220 nm) and a 4.6 × 100 mm Microsorb 5 uM C-8 column; flow rate 20 mL/min.; Buffer A: 0.1% TFA/99.9% water, Buffer B: 0.1% TFA/99.9% CH$_3$CN; gradient from 10% Buffer B to 100% Buffer B over 5 min., hold at 100% B 100% for 1.5 min.

TABLE 2-continued

2-Imino-1,3-thiazolidin-4-ones and 2-Imino-1,3-thiazolidin-5-ones

| Entry | Compound | mp (° C.) | HPL (min.) | TLC $R_f$ | TLC Solvent System | Mass Spec. [Source] | Synth. Method |
|---|---|---|---|---|---|---|---|

(j) Ranin Dynamax HPLC equipped with UV-DII dual wavelength detector (254 and 220 nm) and a 21 × 2500 mm Microsorb 5 uM C-18 column; flow rate 20 mL/min.; Buffer A: 0.1% TFA/99.9% water, Buffer B: 0.1% TFA/99.9% CH$_3$CN; gradient from 20% Buffer B to 100% Buffer B over 30 min., hold at 100% B 100% for 7 min.

TABLE 3

2-Imino-1,3-oxazolidines

| Entry | Compound | mp (° C.) | HPLC (min.) | TLC $R_f$ | TLC Solvent System | Mass Spec. [Source] | Synth. Method |
|---|---|---|---|---|---|---|---|
| 314 | | | | 0.30 | 30% EtOAc/hex | 276 (M + H) + [CI] | B8a C5a |
| 315 | | | 6.77 (c) | 0.30 | 20% EtOAc/hex | 319 (M+) [EI] | B1b B4c B7b C4a |
| 316 | | | 7.42 (c) | 0.25 | 30% EtOAc/hex | 334 (M + H) + [CI] | B1b B4c B7b C4a |
| 317 | | | | 0.35 | 10% EtOAc/hex | 328 (M + H) + [HPLC ES-MS] | A3a B1b B4c C7b |
| 318 | | 134–136 | | 0.55 | 15% EtOAc/hex | 318 (M + H) + [CI] | A3a B4c C7a |
| 319 | | 112–114 | | 0.60 | 15% EtOAc/hex | 312 (M + H) + [CI] | A3a, B4c, C7a |

TABLE 3-continued

2-Imino-1,3-oxazolidines

| Entry | Compound | mp (° C.) | HPLC (min.) | TLC $R_f$ | TLC Solvent System | Mass Spec. [Source] | Synth. Method |
|---|---|---|---|---|---|---|---|
| 320 | 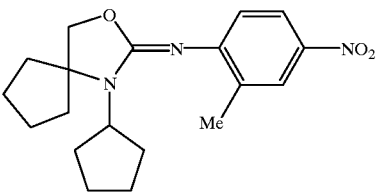 | | 8.25 (b) | | | 344 (M + H) + [CI] | B1c, B4d, B7b, C4a |
| 321 | 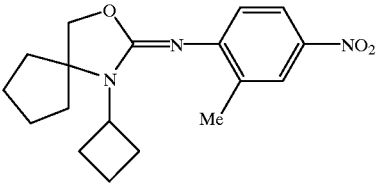 | | 7.83 (b) | | | | B1c, B4a, B7b, C4a |
| 322 | 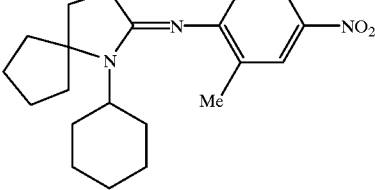 | | 8.30 (b) | | | 358 (M + H) + [CI] | B1c, B4a, B7b, C4a |
| 323 | 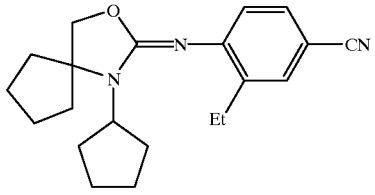 | | | 0.38 | 10% EtOAc/hex | 338 (M + H) + [FAB] | A3a, B1c, B4d, C7a |

(a) Hewlett Packard 1100 HPLC equipped with a Finnigan LCQ MS detector and a 2 × 300 mm Phenomenex 3 uM C-18 column; flow rate 1.0 mL/min.; Buffer A: 0.02% TFA/2% CH$_3$CN/water, Buffer B: 0.018% TFA/98% CH$_3$CN/water; hold at 100% Buffer A for 1 min., gradient from 100% Buffer A to 100% Buffer B over 3 min., hold at 100% Buffer B 1 min., gradient from 100% Buffer B to 100% Buffer A over 0.5 min., hold at 100% Buffer A 1.5 min.
(b) Ranin Dynamax HPLC equipped with UV-DII dual wavelength detector (254 and 220 nm) and a 4 × 100 mm Dynamax 3 uM C-18 column; flow rate 1.5 mL/min.; Buffer A: 0.5% TFA/water, Buffer B: 0.5% TFA/CH$_3$CN; gradient from 100% Buffer A to 100% Buffer B over 10 min, hold at 100% Buffer B 5 min.
(c) Hewlett Packard 1090 HPLC equipped with UV detector (210 nM) and a 4 × 125 mm Nucleosil 3 uM C-18 column; flow rate 2.0 mL/min.; Buffer A: 0.01 mol % H$_3$PO$_4$/water, Buffer B: 0.01 mol % H$_3$PO$_4$/CH$_3$CN; 10% Buffer B for 1 min., gradient from 10 Buffer B to 90% Buffer B over 8 min., gradient from 90% Buffer B to 10% Buffer B over 4 min.
(d) Ranin Dynamax HPLC equipped with UV-DII dual wavelength detector (254 and 220 nm) and a 2500 mm Dynamax 8 uM C-18 column; flow rate 18 mL/min.; Buffer A: 0.1% TFA/99.9% water, Buffer B: 0.1% TFA/99.9% CH$_3$CN; gradient from 30% Buffer B to 100% Buffer B over 25 min., hold at 100% Buffer B 30 min.
(e) Ranin Dynamax HPLC equipped with UV-DII dual wavelength detector (254 and 220 nm) and a 2500 mm Dynamax 8 uM C-18 column; flow rate 18 mL/min.; Buffer A: 0.1% TFA/99.9% water, Buffer B: 0.1% TFA/99.9% CH$_3$CN; gradient from 50% Buffer B to 60% Buffer B over 25 min., gradient from 60% to 100% over 32 min.
(f) Ranin Dynamax HPLC equipped with UV-DII dual wavelength detector (254 and 220 nm) and a 21 × 2500 mm Microsorb 5 uM C-18 column; flow rate 20 mL/min.; Buffer A: 0.1% TFA/99.9% water, Buffer B: 0.1% TFA/99.9% CH$_3$CN; gradient from 30% Buffer B to 100% Buffer B over 25 min., hold at 100% B 100% for 30 min.
(g) Ranin Dynamax HPLC equipped with UV-DII dual wavelength detector (254 and 220 nm) and a 21 × 2500 mm Microsorb 5 uM C-18 column; flow rate 20 mL/min.; Buffer A: 0.1% TFA/99.9% water, Buffer B: 0.1% TFA/99.9% CH$_3$CN; gradient from 50% Buffer B to 100% Buffer B over 25 min., hold at 100% B 100% for 7 min.
(h) Ranin Dynamax HPLC equipped with UV-DII dual wavelength detector (254 and 220 nm) and a 21 × 2500 mm Microsorb 5 uM C-18 column; flow rate 20 mL/min.; Buffer A: 0.1% TFA/99.9% water, Buffer B: 0.1% TFA/99.9% CH$_3$CN; gradient from 10% Buffer B to 100% Buffer B over 30 min., hold at 100% B 100% for 7 min.
(i) Ranin Dynamax HPLC equipped with UV-DII dual wavelength detector (254 and 220 nm) and a 4.6 × 100 mm Microsorb 5 uM C-8 column; flow rate 20 mL/min.; Buffer A: 0.1% TFA/99.9% water, Buffer B: 0.1% TFA/99.9% CH$_3$CN; gradient from 10% Buffer B to 100% Buffer B over 5 min., hold at 100% B 100% for 1.5 min.
(j) Ranin Dynamax HPLC equipped with UV-DII dual wavelength detector (254 and 220 nm) and a 21 × 2500 mm Microsorb 5 uM C-18 column; flow rate 20 mL/min.; Buffer A: 0.1% TFA/99.9% water, Buffer B: 0.1% TFA/99.9% CH$_3$CN; gradient from 20% Buffer B to 100% Buffer B over 30 min., hold at 100% B 100% for 7 min.

TABLE 4

Additional Examples

| Entry | Compound | mp (° C.) | HPLC (min.) | TLC R$_f$ | TLC Solvent System | Mass Spec. [Source] | Synth. Meth. |
|---|---|---|---|---|---|---|---|
| 324 | (structure: 4-isobutyl-1-isobutyl-imidazoline-2-thio-4-nitrophenyl) | | | 0.67 | 30% EtOAc/hex | 336 (M + H) + [HPLC ES-MS] | B1b, B4c, B7c, C1f |
| 325 | (structure: isobutyl-thiazoline-N-(2-methyl-4-nitrophenyl)-N-(heptan-4-yl)) | | | 0.81 | 30% EtOAc/hex | 392 (M + H) + [FAB] | B7a, C1a, D2a |
| 326 | (structure: isobutyl-thiazoline-N-(2-methyl-4-nitrophenyl)-N-isobutyl, HCl) | 7.99 (b) | | 0.59 | 20% EtOAc/hex | 350 (M + H) + [FAB] | B1b B7a, C1a, D2a |
| 327 | (structure: isobutyl-thiazoline-N-(2-methyl-4-nitrophenyl)-N-neopentyl) | | | 0.81 | 30% EtOAc/hex | 364 (M + H) + [FAB] | B7a, C1a, D2a |
| 328 | (structure: isobutyl-thiazoline-N-(2,3-dichlorophenyl)-N-(pentan-3-yl)) | | | .74 | 30% EtOAc/hex | 387 (M + H) + [FAB] | B7a, C1a, D2a |

(a) Hewlett Packard 1100 HPLC equipped with a Finnigan LCQ MS detector and a 2 × 300 mm Phenomenex 3 uM C-18 column; flow rate 1.0 mL/min.; Buffer A: 0.02% TFA/2% CH$_3$CN/water, Buffer B: 0.018% TFA/98% CH$_3$CN/water; hold at 100% Buffer A for 1 min., gradient from 100% Buffer A to 100% Buffer B over 3 min., hold at 100% Buffer B 1 min., gradient from 100% Buffer B to 100% Buffer A over 0.5 min., hold at 100% Buffer A 1.5 min.
(b) Ranin Dynamax HPLC equipped with UV-DII dual wavelength detector (254 and 220 nm) and a 4 × 100 mm Dynamax 3 uM C-18 column; flow rate 1.5 mL/min.; Buffer A: 0.5% TFA/water, Buffer B: 0.5% TFA/CH$_3$CN; gradient from 100% Buffer A to 100% Buffer B over 10 min, hold at 100% Buffer B 5 min.
(c) Hewlett Packard 1090 HPLC equipped with UV detector (210 nM) and a 4 × 125 mm Nucleosil 3 uM C-18 column; flow rate 2.0 mL/min.; Buffer A: 0.01 mol % H$_3$PO$_4$/water, Buffer B: 0.01 mol % H$_3$PO$_4$/CH$_3$CN; 10% Buffer B for 1 min., gradient from 10 Buffer B to 90% Buffer B over 8 min., gradient from 90% Buffer B to 10% Buffer B over 4 min.
(d) Ranin Dynamax HPLC equipped with UV-DII dual wavelength detector (254 and 220 nm) and a 2500 mm Dynamax 8 uM C-18 column; flow rate 18 mL/min.; Buffer A: 0.1% TFA/99.9% water, Buffer B: 0.1% TFA/99.9% CH$_3$CN; gradient from 30% Buffer B to 100% Buffer B over 25 min., hold at 100% Buffer B 30 min.
(e) Ranin Dynamax HPLC equipped with UV-DII dual wavelength detector (254 and 220 nm) and a 2500 mm Dynamax 8 uM C-18 column; flow rate 18 mL/min.; Buffer A: 0.1% TFA/99.9% water, Buffer B: 0.1% TFA/99.9% CH$_3$CN; gradient from 50% Buffer B to 60% Buffer B over 25 min., gradient from 60% to 100% over 32 min.
(f) Ranin Dynamax HPLC equipped with UV-DII dual wavelength detector (254 and 220 nm) and a 21 × 2500 mm Microsorb 5 uM C-18 column; flow rate 20 mL/min.; Buffer A: 0.1% TFA/99.9% water, Buffer B: 0.1% TFA/99.9% CH$_3$CN; gradient from 30% Buffer B to 100% Buffer B over 25 min., hold at 100% B 100% for 30 min.
(g) Ranin Dynamax HPLC equipped with UV-DII dual wavelength detector (254 and 220 nm) and a 21 × 2500 mm Microsorb 5 uM C-18 column; flow rate 20 mL/min.; Buffer A: 0.1% TFA/99.9% water, Buffer B: 0.1% TFA/99.9% CH$_3$CN; gradient from 50% Buffer B to 100% Buffer B over 25 min., hold at 100% B 100% for 7 min.
(h) Ranin Dynamax HPLC equipped with UV-DII dual wavelength detector (254 and 220 nm) and a 21 × 2500 mm Microsorb 5 uM C-18 column; flow rate 20 mL/min.; Buffer A: 0.1% TFA/99.9% water, Buffer B: 0.1% TFA/99.9% CH$_3$CN; gradient from 10% Buffer B to 100% Buffer B over 30 min., hold at 100% B 100% for 7 min.

TABLE 4-continued

Additional Examples

| Entry | Compound | mp (° C.) | HPLC (min.) | TLC $R_f$ | TLC Solvent System | Mass Spec. [Source] | Synth. Meth. |
|---|---|---|---|---|---|---|---|

(i) Ranin Dynamax HPLC equipped with UV-DII dual wavelength detector (254 and 220 nm) and a 4.6 × 100 mm Microsorb 5 uM C-8 column; flow rate 20 mL/min.; Buffer A: 0.1% TFA/99.9% water, Buffer B: 0.1% TFA/99.9% $CH_3CN$; gradient from 10% Buffer B to 100% Buffer B over 5 min., hold at 100% B 100% for 1.5 min.

(j) Ranin Dynamax HPLC equipped with UV-DII dual wavelength detector (254 and 220 nm) and a 21 × 2500 mm Microsorb 5 uM C-18 column; flow rate 20 mL/min.; Buffer A: 0.1% TFA/99.9% water, Buffer B: 0.1% TFA/99.9% $CH_3CN$; gradient from 20% Buffer B to 100% Buffer B over 30 min., hold at 100% B 100% for 7 min.

Biological Protocol

The activity of a given compound to bind to the progesterone receptor can be assayed routinely according to procedure disclosed below. This procedure was used to determine the progesterone binding activities of the compounds of the invention.

Progesterone Receptor Binding Assay

To siliconized glass test tubes cooled over an ice water bath was added binding buffer (100 mL; 50 mM Tris, pH 7.4, 10 mM molybdic acid, 2 mM EDTA, 150 mM NaCl, 5% Glycerol, 1% DMSO) containing various concentrations of a compound to be assayed, T47D cell cytosol (100 μL of a solution which will give at least 4000 cpm of binding) and $^3$H-progesterone (50 μL, 10 nM, NET-381). The mixture was incubated for 16 h at 4° C., and treated with charcoal (250 μL of a 0.5% mixture of 0.05% dextran-coated charcoal which had been washed twice with binding buffer). The resulting mixture was incubated for 10 min. at 4° C. The tubes were centrifuged (20 min at 2800×g) at 4° C. The supernatant was transferred into scintillation vials containing scintillation fluid (4 mL). Remaining $^3$H-progesterone was determined with a Packard 1900TR beta counter. Each assay included the following control groups: 1) total binding group (without compound), 2) non-specific binding group (with 400 nM progesterone), and 3) positive control group (with 2 nM progesterone or a known inhibitor).

The compounds of the present invention were found to cause greater than or equal to 30% inhibition of binding of $^3$H-progesterone to the progesterone receptor at a compound concentration of 200 nM. Activity ranges of the compounds of the present invention in the Progesterone Receptor Binding Assay at a compound concentration of 20 nM are listed in Table 5.

TABLE 5

Inhibitory Activity of Exemplified Compounds

| Compounds Which Cause 30–59% Inhibition at 200 nM (Entry Number) | Compounds Which Cause 60–79% Inhibition at 200 nM (Entry Number) | Compounds Which Cause 80–100% Inhibition at 200 nM (Entry Number) |
|---|---|---|
| 1 | 2 | 3 |
| 5 | 4 | 8 |
| 6 | 9 | 11 |
| 7 | 15 | 14 |
| 10 | 16 | 17 |
| 12 | 19 | 18 |
| 13 | 26 | 20 |
| 27 | 29 | 21 |
| 34 | 30 | 22 |
| 43 | 31 | 23 |
| 45 | 32 | 24 |
| 48 | 35 | 25 |
| 49 | 36 | 28 |
| 56 | 37 | 33 |
| 57 | 38 | 40 |
| 59 | 39 | 41 |
| 61 | 42 | 44 |
| 64 | 46 | 47 |
| 66 | 54 | 50 |
| 67 | 60 | 51 |
| 74 | 63 | 52 |
| 75 | 71 | 53 |
| 79 | 73 | 55 |
| 83 | 77 | 58 |
| 84 | 78 | 62 |
| 87 | 81 | 65 |
| 89 | 82 | 68 |
| 92 | 86 | 69 |
| 94 | 88 | 70 |
| 96 | 95 | 72 |
| 108 | 103 | 76 |
| 113 | 106 | 80 |
| 120 | 110 | 85 |
| 123 | 112 | 90 |
| 129 | 114 | 91 |
| 130 | 119 | 93 |
| 131 | 134 | 97 |
| 135 | 144 | 99 |
| 136 | 149 | 102 |
| 141 | 150 | 104 |
| 143 | 153 | 105 |
| 146 | 154 | 107 |
| 147 | 155 | 109 |
| 148 | 160 | 111 |
| 151 | 162 | 115 |
| 152 | 164 | 116 |
| 156 | 166 | 117 |
| 157 | 170 | 118 |
| 158 | 174 | 121 |
| 159 | 180 | 122 |
| 161 | 188 | 125 |
| 163 | 193 | 126 |
| 169 | 198 | 127 |
| 175 | 200 | 128 |
| 181 | 201 | 132 |
| 182 | 210 | 133 |
| 183 | 211 | 137 |
| 184 | 212 | 138 |
| 185 | 225 | 139 |
| 186 | 236 | 140 |
| 187 | 241 | 145 |
| 189 | 242 | 165 |
| 190 | 246 | 167 |
| 191 | 258 | 168 |
| 192 | 260 | 171 |
| 194 | 261 | 172 |
| 195 | 269 | 173 |

TABLE 5-continued

Inhibitory Activity of Exemplified Compounds

| Compounds Which Cause 30–59% Inhibition at 200 nM (Entry Number) | Compounds Which Cause 60–79% Inhibition at 200 nM (Entry Number) | Compounds Which Cause 80–100% Inhibition at 200 nM (Entry Number) |
|---|---|---|
| 199 | 277 | 176 |
| 202 | 279 | 177 |
| 203 | 290 | 178 |
| 204 | 294 | 179 |
| 205 | 296 | 196 |
| 207 | 297 | 197 |
| 226 | 300 | 206 |
| 227 | 301 | 208 |
| 228 | 317 | 209 |
| 229 |  | 213 |
| 238 |  | 215 |
| 254 |  | 218 |
| 257 |  | 219 |
| 262 |  | 220 |
| 263 |  | 221 |
| 264 |  | 223 |
| 265 |  | 224 |
| 266 |  | 230 |
| 270 |  | 231 |
| 272 |  | 232 |
| 273 |  | 233 |
| 308 |  | 234 |
| 309 |  | 235 |
| 310 |  | 237 |
| 312 |  | 240 |
| 313 |  | 243 |
| 314 |  | 244 |
| 321 |  | 245 |
| 324 |  | 247 |
| 326 |  | 248 |
| 327 |  | 249 |
| 328 |  | 250 |
|  |  | 251 |
|  |  | 252 |
|  |  | 253 |
|  |  | 255 |
|  |  | 256 |
|  |  | 259 |
|  |  | 267 |
|  |  | 268 |
|  |  | 271 |
|  |  | 274 |
|  |  | 275 |
|  |  | 276 |
|  |  | 278 |
|  |  | 280 |
|  |  | 281 |
|  |  | 282 |
|  |  | 283 |
|  |  | 284 |
|  |  | 285 |
|  |  | 286 |
|  |  | 287 |
|  |  | 288 |
|  |  | 289 |
|  |  | 291 |
|  |  | 292 |
|  |  | 293 |
|  |  | 295 |
|  |  | 298 |
|  |  | 299 |
|  |  | 302 |
|  |  | 303 |
|  |  | 304 |
|  |  | 305 |
|  |  | 306 |
|  |  | 307 |
|  |  | 311 |
|  |  | 315 |
|  |  | 316 |
|  |  | 318 |
|  |  | 319 |
|  |  | 320 |
|  |  | 322 |
|  |  | 323 |
|  |  | 325 |

The preceeding examples can be repeated with similar success by substituting the generically or specifically described reactants and/or operating conditions of this invention for those used in the preceeding examples.

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

We claim:

1. A compound having the formula $$(T)_tR\diagdown N=\diagup^{R^1(G)_g}$$
(with X, $(Q)_qR^2$, $(Q)_qR^3$, $(Q)_qR^4$, $(C_nH_{2n-p})$ in a ring)

wherein

R is
  substituted phenyl, wherein the substituent is selected from T; or
  substituted pyridyl, wherein the substituent is selected from T;

R¹ is
  alkyl of 1–10 carbons;
  cycloalkyl of 3–12 carbons and containing 1–3 rings;
  alkenyl of 2–10 carbons;
  cycloalkenyl of 5–12 carbons and containing 1–3 rings; or
  alkynyl of 3–10 carbons;

$R^2$, $R^3$, and $R^4$ are independently selected from the group consisting of
  H;
  alkyl of 1–10 carbons;
  cycloalkyl of 3–12 carbons;
  alkenyl of 2–10 carbons;
  cycloalkenyl of 5–12 carbons; and
  =O, representing two of the groups $R^2$, $R^3$, and $R^4$;

X is $S(O)_y$; wherein
  y is 0, 1, or 2;
n is 2;
p is the sum of non-H substituents $R^2$, $R^3$, and $R^4$;
T is a substituent selected from the group consisting of
  alkyl of 1–4 carbons;
  alkoxy of 1–4 carbons;
  alkenyl of 2–4 carbons;
  alkynyl of 2–4 carbons;

NO$_2$;
CN; and
halogen;

t is 1–5;
provided that when substituent moiety T is alkyl of 1–4 carbons, alkoxy of 1–4 carbons, alkenyl of 2–4 carbons, or alkynyl of 2–4 carbons, then T optionally may bear secondary substituents selected from the group consisting of
alkyl of 1–4 carbons;
alkoxy of 1–4 carbons;
CO$_2$R$^5$; wherein
R$^5$ is alkyl of 1–4 carbons, haloalkyl of 1–4 carbons, cycloalkyl of 3–6 carbons, or halocycloalkyl of 3–6 carbons;
CO$_2$H;
C(O)N(R$^6$)(R$^7$); wherein
R$^6$ is H or alkyl of 1–5 carbons; and
R$^7$ is H or alkyl of 1–5 carbons;
CHO;
OH;
NO$_2$;
CN
halogen;
S(O)yR$^8$; wherein
R$^8$ is alkyl of 1–5 carbons; and
=O, representing two secondary substituents;
the number of said secondary substituents being 1 or 2 with the exception of halogen, which may be employed up to the perhalo level;

G is a substituent selected from the group consisting of
halogen;
OR$^5$;
alkyl of 1–4 carbons;
alkenyl of 1–4 carbons;
cycloalkyl of 3–7 carbons;
cycloalkenyl of 5–7 carbons;
aryl of 6–10 carbons; and
CN;

g is 0–4, with the exception of halogen, which may be employed up to the perhalo level;
provided that when substituent G is alkyl of 1–4 carbons, alkenyl of 1–4 carbons, cycloalkyl of 3–7 carbons, or cycloalkenyl of 5–7 carbons, then G optionally may bear secondary substituents of halogen up to the perhalo level; and when substituent G is aryl, then G optionally may bear secondary substituents independently selected from the group consisting of alkyl of 1–4 carbons and halogen, the number of said secondary substituents being up to 3 for alkyl moieties, and up to the perhalo level for halogen;

Q is a substituent selected from the group consisting of
alkyl of 1–4 carbons;
haloalkyl of 1–4 carbons;
cycloalkyl of 3–8 carbons;
alkoxy of 1–8 carbons;
alkenyl of 2–5 carbons;
cycloalkenyl of 5–8 carbons;
CO$_2$R$^5$;
=O, representing two substituents Q;
OH;
halogen;
N(R$^6$)(R$^7$); and
S(O)$_y$R$^8$;

q is 0–4; and
with the further provisos that:
a) two of (Q)$_q$R$^1$, (Q)$_q$R$^2$ (Q)$_q$R$^3$, and (Q)$_q$R$^4$ may be joined, and taken together with the atom(s) to which they are attached, form a spiro or nonspiro nonaromatic ring of 3–8 members containing 0–2 heteroatoms selected from the group consisting of N, O, and S;
b) at least one of R$^2$, R$^3$, and R$^4$ is other than H;
c) the sum of non-hydrogen atoms in R$^1$, R$^2$, R$^3$, and R$^4$ is at least 5; and
d) when the 4-position of the 1,3-thiazolidine ring bears a carbonyl group, R$^1$ is a substituted methyl group, and G is a phenyl group, then said phenyl group bears a secondary substituent;
and pharmaceutically acceptable salts thereof.

2. A compound having the formula wherein
R is
substituted phenyl, wherein the substituent is selected from T; or
substituted pyridyl, wherein the substituent is selected from T;
R$^1$ is
alkyl of 1–10 carbons;
cycloalkyl of 3–12 carbons and containing 1–3 rings;
alkenyl of 2–10 carbons; or
cycloalkenyl of 5–12 carbons and containing 1–3 rings;
R$^2$, R$^3$, and R$^4$ are independently selected from the group consisting of
H;
alkyl of 1–10 carbons;
cycloalkyl of 3–12 carbons;
alkenyl of 2–10 carbons; and
cycloalkenyl of 5–12 carbons;
X is S(O)$_y$; wherein
y is 0, 1, or 2;
n is 2;
p is the sum of non-H substituents R$^2$, R$^3$, and R$^4$;
T is a substituent selected from the group consisting of
alkyl of 1–4 carbons;
alkenyl of 2–4 carbons;
NO$_2$;
CN; and
halogen;
t is 1–5;
provided that when substituent moiety T is alkyl of 1–4 carbons, or alkenyl of 2–4 carbons, then T optionally may bear secondary substituents selected from the group consisting of
alkyl of 1–4 carbons;
alkoxy of 1–4 carbons;
CO$_2$R$^5$; wherein
R$^5$ is alkyl of 1–4 carbons, haloalkyl of 1–4 carbons, cycloalkyl of 3–6 carbons, or halocycloalkyl of 3–6 carbons;

CO$_2$H;
C(O)N(R$^6$)(R$^7$); wherein
   R$^6$ is H or alkyl of 1–5 carbons; and
   R$^7$ is H or alkyl of 1–5 carbons;
CHO;
OH;
NO$_2$;
CN;
halogen;
S(O)$_x$R$^8$; wherein
   R$^8$ is alkyl of 1–5 carbons; and
=O;
   the number of said secondary substituents being 1 or 2 with the exception of halogen, which may be employed up to the perhalo level;
G is a substituent selected from the group consisting of
halogen;
alkyl of 1–4 carbons;
alkenyl of 1–4 carbons;
cycloalkyl of 3–7 carbons;
cycloalkenyl of 5–7 carbons; and
aryl of 6–10 carbons;
g is 0–4, with the exception of halogen, which may be employed up to the perhalo level;
   provided that when substituent G is alkyl of 1–4 carbons, alkenyl of 1–4 carbons, cycloalkyl of 3–7 carbons, or cycloalkenyl of 5–7 carbons, then G optionally may bear secondary substituents of halogen up to the perhalo level; and when substituent G is aryl, then G optionally may bear secondary substituents independently selected from the group consisting of alkyl of 1–4 carbons and halogen, the number of said secondary substituents being up to 3 for alkyl moieties, and up to the perhalo level for halogen;
Q is a substituent selected from the group consisting of
alkyl of 1–4 carbons;
haloalkyl of 1–4 carbons;
cycloalkyl of 3–8 carbons;
alkoxy of 1–8 carbons;
alkenyl of 2–5 carbons;
cycloalkenyl of 5–8 carbons; and
halogen;
q is 0–4; and
with the further provisos that:
a) two Of (Q)$_q$R$^1$, (Q)$_q$R$^2$, (Q)$_q$R$^3$, and (Q)$_q$R$^4$ may be joined, and taken together with the atom(s) to which they are attached, form a spiro or nonspiro nonaromatic ring of 3–8 members containing 0–2 heteroatoms selected from the group consisting of N, O, and S;
b) at least one of R$^2$, R$^3$, and R$^4$ is other than H;
c) the sum of non-hydrogen atoms in R$^1$, R$^2$, R$^3$, and R$^4$ is at least 5; and pharmaceutically acceptable salts thereof.

3. A compound of claim 1, selected from the group consisting of:
(4S)-2-(2-methyl-4-nitrophenylimino)-3-isobutyl-4-isopropyl-1,3-thiazolidine;
(4S)-2-(2-methyl-4-nitrophenylimino)-3,4-diisobutyl-1,3-thiazolidine;
(4S)-2-(2-methyl-4-nitrophenylimino)-3-isobutyl-4-(trifluoromethyl)-1,3-thiazolidine;
(4S)-2-(2-methyl-4-nitrophenylimino)-3-cyclopentyl-4-isobutyl-1,3-thiazolidine;
(4S)-2-(2-methyl-4-nitrophenylimino)-3-isobutyl-4-isopropyl-1,3-thiazolidine;
(4S)-2-(2-methyl-4-nitrophenylimino)-3-cyclopentyl-4-isopropyl-1,3-thiazolidine;
2-(4-cyano-2-methylphenylimino)-1-cyclopentyl-3-thia-1-azaspiro[4.4]nonane;
2-(4-cyano-2-ethylphenylimino)-1-cyclopentyl-3-thia-1-azaspiro[4.4]nonane;
2-(4-cyanophenylimino)-1-cyclopentyl-3-thia-1-azaspiro[4.4]nonane;
2-(4-cyano-2-methylphenylimino)-1-isobutyl-3-thia-1-azaspiro [4.4]nonane;
2-(4-cyano-2,3-dimethylphenylimino)-1-isobutyl-3-thia-1-azaspiro[4.4]nonane;
2-(4-cyano-2-methylphenylimino)-1-(1-ethyl-1-propyl)-3-thia-1-azaspiro[4.4]nonane;
2-(2-methyl-4-nitrophenylimino)-1-(prop-2-en-1-yl)-3-thia-1-azaspiro[4.4]nonane;
2-(2-methyl-4-nitrophenylimino)-1-isopropyl-3-thia-1-azaspiro[4.4]nonane;
2-(2-methyl-4-nitrophenylimino)-1-isobutyl-3-thia-1-azaspiro[4.4]nonane;
2-(2-methyl-4-nitrophenylimino)-1-cyclopentyl-3-thia-1-azaspiro[4.4]nonane;
2-(3-methyl-4-nitrophenylimino)-1-cyclopentyl-3-thia-1-azaspiro[4.4]nonane;
2-(2-methyl-4-nitrophenylimino)-1-cyclohexyl-3-thia-1-azaspiro[4.4]nonane;
2-(2,3-dimethyl-4-nitrophenylimino)-1-cyclopentyl-3-thia-1-azaspiro[4.4]nonane; and
2-(4-cyano-2,3-dimethylphenylimino)-1-cyclopentyl-3-thia-1-azaspiro[4.4]nonane.

4. A compound of claim 1, selected from the group consisting of:
2-(2-methyl-4-nitrophenylimino)-3-isobutyl-1,3-thiazolidin-4-one;
2-(3-methyl-4-nitrophenylimino)-3-isobutyl-1,3-thiazolidin-4-one;
2-(2-methyl-4-nitrophenylimino)-3-benzyl-1,3-thiazolidin-4-one;
2-(3-methyl-4-nitrophenylimino)-3-benzyl-1,3-thiazolidin-4-one;
2-(2-methyl-4-nitrophenylimino)-3-(2-methyl-1-butyl)-1,3-thiazolidin-4-one;
2-(3-methyl-4-nitrophenylimino)-3-(2-methyl-1-butyl)-1,3-thiazolidin-4-one;
2-(2-methyl-4-nitrophenylimino)-3-( 1-cyclohexyl-1-ethyl)-1,3-thiazolidin-4-one;
2-(3-methyl-4-nitrophenylimino)-3-(1-cyclohexyl-1-ethyl)-1,3-thiazolidin-4-one;
2-(2-methyl-4-nitrophenylimino)-3-(2-ethyl-1-butyl)-1,3-thiazolidin-4-one; and
2-(2-methyl-4-nitrophenylimino)-3-isobutyl-5-methyl-1,3-thiazolidin-4-one.

5. A pharmaceutical composition comprising a compound of claim 1, 2, 3, or 4, and a pharmaceutically acceptable carrier.

6. A method of treating a mammal by administering to said mammal an effective amount of a compound for:
A1) enhancement of bone formation in bone weakening diseases for the treatment or prevention of osteopenia or osteoporosis;
A2) enhancement of fracture healing;
B1) use as a female contragestive agent;
B2) prevention of endometrial implantation;
B3) induction of labor;
B4) treatment of luteal deficiency;
B5) enhanced recognition and maintenance of pregnancy;
B6) counteracting of preeclampsia, eclampsia of pregnancy, and preterm labor;

B7) treatment of infertility, including promotion of spermatogenesis, induction of the acrosome reaction, maturation of oocytes, or in vitro fertilization of oocytes;
C1) treatment of dysmenorrhea;
C2) treatment of dysfunctional uterine bleeding;
C3) treatment of ovarian hyperandrogynism;
C4) treatment of ovarian hyperaldosteronism;
C5) alleviation of premenstral syndrome and of premenstral tension;
C6) alleviation of perimenstrual behavior disorders;
C7) treatment of climeracteric disturbance, including, menopause transition, mood changes, sleep disturbance, and vaginal dryness;
C9) treatment of post menopausal urinary incontinence;
C10) improvement of sensory and motor functions;
C12) alleviation of postpartum depression;
C13) treatment of genital atrophy;
C14) prevention of postsurgical adhesion formation;
C15) regulation of uterine immune function;
D1) hormone replacement;
E1) treatment of breast cancer, uterine cancer, ovarian cancer, or endometrial cancer;
E2) treatment of endometriosis;
E3) treatment of uterine fibroids;
F1) treatment of hirsutism;
F2) inhibition of hair growth;
G1) activity as a male contraceptive; and
G2) activity as an abortifacient;
wherein said compound has the general formula

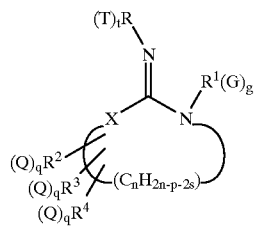

wherein
R is
  substituted aryl of 6–14 carbons, wherein the substituent is selected from T; or
  heteroaryl of 3–10 carbons and containing 1–3 heteroatoms selected from the group consisting of N, O, and S, with the proviso that R is other than benzofuran or benzothiophene;
$R^1$ is
  alkyl of 1–10 carbons;
  cycloalkyl of 3–12 carbons and containing 1–3 rings;
  heterocycloalkyl of 4–7 carbons and containing 1–3 rings and 1–3 heteroatoms selected from the group consisting of N, O, and S;
  substituted aryl of 6–10 carbons, wherein the substituent is selected from G;
  heteroaryl of 3–9 carbons and containing 1–3 rings and 1–3 heteroatoms selected from the group consisting of N, O, and S;
  alkenyl of 2–10 carbons;
  cycloalkenyl of 5–12 carbons and containing 1–3 rings; or alkynyl of 3–10 carbons;
$R^2$, $R^3$, and $R^4$ are independently selected from the group consisting of
  H;
  alkyl of 1–10 carbons;
  cycloalkyl of 3–12 carbons;
  alkenyl of 2–10 carbons;
  cycloalkenyl of 5–12 carbons;
  aryl of 6–13 carbons;
  heteroaryl of 3–9 carbons and containing 1–3 heteroatoms selected from the group consisting of N, O, and S;
  $CO_2R^5$; wherein
    $R^5$ is alkyl of 1–4 carbons, haloalkyl of 1–4 carbons, cycloalkyl of 3–6 carbons, or halocycloalkyl of 3–6 carbons;
  halogen; and
  =O, representing two of the groups $R^2$, $R^3$, and $R^4$;
X is $S(O)_y$; wherein
  y is 0, 1, or 2;
n is 2;
p is the sum of non-H substituents $R^2$, $R^3$, and $R^4$;
s represents the number of double bonds in the ring, and is 0, 1, or 2;
T is a substituent selected from the group consisting of
  alkyl of 1–4 carbons;
  alkoxy of 1–4 carbons;
  aryl of 6–10 carbons;
  $CO_2H$;
  $CO_2R^5$;
  alkenyl of 2–4 carbons;
  alkynyl of 2–4 carbons;
  $C(O)C_6H_5$;
  $C(O)N(R^6)(R^7)$; wherein
    $R^6$ is H or alkyl of 1–5 carbons; and
    $R^7$ is H or alkyl of 1–5 carbons;
  $S(O)_{y'}R^8$; wherein
    y' is 1 or 2; and
    $R^8$ is alkyl of 1–5 carbons;
  $SO_2F$;
  CHO;
  OH;
  $NO_2$;
  CN;
  halogen;
  $OCF_3$;
  N-oxide;
  O—$C(R^9)_2$—O, the oxygens being connected to adjacent positions on R; and
    wherein $R^9$ is H, halogen, or alkyl of 1–4 carbons;
  C(O)NHC(O), the carbons being connected to adjacent positions on R; and
  $C(O)C_6H_4$, the carbonyl carbon and the ring carbon ortho to the carbonyl being connected to adjacent positions on R;
t is 1–5;
provided that when substituent moiety T is alkyl of 1–4 carbons; alkoxy of 1–4 carbons; aryl of 6–10 carbons; $CO_2R^5$; alkenyl of 2–4 carbons; alkynyl of 2–4 carbons; $C(O)C_6H_5$; $C(O)N(R^6)(R^7)$; $S(O)_{y'}R^8$; O—$C(R^9)_2$—O, or $C(O)C_6H_4$, then T optionally may bear secondary substituents selected from the group consisting of alkyl of 1–4 carbons; alkoxy of 1–4 carbons; $CO_2R^5$; $CO_2H$; $C(O)N(R^6)(R^7)$; CHO; OH; $NO_2$; CN; halogen; $S(O)yR^8$; or =O, the number of said secondary substituents being 1 or 2 with the exception of halogen, which may be employed up to the perhalo level;
G is a substituent selected from the group consisting of
  halogen;
  OH;
  $OR^5$;
  =O, representing two substituents G;

alkyl of 1–4 carbons;
alkenyl of 1–4 carbons;
cycloalkyl of 3–7 carbons;
heterocycloalkyl of 3–5 carbons and 1–3 heteroatoms selected from the group consisting of N, O, and S;
cycloalkenyl of 5–7 carbons;
heterocycloalkenyl of 4–6 carbons and 1–3 heteroatoms selected from the group consisting of N, O, and S;
$CO_2R^5$;
$C(O)N(R^6)(R^7)$;
aryl of 6–10 carbons;
heteroaryl of 3–9 carbons and 1–3 heteroatoms selected from the group consisting of N, O, and S;
$NO_2$;
CN;
$S(O)_yR^8$;
$SO_3R^8$; and
$SO_2N(R^6)(R^7)$;

g is 0–4, with the exception of halogen, which may be employed up to the perhalo level;
provided that when substituent G is alkyl of 1–4 carbons, alkenyl of 1–4 carbons, cycloalkyl of 3–7 carbons, heterocycloalkyl of 3–5 carbons, cycloalkenyl of 5–7 carbons, or heterocycloalkenyl of 4–6 carbons, then G optionally may bear secondary substituents of halogen up to the perhalo level; and when substituent G is aryl or heteroaryl, then G optionally may bear secondary substituents independently selected from the group consisting of alkyl of 1–4 carbons and halogen, the number of said secondary substituents being up to 3 for alkyl moieties, and up to the perhalo level for halogen;

Q is a substituent selected from the group consisting of alkyl of 1–4 carbons;
haloalkyl of 1–4 carbons;
cycloalkyl of 3–8 carbons;
alkoxy of 1–8 carbons;
alkenyl of 2–5 carbons;
cycloalkenyl of 5–8 carbons;
aryl of 6–10 carbons;
heteroaryl of 3–9 carbons and containing 1–3 heteroatoms selected from the group consisting of N, O, and S;
$CO_2R^5$
=O, representing two substituents Q;
OH;
halogen;
$N(R^6)(R^7)$;
$S(O)_yR^8$;
$SO_3R^8$; and
$SO_2N(R^6)(R^7)$;

q is 0–4
provided that when substituent Q is aryl or heteroaryl, then Q optionally may bear secondary substituents independently selected from the group consisting of alkyl of 1–4 carbons and halogen, the number of said secondary substituents being up to 3 for alkyl moieties and up to the perhalo level for halogen; and with the firer proviso that two of $(Q)_qR^1$, $(Q)_qR^2$, $(Q)_qR^3$, and $(Q)_qR^4$ may be joined, and taken together with the atom(s) to which they are attached, form a spiro or nonspiro nonaromatic ring of 3–8 members containing 0–2 heteroatoms selected from the group consisting of N, O, and S;

and pharmaceutically acceptable salts thereof.

7. The method of claim 6 wherein said mammal is a human.

\* \* \* \* \*